(12) United States Patent
Akritopoulou-Zanze et al.

(10) Patent No.: US 8,648,069 B2
(45) Date of Patent: Feb. 11, 2014

(54) 5-SUBSTITUTED INDAZOLES AS KINASE INHIBITORS

(75) Inventors: Irini Akritopoulou-Zanze, Libertyville, IL (US); Brian D. Wakefield, Vernon Hills, IL (US); Helmut Mack, Ludwigshafen (DE); Sean C. Turner, Mannheim (DE); Alan F. Gasiecki, Vernon Hills, IL (US); Vijaya J. Gracias, West Newton, IN (US); Kathy A. Sarris, Deerfield, IL (US); Douglas M. Kalvin, Buffalo Grove, IL (US); Melissa J. Michmerhuizen, Beach Park, IL (US); Qi Shuai, Dekalb, IL (US); Jyoti R. Patel, Libertyville, IL (US); Margaretha Bakker, Seeheim-Jugenheim (DE); Nicole Teusch, Wuelfrath (DE); Eric F. Johnson, Temecula, CA (US); Peter J. Kovar, Chicago, IL (US); Stevan W. Djuric, Libertyville, IL (US); Andrew J. Long, Chelmsford, MA (US); Anil Vasudevan, Union Grove, WI (US); Dawn George, Charlton, MA (US); Lu Wang, Worcester, MA (US); Biqin Li, Northborough, MA (US); N. St. John Moore, Shrewsbury, MA (US); Adrian D. Hobson, Shrewsbury, MA (US); Keith W. Woods, Libertyville, IL (US); Julie M. Miyashiro, Morton Grove, IL (US); Steven L. Swann, Jr., Antioch, IL (US); Thomas D. Penning, Elmhurst, IL (US)

(73) Assignee: AbbVie Inc., North Chicago, IL (US)

( * ) Notice: Subject to any disclaimer, the term of this patent is extended or adjusted under 35 U.S.C. 154(b) by 368 days.

(21) Appl. No.: 12/327,991

(22) Filed: Dec. 4, 2008

(65) Prior Publication Data

US 2009/0203690 A1 Aug. 13, 2009

Related U.S. Application Data

(63) Continuation-in-part of application No. 12/132,993, filed on Jun. 4, 2008, now abandoned.

(60) Provisional application No. 60/933,960, filed on Jun. 8, 2007.

(51) Int. Cl.
| | | |
|---|---|---|
| *A61K 31/541* | (2006.01) | |
| *A61K 31/5377* | (2006.01) | |
| *A61K 31/496* | (2006.01) | |
| *A61K 31/454* | (2006.01) | |
| *A61K 31/4192* | (2006.01) | |
| *C07D 417/14* | (2006.01) | |
| *C07D 405/14* | (2006.01) | |
| *C07D 401/14* | (2006.01) | |
| *C07D 403/04* | (2006.01) | |
| *C07D 403/14* | (2006.01) | |

(52) U.S. Cl.
USPC ............... 514/228.2; 514/234.8; 514/254.06; 514/322; 514/403; 514/405; 544/58.2; 544/140; 544/371; 546/199

(58) Field of Classification Search
None
See application file for complete search history.

(56) References Cited

U.S. PATENT DOCUMENTS

| | | | |
|---|---|---|---|
| 7,115,627 B2 * | 10/2006 | Pinto et al. ................... | 514/303 |
| 2005/0090529 A1 | 4/2005 | McAlpine et al. | |
| 2006/0258706 A1 | 11/2006 | Saindane et al. | |
| 2008/0090882 A1 * | 4/2008 | Dorsch et al. ................. | 514/365 |

FOREIGN PATENT DOCUMENTS

| | | |
|---|---|---|
| WO | WO-0153268 A2 | 7/2001 |
| WO | WO2003066630 | 8/2003 |
| WO | 2004031158 A1 | 4/2004 |
| WO | WO-2004039325 A2 | 5/2004 |
| WO | WO2004094388 | 11/2004 |
| WO | WO-2004013140 A1 | 12/2004 |
| WO | WO-2004113304 A1 | 12/2004 |
| WO | WO-2005009997 A1 | 2/2005 |

(Continued)

OTHER PUBLICATIONS

Kiselyov et al. Chem. Biol. Drug Des., 2007, 69, pp. 331-337.*
"IUPAC Commission on Nomenclature of Organic Chemistry: Rules for the Nomenclature of Organic Chemistry, Section E: Stereochemistry (Recommendations 1974)," Pure Appl Chem, 1976, 13-30, vol. 45.

(Continued)

*Primary Examiner* — Alicia L Otton
(74) *Attorney, Agent, or Firm* — Susan L. Steele

(57) ABSTRACT

The present invention relates to compounds of formula (I) or pharmaceutical acceptable salts,

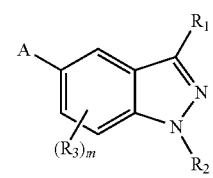

wherein A, $R_1$, $R_2$, $R_3$ and m, are defined in the description. The present invention relates also to methods of making said compounds, and compositions containing said compounds which are useful for inhibiting kinases such as Glycogen Synthase kinase 3 (GSK-3), Rho kinase (ROCK), Janus Kinases (JAK), Cdc7, AKT, PAK4, PLK, CK2, KDR, MK2, JNK1, aurora, pim 1 and nek 2.

7 Claims, No Drawings

(56) References Cited

FOREIGN PATENT DOCUMENTS

| WO | WO2005065050 | | 7/2005 | |
| --- | --- | --- | --- | --- |
| WO | WO2005074642 | | 8/2005 | |
| WO | WO-2005099703 A1 | | 10/2005 | |
| WO | WO 2005/123688 | * | 12/2005 | ........... C07D 231/00 |
| WO | WO2005123680 | | 12/2005 | |
| WO | WO2006001894 | | 1/2006 | |
| WO | WO2006044860 | | 4/2006 | |
| WO | WO 2006/045350 | * | 5/2006 | ........... C07D 233/90 |
| WO | WO 2006/058007 | * | 6/2006 | ........... A61K 31/416 |
| WO | WO2006071548 | | 7/2006 | |
| WO | 2006130297 A2 | | 12/2006 | |
| WO | WO2007056468 | | 5/2007 | |
| WO | WO2008063287 | | 5/2008 | |
| WO | WO2008086854 | | 7/2008 | |
| WO | WO 2008/154241 | * | 12/2008 | ........... C07D 403/04 |

OTHER PUBLICATIONS

Abstract S023, 8th World Congress on Inflammation, Copenhagen, Denmark, Jun. 16-20, 2007.

Barr et al., "MAPK-specific tyrosine phosphatases: new targets for drug discovery?," Trends in Pharmacological Sciences, 2006, pp. 525-530, vol. 27 (10).

Bennett and Xie "A peripheral mononeuropathy in rat that produces disorders of pain sensation like those seen in man," (Binary/Image), 1988, 87-107, vol. 33.

Berven L. A. et al., "Cellular function of p70S6K: a role in regulating cell motility," Immunol. Cell Biol., 2000, pp. 447-51, vol. 78 (4).

Cho Wh, Lee Yj, Kong Si, et al., "CDC7 kinase phosphorylates serine residues adjacent to acidic amino acids in the minichromosome maintenance 2 protein.", Proc Natl Aced Sci USA, 2006, 103/31, 11521-6.

Clark et al., "The serine/threonine protein kinase, p90 ribosomal S6 kinase, is an important regulator of prostate cancer cell proliferation," Cancer Research, 2005, pp. 3108-3116, vol. 65 (8).

Cohen, P. , "Protein kinases—the major drug targets of the twenty-first century?," Nature.
Reviews Drug Discovery, 2002, pp. 309-315, vol. 1 (4).

Dergham, P. et al., "Rho signaling pathway targeted to promote spinal cord repair," J. Neurosci., 2002, pp. 6570-6577, vol. 22 (15).

Fabbro et al., "Protein kinases as targets for anticancer agents: from inhibitors to useful drugs," Pharmacology & Therapeutics, 2002, pp. 79-98, vol. 93 (2-3).

Frodin et al., "Role and regulation of 90 kDa ribosomal S6 kinase (RSK) in signal transduction," Mol. Cell. Endocrinol, 1999, pp. 65-77, vol. 151 (1-2).

Fujishiro et al., Recent Research Developments in Physiology, 2003, pp. 801-812, vol. 1 (Pt. 2).

Gartner et al., "Neuronal polarity is regulated by glycogen synthase kinase-3 (GSK-3beta) independently of Akt/PKB serine phosphorylation," J. Cell Science, 2006, pp. 3927-3934, vol. 119 (Pt 19).

Girdler F., "Validating Aurora B as an anti-cancer drug target," Journal of Cell Science, 2006, pp. 3664-3675, vol. 119.

Gould, Todd D., "Targeting Glycogen Synthase Kinase-3 in the CNS: Implications for the Development of New Treatments for Mood Disorders," Current Drug Targets, 2006, pp. 1399-1409, vol. 7 (11).

Greene, T.W. et al., "Protective Groups in Organic Synthesis", 1999, 3 rd Ed, pp. 494-653, John Wiley & Sons.

Gross et al., "A constitutively active form of the protein kinase p9ORsk1 is sufficient to trigger the G2/M transition in Xenopus oocytes," J. Biol. Chem., 2001, pp. 46099-46103, vol. 276 (49).

Hara, M. et al. , "Protein kinase inhibition by fasudil hydrochloride promotes neurological recovery after spinal cord injury in rats," J. Neurosurg. Spine, 2000, pp. 94-101, vol. 93.

Hartwell et al., "Cell cycle control and cancer," Science, 1994, pp. 1821-1828, vol. 266 (5192).

Huang, "Multiple Roles for Glycogen Synthase Kinase-3 as a Drug Target in Alzheimer's Disease," Current Drug Targets, 2006, pp. 1389-1397, vol. 7 (11), Bentham Science Publishers.

Inoue, M. et al., "Initiation of neuropathic pain requires lysophosphatidic acid receptor signaling," Nature Med., 2004, pp. 712-718, vol. 10 (7).

Kidwai M., "An Expeditious Solventless Synthesis of Isoxazoles ," Organic Preparations and Procedures International, 2001, pp. 381-386, vol. 33 (4).

Kim, J. M. et al. , "Functions of mammalian Cdc7 kinase in initiation/monitoring of DNA replication and development," Mutat. Res., 2003, pp. 29-40, vol. 532 (1-2).

Kim, S.H. & Chung, J.M. "An experimental model for peripheral neuropathy produced by segmental spinal nerve ligation in the rat," (Binary/Image), 1992, 355-363, vol. 50-Issue 3.

Kitaoka, Y. et al. , "Involvement of RhoA and possible neuroprotective effect of fasudil, a Rock inhibitor, in NMDA-induced neurotoxicity in the rat retina," Brain Res., 2004, pp. 111-118, vol. 1018 (15).

Kockeritz et al., "Glycogen Synthase Kinase-3—An Overview of an Over-Achieving Protein Kinase," Current Drug Targets, 2006, pp. 1377-1388, vol. 7 (11).

Kumagai A. et al., "How cells activate ATR," Cell Cycle, 2006, pp. 1265-1268, vol. 5 (12).

Lau, E. et al., "Is there a pre-Rc checkpoint that cancer cells lack?," Cell Cycle, 2006, pp. 1602-1606, vol. 5 (15).

Lau, E. et al., "The functional role of Cdc6 in S-G2/M in mammalian cells," EMBO Rep., 2006, pp. 425-430, vol. 7.

Lau, E. et al., "The role of pre-replicative complex (pre-RC) components in oncogenesis," Faseb J., 2007, pp. 3786-3794, vol. 21 (14).

Lee, J. K. et al., "Nogo receptor antagonism promotes stroke recovery by enhancing axonal plasticity," J. Neurosci., 2004, pp. 6209-6217, vol. 24 (27).

Li et al., "The Ras-JNK pathway is involved in shear-induced gene expression," Mol. Cell. Biol., 1996, pp. 5947-5954, vol. 16 (11).

Mathis, "HTRF® Technology," Journal of Biomolecular Screening, Apr. 1999—issue 6, pp. 309-314.

Matter, A., "Tumor angiogenesis as a therapeutic target," Drug Discov. Today, 2001, pp. 1005-1023, vol. 6 (19).

Montagnoli et al., "Identification of Mcm2 phosphorylation sites by S-phase-regulating kinases.", J Biol Chem, 2006, 281/15, 10281-90.

Montagnoli, A. et al. , "Cdc7 inhibition reveals a p53- dependent replication checkpoint that is defective in cancer cells," Cancer Res, 2004, pp. 7110-7116, vol. 64.

Mueller et al., "Rho kinase, a promising drug target for neurological disorders," Nature Reviews Drug Discovery, 2005, pp. 387-398, vol. 4 (5).

Nurse P. et al., "Checkpoint pathways come of age," Cell, 1997, pp. 865-867, vol. 91 (7).

Pallas et al., "Inhibitors of Cyclin-Dependent Kinases: Potential Drugs for the Treatment of Neurodegenerative Disorders? ," Current Medicinal Chemistry—Central Nervous System Agents, 2005, pp. 101-109, vol. 5 (2).

Pearson M, Garcia-Echeverria C, Fabbro D. "Protein Tyrosine Kinases as Targets for Cancer and Other Indications" in Protein Tyrosine Kinases: From Inhibitors to Useful Drugs. Fabbro D and McCormick F, eds. Human Press, 2006.

Pearson R. B et al., "Regulation of p70s6k/p85s6k and its role in the cell cycle," Prog Cell Cycle Res, 1995, pp. 21-32, vol. 1.

Pombo et al., "The stress-activated protein kinases are major c-Jun amino-terminal kinases activated by ischemia and reperfusion," J. Biol. Chem., 1994, pp. 26546-26551, vol. 269 (42).

Prescott, et al., "Lipid Vesicles as Carriers for Introducing Biologically Active Materials into Cells," Methods in Cell Biology, 1976, 33-71, vol. 14, Academic Press.

Qi et al., "MAP kinase pathways," Journal of Cell Science, 2005, pp. 3569-3572, vol. 118 (16).

Risau, W., "Mechanisms of angiogenesis," Nature, 1997, pp. 671-674, vol. 386 (6626).

Robertson et al., "RTK mutations and human syndromeswhen good receptors turn bad," Trends Genet, 2000, pp. 265-271, vol. 16 (6).

Robinson et al., "The protein tyrosine kinase family of the human genome," Oncogene, 2000, pp. 5548-5557, vol. 19 (49).

Rowell et al., "The role of cyclin-dependent kinases in T-cell development, proliferation, and function," Critical Reviews in Immunology, 2006, pp. 189-212, vol. 26 (3).

(56) References Cited

OTHER PUBLICATIONS

Satoh, S. et al., "Pharmacological profile of hydroxy fasudil as a selective Rock inhibitor on ischemic brain damage," Life Sci., 2001, pp. 1441-1453, vol. 69.
Shimokawa et al., "Rho-kinase is an important therapeutic target in cardiovascular medicine," Arteriosclerosis,Thrombosis, and Vascular Biology, 2005, pp. 1767-1775, vol. 25 (9).
Sridhar et al., "Protein kinases as therapeutic targets," Pharmaceutical Research, 2000, pp. 1345-1353, vol. 17 (11).
Stillman, B., "Origin recognition and the chromosome cycle," FEBS Lett., 2005, pp. 877-884, vol. 579.
Sung, J. K. et al., "A possible role of RhoA/Rho-kinase in experimental spinal cord injury in rat," Brain Res., 2003, pp. 29-38, vol. 959 (1).
Tanaka, H. et al., "Cytoplasmic p21(Cip1/WAF1) enhances axonal regeneration and functional recovery after spinal cord injury in rats," Neuroscience, 2004, pp. 155-164, vol. 127 (1).
Tatsumi, S. et al., "Involvement of Rho-kinase in inflammatory and neuropathic pain through phosphorylation of myristoylated alanine-rich C-kinase substrate (MARCKS)," Neuroscience, 2005, pp. 491-498, vol. 131 (2).
Thomas et al., "Identification of a novel 3,5-disubstituted pyridine as a potent, selective, and orally active inhibitor of Akt1 kinase," Bioorganic & Medicinal Chemistry Letters, 2003, 16, pp. 3740-3744.
Tsuji T, Ficarro SB, Jiang W, "Essential Role of Phosphorylation of MCM2 by Cdc7/Dbf4 in the Initiation of DNA Replication in Mammalian Cells", Molecular Biology of the Cell, 2006, 17, 4459-4472.
Wiessner, C. et al., "Anti-Nogo-A antibody infusion 24 hours after experimental stroke improved behavioral outcome and corticospinal plasticity in normotensive and spontaneously hypertensive rats," J. Cereb. Blood FlowMetab., 2003, pp. 154-165, vol. 23 (2).
Wrzeciono, U. et al., Pharmazie, 1986, pp. 472-474, vol. 41.
Xiao et al., "Differential roles of checkpoint kinase 1, checkpoint kinase 2, and mitogen-activated protein kinase-activated protein kinase 2 in mediating DNA damage-induced cell cycle arrest: implications for cancer therapy," Molecular Cancer Therapeutics, 2006, pp. 1935-1943, vol. 5 (8).
Yang et al., "Differentiation of CD4+ T cells to Th1 cells requires MAP kinase JNK2," Immunity, 1998, pp. 575, vol. 9 (4).
Zhou et al., "NGF-induced axon growth is mediated by localized inactivation of GSK-3beta and functions of the microtubule plus end binding protein APC," Neuron, 2004, pp. 897-912, vol. 42 (6).
Abstract 1216, 8th World Congress on Inflammation, Copenhagen, Denmark, Jun. 16-20, 2007.
Cuzzocrea et al., "Glycogen synthase kinase-3β inhibition attenuates the degree of arthritis caused by type II collagen in the mouse," Clinical Immunology, 2006, pp. 57-67, vol. 120 (1).
Feng, D. et al., "Inhibiting the expression of DNA replication-initiation proteins induces apoptosis in human cancer cells," Cancer Res., 2003, pp. 7356-7364, vol. 63.
Fournier, A. E. et al., "Rho Kinase Inhibition Enhances Axonal Regeneration in the Injured CNS," J. Neurosci., 2003, pp. 1416-1423, vol. 23 (4).
International Search Report for PCT/US2008/065727, mailed Nov. 25, 2008.
Kim, J. M. et al., "Genetic dissection of mammalian Cdc7 kinase: cell cycle and developmental roles," Cell Cycle, 2004, pp. 300-304, vol. 3 (3).
Toshima Y. et al., "A new model of cerebral microthrombosis in rats and the neuroprotective effect of a Rho-kinase inhibitor," Stroke, 2000, pp. 2245-2250, vol. 31 (9).
Woods et al., "Synthesis and SAR of indazole-pyridine based protein kinase B/Akt inhibitors ," Bioorganic & Medicinal Chemistry, 2006, pp. 6832-6846, 14.
Zhou, Y. et al., "Nonsteroidal anti-inflammatory drugs can lower amyloidogenic Aβ 42 by inhibiting Rho," Science, 2003, pp. 1215-1217, vol. 302.
Ziu et al., "Syntheses of Potent, Selective, and Orally Bioavailable Indazole-pyridine Series of Protein Kinase B/Akt Inhibitors with Reduced Hypotension," Journal of Medicinal Chemistry, 2007, vol. 50 (13), pp. 2990-3003..

\* cited by examiner

5-SUBSTITUTED INDAZOLES AS KINASE INHIBITORS

RELATED APPLICATION INFORMATION

This application is a continuation-in-part of U.S. application Ser. No. 12/132,993 filed on Jun. 4, 2008 which claims priority to provisional application Ser. No. 60/933,960 filed on, Jun. 8, 2007, the contents of each of which are herein incorporated by reference.

TECHNICAL FIELD

The present invention relates to 5-substituted indazole containing compounds, methods of making the compounds, compositions containing the compounds which are useful for inhibiting kinases such as Glycogen Synthase kinase 3 (GSK-3), Rho kinase (ROCK), Janus Kinases (JAK), Cdc7, AKT, PAK4, PLK, CK2, KDR, MK2, JNK1, aurora, pim 1 and nek 2.

BACKGROUND OF THE INVENTION

Protein kinases are a class of enzymes that catalyze the transfer of a phosphate group from ATP to a tyrosine, serine, threonine, or histidine residue located on a protein substrate. Protein kinases clearly play a role in normal cell growth. Many of the growth factor receptor proteins have intracellular domains that function as protein kinases and it is through this function that they effect signaling. The interaction of growth factors with their receptors is a necessary event in the normal regulation of cell growth, and the phosphorylation state of substrate proteins often is related to the modulation of cell growth.

It is widely known that abnormal protein phosphorylation may be directly linked to certain disease states or may be a contributing factor in the onset of such diseases. As a result, protein kinases have become the targets of new pharmaceutical research (Cohen, P. Nature Reviews Drug Discovery, 1:309-315, 2002). Various protein kinase inhibitors have been used clinically in the treatment of a wide variety of diseases, such as cancer, chronic inflammatory diseases, diabetes and stroke.

The protein kinases are a large and diverse family of enzymes that catalyze protein phosphorylation and play a key role in cellular signaling. Protein kinases may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. As a result, malfunctions of cellular signaling have been associated with many diseases, the most characterized of which include cancer and diabetes. The regulation of signal transduction by cytokines and the association of signal molecules with proto-oncogenes and tumor suppressor genes have been well documented. Similarly, the connection between diabetes, viral infections and the conditions related thereto has also been associated with the regulation of protein kinases.

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as, but not limited to, cancer, inflammatory diseases, abnormal angiogenesis and diseases related thereto, atherosclerosis, macular degeneration, diabetes, obesity, and pain.

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways.

It has therefore been suggested that due to the complexity of intracellular signaling cascades of protein kinase pathways, agents that affect multiple pathways simultaneously may be required for meaningful clinical activity. Although it has been suggested that a single agent that provides combinatorial effects is an attractive notion, there is a need to identify and use single agents that target the right combination of multiple pathways that are clinically effective in a particular disease setting.

Glycogen synthase kinase-3 (GSK-3) is a serine/threonine kinase encoded by two isoforms, GSK-3α and GSK-3β with molecular weights of 51 and 47 kDa, respectively. These share 97% sequence similarity in their kinase catalytic domains. The GSK-3α isoform has an extended glycine-rich N-terminal tail. A minor splice variant of GSK-3β has been identified (expressed at ~15% of total) with a 13 amino acid insert within the kinase domain. This variant had a reduced activity towards tau. GSK-3 is highly conserved throughout evolution, and found in all mammals thus far with high homology in the kinase domain. Both isoforms are ubiquitously expressed in mammalian tissues, including the brain. Pharmacological GSK-3 inhibitors are not able to selectively inhibit one of the isoforms.

GSK-3β plays an important role in the control of metabolism, differentiation and survival. It was initially identified as an enzyme able to phosphorylate and hence inhibit glycogen synthase. Subsequently, it was recognized that GSK-3β was identical to tau protein kinase 1 (TPK1), an enzyme that phosphorylates tau protein in epitopes that are also found to be hyperphosphorylated in Alzheimer's disease and in several taupathies.

Interestingly, protein kinase B (AKT) phosphorylation of GSK-3β results in a loss of kinase activity, and it has been proposed that this inhibition may mediate some of the effects of neurotrophic factors. Moreover, phosphorylation of β-catenin (a protein involved in cell survival) by GSK-3β, results in its degradation by an ubiquitinilation dependent proteasome pathway.

Therefore it appears that inhibition of GSK-3β activity may result in neurotrophic activity. There is evidence that lithium, an uncompetitive inhibitor of GSK-3β, enhances neuritogenesis in some models and can also increase neuronal survival, through the induction of survival factors such as Bcl-2 and the inhibition of the expression of proapoptotic factors such as P53 and Bax.

Further studies have shown that β-amyloid increases GSK-3β activity and tau protein phosphorylation. Moreover, this hyperphosphorylation as well as the neurotoxic effects of β-amyloid are blocked by lithium chloride and by a GSK-3β antisense mRNA. These observations taken together suggest that GSK-3β may be the link between the two major pathological processes in Alzheimer's disease: abnormal APP (Amyloid Precursor Protein) processing and tau protein hyperphosphorylation.

These experimental observations indicate that GSK-3β may find application in the prevention and treatment of the neuropathological consequences and the cognitive and attention deficits associated with Alzheimer's disease, as well as other acute and chronic neurodegenerative diseases. These include, but are not limited to: Parkinson's disease, tauopathies (e.g. frontotemporoparietal dementia, corticobasal degeneration, Pick's disease, progressive supranuclear palsy) and other dementia including vascular dementia; acute stroke and other traumatic injuries; cerebrovascular accidents (e.g. age related macular degeneration); brain and spinal cord trauma; peripheral neuropathies; retinopathies and glaucoma.

GSK-3β may also have utility in the treatment of other diseases such as: non-insulin dependent diabetes and obesity; manic depressive illness; schizophrenia; alopecia; inflammation; cancers such as breast cancer, non-small cell lung carcinoma, thyroid cancer, T or B-cell leukemia and several virus-induced tumors.

Rho kinases (ROCKs), the first Rho effectors to be described, are serine/threonine kinases that are important in fundamental processes of cell migration, cell proliferation and cell survival. Abnormal activation of the Rho/ROCK pathway has been observed in various disorders. Examples of disease states in which compounds of the present invention have potentially beneficial therapeutic effects due to their anti vasospasm activity includes cardiovascular diseases such as hypertension, chronic and congestive heart failure, cardiac hypertrophy, restenosis, chronic renal failure, cerebral vasospasm after subarachnoid bleeding, pulmonary hypertension and atherosclerosis. The muscle relaxing property is also beneficial for treating asthma, male erectile dysfunctions, female sexual dysfunction, and over-active bladder syndrome. Injury to the adult vertebrate brain and spinal cord activates ROCKs, thereby inhibiting neurite growth and sprouting. Inhibition of ROCKs results in induction of new axonal growth, axonal rewiring across lesions within the CNS, accelerated regeneration and enhanced functional recovery after acute neuronal injury in mammals (spinal-cord injury, traumatic brain injury). Inhibition of the Rho/ROCK pathway has also proved to be efficacious in other animal models of neurodegeneration like stroke, inflammatory and demyelinating diseases, Alzheimer's disease as well as the treatment of pain. Rho/ROCK pathway inhibitors therefore have potential for preventing neurodegeneration and stimulating neuroregeneration in various neurological disorders, including spinal-cord injury, Alzheimer's disease, stroke, multiple sclerosis, amyotrophic lateral sclerosis, as well as the treatment of pain. ROCK inhibitors have been shown to possess anti-inflammatory properties. Thus, compounds of the invention can be used as treatment for neuroinflammatory diseases such as stroke, multiple sclerosis, Alzheimer's disease, Huntington's disease, Parkinson's disease, amyotrophic lateral sclerosis, and inflammatory pain, as well as other inflammatory diseases such as rheumatoid arthritis, osteoarthritis, asthma, irritable bowel syndrome, Crohn's disease, psoriasis, ulcerative colitis, Lupus, and inflammatory bowel disease. Since ROCK inhibitors reduce cell proliferation and cell migration, they could be useful in treating cancer and tumor metastasis. Further more, there is evidence suggesting that ROCK inhibitors suppress cytoskeletal rearrangement upon virus invasion, thus they also have potential therapeutic value in anti-viral and anti-bacterial applications. ROCK inhibitors are also useful for the treatment of insulin resistance and diabetes. Further, ROCK inhibitors have been shown to ameliorate progression of cystic fibrosis (Abstract S02.3, 8th World Congress on Inflammation, Copenhagen, Denmark, Jun. 16-20, 2007).

In addition, Rho-associated coiled-coil forming protein kinases (ROCK)-1 and -2, have been shown to enhance myosin light chain (MLC) phosphorylation by inhibiting MLC phosphatase as well as phosphorylating MLC. This results in the regulation of actin-myosin contraction. Recent reports have demonstrated that inhibition of ROCK results in disruption of inflammatory cell chemotaxis as well as inhibition of smooth muscle contraction in models of pulmonary inflammation associated with asthma. Therefore, the inhibitors of the Rho/ROCK pathway should be useful for the treatment of asthma.

The Janus kinases (JAKs) are an important family of intracellular protein tyrosine kinases (PTKs), with 4 mammalian members, JAK1, JAK2, JAK3, and TYK2, as well as homologs in chicken, fish, and *Drosophila*. The JAKs play critical roles in several important intracellular signaling pathways, including the eponymous JAK/STAT pathway, central to the mediation of cytokine signaling. It is this pivotal role in cytokine signaling that underpins the notion that specific JAK inhibitors may be therapeutically deployed in situations where cytokine activity results in disease. Important examples of this include autoimmune diseases such as rheumatoid arthritis and psoriasis, myeloproliferative syndromes such as, leukemias, lymphomas, and cardiovascular diseases.

JAK2, a member of the Janus kinase (JAK) family of protein tyrosine kinases (PTKs), is an important intracellular mediator of cytokine signaling. Mutations of the JAK2 gene are associated with hematologic cancers, and aberrant JAK activity is also associated with a number of immune diseases, including rheumatoid arthritis.

Aurora kinases are a family of multigene mitotic serine-threonine kinases that functions as a class of novel oncogenes. These kinases comprise aurora-A, aurora-B, and aurora-B members. These are hyperactivated and/or overexpressed in several solid tumors including but not limited to breast, ovary, prostate, pancreas, and colorectal cancers. In particular aurora-A is a centrosome kinase, and its localization depends on the cell cycle and plays an important role cell cycle progression and cell proliferation. Aurora-A is located in the 20q13 chromosome region that is frequently amplified in several different types of malignant tumors such as colorectal, breast and bladder cancers. Inhibition of aurora kinase activity could help to reduce cell proliferation, tumor growth and potentially tumorigenesis.

Eukaryotic cells divide by a directed, step-wise process referred to as the cell cycle. Cells must first replicate their DNA in S phase before separating their sister chromatids in mitosis (karyokinesis) and splitting off into two daughter cells (cytokinesis). In mammalian cells, DNA replication must be initiated at multiple sites (replication origins) throughout the genome to ensure that all the genetic material is duplicated prior to mitosis. To maintain genome integrity, DNA must be replicated only once per cell cycle, and so this process is highly regulated and governed by checkpoints. Before replication is initiated, origins must be licensed through the formation of pre-replication complexes (pre-RCs) in early G1. Formation of pre-RCs involves the step-wise binding of the origin recognition complex (ORC) to origins followed by the binding of the loading factors Cdc6 and Cdt1. These proteins then recruit the putative DNA replicative helicase complex, MCM2-7. Once this pre-RC is formed, replication initiation requires the activation of S-phase-promoting serine/threonine kinases, Cyclin/Cdks and Cdc7/Dbf4. These kinases consist of an enzymatic sub-unit (CDKs and Cdc7) and a regulatory sub-unit (Cyclins for CDKs; Dbf4 or Drf1 for Cdc7). They phosphorylate multiple MCMs in pre-RCs in a sequential manner, thereby activating the helicase and recruiting other DNA replication factors (Cdc45, GINS complex, etc.) for DNA synthesis (for reviews, see Kim, J. M., et al. (2003). Functions of mammalian Cdc7 kinase in initiation/monitoring of DNA replication and development. *Mutat. Res.* 532, 29-40; Kim, J. M., et al. (2004). Genetic dissection of mammalian Cdc7 kinase: cell cycle and developmental roles. *Cell Cycle* 3, 300-304; Lau, E., et al. (2006). The functional role of Cdc6 in S-G2/M in mammalian cells. *EMBO Rep.* 7, 425-430; Lau, E., et al. (2007). The role of pre-replicative complex (pre-RC) components in oncogenesis. *Faseb J.* 21, 3786-3794; Stillman, B. (2005). Origin recognition and the chromosome cycle. *FEBS Lett.* 579, 877-884). MCM2 Serine-40 and Serine-53 are well-characterized phosphorylation sites for Cdc7/Dbf4 (Cho et al., 2006; Montagnoli et al., 2006; Tsuji et al., 2006).

Inhibiting regulators of replication initiation, such as Cdc6, Cdc7/Dbf4 or Cdc7/Drf1, has lethal consequences in cancerous cells, whereas normal cells are able to arrest and resume normal divisions once initiation activity is restored (Feng, D., et al. (2003). Inhibiting the expression of DNA replication-initiation proteins induces apoptosis in human cancer cells. *Cancer Res.* 63, 7356-7364; Montagnoli, A., et al. (2004). Cdc7 inhibition reveals a p53-dependent replication checkpoint that is defective in cancer cells. *Cancer Res* 64, 7110-7116; see Lau, E., et al. (2006). Is there a pre-RC checkpoint that cancer cells lack? *Cell Cycle* 5, 1602-1606, for review). Small molecule inhibitors of the protein kinase Cdc7 are thus attractive candidates for therapeutic intervention in cancer, inflammation and other cell proliferative disorders.

Accordingly, there remains a need for the development of methods comprising the use of a single agent drug capable of targeting specific sets of kinases or kinase pathways. In particular such methods affect the right combination of multiple targets thereby achieving clinical efficacy.

SUMMARY OF THE INVENTION

In the principle embodiment, the present invention provides compounds of Formula (I),

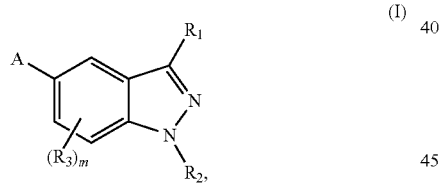

(I)

or a pharmaceutically acceptable salt thereof, wherein
A is

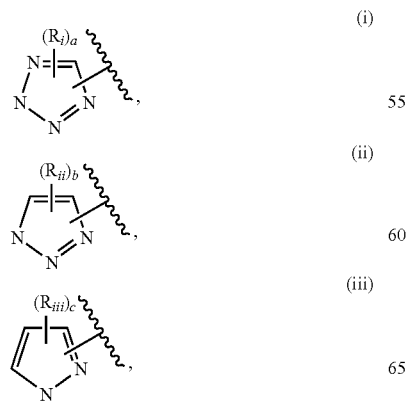

-continued

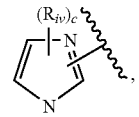
(iv)

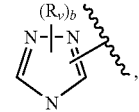
(v)

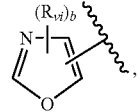
(vi)

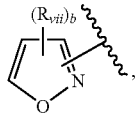
(vii)

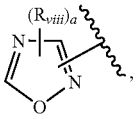
(viii)

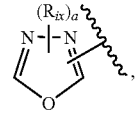
(ix)

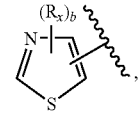
(x)

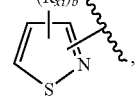
(xi)

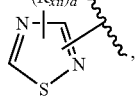
(xii)

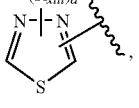
(xiii)

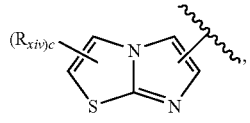
(xiv)

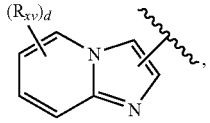
(xv)

-continued

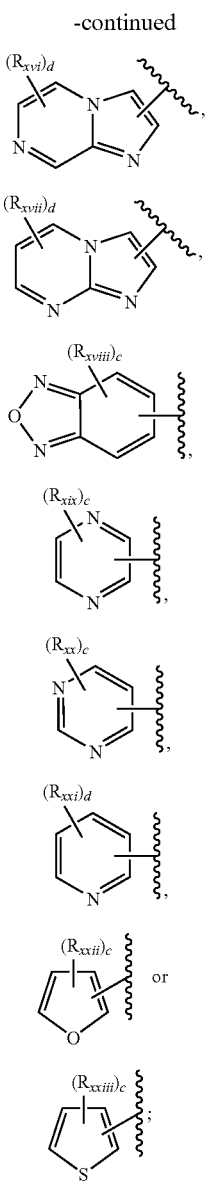

R₁ is hydrogen, alkoxycarbonyl, alkyl, aryl, heterocycle, heteroaryl, $R_aR_bN-$, $R_cR_dN-C(O)-$ or $R_cR_dN-S(O)_2-$;

R₂ is hydrogen, alkoxycarbonyl, alkyl, alkylcarbonyl, arylcarbonyl, heterocyclecarbonyl or $R_eR_fN\text{-alkyl-}C(O)-$;

R₃ is alkyl, alkoxy, aryl, cyano, cycloalkyl, halogen, haloalkyl, heteroaryl, nitro, or $R_gR_hN-$;

R₄ is alkyl, alkoxyalkyl, aryl, cycloalkyl, heteroaryl, heterocycle, heterocyclealkyl, $R_jR_kN-$ or $R_jR_kN\text{-alkyl-}$;

R₅ is alkyl, aryl, or heteroaryl;

R₆ is alkyl, alkoxyalkyl, $R_jR_kN\text{-alkyl-}$, aryl, cycloalkyl or heteroaryl;

R₇ is alkyl, aryl or heteroaryl;

$R_a$ and $R_b$ are each independently hydrogen, alkyl, arylalkyl, cycloalkyl, cycloalkylalkyl, heteroarylalkyl, heterocyclealkyl, $R_4-C(O)-$, or $R_5-S(O)_2-$;

$R_c$ and $R_d$ are each independently hydrogen, alkyl or heteroaryl;

$R_e$ and $R_f$ are each independently hydrogen, alkyl, arylalkyl, heteroarylalkyl, $R_6-C(O)-$, or $R_7-S(O)_2-$;

$R_g$ and $R_h$ are each independently hydrogen, alkyl, or alkylcarbonyl;

$R_j$ and $R_k$ are each independently hydrogen, alkyl, aryl, arylalkyl, cycloalkyl, heteroaryl, or heterocycle;

$R_i$, $R_{ii}$, $R_{iii}$, $R_{iv}$, $R_v$, $R_{vi}$, $R_{vii}$, $R_{viii}$, $R_{ix}$, $R_x$, $R_{xi}$, $R_{xii}$, $R_{xiii}$, $R_{xiv}$, $R_{xv}$, $R_{xvi}$, $R_{xvii}$, $R_{xviii}$, $R_{xix}$, $R_{xx}$, $R_{xxi}$, $R_{xxii}$, and $R_{xxiii}$ are each independently alkyl, alkoxy, alkoxyalkyl, alkoxycarbonyl, alkoxycarbonylalkyl, aryl, arylalkyl, aryl(hydroxy)alkyl, aryloxyalkyl, arylcarbonyl, arylthioalkyl, carboxy, carboxyalkyl, cyanoalkyl, cycloalkyl, cycloalkylalkyl, cycloalkylcarbonyl, halogen, heteroaryl, heteroarylalkyl, heterocycle, heterocyclealkyl, heterocyclecarbonyl, hydroxyalkyl, trialkylsilylalkyl, $H_2NC(O)\text{-alkyl}$, $Z_aZ_bN-$, $Z_aZ_b\text{Nalkyl}$, $Z_cZ_dNC(O)-$ or $Z_cZ_dNS(O)_2-$ wherein $R_{xiv}$, $R_{xv}$, $R_{xvi}$, and $R_{xvii}$ may occur at any open valence on compounds (xiv), (xv), (xvi) or (xvii);

$Z_a$ and $Z_b$ are each independently hydrogen, alkyl, alkoxycarbonylalkyl, aryl, arylalkyl, cycloalkyl, $H_2NC(O)-$, $H_2\text{Nalkyl}C(O)-$, $H_2NC(O)\text{-alkyl}$, dialkylNC(O)— or dialkylNC(O)-alkyl-;

$Z_c$ and $Z_d$ are each independently hydrogen, alkyl, alkoxyalkyl, aryl, arylalkyl, aryl(hydroxy)alkyl, cycloalkyl, cycloalkylalkyl, heteroarylalkyl, heterocycle, heterocyclealkyl, hydroxyalkyl, $H_2NC(O)\text{-alkyl-}$, dialkylNC(O)-alkyl-, dialkylN-alkyl-, or $CHZ_eZ_f$;

$Z_e$ is aryl or heteroaryl;

$Z_f$ is heteroarylalkyl, heterocyclealkyl, or $Z_1Z_2N\text{-alkyl-}$;

m is 0, 1 or 2;
a is 0 or 1;
b is 0, 1, or 2;
c is 0, 1, 2 or 3; and
d is 0, 1, 2, 3 or 4.

Also provided are pharmaceutically acceptable compositions comprising a therapeutically effective amount of a compound of formula (I) in combination with a pharmaceutically suitable carrier.

The object of the present invention is to provide compounds that are useful for the preventive of or treatment of diseases caused by abnormal protein kinase activity. In addition, the invention also provides pharmaceutically effective compositions of the compounds of the present invention that are useful for the prevention of or treatment of said diseases.

The present invention also relates to a pharmaceutical composition which comprises at least one 5-substituted indazole compound of the formula (I) which may exist as a pharmaceutically acceptable salt or prodrug thereof, in the presence or absence of pharmaceutically acceptable carriers, dragees, adjuvants or other auxiliary substances.

The compounds of the present invention have inhibitory activity against GSK-3, ROCK-1, ROCK-2, JAK2, Cdc7 as well as other kinases and are useful for the inhibition of such kinases. Certain compounds of the present invention are selective toward one or more kinases and may be useful for the selective inhibition of such kinases. Accordingly, the compounds of the present invention are useful as an active ingredient for the preparation of a composition, which enables preventive and/or therapeutic treatment of a disease caused by abnormal GSK-3 activity and more particularly, of neurodegenerative diseases such as Alzheimer's disease. In addition, the compounds of the present invention are also useful as an active ingredient for the preparation of a composition for preventive and/or therapeutic treatment of neurodegenerative diseases such as Parkinson's disease, tauopathies (e.g. frontotemporoparietal dementia, corticobasal degeneration, Pick's disease, progressive supranuclear palsy) and other dementia including vascular dementia; acute stroke and other traumatic injuries; cerebrovascular accidents (e.g. age related macular degeneration); brain and spinal cord trauma; peripheral neuropathies; retinopathies and glaucoma; and other diseases such as non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors. Certain compounds of the present invention are useful as an active ingredient for the preparation of a composition, which enables preventive and/or therapeutic treatment of a disease caused by abnormal Cdc7 activity and more particularly, cancer such as bladder cancer, breast cancer, colon cancer, kidney cancer, liver cancer, lung cancer, esophagus cancer, gallbladder cancer, ovarian cancer, pancreatic cancer, stomach cancer, cervical cancer, thyroid cancer, prostate cancer, skin cancer, including squamous cell carcinoma, hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, Burkitt's lymphoma, hematopoietic tumors of myeloid lineage, including acute and chronic myelogenous leukemias, myelodysplastic syndrome and promyelocytic leukemia, tumors of mesenchymal origin, including fibrosarcoma and rhabdomyosarcoma, tumors of the central and peripheral nervous system, including astrocytoma, neuroblastoma, glioma and schwannomas, other tumors, including melanoma, seminoma, teratocarcinoma, osteosarcoma, xeroderma pegmentosum, keratoxanthoma, thyroid follicular cancer and Kaposi's sarcoma. In addition, the compounds of the present invention are also useful as an active ingredient for the preparation of a composition for preventive and/or therapeutic treatment of proliferative diseases such as benign prostate hyperplasia, familial adenomatosis, polyposis, neurofibromatosis, psoriasis, vascular smooth cell proliferation associated with atherosclerosis, pulmonary fibrosis, arthritis, glomerulonephritis, and post-surgical stenosis and restenosis caused by abnormal Cdc7 activity.

DETAILED DESCRIPTION OF THE INVENTION

Compounds of the present invention have the formula (I) as described above. More particularly, compounds of formula (I) can include, but are not limited to, compounds wherein A is (ii), (iii), (iv), (vii), (x), (xiv), (xv), (xvi), (xvii), (xviii), (xix), (xx), (xxi), (xxii), or (xxiii).

In another embodiment of the present invention there is disclosed a compound of formula (I), wherein A is (ii),

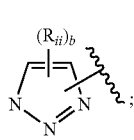

(ii)

$R_1$ is hydrogen, alkoxyalkyl, alkyl, aryl, heteroaryl, heterocycle, $R_aR_bN$— or $R_cR_dN$—C(O)—; $R_2$ is hydrogen, alkoxycarbonyl, arylcarbonyl, heterocyclecarbonyl, alkylcarbonyl, or $R_eR_fN$-alkyl-C(O)—; $R_4$ is alkyl, alkoxyalkyl, aryl, cycloalkyl, heterocycle, heterocyclealkyl, $R_jR_kN$—, or $R_jR_kN$-alkyl-; $R_5$ is alkyl, aryl, or heteroaryl; $R_a$ and $R_b$ are each independently hydrogen, alkyl, arylalkyl, cycloalkylalkyl, heterocyclealkyl, $R_4$—C(O)—, or $R_5$—S(O)$_2$—; $R_c$, and $R_d$ are each independently hydrogen, alkyl, or heteroaryl, $R_e$ and $R_f$ are each independently hydrogen or alkyl, $R_j$ and $R_k$ are each independently hydrogen, alkyl, aryl, arylalkyl, cycloalkyl, or heterocycle; $R_{ii}$ is alkyl, alkoxyalkyl, alkoxycarbonyl, aryl, arylalkyl, aryl(hydroxy)alkyl, aryloxyalkyl, arylcarbonyl, alkoxycarbonylalkyl, arylthioalkyl, carboxy, carboxyalkyl, cycloalkyl, cycloalkylalkyl, cycloalkylcarbonyl, halogen, heteroaryl, heteroarylalkyl, heterocycle, heterocyclealkyl, heterocyclecarbonyl, hydroxyalkyl, trialkylsilylalkyl, $Z_aZ_bN$—, $Z_aZ_b$Nalkyl-, or $Z_cZ_dNC(O)$—; $Z_a$ and $Z_b$ are each independently hydrogen, alkyl, or $H_2$NalkylC(O)—; $Z_c$ and $Z_d$ are each independently hydrogen, alkyl, alkoxyalkyl, aryl, arylalkyl, cycloalkyl, cycloalkylalkyl, heteroarylalkyl, heterocyclealkyl, hydroxyalkyl, or dialkylN-alkyl-; m is 0; and b is 0, 1, or 2.

In another embodiment of the present invention, there is disclosed a compound of formula (I), wherein A is (iii),

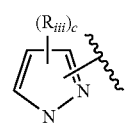

(iii)

$R_1$ is hydrogen or $R_aR_bN$—; $R_2$ is hydrogen; $R_4$ is $R_jR_kN$-alkyl-; $R_a$ and $R_b$ are each independently hydrogen or $R_4$—C(O)—; $R_j$ and $R_k$ are each alkyl; $R_{iii}$ is alkoxycarbonylalkyl, alkyl, arylalkyl, cyanoalkyl, heterocyclealkyl, or $H_2NC(O)$-alkyl-; c is 0, 1, or 2; and m is 0.

In another embodiment of the present invention, there is disclosed a compound of formula (I), wherein A is (iv),

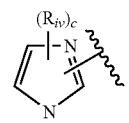

(iv)

$R_1$ is hydrogen or $R_aR_bN$—; $R_2$ is hydrogen; $R_a$ and $R_b$ are each hydrogen; $R_{iv}$ is aryl, arylalkyl, heterocycle, heterocyclealkyl, $Z_aZ_b$Nalkyl or $Z_cZ_dNS(O)_2$—; $Z_a$ and $Z_b$ are each independently hydrogen or alkyl; $Z_c$ and $Z_d$ are each alkyl; c is 0, 1, or 2; and m is 0.

In another embodiment of the present invention, there is disclosed a compound of formula (I), wherein A is (vii),

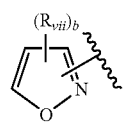

(vii)

$R_1$ is hydrogen, alkyl, or $R_aR_bN$; $R_2$ is hydrogen; $R_a$ and $R_b$ are each hydrogen; $R_{vii}$ is alkyl, alkoxycarbonyl, aryl, arylalkyl, cycloalkyl, heterocyclealkyl, heterocyclecarbonyl, hydroxyalkyl, or $Z_cZ_dNC(O)$—; $Z_c$ and $Z_d$ are each independently hydrogen, alkyl, alkoxyalkyl, aryl, arylalkyl, aryl(hydroxy)alkyl, cycloalkyl, cycloalkylalkyl, heteroarylalkyl, heterocycle, heterocyclealkyl, hydroxyalkyl, or $CHZ_eZ_f$; $Z_e$ is aryl or heteroaryl, $Z_f$ is heteroarylalkyl, heterocyclealkyl, or $Z_1Z_2N$-alkyl-; b is 1; and m is 0.

In another embodiment of the present invention, there is disclosed a compound of formula (I), wherein A is (x),

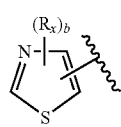

(x)

$R_1$ is hydrogen; $R_2$ is hydrogen; $R_x$ is alkyl, aryl, $Z_aZ_bN-$, or $Z_cZ_dNC(O)-$; $Z_a$ and $Z_b$ are each independently hydrogen, alkyl, aryl, or arylalkyl; $Z_c$ and $Z_d$ are each independently hydrogen or arylalkyl; b is 1 or 2; and m is 0.

In another embodiment of the present invention, there is disclosed a compound of formula (I), wherein A is (xiv),

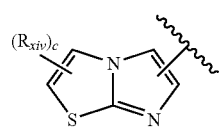

(xiv)

$R_1$ is hydrogen; $R_2$ is hydrogen; $R_{xiv}$ is $Z_aZ_bN-$; $Z_a$ and $Z_b$ are each independently hydrogen or cycloalkyl; c is 1; and m is 0.

In another embodiment of the present invention, there is disclosed a compound of formula (I), wherein A is (xv),

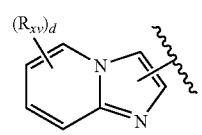

(xv)

$R_1$ is hydrogen or $R_aR_bN-$; $R_2$ is hydrogen; $R_a$ and $R_b$ are each hydrogen; $R_{xv}$ is $Z_aZ_bN-$; $Z_a$ and $Z_b$ are each independently hydrogen, alkoxycarbonylalkyl, aryl, arylalkyl, or cycloalkyl; d is 0 or 1; and m is 0.

In another embodiment of the present invention, there is disclosed a compound of formula (I), wherein A is (xvi),

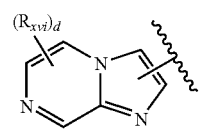

(xvi)

$R_1$ is hydrogen; $R_2$ is hydrogen; $R_{xvi}$ is $Z_aZ_bN-$; $Z_a$ and $Z_b$ are each independently hydrogen or cycloalkyl; d is 1; and m is 0.

In another embodiment of the present invention, there is disclosed a compound of formula (I), wherein A is (xvii),

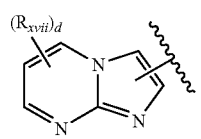

(xvii)

$R_1$ is hydrogen; $R_2$ is hydrogen; $R_{xvii}$ is aryl or $Z_aZ_bN-$; $Z_a$ and $Z_b$ are each independently hydrogen, alkyl, alkoxycarbonylalkyl, aryl, arylalkyl, cycloalkyl, or $H_2NC(O)$-alkyl; d is 0 or 1; and m is 0.

In another embodiment of the present invention, there is disclosed a compound of formula (I), wherein A is (xviii),

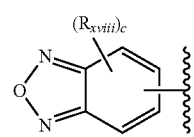

(xviii)

$R_1$ is $R_aR_bN-$; $R_2$ is hydrogen; $R_a$ and $R_b$ are each hydrogen; c is 0; and m is 0.

In another embodiment of the present invention, there is disclosed a compound of formula (I), wherein A is (xix),

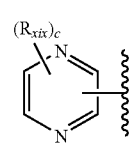

(xix)

$R_1$ is $R_aR_bN-$; $R_2$ is hydrogen; $R_a$ and $R_b$ are each independently hydrogen; c is 0; and m is 0.

In another embodiment of the present invention, there is disclosed a compound of formula (I), wherein A is (xx),

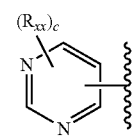

(xx)

$R_1$ is $R_aR_bN-$; $R_2$ is hydrogen; $R_4$ is $R_jR_kN$-alkyl-; $R_a$ and $R_b$ are each hydrogen or $R_4-C(O)-$; $R_j$ and $R_k$ are independently alkyl; $R_{xx}$ is $Z_aZ_bN-$ or heterocycle; $Z_a$ and $Z_b$ are independently hydrogen or alkyl; c is 0 or 1; and m is 0.

In another embodiment of the present invention, there is disclosed a compound of formula (I), wherein A is (xxi),

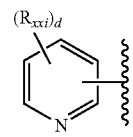

(xxi)

$R_1$ is $R_aR_bN-$; $R_2$ is hydrogen; $R_a$ and $R_b$ are each hydrogen; $R_{xxi}$ is alkoxy; d is 1; and m is 0.

In another embodiment of the present invention, there is disclosed a compound of formula (I), wherein A is (xxii),

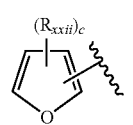

(xxii)

$R_1$ is $R_aR_bN-$; $R_2$ is hydrogen; $R_4$ is $R_jR_kN$-alkyl-; $R_a$ and $R_b$ are each independently hydrogen or $R_4-C(O)-$; $R_j$ and $R_k$ are each alkyl; c is 0 and m is 0.

In another embodiment of the present invention, there is disclosed a compound of formula (I), wherein A is (xxiii),

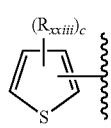

(xxiii)

R$_1$ is R$_a$R$_b$N—; R$_2$ is hydrogen; R$_a$ and R$_b$ are each hydrogen; c is 0; and m is 0.

Specific embodiments contemplated as part of the invention include, but are not limited to, compounds of formula (I), for example:

5-(1-benzyl-1H-1,2,3-triazol-5-yl)-1H-indazole compound with 5-(1-benzyl-1H-1,2,3-triazol-4-yl)-1H-indazole;
5-(1H-1,2,3-triazol-5-yl)-1H-indazole;
5-(1-benzyl-1H-1,2,3-triazol-4-yl)-1H-indazole;
5-[1-(2-methylbenzyl)-1H-1,2,3-triazol-4-yl]-1H-indazole;
5-[1-(3-methylbenzyl)-1H-1,2,3-triazol-4-yl]-1H-indazole;
5-[1-(4-methylbenzyl)-1H-1,2,3-triazol-4-yl]-1H-indazole;
5-[1-(3-methoxybenzyl)-1H-1,2,3-triazol-4-yl]-1H-indazole;
5-[1-(2-fluorobenzyl)-1H-1,2,3-triazol-4-yl]-1H-indazole;
5-[1-(3-fluorobenzyl)-1H-1,2,3-triazol-4-yl]-1H-indazole;
5-[1-(4-fluorobenzyl)-1H-1,2,3-triazol-4-yl]-1H-indazole;
5-[1-(2-chlorobenzyl)-1H-1,2,3-triazol-4-yl]-1H-indazole;
5-[1-(3-chlorobenzyl)-1H-1,2,3-triazol-4-yl]-1H-indazole;
5-[1-(4-chlorobenzyl)-1H-1,2,3-triazol-4-yl]-1H-indazole;
5-[1-(2-bromobenzyl)-1H-1,2,3-triazol-4-yl]-1H-indazole;
5-[1-(2-nitrobenzyl)-1H-1,2,3-triazol-4-yl]-1H-indazole;
5-[1-(3-nitrobenzyl)-1H-1,2,3-triazol-4-yl]-1H-indazole;
5-[1-(4-nitrobenzyl)-1H-1,2,3-triazol-4-yl]-1H-indazole;
2-{[4-(1H-indazol-5-yl)-1H-1,2,3-triazol-1-yl]methyl}benzonitrile;
3-{[4-(1H-indazol-5-yl)-1H-1,2,3-triazol-1-yl]methyl}benzonitrile;
4-{[4-(1H-indazol-5-yl)-1H-1,2,3-triazol-1-yl]methyl}benzonitrile;
5-{1-[2-(trifluoromethyl)benzyl]-1H-1,2,3-triazol-4-yl}-1H-indazole;
5-{1-[3-(trifluoromethyl)benzyl]-1H-1,2,3-triazol-4-yl}-1H-indazole;
5-{1-[4-(trifluoromethyl)benzyl]-1H-1,2,3-triazol-4-yl}-1H-indazole;
5-{1-[3-(trifluoromethoxy)benzyl]-1H-1,2,3-triazol-4-yl}-1H-indazole;
5-{1-[4-(trifluoromethoxy)benzyl]-1H-1,2,3-triazol-4-yl}-1H-indazole;
5-[1-(4-tert-butylbenzyl)-1H-1,2,3-triazol-4-yl]-1H-indazole;
methyl 3-{[4-(1H-indazol-5-yl)-1H-1,2,3-triazol-1-yl]methyl}benzoate;
methyl 4-{[4-(1H-indazol-5-yl)-1H-1,2,3-triazol-1-yl]methyl}benzoate;
5-[1-(2,4-dimethylbenzyl)-1H-1,2,3-triazol-4-yl]-1H-indazole;
5-[1-(3,5-dimethylbenzyl)-1H-1,2,3-triazol-4-yl]-1H-indazole;
5-[1-(2,3-dichlorobenzyl)-1H-1,2,3-triazol-4-yl]-1H-indazole;
5-[1-(2,4-dichlorobenzyl)-1H-1,2,3-triazol-4-yl]-1H-indazole;
5-[1-(2,5-dichlorobenzyl)-1H-1,2,3-triazol-4-yl]-1H-indazole;
5-[1-(3,5-dichlorobenzyl)-1H-1,2,3-triazol-4-yl]-1H-indazole;
5-{1-[2,4-bis(trifluoromethyl)benzyl]-1H-1,2,3-triazol-4-yl}-1H-indazole;
N-cyclohexyl-6-(1H-indazol-5-yl)imidazo[2,1-b][1,3]thiazol-5-amine;
N-cyclohexyl-2-(1H-indazol-5-yl)imidazo[1,2-a]pyridin-3-amine;
N-cyclohexyl-2-(1H-indazol-5-yl)imidazo[1,2-a]pyrazin-3-amine;
5-[1-benzyl-4-(4-fluorophenyl)-1H-imidazol-5-yl]-1H-indazole;
N-{3-[4-(4-fluorophenyl)-5-(1H-indazol-5-yl)-1H-imidazol-1-yl]propyl}-N,N-dimethylamine;
N-cyclohexyl-2-(1H-indazol-5-yl)imidazo[1,2-a]pyrimidin-3-amine;
5-[4-(4-fluorophenyl)-1-(1-phenylethyl)-1H-imidazol-5-yl]-1H-indazole;
2-(1H-indazol-5-yl)-N-isopropylimidazo[1,2-a]pyrimidin-3-amine;
4-(1H-indazol-5-yl)-N-phenyl-1,3-thiazol-2-amine;
5-(2-methyl-1,3-thiazol-4-yl)-1H-indazole;
N-ethyl-4-(1H-indazol-5-yl)-1,3-thiazol-2-amine;
N-benzyl-4-(1H-indazol-5-yl)-1,3-thiazol-2-amine;
4-(1H-indazol-5-yl)-1,3-thiazol-2-amine;
4-(1H-indazol-5-yl)-N-(2-phenylethyl)-1,3-thiazol-2-amine;
N-benzyl-2-(1H-indazol-5-yl)imidazo[1,2-a]pyrimidin-3-amine;
N-butyl-2-(1H-indazol-5-yl)imidazo[1,2-a]pyrimidin-3-amine;
N-(4-chlorophenyl)-2-(1H-indazol-5-yl)imidazo[1,2-a]pyrimidin-3-amine;
2-(1H-indazol-5-yl)-N-(4-methoxyphenyl)imidazo[1,2-a]pyrimidin-3-amine;
2-(1H-indazol-5-yl)imidazo[1,2-a]pyrimidine;
methyl N-[2-(1H-indazol-5-yl)imidazo[1,2-a]pyridin-3-yl]glycinate;
N-benzyl-2-(1H-indazol-5-yl)imidazo[1,2-a]pyridin-3-amine;
N-(4-chlorophenyl)-2-(1H-indazol-5-yl)imidazo[1,2-a]pyridin-3-amine;
2-(1H-indazol-5-yl)-N-(4-methoxyphenyl)imidazo[1,2-a]pyridin-3-amine;
tert-butyl 4-[4-(4-fluorophenyl)-5-(1H-indazol-5-yl)-1H-imidazol-1-yl]piperidine-1-carboxylate;
3,5-bis(1-benzyl-1H-1,2,3-triazol-4-yl)-1H-indazole;
5-(1-benzyl-1H-1,2,3-triazol-4-yl)-3-phenyl-1H-indazole;
5-(1-benzyl-1H-1,2,3-triazol-4-yl)-1H-indazol-3-amine;
5-(1-benzyl-1H-1,2,3-triazol-4-yl)-1-[(1-methylpiperidin-4-yl)carbonyl]-1H-indazol-3-amine;
N-[5-(1-benzyl-1H-1,2,3-triazol-4-yl)-1H-indazol-3-yl]-2-methoxyacetamide;
N$^1$-[5-(1-benzyl-1H-1,2,3-triazol-4-yl)-1H-indazol-3-yl]-N$^2$,N$^2$-dimethylglycinamide;
N-[5-(1-benzyl-1H-1,2,3-triazol-4-yl)-1H-indazol-3-yl]butanamide;
5-[4-(4-fluorophenyl)-1-piperidin-4-yl-1H-imidazol-5-yl]-1H-indazole;
5-{4-(4-fluorophenyl)-1-[2-(1-methylpyrrolidin-2-yl)ethyl]-1H-imidazol-5-yl}-1H-indazole;
5-{4-(4-fluorophenyl)-1-[3-(4-methylpiperazin-1-yl)propyl]-1H-imidazol-5-yl}-1H-indazole;
ethyl 5-(1H-indazol-5-yl)isoxazole-3-carboxylate;
5-(1H-indazol-5-yl)-N-methylisoxazole-3-carboxamide;
5-(3-benzylisoxazol-5-yl)-1H-indazole;
N-[5-(1-benzyl-1H-1,2,3-triazol-4-yl)-1H-indazol-3-yl]benzamide;
5-(3-propylisoxazol-5-yl)-1H-indazole;

N-benzyl-4-(1H-indazol-5-yl)-5-phenyl-1,3-thiazol-2-amine;
4-(1H-indazol-5-yl)-N,5-diphenyl-1,3-thiazol-2-amine;
5-(1-benzyl-5-cyclopropyl-1H-1,2,3-triazol-4-yl)-1H-indazole;
5-(1-benzyl-4-cyclopropyl-1H-1,2,3-triazol-5-yl)-1H-indazole;
2-(1H-indazol-5-yl)-3-phenylimidazo[1,2-a]pyrimidine;
5-[1-(tetrahydro-2H-pyran-4-ylmethyl)-1H-1,2,3-triazol-4-yl]-1H-indazole;
5-[3-(piperidin-1-ylcarbonyl)isoxazol-5-yl]-1H-indazole;
5-(1H-indazol-5-yl)-N-phenylisoxazole-3-carboxamide;
N-cyclohexyl-5-(1H-indazol-5-yl)isoxazole-3-carboxamide;
5-[3-(piperidin-1-ylmethyl)isoxazol-5-yl]-1H-indazole;
[5-(1H-indazol-5-yl)isoxazol-3-yl]methanol;
5-(1H-indazol-5-yl)-N-(2-methoxyethyl)isoxazole-3-carboxamide;
5-(1-benzyl-5-phenyl-1H-1,2,3-triazol-4-yl)-1H-indazole;
5-(4-benzyl-1H-1,2,3-triazol-1-yl)-1H-indazole;
5-(1-benzyl-5-cyclopropyl-1H-1,2,3-triazol-4-yl)-1H-indazol-3-amine;
5-(1-benzyl-4-cyclopropyl-1H-1,2,3-triazol-5-yl)-1H-indazol-3-amine;
5-(3-isobutylisoxazol-5-yl)-1H-indazol-3-amine;
5-(3-benzylisoxazol-5-yl)-1H-indazol-3-amine;
N-{2-[4-(4-fluorophenyl)-5-(1H-indazol-5-yl)-1H-imidazol-1-yl]ethyl}-N,N-dimethylamine;
5-[4-(4-fluorophenyl)-1-(3-morpholin-4-ylpropyl)-1H-imidazol-5-yl]-1H-indazole;
5-[4-(4-fluorophenyl)-1-(3-pyrrolidin-1-ylpropyl)-1H-imidazol-5-yl]-1H-indazole;
5-{4-(4-fluorophenyl)-1-[2-(4-methylpiperidin-1-yl)ethyl]-1H-imidazol-5-yl}-1H-indazole;
5-[1-(1-benzylpiperidin-4-yl)-4-(4-fluorophenyl)-1H-imidazol-5-yl]-1H-indazole;
5-[4-(4-fluorophenyl)-1-(2-morpholin-4-ylethyl)-1H-imidazol-5-yl]-1H-indazole;
5-[1-(1-benzylpyrrolidin-3-yl)-4-(4-fluorophenyl)-1H-imidazol-5-yl]-1H-indazole;
2-{4-[4-(4-fluorophenyl)-5-(1H-indazol-5-yl)-1H-imidazol-1-yl]piperidin-1-yl}-2-oxoethanol;
5-(1-benzyl-5-phenyl-1H-1,2,3-triazol-4-yl)-1H-indazol-3-amine;
2-[1-(1H-indazol-5-yl)-1H-1,2,3-triazol-4-yl]propan-2-ol;
5-[4-(methoxymethyl)-1H-1,2,3-triazol-1-yl]-1H-indazole;
1-[1-(1H-indazol-5-yl)-1H-1,2,3-triazol-4-yl]-1-phenylethanol;
5-(4-propyl-1H-1,2,3-triazol-1-yl)-1H-indazole;
1-[1-(1H-indazol-5-yl)-1H-1,2,3-triazol-4-yl]propan-2-ol;
3-[1-(1H-indazol-5-yl)-1H-1,2,3-triazol-4-yl]propan-1-ol;
1-{[1-(1H-indazol-5-yl)-1H-1,2,3-triazol-4-yl]methyl}-1H-1,2,3-benzotriazole;
5-{4-[(phenylthio)methyl]-1H-1,2,3-triazol-1-yl}-1H-indazole;
5-(4-cyclopropyl-1H-1,2,3-triazol-1-yl)-1H-indazole;
5-[4-(2-phenylethyl)-1H-1,2,3-triazol-1-yl]-1H-indazole;
5-[4-(cyclohexylmethyl)-1H-1,2,3-triazol-1-yl]-1H-indazole;
5-(4-cyclopentyl-1H-1,2,3-triazol-1-yl)-1H-indazole;
1-[1-(1H-indazol-5-yl)-1H-1,2,3-triazol-4-yl]cyclohexanol;
5-[4-(phenoxymethyl)-1H-1,2,3-triazol-1-yl]-1H-indazole;
5-{4-[(1,1-dioxidothiomorpholin-4-yl)methyl]-1H-1,2,3-triazol-1-yl}-1H-indazole;
5-[4-(3-phenylpropyl)-1H-1,2,3-triazol-1-yl]-1H-indazole;
[1-benzyl-4-(1H-indazol-5-yl)-1H-1,2,3-triazol-5-yl](phenyl)methanone;
N,N-diethyl-N-{[1-(1H-indazol-5-yl)-1H-1,2,3-triazol-4-yl]methyl}amine;
ethyl N-[2-(1H-indazol-5-yl)imidazo[1,2-a]pyrimidin-3-yl]-beta-alaninate;
5-(1-benzyl-5-methyl-1H-1,2,3-triazol-4-yl)-1H-indazole;
5-(1-benzyl-5-methyl-1H-1,2,3-triazol-4-yl)-1H-indazol-3-amine;
$N^3$-[2-(1H-indazol-5-yl)imidazo[1,2-a]pyrimidin-3-yl]-β-alaninamide;
5-(1-benzyl-5-iodo-1H-1,2,3-triazol-4-yl)-1H-indazol-3-amine;
N-{3-[4-(3-amino-1H-indazol-5-yl)-1-benzyl-1H-1,2,3-triazol-5-yl]phenyl}-N'-(3-methylphenyl)urea;
5-(1H-indazol-5-yl)-N-(2-isopropoxyethyl)isoxazole-3-carboxamide;
5-[3-(morpholin-4-ylcarbonyl)isoxazol-5-yl]-1H-indazole;
5-(1H-indazol-5-yl)-N-(3-morpholin-4-ylpropyl)isoxazole-3-carboxamide;
N-[2-(1H-imidazol-4-yl)ethyl]-5-(1H-indazol-5-yl)isoxazole-3-carboxamide;
(3R)-1-{[5-(1H-indazol-5-yl)isoxazol-3-yl]carbonyl}piperidin-3-ol;
1-{[5-(1H-indazol-5-yl)isoxazol-3-yl]carbonyl}piperidine-3-carboxamide;
2-[2-(4-{[5-(1H-indazol-5-yl)isoxazol-3-yl]carbonyl}piperazin-1-yl)ethoxy]ethanol;
5-{3-[(4-methyl-1,4-diazepan-1-yl)carbonyl]isoxazol-5-yl}-1H-indazole;
N-(3-hydroxypropyl)-5-(1H-indazol-5-yl)isoxazole-3-carboxamide;
N-[(1R)-2-hydroxy-1-phenylethyl]-5-(1H-indazol-5-yl)isoxazole-3-carboxamide;
N-[3-(1H-imidazol-1-yl)propyl]-5-(1H-indazol-5-yl)isoxazole-3-carboxamide;
5-(1H-indazol-5-yl)-N-[3-(2-oxopyrrolidin-1-yl)propyl]isoxazole-3-carboxamide;
N-{2-[4-(aminosulfonyl)phenyl]ethyl}-5-(1H-indazol-5-yl)isoxazole-3-carboxamide;
[1-benzyl-4-(1H-indazol-5-yl)-1H-1,2,3-triazol-5-yl](3-chlorophenyl)methanone;
[1-benzyl-4-(1H-indazol-5-yl)-1H-1,2,3-triazol-5-yl](cyclopropyl)methanone;
5-[5-cyclopropyl-1-(tetrahydro-2H-pyran-4-ylmethyl)-1H-1,2,3-triazol-4-yl]-1H-indazole;
$N^1$-{[1-benzyl-4-(1H-indazol-5-yl)-1H-1,2,3-triazol-5-yl]methyl}glycinamide;
(4-fluorophenyl)[4-(1H-indazol-5-yl)-1-(tetrahydro-2H-pyran-4-ylmethyl)-1H-1,2,3-triazol-5-yl]methanone;
(4-chlorophenyl)[4-(1H-indazol-5-yl)-1-(tetrahydro-2H-pyran-4-ylmethyl)-1H-1,2,3-triazol-5-yl]methanone;
(3-chlorophenyl)[4-(1H-indazol-5-yl)-1-(tetrahydro-2H-pyran-4-ylmethyl)-1H-1,2,3-triazol-5-yl]methanone;
(2-chlorophenyl)[4-(1H-indazol-5-yl)-1-(tetrahydro-2H-pyran-4-ylmethyl)-1H-1,2,3-triazol-5-yl]methanone;
cyclopentyl[4-(1H-indazol-5-yl)-1-(tetrahydro-2H-pyran-4-ylmethyl)-1H-1,2,3-triazol-5-yl]methanone;
1-benzyl-4-(1H-indazol-5-yl)-1H-1,2,3-triazole-5-carboxylic acid;
5-{5-(4-fluorophenyl)-1-[4-(trifluoromethyl)benzyl]-1H-1,2,3-triazol-4-yl}-1H-indazol-3-amine;
5-[1-benzyl-5-(4-fluorophenyl)-1H-1,2,3-triazol-4-yl]-1H-indazol-3-amine;
[4-(1H-indazol-5-yl)-1-(tetrahydro-2H-pyran-4-ylmethyl)-1H-1,2,3-triazol-5-yl](tetrahydro-2H-pyran-4-yl)methanone;
5-[1-benzyl-5-(2-methylphenyl)-1H-1,2,3-triazol-4-yl]-1H-indazole;

5-{1-benzyl-5-[(4-methylpiperazin-1-yl)carbonyl]-1H-1,2,3-triazol-4-yl}-1H-indazole;
1-{[1-benzyl-4-(1H-indazol-5-yl)-1H-1,2,3-triazol-5-yl]carbonyl}piperidin-4-ol;
1-acetyl-5-[5-(4-fluorophenyl)-1-(tetrahydro-2H-pyran-4-ylmethyl)-1H-1,2,3-triazol-4-yl]-1H-indazole;
1-benzyl-4-(1H-indazol-5-yl)-N,N-dimethyl-1H-1,2,3-triazole-5-carboxamide;
N,1-dibenzyl-4-(1H-indazol-5-yl)-1H-1,2,3-triazole-5-carboxamide;
N-(2-hydroxy-2-phenylethyl)-5-(1H-indazol-5-yl)-N-methylisoxazole-3-carboxamide;
N-[(1S)-2-hydroxy-1-phenylethyl]-5-(1H-indazol-5-yl)isoxazole-3-carboxamide;
N-benzyl-N-(2-hydroxyethyl)-5-(1H-indazol-5-yl)isoxazole-3-carboxamide;
5-[1-benzyl-5-(2-methylphenyl)-1H-1,2,3-triazol-4-yl]-3-methyl-1H-indazole;
5-[1-benzyl-5-(2-methylphenyl)-1H-1,2,3-triazol-4-yl]-1H-indazol-3-amine;
2-{2-[1-(1H-indazol-5-yl)-1H-1,2,3-triazol-4-yl]ethyl}-1H-isoindole-1,3(2H)-dione;
5-{4-[(2,4-dichlorophenoxy)methyl]-1H-1,2,3-triazol-1-yl}-1H-indazole;
5-{4-[(2,6-dichlorophenoxy)methyl]-1H-1,2,3-triazol-1-yl}-1H-indazole;
5-[5-(4-fluorophenyl)-1-(tetrahydro-2H-pyran-4-ylmethyl)-1H-1,2,3-triazol-4-yl]-1H-indazole;
1-{[1-(1H-indazol-5-yl)-1H-1,2,3-triazol-4-yl]methyl}-1H-indazole;
5-[1-benzyl-5-(piperidin-1-ylcarbonyl)-1H-1,2,3-triazol-4-yl]-1H-indazole;
5-[5-(2-methylphenyl)-1-(tetrahydro-2H-pyran-4-ylmethyl)-1H-1,2,3-triazol-4-yl]-1H-indazole;
5-[5-(2-methylphenyl)-1-(tetrahydro-2H-pyran-4-ylmethyl)-1H-1,2,3-triazol-4-yl]-1H-indazol-3-amine;
5-[1-benzyl-5-(morpholin-4-ylcarbonyl)-1H-1,2,3-triazol-4-yl]-1H-indazole;
5-[1-benzyl-5-(4-methoxyphenyl)-1H-1,2,3-triazol-4-yl]-1H-indazol-3-amine;
N-[(1S)-1-benzyl-2-hydroxyethyl]-5-(1H-indazol-5-yl)isoxazole-3-carboxamide;
N-[(1S,2R)-2-hydroxy-2,3-dihydro-1H-inden-1-yl]-5-(1H-indazol-5-yl)isoxazole-3-carboxamide;
5-{3-[(3-phenylmorpholin-4-yl)carbonyl]isoxazol-5-yl}-1H-indazole;
N-benzyl-5-(1H-indazol-5-yl)isoxazole-3-carboxamide;
((1S)-2-{[5-(1H-indazol-5-yl)isoxazol-3-yl]carbonyl}-6,7-dimethoxy-1,2,3,4-tetrahydroisoquinolin-1-yl)methanol;
N-[(1R)-3-hydroxy-1-phenylpropyl]-5-(1H-indazol-5-yl)isoxazole-3-carboxamide;
N-[(1S)-3-hydroxy-1-phenylpropyl]-5-(1H-indazol-5-yl)isoxazole-3-carboxamide;
N-2,3-dihydro-1H-inden-1-yl-5-(1H-indazol-5-yl)isoxazole-3-carboxamide;
N-2,3-dihydro-1H-inden-2-yl-5-(1H-indazol-5-yl)isoxazole-3-carboxamide;
5-(1H-indazol-5-yl)-N-(1-phenylpropyl)isoxazole-3-carboxamide;
5-{1-benzyl-5-[3-(dimethylamino)phenyl]-1H-1,2,3-triazol-4-yl}-1H-indazol-3-amine;
5-{1-benzyl-5-[4-(dimethylamino)phenyl]-1H-1,2,3-triazol-4-yl}-1H-indazol-3-amine;
N-{3-[4-(3-amino-1H-indazol-5-yl)-1-benzyl-1H-1,2,3-triazol-5-yl]phenyl}acetamide;
N-{4-[4-(3-amino-1H-indazol-5-yl)-1-benzyl-1H-1,2,3-triazol-5-yl]phenyl}acetamide;
5-{1-benzyl-5-[3-(1H-pyrazol-1-yl)phenyl]-1H-1,2,3-triazol-4-yl}-1H-indazol-3-amine;
5-[1-benzyl-5-(1-methyl-1H-pyrazol-4-yl)-1H-1,2,3-triazol-4-yl]-1H-indazol-3-amine;
3-[4-(3-amino-1H-indazol-5-yl)-1-benzyl-1H-1,2,3-triazol-5-yl]-N-phenylbenzamide;
3-[4-(3-amino-1H-indazol-5-yl)-1-benzyl-1H-1,2,3-triazol-5-yl]-N-benzylbenzamide;
5-[1-benzyl-5-(1-methyl-1H-indol-5-yl)-1H-1,2,3-triazol-4-yl]-1H-indazol-3-amine;
5-[1-benzyl-5-(3-methoxyphenyl)-1H-1,2,3-triazol-4-yl]-1H-indazol-3-amine;
5-[1-benzyl-5-(3-morpholin-4-ylphenyl)-1H-1,2,3-triazol-4-yl]-1H-indazol-3-amine;
5-[3-(1,3-dihydro-2H-isoindol-2-ylcarbonyl)isoxazol-5-yl]-1H-indazole;
5-{3-[(4-methyl-2-phenylpiperazin-1-yl)carbonyl]isoxazol-5-yl}-1H-indazole;
1-{[1-benzyl-4-(1H-indazol-5-yl)-1H-1,2,3-triazol-5-yl]carbonyl}piperidin-4-amine;
N-[5-(1-benzyl-5-phenyl-1H-1,2,3-triazol-4-yl)-1H-indazol-3-yl]benzamide;
N-[5-(1-benzyl-5-phenyl-1H-1,2,3-triazol-4-yl)-1H-indazol-3-yl]benzenesulfonamide;
N-[5-(1-benzyl-5-phenyl-1H-1,2,3-triazol-4-yl)-1H-indazol-3-yl]-N'-(4-methoxyphenyl)urea;
N-[5-(1-benzyl-5-phenyl-1H-1,2,3-triazol-4-yl)-1H-indazol-3-yl]butanamide;
N-[5-(1-benzyl-5-phenyl-1H-1,2,3-triazol-4-yl)-1H-indazol-3-yl]-2-methylpropanamide;
N-[5-(1-benzyl-5-phenyl-1H-1,2,3-triazol-4-yl)-1H-indazol-3-yl]cyclopropanecarboxamide;
N-[1-benzoyl-5-(1-benzyl-5-cyclopropyl-1H-1,2,3-triazol-4-yl)-1H-indazol-3-yl]benzamide;
N-[5-(1-benzyl-5-cyclopropyl-1H-1,2,3-triazol-4-yl)-1H-indazol-3-yl]-3-fluorobenzamide;
N-[5-(1-benzyl-5-cyclopropyl-1H-1,2,3-triazol-4-yl)-1H-indazol-3-yl]benzamide;
N-benzyl-5-(1-benzyl-5-cyclopropyl-1H-1,2,3-triazol-4-yl)-1H-indazol-3-amine;
N-[(1R)-1-benzyl-2-hydroxyethyl]-5-(1H-indazol-5-yl)isoxazole-3-carboxamide;
5-(1-benzyl-1H-pyrazol-4-yl)-1H-indazole;
N-[(1R)-3-hydroxy-1-phenylpropyl]-5-(3-methyl-1H-indazol-5-yl)isoxazole-3-carboxamide;
3-[4-(3-amino-1H-indazol-5-yl)-1-benzyl-1H-1,2,3-triazol-5-yl]phenol;
3-[4-(3-amino-1H-indazol-5-yl)-1-benzyl-1H-1,2,3-triazol-5-yl]benzamide;
5-{1-benzyl-5-[4-(methylsulfonyl)phenyl]-1H-1,2,3-triazol-4-yl}-1H-indazol-3-amine;
N-[5-(1-benzyl-5-cyclopropyl-1H-1,2,3-triazol-4-yl)-1H-indazol-3-yl]-2-chlorobenzamide;
N-[5-(1-benzyl-5-cyclopropyl-1H-1,2,3-triazol-4-yl)-1H-indazol-3-yl]-4-chlorobenzamide;
N-[5-(1-benzyl-5-cyclopropyl-1H-1,2,3-triazol-4-yl)-1H-indazol-3-yl]ethanesulfonamide;
N-[5-(1-benzyl-5-cyclopropyl-1H-1,2,3-triazol-4-yl)-1H-indazol-3-yl]benzenesulfonamide;
N-[5-(1-benzyl-5-cyclopropyl-1H-1,2,3-triazol-4-yl)-1H-indazol-3-yl]-2-chlorobenzenesulfonamide;
N-[5-(1-benzyl-5-cyclopropyl-1H-1,2,3-triazol-4-yl)-1H-indazol-3-yl]-3-chlorobenzenesulfonamide;
N-[5-(1-benzyl-5-cyclopropyl-1H-1,2,3-triazol-4-yl)-1H-indazol-3-yl]-4-chlorobenzenesulfonamide;
N-[5-(1-benzyl-5-cyclopropyl-1H-1,2,3-triazol-4-yl)-1H-indazol-3-yl]-2,5-dimethylfuran-3-sulfonamide;

5-(1-benzyl-5-cyclopropyl-1H-1,2,3-triazol-4-yl)-N-(2-chlorobenzyl)-1H-indazol-3-amine;
5-(1-benzyl-5-cyclopropyl-1H-1,2,3-triazol-4-yl)-N-(3-chlorobenzyl)-1H-indazol-3-amine;
N-[5-(1-benzyl-5-cyclopropyl-1H-1,2,3-triazol-4-yl)-1H-indazol-3-yl]-3-chlorobenzamide;
N-[5-(1-benzyl-5-cyclopropyl-1H-1,2,3-triazol-4-yl)-1H-indazol-3-yl]-2-furamide;
5-(1-benzyl-5-cyclopropyl-1H-1,2,3-triazol-4-yl)-N-ethyl-1H-indazol-3-amine;
5-(1-benzyl-5-cyclopropyl-1H-1,2,3-triazol-4-yl)-N-(4-chlorobenzyl)-1H-indazol-3-amine;
5-(1-benzyl-5-cyclopropyl-1H-1,2,3-triazol-4-yl)-N-(3-furylmethyl)-1H-indazol-3-amine;
N-[5-(1-benzyl-5-cyclopropyl-1H-1,2,3-triazol-4-yl)-1H-indazol-3-yl]-N'-[5-methyl-2-(trifluoromethyl)-3-furyl]urea;
N-[5-(1-benzyl-5-cyclopropyl-1H-1,2,3-triazol-4-yl)-1H-indazol-3-yl]-3-furamide;
5-(1H-indazol-5-yl)-N-[(1S)-1-phenylpropyl]isoxazole-3-carboxamide;
5-(1H-indazol-5-yl)-N-[(1R)-1-phenylpropyl]isoxazole-3-carboxamide;
5-(1-benzyl-1H-pyrazol-4-yl)-1H-indazol-3-amine;
1-benzyl-4-(1H-indazol-5-yl)-N-[(2S)-tetrahydrofuran-2-ylmethyl]-1H-1,2,3-triazole-5-carboxamide;
1-benzyl-4-(1H-indazol-5-yl)-N-(2-isopropoxyethyl)-1H-1,2,3-triazole-5-carboxamide;
1-benzyl-4-(1H-indazol-5-yl)-N-[(2R)-tetrahydrofuran-2-ylmethyl]-1H-1,2,3-triazole-5-carboxamide;
1-benzyl-4-(1H-indazol-5-yl)-N-(tetrahydrofuran-3-ylmethyl)-1H-1,2,3-triazole-5-carboxamide;
1-benzyl-N-cyclopentyl-4-(1H-indazol-5-yl)-1H-1,2,3-triazole-5-carboxamide;
1-benzyl-N-(cyclopentylmethyl)-4-(1H-indazol-5-yl)-1H-1,2,3-triazole-5-carboxamide;
1-benzyl-N-ethyl-4-(1H-indazol-5-yl)-N-methyl-1H-1,2,3-triazole-5-carboxamide;
1-benzyl-4-(1H-indazol-5-yl)-N-isopropyl-N-methyl-1H-1,2,3-triazole-5-carboxamide;
1-benzyl-4-(1H-indazol-5-yl)-N-(2-methoxyethyl)-N-methyl-1H-1,2,3-triazole-5-carboxamide;
1-benzyl-4-(1H-indazol-5-yl)-N-phenyl-1H-1,2,3-triazole-5-carboxamide;
1-benzyl-N-(4-chlorophenyl)-4-(1H-indazol-5-yl)-1H-1,2,3-triazole-5-carboxamide;
1-benzyl-4-(1H-indazol-5-yl)-N-(2-morpholin-4-ylethyl)-1H-1,2,3-triazole-5-carboxamide;
1-benzyl-N-[2-(dimethylamino)ethyl]-4-(1H-indazol-5-yl)-N-methyl-1H-1,2,3-triazole-5-carboxamide;
1-benzyl-N-(2-hydroxyethyl)-4-(1H-indazol-5-yl)-N-propyl-1H-1,2,3-triazole-5-carboxamide;
1-benzyl-N-[3-(dimethylamino)propyl]-4-(1H-indazol-5-yl)-N-methyl-1H-1,2,3-triazole-5-carboxamide;
1-benzyl-N-[2-(diethylamino)ethyl]-4-(1H-indazol-5-yl)-N-methyl-1H-1,2,3-triazole-5-carboxamide;
N,1-dibenzyl-N-ethyl-4-(1H-indazol-5-yl)-1H-1,2,3-triazole-5-carboxamide;
N,1-dibenzyl-N-(2-hydroxyethyl)-4-(1H-indazol-5-yl)-1H-1,2,3-triazole-5-carboxamide;
(3R)-1-{[1-benzyl-4-(1H-indazol-5-yl)-1H-1,2,3-triazol-5-yl]carbonyl}piperidin-3-ol;
1-{[1-benzyl-4-(1H-indazol-5-yl)-1H-1,2,3-triazol-5-yl]carbonyl}piperidine-4-carboxamide;
5-{1-benzyl-5-[(2,6-dimethylmorpholin-4-yl)carbonyl]-1H-1,2,3-triazol-4-yl}-1H-indazole;
5-{5-[(4-acetylpiperazin-1-yl)carbonyl]-1-benzyl-1H-1,2,3-triazol-4-yl}-1H-indazole;
5-{1-benzyl-5-[(4-phenylpiperazin-1-yl)carbonyl]-1H-1,2,3-triazol-4-yl}-1H-indazole;
1-benzyl-N-[(1R)-1-(hydroxymethyl)-2-methylpropyl]-4-(1H-indazol-5-yl)-1H-1,2,3-triazole-5-carboxamide;
1-benzyl-N-[(1S)-1-(hydroxymethyl)-2-methylpropyl]-4-(1H-indazol-5-yl)-1H-1,2,3-triazole-5-carboxamide;
1-benzyl-N-[3-(1H-imidazol-1-yl)propyl]-4-(1H-indazol-5-yl)-1H-1,2,3-triazole-5-carboxamide;
N-[5-(1-benzyl-5-cyclopropyl-1H-1,2,3-triazol-4-yl)-1H-indazol-3-yl]-N'-ethylurea;
N-[5-(1-benzyl-5-cyclopropyl-1H-1,2,3-triazol-4-yl)-1H-indazol-3-yl]-N'-phenylurea;
N-benzyl-N'-[5-(1-benzyl-5-cyclopropyl-1H-1,2,3-triazol-4-yl)-1H-indazol-3-yl]urea;
N-[5-(1-benzyl-5-cyclopropyl-1H-1,2,3-triazol-4-yl)-1H-indazol-3-yl]-N'-(2-chlorophenyl)urea;
N-[5-(1-benzyl-5-cyclopropyl-1H-1,2,3-triazol-4-yl)-1H-indazol-3-yl]-N'-(3-chlorophenyl)urea;
N-[5-(1-benzyl-5-cyclopropyl-1H-1,2,3-triazol-4-yl)-1H-indazol-3-yl]-N'-(4-chlorophenyl)urea;
N-[5-(1-benzyl-5-iodo-1H-1,2,3-triazol-4-yl)-1H-indazol-3-yl]benzamide;
3-[4-(3-amino-1H-indazol-5-yl)-1H-pyrazol-1-yl]propanenitrile;
2-[4-(3-amino-1H-indazol-5-yl)-1H-pyrazol-1-yl]acetamide;
methyl 3-[4-(3-amino-1H-indazol-5-yl)-1H-pyrazol-1-yl]propanoate;
3-[4-(3-amino-1H-indazol-5-yl)-1H-pyrazol-1-yl]propanamide;
[4-(3-amino-1H-indazol-5-yl)-1H-pyrazol-1-yl]acetonitrile;
4-(3-amino-1H-indazol-5-yl)-N,N-dimethyl-1H-imidazole-1-sulfonamide;
5-pyrazin-2-yl-1H-indazol-3-amine;
5-thien-2-yl-1H-indazol-3-amine;
5-(2-aminopyrimidin-4-yl)-1H-indazol-3-amine;
5-(2-methoxypyridin-3-yl)-1H-indazol-3-amine;
5-imidazo[1,2-a]pyridin-3-yl-1H-indazol-3-amine;
$N^2,N^2$-dimethyl-$N^1$-[5-(1H-1,2,3-triazol-4-yl)-1H-indazol-3-yl]glycinamide;
5-(1H-pyrazol-5-yl)-1H-indazol-3-amine;
5-(4-methyl-1H-imidazol-5-yl)-1H-indazol-3-amine;
5-(1H-imidazol-4-yl)-1H-indazol-3-amine;
$N^2,N^2$-dimethyl-$N^1$-{5-[1-(3-methylbenzyl)-1H-1,2,3-triazol-4-yl]-1H-indazol-3-yl}glycinamide;
5-(1-benzyl-1H-imidazol-4-yl)-1H-indazol-3-amine;
$N^1$-{5-[1-(4-tert-butylbenzyl)-1H-1,2,3-triazol-4-yl]-1H-indazol-3-yl}-$N^2,N^2$-dimethylglycinamide;
$N^2,N^2$-dimethyl-$N^1$-{5-[1-(2-piperidin-1-ylethyl)-1H-1,2,3-triazol-4-yl]-1H-indazol-3-yl}glycinamide;
$N^2,N^2$-dimethyl-$N^1$-{5-[1-(2-morpholin-4-ylethyl)-1H-1,2,3-triazol-4-yl]-1H-indazol-3-yl}glycinamide;
$N^1$-(5-{1-[2-(3,5-dimethylisoxazol-4-yl)ethyl]-1H-1,2,3-triazol-4-yl}-1H-indazol-3-yl)-$N^2,N^2$-dimethylglycinamide;
$N^1$-(5-{1-[2-(3,5-dimethyl-1H-pyrazol-4-yl)ethyl]-1H-1,2,3-triazol-4-yl}-1H-indazol-3-yl)-$N^2,N^2$-dimethylglycinamide;
2-(4-{3-[(N,N-dimethylglycyl)amino]-1H-indazol-5-yl}-1H-1,2,3-triazol-1-yl)-2-methylpropanoic acid;
ethyl (4-{3-[(N,N-dimethylglycyl)amino]-1H-indazol-5-yl}-1H-1,2,3-triazol-1-yl)acetate;
$N^2,N^2$-dimethyl-$N^1$-(5-{1-[(trimethylsilyl)methyl]-1H-1,2,3-triazol-4-yl}-1H-indazol-3-yl)glycinamide;

$N^1$-[5-(3-furyl)-1H-indazol-3-yl]-$N^2,N^2$-dimethylglycinamide;

$N^2,N^2$-dimethyl-$N^1$-[5-(1H-pyrazol-5-yl)-1H-indazol-3-yl]glycinamide;

$N^2,N^2$-dimethyl-$N^1$-(5-pyrimidin-5-yl-1H-indazol-3-yl)glycinamide;

$N^1$-[5-(2,1,3-benzoxadiazol-5-yl)-1H-indazol-3-yl]-$N^2,N^2$-dimethylglycinamide;

$N^2,N^2$-dimethyl-$N^1$-[5-(1H-pyrazol-4-yl)-1H-indazol-3-yl]glycinamide;

$N^2,N^2$-dimethyl-$N^1$-[5-(1-methyl-1H-pyrazol-4-yl)-1H-indazol-3-yl]glycinamide;

$N^1$-[5-(3,5-dimethyl-1H-pyrazol-4-yl)-1H-indazol-3-yl]-$N^2,N^2$-dimethylglycinamide;

$N^1$-{5-[2-(dimethylamino)pyrimidin-5-yl]-1H-indazol-3-yl}-$N^2,N^2$-dimethylglycinamide;

$N^2,N^2$-dimethyl-$N^1$-[5-(2-morpholin-4-ylpyrimidin-5-yl)-1H-indazol-3-yl]glycinamide;

$N^2,N^2$-dimethyl-$N^1$-{5-[1-(2-morpholin-4-ylethyl)-1H-pyrazol-4-yl]-1H-indazol-3-yl}glycinamide;

$N^1$-[5-(1-benzyl-5-cyclopropyl-1H-1,2,3-triazol-4-yl)-1H-indazol-3-yl]-$N^2,N^2$-dimethylglycinamide;

$N^1$-[5-(1-benzyl-1H-pyrazol-4-yl)-1H-indazol-3-yl]-$N^2,N^2$-dimethylglycinamide;

$N^1$-[5-(1-benzyl-1H-1,2,3-triazol-4-yl)-1H-indazol-3-yl]-$N^2$-methylglycinamide;

N-[5-(1-benzyl-1H-1,2,3-triazol-4-yl)-1H-indazol-3-yl]-2-pyrrolidin-1-ylacetamide;

$N^1$-[5-(1-benzyl-1H-1,2,3-triazol-4-yl)-1H-indazol-3-yl]-$N^2$-cyclopentylglycinamide;

$N^1$-[5-(1-benzyl-1H-1,2,3-triazol-4-yl)-1H-indazol-3-yl]-$N^2$-cyclopropylglycinamide;

$N^1$-[5-(1-benzyl-1H-1,2,3-triazol-4-yl)-1H-indazol-3-yl]-$N^2$-tetrahydro-2H-pyran-4-yl)glycinamide;

N-[5-(1-benzyl-1H-1,2,3-triazol-4-yl)-1H-indazol-3-yl]-2-(3-hydroxypyrrolidin-1-yl)acetamide;

N-[5-(1-benzyl-1H-1,2,3-triazol-4-yl)-1H-indazol-3-yl]-2-(3-hydroxypiperidin-1-yl)acetamide;

$N^1$-[5-(1-benzyl-1H-1,2,3-triazol-4-yl)-1H-indazol-3-yl]-$N^3,N^3$-dimethyl-beta-alaninamide;

N-[5-(1-benzyl-1H-1,2,3-triazol-4-yl)-1H-indazol-3-yl]-2-morpholin-4-ylacetamide;

N-[5-(1-benzyl-1H-1,2,3-triazol-4-yl)-1H-indazol-3-yl]-2-(4-methylpiperazin-1-yl)acetamide;

N-[5-(1-benzyl-1H-1,2,3-triazol-4-yl)-1H-indazol-3-yl]-2-(3-oxopiperazin-1-yl)acetamide;

$N^1$-[5-(1-benzyl-1H-1,2,3-triazol-4-yl)-1H-indazol-3-yl]-$N^2$-isopropylglycinamide;

$N^1$-[5-(1-benzyl-1H-1,2,3-triazol-4-yl)-1H-indazol-3-yl]-$N^2$-cyclohexylglycinamide;

N-[5-(1-benzyl-1H-1,2,3-triazol-4-yl)-1H-indazol-3-yl]acetamide;

$N^1$-[5-(1-benzyl-1H-1,2,3-triazol-4-yl)-1H-indazol-3-yl]-$N^2$-cyclobutylglycinamide;

N-[5-(1-benzyl-1H-1,2,3-triazol-4-yl)-1H-indazol-3-yl]-N'-propylurea;

N-[5-(1-benzyl-1H-1,2,3-triazol-4-yl)-1H-indazol-3-yl]ethanesulfonamide;

5-(1-benzyl-1H-1,2,3-triazol-4-yl)-N-(cyclopropylmethyl)-1H-indazol-3-amine;

N-[5-(1-benzyl-1H-1,2,3-triazol-4-yl)-1H-indazol-3-yl]-N'-ethylurea;

1-[5-(1-benzyl-1H-1,2,3-triazol-4-yl)-1H-indazol-3-yl]pyrrolidin-2-one;

N-[5-(1-benzyl-1H-1,2,3-triazol-4-yl)-1H-indazol-3-yl]-4-(dimethylamino)butanamide;

N-3,4-dihydro-1H-isochromen-4-yl-5-(1H-indazol-5-yl)isoxazole-3-carboxamide;

N-(cyclohexylmethyl)-5-(1H-indazol-5-yl)isoxazole-3-carboxamide;

N-(3-chlorobenzyl)-5-(1H-indazol-5-yl)isoxazole-3-carboxamide;

5-(1H-indazol-5-yl)-N-(2-methoxybenzyl)isoxazole-3-carboxamide;

5-(1H-indazol-5-yl)-N-[2-(trifluoromethyl)benzyl]isoxazole-3-carboxamide;

5-(1H-indazol-5-yl)-N-[3-(trifluoromethyl)benzyl]isoxazole-3-carboxamide;

5-(1H-indazol-5-yl)-N-[4-(trifluoromethyl)benzyl]isoxazole-3-carboxamide;

5-(1H-indazol-5-yl)-N-(pyridin-2-ylmethyl)isoxazole-3-carboxamide;

5-(1H-indazol-5-yl)-N-(pyridin-3-ylmethyl)isoxazole-3-carboxamide;

5-(1H-indazol-5-yl)-N-(pyridin-4-ylmethyl)isoxazole-3-carboxamide;

N-(2-chlorobenzyl)-5-(1H-indazol-5-yl)isoxazole-3-carboxamide;

N-(4-chlorobenzyl)-5-(1H-indazol-5-yl)isoxazole-3-carboxamide;

5-(1H-indazol-5-yl)-N-(1-phenyl-2-piperidin-1-ylethyl)isoxazole-3-carboxamide;

N-[2-(1H-imidazol-1-yl)-1-phenylethyl]-5-(1H-indazol-5-yl)isoxazole-3-carboxamide;

5-(1H-indazol-5-yl)-N-(2-morpholin-4-yl-1-phenylethyl)isoxazole-3-carboxamide;

5-(1H-indazol-5-yl)-N-[2-(4-methylpiperazin-1-yl)-1-phenylethyl]isoxazole-3-carboxamide;

5-(1H-indazol-5-yl)-N-(1-phenyl-2-pyrrolidin-1-ylethyl)isoxazole-3-carboxamide;

tert-butyl 2-({[5-(1H-indazol-5-yl)isoxazol-3-yl]carbonyl}amino)-2-phenylethylcarbamate;

5-(1H-indazol-5-yl)-N-(1-naphthylmethyl)isoxazole-3-carboxamide;

5-(1H-indazol-5-yl)-N-(2-phenylethyl)isoxazole-3-carboxamide;

5-(1H-indazol-5-yl)-N-(2-pyridin-2-ylethyl)isoxazole-3-carboxamide;

5-(1H-indazol-5-yl)-N-(2-pyridin-3-ylethyl)isoxazole-3-carboxamide;

5-(1H-indazol-5-yl)-N-(2-pyridin-4-ylethyl)isoxazole-3-carboxamide;

N-[2-(2-chlorophenyl)ethyl]-5-(1H-indazol-5-yl)isoxazole-3-carboxamide;

N-[2-(3-chlorophenyl)ethyl]-5-(1H-indazol-5-yl)isoxazole-3-carboxamide;

N-[2-(4-chlorophenyl)ethyl]-5-(1H-indazol-5-yl)isoxazole-3-carboxamide;

N-benzyl-N-ethyl-5-(1H-indazol-5-yl)isoxazole-3-carboxamide;

5-(1H-indazol-5-yl)-N-methyl-N-(1-naphthylmethyl)isoxazole-3-carboxamide;

5-(1H-indazol-5-yl)-N-methyl-N-(2-phenylethyl)isoxazole-3-carboxamide;

5-(1H-indazol-5-yl)-N-methyl-N-(2-pyridin-2-ylethyl)isoxazole-3-carboxamide;

5-(1H-indazol-5-yl)-N-[(1R)-1-phenylethyl]isoxazole-3-carboxamide;

5-(1H-indazol-5-yl)-N-1,2,3,4-tetrahydronaphthalen-1-ylisoxazole-3-carboxamide;

5-(1H-indazol-5-yl)-N-[(1S)-1-(1-naphthyl)ethyl]isoxazole-3-carboxamide;

5-(1H-indazol-5-yl)-N-[(1R)-1-(1-naphthyl)ethyl]isoxazole-3-carboxamide;
N-[3-(dimethylamino)-1-phenylpropyl]-5-(1H-indazol-5-yl)isoxazole-3-carboxamide;
N-(2,3-dihydro-1,4-benzodioxin-5-ylmethyl)-5-(1H-indazol-5-yl)isoxazole-3-carboxamide;
N-(3,4-dihydro-2H-1,5-benzodioxepin-6-ylmethyl)-5-(1H-indazol-5-yl)isoxazole-3-carboxamide;
5-(1H-indazol-5-yl)-N-[(1-methyl-1H-indol-4-yl)methyl]isoxazole-3-carboxamide;
5-{3-[(3-phenylpyrrolidin-1-yl)carbonyl]isoxazol-5-yl}-1H-indazole;
5-{3-[(2-phenylpyrrolidin-1-yl)carbonyl]isoxazol-5-yl}-1H-indazole;
5-{3-[(2-phenylpiperidin-1-yl)carbonyl]isoxazol-5-yl}-1H-indazole;
5-(1H-indazol-5-yl)-N-[(1S)-1-phenylethyl]isoxazole-3-carboxamide;
5-(1H-indazol-5-yl)-N-[(1R)-1-(4-methylphenyl)ethyl]isoxazole-3-carboxamide;
5-(1H-indazol-5-yl)-N-[(1S)-1-(4-methylphenyl)ethyl]isoxazole-3-carboxamide;
N-[(1R,2S)-2-hydroxy-2,3-dihydro-1H-inden-1-yl]-5-(1H-indazol-5-yl)isoxazole-3-carboxamide;
N-[(1R,2R)-2-hydroxy-2,3-dihydro-1H-inden-1-yl]-5-(1H-indazol-5-yl)isoxazole-3-carboxamide;
N-[(1R)-1-(4-bromophenyl)ethyl]-5-(1H-indazol-5-yl)isoxazole-3-carboxamide;
N-[(1S)-1-(4-bromophenyl)ethyl]-5-(1H-indazol-5-yl)isoxazole-3-carboxamide;
N-[(1R)-1-(4-chlorophenyl)ethyl]-5-(1H-indazol-5-yl)isoxazole-3-carboxamide;
N-[(1S)-1-(4-chlorophenyl)ethyl]-5-(1H-indazol-5-yl)isoxazole-3-carboxamide;
5-(1H-indazol-5-yl)-N-[(1S)-1-(2-naphthyl)ethyl]isoxazole-3-carboxamide;
N-[1-(4-ethoxyphenyl)-2-hydroxyethyl]-5-(1H-indazol-5-yl)isoxazole-3-carboxamide;
N-[2-hydroxy-1-(4-isopropylphenyl)ethyl]-5-(1H-indazol-5-yl)isoxazole-3-carboxamide;
N-[1-(3,4-dimethylphenyl)-2-hydroxyethyl]-5-(1H-indazol-5-yl)isoxazole-3-carboxamide;
N-[2-hydroxy-1-(2-methoxyphenyl)ethyl]-5-(1H-indazol-5-yl)isoxazole-3-carboxamide;
N-[2-hydroxy-1-(4-methylphenyl)ethyl]-5-(1H-indazol-5-yl)isoxazole-3-carboxamide;
5-(1H-indazol-5-yl)-N-[(1R)-1-(2-methoxyphenyl)ethyl]isoxazole-3-carboxamide;
N-[(1S)-1-(3,4-difluorophenyl)ethyl]-5-(1H-indazol-5-yl)isoxazole-3-carboxamide;
5-(1H-indazol-5-yl)-N-[(1R)-1-(3-methoxyphenyl)ethyl]isoxazole-3-carboxamide;
5-(1H-indazol-5-yl)-N-{(1R)-1-[3-(trifluoromethyl)phenyl]ethyl} isoxazole-3-carboxamide;
N-[1-(2,3-dihydro-1,4-benzodioxin-6-yl)ethyl]-5-(1H-indazol-5-yl)isoxazole-3-carboxamide;
N-[1-(3,5-dichlorophenyl)-2-hydroxyethyl]-5-(1H-indazol-5-yl)isoxazole-3-carboxamide;
tert-butyl 5-(1-benzyl-1H-1,2,3-triazol-4-yl)-3-[({[6-(trifluoromethyl)pyridin-2-yl]amino}carbonyl)amino]-1H-indazole-1-carboxylate;
5-(1-benzyl-1H-1,2,3-triazol-4-yl)-1-[(1-methylpiperidin-2-yl)carbonyl]-1H-indazol-3-amine;
5-(1-benzyl-1H-1,2,3-triazol-4-yl)-1-[(dimethylamino)acetyl]-1H-indazol-3-amine;
tert-butyl 3-amino-5-(1-benzyl-1H-1,2,3-triazol-4-yl)-1H-indazole-1-carboxylate;
N-[5-(1-benzyl-1H-1,2,3-triazol-4-yl)-1H-indazol-3-yl]-2-piperidin-1-ylacetamide;
N-[5-(1-benzyl-1H-1,2,3-triazol-4-yl)-1H-indazol-3-yl]-2-morpholin-4-ylacetamide;
N-[5-(1-benzyl-1H-1,2,3-triazol-4-yl)-1H-indazol-3-yl]-1-methylpiperidine-2-carboxamide;
2-(1H-indazol-5-yl)-N-[(1R)-1-(3-methoxyphenyl)ethyl]-1,3-thiazole-5-carboxamide
N-[5-(1-benzyl-1H-1,2,3-triazol-4-yl)-1H-indazol-3-yl]-3-fluorobenzamide;
5-(1-benzyl-1H-1,2,3-triazol-4-yl)-N,N-dimethyl-1H-indazole-3-carboxamide;
methyl 5-(1-benzyl-1H-1,2,3-triazol-4-yl)-1H-indazole-3-carboxylate;
5-(1-benzyl-1H-1,2,3-triazol-4-yl)-3-(1-methyl-1H-imidazol-2-yl)-1H-indazole;
5-(1-benzyl-1H-1,2,3-triazol-4-yl)-3-morpholin-4-yl-1H-indazole;
5-(1-benzyl-1H-1,2,3-triazol-4-yl)-3-(4-methylpiperazin-1-yl)-1H-indazole;
5-(1-benzyl-1H-1,2,3-triazol-4-yl)-3-thien-2-yl-1H-indazole;
5-(1-benzyl-5-cyclohexyl-1H-1,2,3-triazol-4-yl)-1H-indazol-3-amine;
5-[1-benzyl-5-(cyclohexylmethyl)-1H-1,2,3-triazol-4-yl]-1H-indazol-3-amine;
5-(1-benzyl-1H-1,2,3-triazol-4-yl)-3-(1,3-thiazol-2-yl)-1H-indazole;
5-(1,5-dibenzyl-1H-1,2,3-triazol-4-yl)-1H-indazol-3-amine;
5-(1-benzyl-5-thien-2-yl-1H-1,2,3-triazol-4-yl)-1H-indazol-3-amine;
5-(1-benzyl-1H-1,2,3-triazol-4-yl)-N-(2-morpholin-4-ylethyl)-1H-indazol-3-amine;
5-[1-benzyl-5-(4-fluorophenyl)-1H-1,2,3-triazol-4-yl]-3-methyl-1H-indazole;
5-[1-benzyl-5-(cyclopentylmethyl)-1H-1,2,3-triazol-4-yl]-1H-indazol-3-amine;
5-(1-benzyl-1H-1,2,3-triazol-4-yl)-N-butyl-1H-indazol-3-amine;
N-benzyl-5-(1-benzyl-1H-1,2,3-triazol-4-yl)-1H-indazol-3-amine;
5-(1-benzyl-1H-1,2,3-triazol-4-yl)-N-(4-chlorobenzyl)-1H-indazol-3-amine;
5-(1-benzyl-1H-1,2,3-triazol-4-yl)-N-(4-methoxybenzyl)-1H-indazol-3-amine;
5-(1-benzyl-1H-1,2,3-triazol-4-yl)-N-(3-fluorobenzyl)-1H-indazol-3-amine;
4-({[5-(1-benzyl-1H-1,2,3-triazol-4-yl)-1H-indazol-3-yl]amino}methyl)benzonitrile;
5-(1-benzyl-1H-1,2,3-triazol-4-yl)-N-(2,4-difluorobenzyl)-1H-indazol-3-amine;
5-(1-benzyl-1H-1,2,3-triazol-4-yl)-N-(cyclohexylmethyl)-1H-indazol-3-amine; and
5-(1-phenyl-1H-1,2,3-triazol-4-yl)-1H-indazole.

All patents, patent applications, and literature references cited in the specification are herein incorporated by reference in their entirety. In the case of inconsistencies, the present disclosure, including definitions, will prevail.

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkylene group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkylene group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkylene group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, and —$CH_2CH(CH_3)CH_2$—.

The term "alkylene-$NR_g$—" as used herein, means an alkylene group, as defined herein, appended to the parent molecular moiety through a —$NR_g$— group, as defined herein.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" as used herein, means an alkylsulfinyl group, as defined herein, appended to the parent molecular moiety through an alkylene group, as defined herein. Representative examples of alkylsulfinylalkyl include, but are not limited to, methylsulfinylmethyl and ethylsulfinylmethyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl" as used herein, means an alkylsulfonyl group, as defined herein, appended to the parent molecular moiety through an alkylene group, as defined herein. Representative examples of alkylsulfonylalkyl include, but are not limited to, methylsulfonylmethyl and ethylsulfonylmethyl.

The term "alkylthio" as used herein, means an alkyl group, as defined herein, appended to the parent molecular moiety through a sulfur atom. Representative examples of alkylthio include, but are not limited to, methylthio, ethylthio, tert-butylthio, and hexylthio.

The term "alkylthioalkyl" as used herein, means an alkylthio group, as defined herein, appended to the parent molecular moiety through an alkylene group, as defined herein. Representative examples of alkylthioalkyl include, but are not limited to, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "aryl," as used herein, means phenyl, a bicyclic aryl or a tricyclic aryl. The bicyclic aryl is naphthyl, or a phenyl fused to a cycloalkyl, or a phenyl fused to a cycloalkenyl, or a phenyl fused to a monocyclic heteroaryl ring as defined herein, or a phenyl fused to a monocyclic heterocycle as defined herein. The bicyclic aryl of the present invention must be attached to the parent molecular moiety through any available carbon atom contained within the phenyl ring. Representative examples of the bicyclic aryl include, but are not limited to, 2,3-dihydro-1,4-benzodioxin-5-yl, 2,3-dihydro-1,4-benzodioxin-6-yl, 3,4-dihydro-2H-1,5-benzodioxepin-6-yl, dihydroindenyl, indenyl, indol-4-yl, naphthyl, dihydronaphthalenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl. The tricyclic aryl is attached to the parent molecular moiety through any carbon atom contained within the tricyclic aryl. Representative examples of tricyclic aryl ring include, but are not limited to, azulenyl, dihydroanthracenyl, fluorenyl, and tetrahydrophenanthrenyl.

The aryl groups of this invention are optionally substituted with 1, 2, 3, 4 or 5 substituents independently selected from alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkylcarbonyloxy, alkylsulfinyl, alkylsulfinylalkyl, alkylsulfonyl, alkylsulfonylalkyl, alkylthio, alkylthioalkyl, alkynyl, aryl*NC(O)—, aryl*NHC(O)NH—, carboxy, carboxyalkyl, cyano, cyanoalkyl, formyl, formylalkyl, halogen, haloalkyl, heteroaryl, hydroxy, hydroxyalkyl, mercapto, morpholino, nitro, $Z_1Z_2N$—, or $(Z_3Z_4N)$carbonyl. Aryl* is optionally substituted with 1, 2 or 3 substituents independently selected from alkyl, halo, cyano or nitro. $Z_1$ and $Z_2$ are each independently selected from hydrogen, alkyl or alkylcarbonyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl" as used herein, means an aryloxy group, as defined herein, appended to the parent molecular moiety through an alkyl group, as defined herein. Representative examples of aryloxyalkyl include, but are not limited to, 2-phenoxyethyl, 3-naphth-2-yloxypropyl and 3-bromophenoxymethyl.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "aryl(hydroxy)alkyl" as used herein, means an aryl group, as defined herein, appended to the parent molecular moiety through an alkylene group bearing one hydroxy group, as defined herein. Representative examples of aryl(hydroxy)alkyl include, but are not limited to, 2-phenylethanol-2-yl and 2-hydroxy-2-phenylethanyl.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "arylthio" as used herein, means an aryl group, as defined herein, appended to the parent molecular moiety through a sulfur atom. Representative examples of arylthio include, but are not limited to, phenylthio and 2-naphthylthio.

The term "arylthioalkyl" as used herein, means an arylthio group, as defined herein, appended to the parent molecular moiety through an alkylene group, as defined herein. Representative examples of arylthioalkyl include, but are not limited to, phenylthiomethyl, 2-naphth-2-ylthioethyl, and 5-phenylthiomethyl.

The term "azido" as used herein, means a —$N_3$ group.

The term "azidoalkyl" as used herein, means an azido group, as defined herein, appended to the parent molecular moiety through an alkylene group, as defined herein.

The term "carbonyl" as used herein, means a —C(O)— group.

The term "carboxy" as used herein, means a —$CO_2H$ group.

The term "carboxyalkyl" as used herein, means a carboxy group, as defined herein, appended to the parent molecular moiety through an alkylene group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkenyl" as used herein, means a monocyclic or bicyclic ring system containing from 3 to 10 carbons and containing at least one carbon-carbon double bond formed by the removal of two hydrogens. Representative examples of monocyclic ring systems include, but are not limited to, 2-cyclohexen-1-yl, 3-cyclohexen-1-yl, 2,4-cyclohexadien-1-yl and 3-cyclopenten-1-yl. Bicyclic ring systems are exemplified by a monocyclic cycloalkenyl ring system which is fused to another monocyclic cycloalkyl ring as defined herein, a monocyclic aryl ring as defined herein, a monocyclic heterocycle as defined herein or a monocyclic heteroaryl as defined herein. The bicyclic ring systems of the present invention must be appended to the parent molecular moiety through an available carbon atom within the cycloalkenyl ring. Representative examples of bicyclic ring systems include, but are not limited to, 4,5-dihydro-benzo[1,2,5]oxadiazole, 3a,4,5,6,7,7a-hexahydro-1H-indenyl, 1,2,3,4,5,6-hexahydro-pentalenyl, 1,2,3,4,4a,5,6,8a-octahydro-pentalenyl.

The term "cycloalkyl" as used herein, means a monocyclic, bicyclic, or spirocyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic cycloalkyl groups of the present invention are exemplified by a monocyclic cycloalkyl ring fused to another monocyclic cycloalkyl ring, or a monocyclic cycloalkyl ring fused cycloalkenyl, or a monocyclic cycloalkyl ring fused to a phenyl ring, or a monocyclic cycloalkyl ring fused to a monocyclic heteroaryl ring as defined herein, or a monocyclic cycloalkyl ring fused to a monocyclic heterocycle as defined herein. The bicyclic cycloalkyl ring systems of the present invention must be appended to the parent molecular moiety through an available carbon atom within the monocycloalkyl ring.

The cycloalkyl groups of the present invention are optionally substituted with 1, 2, 3, or 4 substituents selected from alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkylthioalkyl, alkynyl, carboxy, cyano, formyl, haloalkoxy, haloalkyl, halogen, hydroxy, hydroxyalkyl, mercapto, oxo, $Z_1Z_2N$—, or $(Z_3Z_4N)$carbonyl.

The term "cycloalkylalkyl," as used herein, means a cycloalkyl group appended to the parent molecular moiety through an alkyl group, as defined herein.

The term "cycloalkylcarbonyl" as used herein, means cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl, and cyclohexylcarbonyl.

The term "formyl" as used herein, means a —C(O)H group.

The term "formylalkyl" as used herein, means a formyl group, as defined herein, appended to the parent molecular moiety through an alkylene group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkylene group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic heteroaryl. The monocyclic heteroaryl is a 5 or 6 membered ring containing at least one heteroatom independently selected from O, N, or S. The 5 membered ring contains two double bonds may contain one, two, three or four heteroatoms. The 6 membered ring contains three double bonds may contain one, two, three or four heteroatoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a monocyclic aryl ring as defined herein, a monocyclic cycloalkyl ring as defined herein, a monocyclic cycloalkenyl ring as defined herein, another monocyclic heteroaryl or a monocyclic heterocycle ring as defined herein. The bicyclic heteroaryl ring systems of the present invention must be appended to the parent molecular moiety through an available carbon atom within the heteroaryl ring. The bicyclic heteroaryl is connected to the parent molecular moiety through any carbon atom or any nitrogen atom contained within the bicyclic heteroaryl. Representative examples of bicyclic heteroaryl include, but are not limited to, benzofuranyl, benzoxadiazolyl, 1,3-benzothiazolyl, benzimidazolyl, benzodioxolyl, benzothiophenyl, chromenyl, cinnolinyl, furopyridine, indolyl, indazolyl, isoindolyl, isoquinolinyl, naphthyridinyl, oxazolopyridine, quinolinyl, thienopyridine and thienopyridinyl.

The heteroaryl groups of the present invention are optionally substituted with 1, 2, 3, or 4 substituents independently selected from alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, benzyl, carboxy, carboxyalkyl, cyano, cyanoalkyl, formyl, haloalkoxy, haloalkyl, halogen, hydroxy, hydroxyalkyl, mercapto, nitro, $Z_1Z_2N$—, or $(Z_3Z_4N)$carbonyl. Heteroaryl groups of the present invention that are substituted may be present as tautomers. The present invention encompasses all tautomers including non-aromatic tautomers.

The term "heteroarylalkyl," as used herein, means a heteroaryl group appended to the parent molecular moiety through an alkyl group, as defined herein.

The term "heterocycle" or "heterocyclic" as used herein, refers to a monocyclic, bicyclic, tricyclic or a spirocyclic ring system that contains at least one heteroatom. The monocyclic heterocycle is a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, isoindoline-1,3-dione, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle of the present invention is defined as a monocyclic heterocycle fused to a phenyl group, a cycloalkyl group as defined herein, a cycloalkenyl group as defined herein, another monocyclic heterocycle group as defined herein, or a spirocyclic ring wherein one carbon atom of the monocyclic heterocycle is bridged by two ends of an alkylene chain. The bicyclic heterocycle of the present invention is connected to the parent molecular moiety through any carbon atom or any nitrogen atom contained within the heterocyclic ring. Representative examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 3,4-dihydro-1H-isochromen-4-yl, 2,3-dihydro-1H-indolyl, succinmimidyl, and 1,2,3,4-tetrahydroquinolinyl. The tricyclic heterocycle is a bicyclic heterocycle fused to a phenyl, or a bicyclic heterocycle fused to a cycloalkyl, or a bicyclic heterocycle fused to a cycloalkenyl, or a bicyclic heterocycle fused to a monocyclic heterocycle. The tricyclic heterocycle is connected to the parent molecular moiety through any carbon atom or any nitrogen atom contained within the tricyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

The heterocycles of this invention are optionally substituted with 1, 2, or 3 substituents independently selected from alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, aryl, benzyl, carboxy, carboxyalkyl, cyano, cyanoalkyl, formyl, haloalkoxy, haloalkyl, halogen, hydroxy, hydroxyalkyl, hydroxyalkylcarbonyl, hydroxyalkoxyalkyl, mercapto, oxo, $Z_1Z_2N$—, or $(Z_3Z_4N)$carbonyl.

The term "heterocyclealkyl," as used herein, means a heterocycle group appended to the parent molecular moiety through an alkyl group, as defined herein.

The term "heterocyclecarbonyl" as used herein, means a heterocycle, as defined herein, appended to the parent molecular moiety through a carbonyl group, as defined herein.

The term "hydroxy" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "hydroxyalkylcarbonyl" as used herein, means a hydroxyalkyl group, as defined herein, as appended to the parent molecular moiety through a carbonyl group, as defined herein. Representative examples include, but are not limited to, 2-hydroxyacetyl, and 4-hydroxybutanoyl.

The term "hydroxyalkoxyalkyl" as used herein, means a hydroxyalkoxy group, as defined herein, appended to the parent molecular moiety through an alkylene group, as defined herein. Representative examples of hydroxyalkoxyalkyl include, but are not limited to, (2-hydroxy-ethoxy)-ethyl, and (3-hydroxyl-propoxyl)-ethyl.

The term "hydroxy-protecting group" or "O-protecting group" means a substituent that protects hydroxyl groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. W. Greene and P. G. M. Wuts, Protective Groups in Organic Synthesis, 3rd edition, John Wiley & Sons, New York (1999).

The term "mercapto" as used herein, means a —SH group.

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

The term "nitro" as used herein, means a —NO$_2$ group.

The term "trialkylsilyl" as used herein, means three independently selected alkyl groups, as defined herein, appended to the parent molecular moiety through a silicon atom. Representative examples of trialkylsilyl include, but are not limited to, trimethylsilyl, triethylsilyl, t-butyldimethylsilyl and triisopropylsilyl.

The term "trialkylsilylalkyl" as used herein, means a trialkylsilyl group, as defined herein, appended to the parent molecular through an alkylene group, as defined herein. Representative examples of trialkylsilylalkyl include, but are not limited to, trimethylsilylmethyl, 2-trimethylsilylethyl, and 2-t-butyldimethylsilylethyl.

The term "$Z_1Z_2N$" as used herein, means two groups, $Z_1$ and $Z_2$, which are appended to the parent molecular moiety through a nitrogen atom. $Z_1$ and $Z_2$ are each independently hydrogen, alkoxycarbonyl, alkyl, alkylcarbonyl, aryl, arylalkyl and formyl. In certain instances within the present invention, $Z_1$ and $Z_2$ taken together with the nitrogen atom to which they are attached form a heterocyclic ring. Representative examples of $Z_1Z_2N$ include, but are not limited to, amino, methylamino, acetylamino, acetylmethylamino, phenylamino, benzylamino, azetidinyl, pyrrolidinyl and piperidinyl.

The term "$Z_3Z_4N$" as used herein, means two groups, $Z_3$ and $Z_4$, which are appended to the parent molecular moiety through a nitrogen atom. $Z_3$ and $Z_4$ are each independently hydrogen, alkyl, aryl and arylalkyl. Representative examples of $Z_3Z_4N$ include, but are not limited to, amino, methylamino, phenylamino and benzylamino.

The term "($Z_3Z_4N$)carbonyl" as used herein, means a $NZ_3Z_4$ group, as defined herein, appended to the parent molecular moiety through a carbonyl group, as defined herein. Representative examples of ($Z_3Z_4N$)carbonyl include, but are not limited to, aminocarbonyl, (methylamino)carbonyl, (dimethylamino)carbonyl, and (ethylmethylamino)carbonyl.

The term "oxo" as used herein, means a =O moiety.

The term "sulfinyl" as used herein, means a —S(O)— group.

The term "sulfonyl" as used herein, means a —SO$_2$— group.

The term "sulfonamide" as used herein means a —SO$_2$NH$_2$ group.

The term "tautomer" as used herein means a proton shift from one atom of a compound to another atom of the same compound wherein two or more structurally distinct compounds are in equilibrium with each other.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The present invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the present invention may be prepared synthetically from commercially available starting materials that contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary; or (2) direct separation of the mixture of optical enantiomers on chiral chromatographic columns.

The compounds and processes of the present invention will be better understood by reference to the following Examples, which are intended as an illustration of and not a limitation upon the scope of the invention. Further, all citations herein are incorporated by reference.

Compound names are assigned by using Name Pro naming software, which is provided by ACD/Labs. Alternatively, compound names are assigned using AutoNom naming software, which is provided by MDL Information Systems GmbH (formerly known as Beilstein Informationssysteme) of Frankfurt, Germany, and is part of the CHEMDRAW® ULTRA v. 6.0.2 software suite and ISIS Draw v. 2.5. Also, compound names are assigned using Struct=Name naming algorithm, which is part of the CHEMDRAW® ULTRA v. 9.0.7 software suite.

Abbreviations

Abbreviations which have been used in the descriptions of the Schemes and the Examples that follow are: DMF for N,N-dimethylformamide, DMSO for dimethyl sulfoxide, EtOAc for ethyl acetate, CHCl$_3$ for chloroform, CH$_2$Cl$_2$ for dichloromethane, CH$_3$CN for acetonitrile, THF for tetrahydrofuran, HATU for O-(7-azabenzotriazol-1-yl)-N,N,N',N'-tetramethyluronium hexafluorophosphate, EDC or EDCI for 1-(3-dimethylaminopropyl)-3-ethylcarbodiimide hydrochloride, LC/MS for liquid chromatography/mass spectroscopy, NH$_4$OAc for ammonium acetate, NaBH(OAc)$_3$ for sodium triacetoxyborohydride, PBS for phosphate buffered saline, TMS for trimethylsilyl, MW for microwave, DMAP for 4-(dimethylamino)pyridine, dppf for 1,1'-bis(diphenylphosphino)ferrocene, TFA for trifluoroacetic acid, BINAP for 2,2'-bis(diphenylphosphino)-1,1'-binaphyl, TBAF for tetrabutylammonium fluoride, Tween for polyoxoethylenesorbitan monolaurate HPLC for high pressure liquid chromatography, DME for 1,2-dimethoxyethane, Boc for tert-butoxycarbonyl, BSA for bovine serum albumin, DTT for dithiothreitol, ATP for adenosine triphosphate, EDTA for ethylenediaminetetraacetic acid, HPMC for hydroxypropylmethylcellulose, TMB for 3,3',5,5'-tetramethylbenzidine and HEPES for 4-(2-hydroxyethyl)-1-piperazineethanesulfonic acid.

PREPARATION OF COMPOUNDS OF THE PRESENT INVENTION

The compounds and processes of the present invention will be better understood in connection with the following synthetic Schemes and Examples that illustrate a means by which the compounds of the present invention can be prepared.

Scheme 1

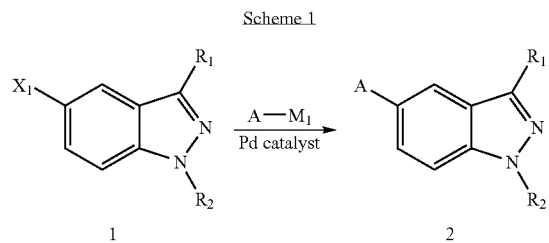

As shown in Scheme 1, compounds of formula 2 which are representative of compounds of formula (I), may be made accordingly. Compounds of formula 1, wherein $R_1$ and $R_2$ are as defined in formula (I), and $X_1$ is iodo, bromo or chloro, and which may be obtained from commercial sources or may be synthesized according to methods known in the literature, when treated with reagent $A-M_1$, wherein A is defined in formula (I) and $M_1$ is $—Sn(R_z)_3$ or $—B(OR_y)_2$, wherein $R_z$ is alkyl or aryl, and $R_y$ is hydrogen, alkyl, aryl or the two $R_y$ groups together with the boron atom to which they are attached form a 1,3-dioxoborolane, in the presence of a palladium catalyst will provide compounds of formula 2. Such reactions between compounds of formula 1 and compounds of formula $A-Sn(R_z)_3$, commonly known as Stille couplings, utilize a palladium catalyst such as, but not limited to, tetrakis(triphenylphosphine)palladium(0), dichlorobis(triphenylphosphine)palladium(II), tris(dibenzylidineacetone)dipalladium or palladium diacetate, in the presence or absence of a ligand such as tri(2-furyl)phosphine or triphenylarsine in a solvent such as toluene or DMF at a temperature from about 25° C. to about 150° C. In addition, Li(I), Cu(I), or Mn(II) salts may be added to improve reactivity or specificity. Reactions between compounds of formula 1 and compounds of formula $A-B(OR_y)_2$, commonly known as Suzuki couplings utilize palladium catalysts such as, but not limited to, tetrakis(triphenylphosphine)palladium(0), dichlorobis(triphenylphosphine)palladium(II), tris(dibenzylidineacetone)dipalladium or palladium diacetate. A palladium ligand may be added such as 2-(dicyclohexylphosphino)biphenyl, tri-t-butylphosphine, or tris(2-furyl)phosphine and a base such as, but not limited to, aqueous $K_3PO_4$, cesium carbonate, potassium carbonate or $Na_2CO_3$ in solvents such as toluene, dimethoxyethane, dioxane, water or DMF at a temperature from about 25° C. to about 150° C. The reaction may also be achieved with heating in a microwave reactor oven.

Although many organo stannanes are commercially available or described in the literature, it is also possible to prepare additional stannanes from A-halides or A-triflates by treatment with a hexa-alkyldistannane of formula $((R_z)_3Sn)_2$ in the presence of $Pd(Ph_3P)_4$. Similarly, in the absence of commercially available organoboron reagents, $A-B(OR_y)_2$ may be prepared from the corresponding halides or triflates (A-halo or A-triflate) via metal exchange with an organolithium followed by the addition of the alkyl borate.

Scheme 2

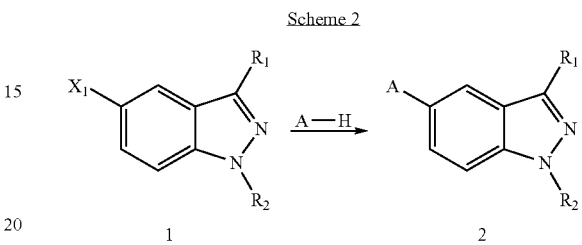

Compounds of formula 2, wherein $R_1$ and $R_2$ are as defined in formula (I) and A is a heteroaryl ring linked to the parent moiety through a nitrogen atom may be prepared as illustrated in Scheme 2. The treatment of compounds of formula 1 with a reagent of formula A-H, wherein the H is a hydrogen on a nitrogen atom contained within the heteroaryl ring A, in the presence of a base such as, but not limited to, sodium t-butoxide or cesium carbonate and a metal catalyst such as, but not limited to, copper metal, CuI or palladium diacetate and optionally with a ligand such as, but not limited to, BINAP, or tri-tertbutylphosphine will provide compounds of formula 2.

Scheme 3

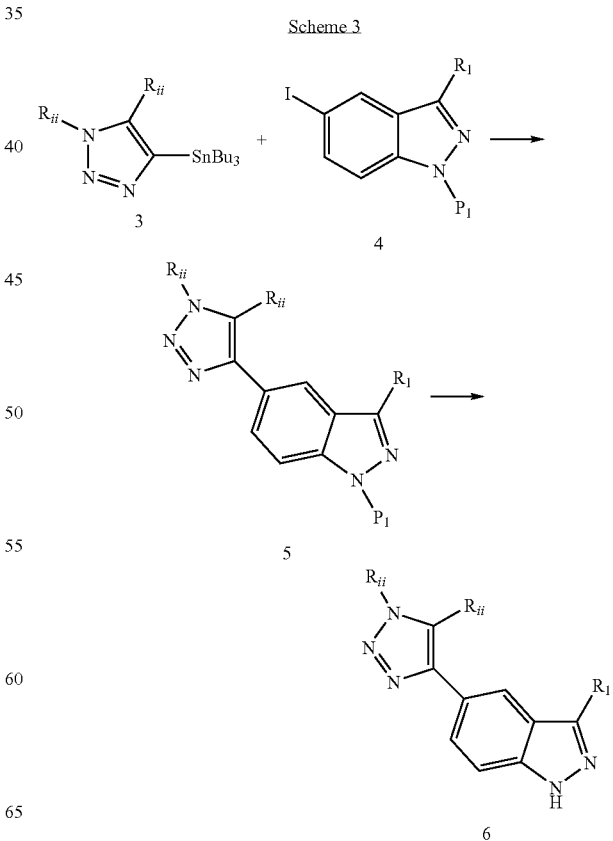

As previously mentioned in Scheme 1, compounds of formula (I) may be synthesized utilizing Stille couplings as described in Scheme 3. Compounds of formula 3, wherein $R_{ii}$ is defined in formula (I), when treated with compounds of formula 4, wherein $R_1$ is defined in formula (I) and $P_1$ is a nitrogen protecting group such as, but not limited to, tert-butyloxycarbonyl or acetyl, in the presence of dichlorobis(triphenylphosphine)palladium(II) and (thiophene-2-carbonyloxy)copper in toluene under heated conditions will provide compounds of formula 5. Compounds of formula 5 when treated with conditions known to remove the protecting group such as hydrochloric acid or trifluoroacetic acid in a solvent such as acetic acid or dioxane when the protecting group is tert-butyloxycarbonyl or sodium hydroxide, lithium hydroxide, or potassium hydroxide in an aqueous mixture of THF, isopropanol, or dioxane when the protecting group is acetyl will provide compounds of formula 6 which are representative of compounds of formula (I) wherein A is (ii).

Compounds of formula 3 utilized in Scheme 3 to generate compounds of formula (I) may be prepared as outlined in Scheme 4. Compounds of formula 7, which are obtained from commercial sources or may be prepared according to methods known to one skilled in the art, when treated with either 1,1,1-tributyl-N,N-dimethylstannamine or methyl ethyl (tributylstannyl)carbamate will provide compounds of formula 8. Alkynes of formula 8 when heated in the presence of compounds of formula 9, wherein $R_{ii}$ is defined in formula (I) and $N_3$ is an azide, will provide compounds of formula 3.

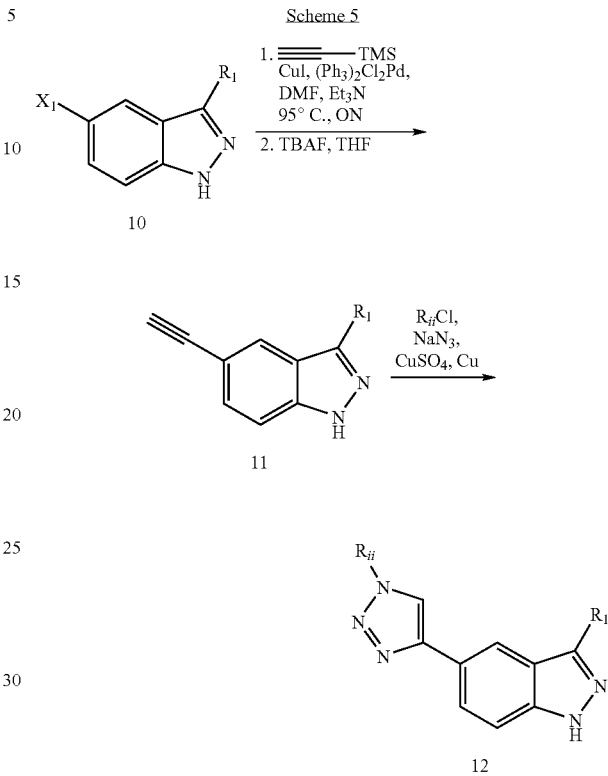

As outlined in Scheme 5, compounds of formula 12 which are representative of compounds of formula (I), wherein A is (ii) may be prepared accordingly. Compounds of formula 10 wherein $R_1$ is defined in formula (I) and $X_1$ is iodo, bromo, chloro, or triflate, when treated with TMS acetylene in the presence of copper iodide, dichlorobis(triphenylphosphine)palladium(II) and triethylamine followed by treatment with tetrabutylammonium fluoride or potassium hydroxide will provide compounds of formula 11. The reaction may be done in a solvent such as, but not limited to, DMF at ambient temperature or under heated conditions. Compounds of formula 11 when treated with $R_{ii}$—Cl, sodium azide, copper sulfate, and optionally with metallic copper, or sodium carbonate, L-proline, and sodium ascorbate under heated conditions in a solvent such as dioxane or water, will provide compounds of formula 12 which are representative of compounds of formula (I) wherein A is (ii).

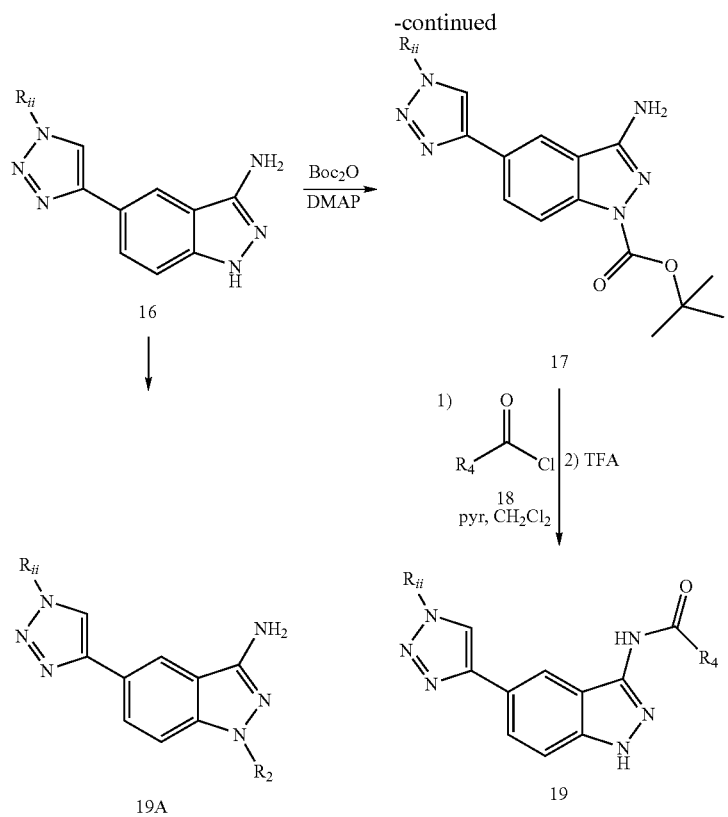

Alternatively, compounds of formula 13 when treated with TMS-acetylene in the presence of copper iodide, dichlorobis (triphenylphosphine)palladium(II) and triethylamine followed by treatment with tetrabutylammonium fluoride or potassium hydroxide will provide compounds of formula 14. The reaction may be done in a solvent such as, but not limited to, DMF at ambient temperature or under heated conditions. Compounds of formula 14 when treated with compounds of formula A wherein $R_{ii}$ is defined in formula (I), or sodium azide, copper sulfate and metallic copper under heated conditions will provide compounds of formula 15. Compounds of formula 15 when heated in the presence of hydrazine in ethanol, will provide compounds of formula 16. Compounds of formula 16 when treated with di-tert-butyldicarbonate and a catalytic amount of DMAP in a solvent such as THF or acetonitrile will provide compounds of formula 17. Compounds of formula 17 when treated with compounds of formula 18 in the presence of a base such as, but not limited to, pyridine in a solvent such as dichloromethane followed by treatment with trifluoroacetic acid will provide compounds of formula 19. Compounds of formula 16 when treated with a carboxylic acid using carboxylic acid-amine coupling conditions known to one skilled in the art will provide compounds of formula 19A. Standard carboxylic acid amine coupling conditions include adding a coupling reagent such as, but not limited to, 1-(3-dimethylaminopropyl)-3-ethylcarbodiimide hydrochloride (EDCI), 1,3dicyclohexylcarbodiimide (DCC), Bis(2-oxo-3-oxazolidinyl)phosphinic chloride (BOPCl), O-(7-azabenzotriazol-1-yl)-N,N,N',N'-tetramethyluronium hexafluorophosphate (HATU) or O-benzotriazol-1-yl-N,N,N',N'-tetramethyluronium tetrafluoroborate (TBTU) with or without an auxiliary reagent such as, but not limited to, 1-hydroxy-7-azabenzotriazole (HOAT) or 1-hydroxybenzotriazole hydrate (HOBT) in a solvent such as, but not limited to, dichloromethane.

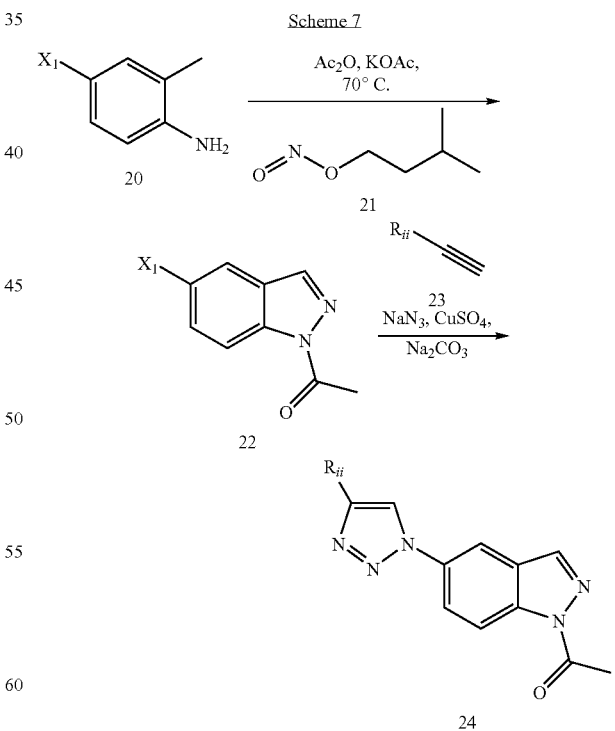

Compounds of formula 24 which are representative of compounds of formula (I) may be prepared accordingly. Compounds of formula 20 wherein $X_1$ is halo or triflate, when treated with the compound of formula 21, acetic anhydride and a base such as, but not limited to, potassium acetate under heated conditions will provide compounds of formula 22. Compounds of formula 22 when treated with sodium azide, copper sulfate, a base such as sodium carbonate and compounds of formula 23, wherein $R_{ii}$ is defined in formula (I) and are either available from commercial sources or may be prepared by one skilled in the art, will provide compounds of formula 24.

Scheme 8

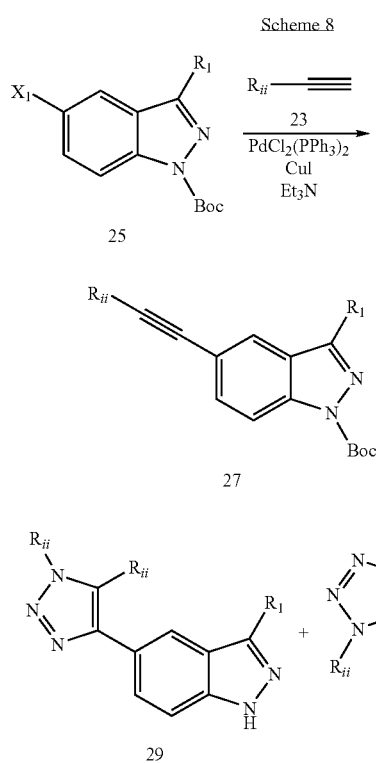

As outlined in Scheme 8, compounds of formula 29 and 30, which are representative of compounds of formula (I), may be prepared accordingly. Compounds of formula 25, wherein $R_1$ is defined in formula (I) and $X_1$ is halo or triflate, when treated with compounds of formula 23 copper iodide, dichlorobis(triphenylphosphine)palladium(II) and triethylamine in DMF at ambient temperature or under heated conditions will provide compounds of formula 27. Compounds of formula 27 when treated with compounds of formula 9, under heated conditions, and either neat or in a solvent such as, but not limited to, dioxane, will provide compounds of formula 29 and 30.

Scheme 9

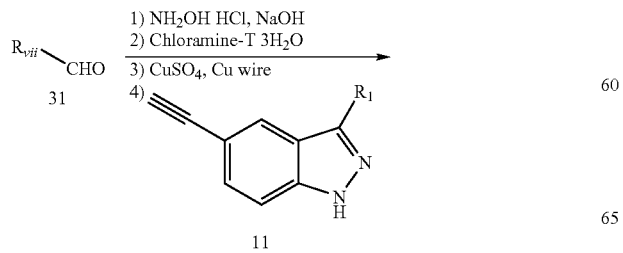

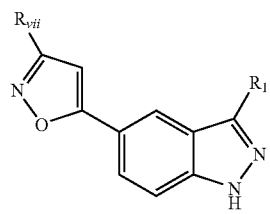

Compounds of formula 32 which are representative of compounds of formula (I), wherein A is (vii), and $R_1$ and $R_{vii}$ are defined in formula (I), may be prepared accordingly. Aldehydes of formula 31, wherein $R_{vii}$ is defined in formula (I) which may be obtained from commercial sources, when treated with hydroxylamine hydrochloride and aqueous sodium hydroxide will provide an oxime intermediate which when oxidized with Chloramine T trihydrate, followed by treatment with copper sulfate and copper wire and compounds of formula 11 will provide compounds of formula 32.

Scheme 10

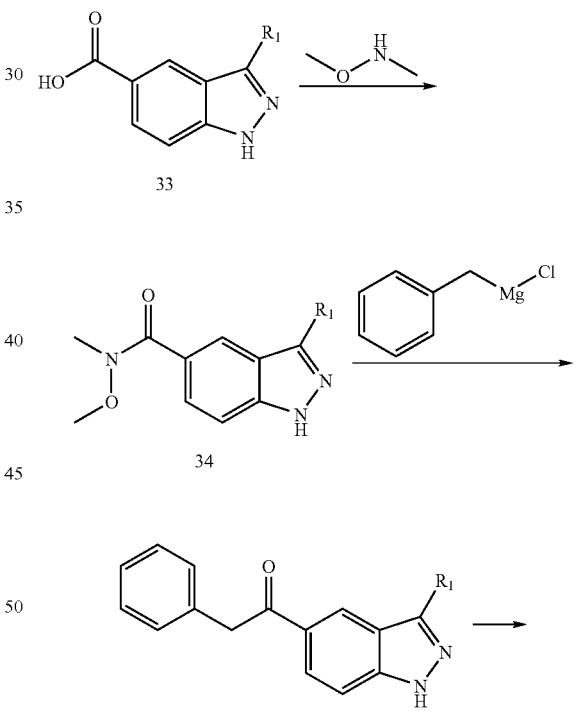

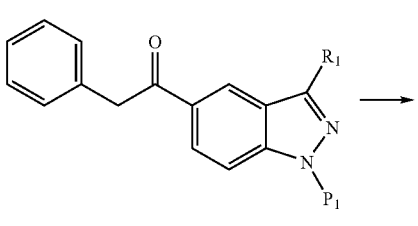

-continued

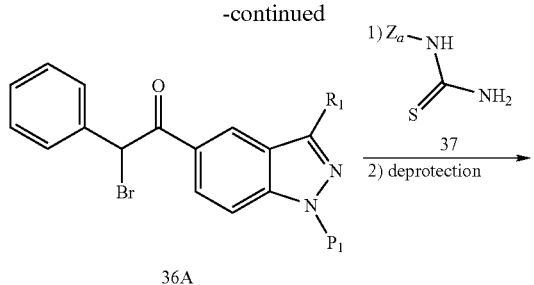

36A

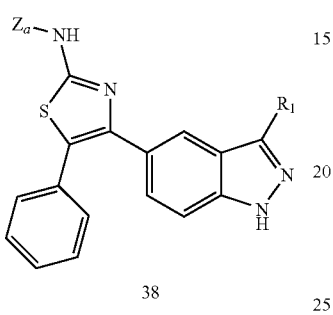

38

Compounds of formula 38 which are representative of compounds of formula (I) wherein A is (x), are prepared accordingly. Compounds of formula 33 wherein $R_1$ is defined in formula (I) which may be obtained from commercial sources or prepared by one skilled in the art, when treated with N,O-dimethylhydroxylamine using acid coupling conditions known to one skilled in the art will provide compounds of formula 34. Standard carboxylic acid-amine coupling conditions include adding a coupling reagent such as, but not limited to, 1-(3-dimethylaminopropyl)-3-ethylcarbodiimide hydrochloride (EDCI), 1,3-dicyclohexylcarbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU) or O-benzotriazol-1-yl-N,N,N',N'-tetramethyluronium tetrafluoroborate (TBTU) with or without an auxiliary reagent such as, but not limited to, 1-hydroxy-7-azabenzotriazole (HOAT) or 1-hydroxybenzotriazole hydrate (HOBT) in a solvent such as, but not limited to, dichloromethane. Compounds of formula 34 when treated with a Grignard reagent such as benzylmagnesium bromide in a solvent such as tetrahydrofuran below ambient temperature will provide compounds of formula 35. Compounds of formula 35 when treated with a protecting group reagent such as, but not limited to, di-tert-butyldicarbonate and a catalytic amount of DMAP in a solvent such as THF or acetonitrile will provide compounds of formula 36. Compounds of formula 36 when treated with pyridinium tribromide in a solvent such as, but not limited to, THF with or without the use of heat will provide compounds of formula 36A. Compounds of formula 36A when treated with compounds of formula 37 with or without the use of heat followed by treating the product with conditions that will remove the nitrogen protecting group will provide compounds of formula 38. Commonly used nitrogen-protecting groups as well as methods to remove them are disclosed in T. W. Greene and P. G. M. Wuts, Protective Groups in Organic Synthesis, 3rd edition, John Wiley & Sons, New York (1999).

Scheme 11

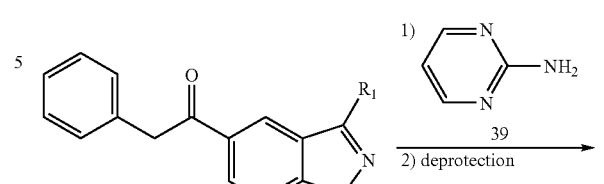

36

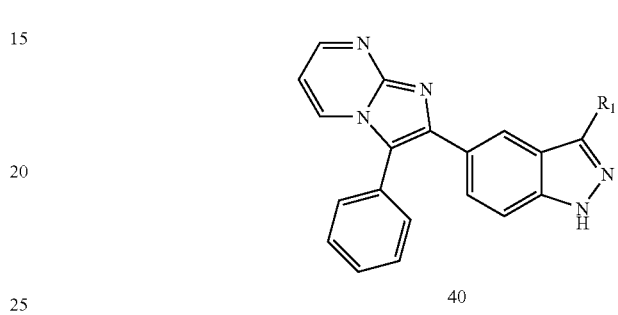

40

Compounds of formula 36, wherein $R_1$ is defined in formula (I) and $P_1$ is a nitrogen protecting group, when treated with compounds of formula 39 under heated conditions followed by treating the product with conditions known to one skilled in the art that will remove a nitrogen protecting group or as outlined in the literature, will provide compounds of formula 40 which are representative of compounds of formula (I) wherein A is (xvii).

Scheme 12

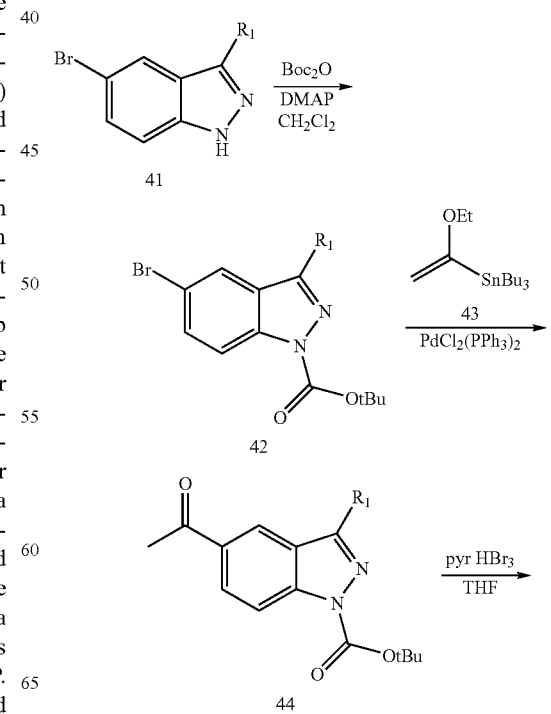

43

-continued

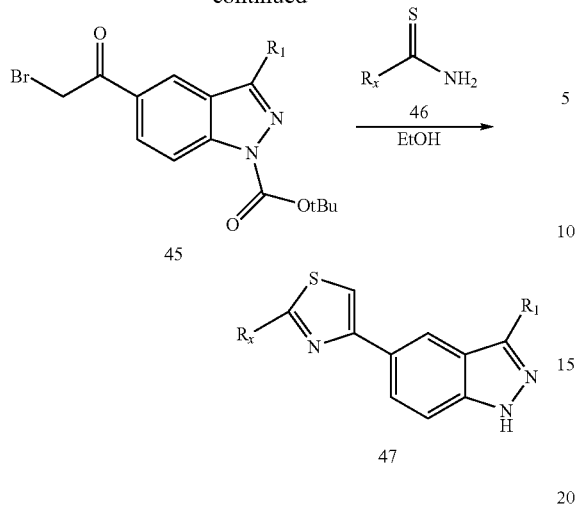

As outlined in Scheme 12, compounds of formula 47 which are representative of compounds of formula (I), wherein A is (x) may be prepared accordingly. Compounds of formula 41, wherein $R_1$ is defined in formula (I), when treated with di-tert-butyldicarbonate and a catalytic amount of DMAP in a solvent such as THF or acetonitrile will provide compounds of formula 42. Treatment of compounds of formula 42 with tributyl(1-ethoxyvinyl)stannane and dichlorobis(triphenylphosphine)palladium(II) will provide compounds of formula 44. Compounds of formula 44 when treated with pyridinium tribromide in THF will provide compounds of formula 45. Compounds of formula 45 when treated with compounds of formula 46 in a solvent such as, but not limited to, ethanol, wherein $R_x$ is defined in formula (I), will provide compounds of formula 47.

Scheme 13

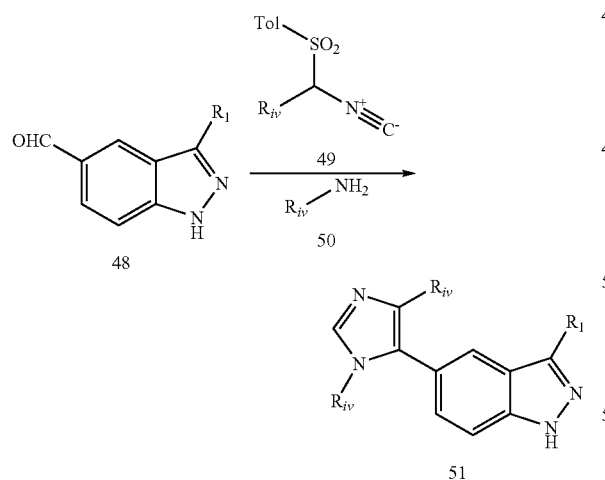

As shown in Scheme 13, compounds of formula 51 which are representative of compounds of formula (I), wherein A is (iv), may be prepared accordingly. Compounds of formula 48, wherein $R_1$ is defined in formula (I), and which are either available through commercial sources or may be prepared according to literature procedures or as outlined herein, when heated in the presence of both compounds of formula 49 and compounds of formula 50, both of which are either commercially available or may be prepared by one skilled in the art using procedures described in the literature, will provide compounds of formula 51.

Scheme 14

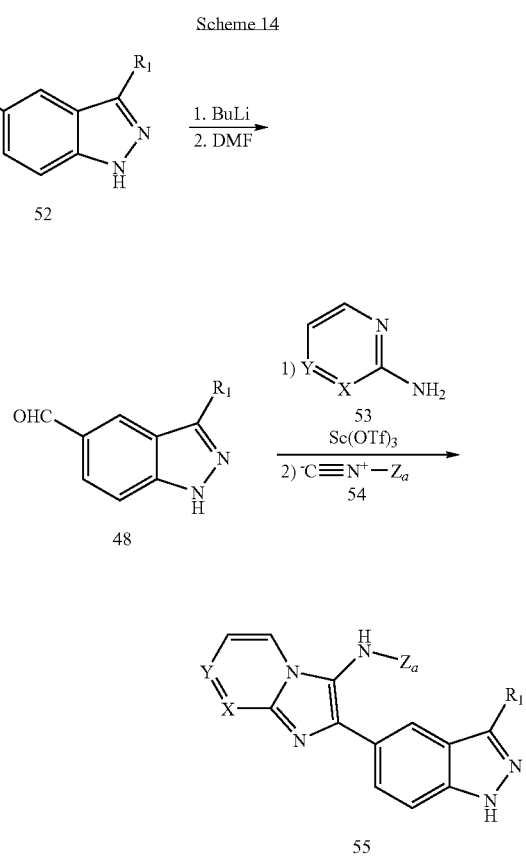

X = CH, N, S
Y = CH, N, bond

As outlined in Scheme 14, compounds of formula 55 which are representative of compounds of formula (I) wherein A is (xiv), (xv), (xvi) or (xvii), may be prepared accordingly. Compounds of formula (52), wherein $R_1$ is defined in formula (I), when treated with butyllithium followed by treatment with DMF followed by an acidic work up will provide compounds of formula 48. Compounds of formula 48 when treated with compounds of formula 53, wherein X is —CH—, —N— or —S—, Y is —CH—, —N— or a bond, and scandium tri(triflate) followed by treatment with compounds of formula 54, wherein $Z_a$ is define in formula (I) will provide compounds of formula 55.

Scheme 15

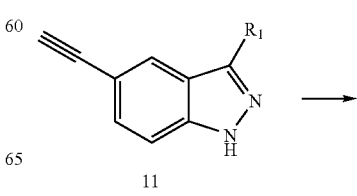

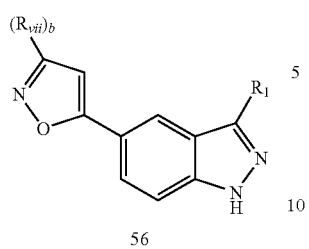

56

As outlined in Scheme 15, compounds of formula 56 which are representative of compounds of formula (I) wherein A is (vii) may be prepared accordingly. Compounds of formula (II), wherein $R_1$ is defined in formula (I), when treated with a reagent such as, but not limited to, ethyl 2-chloro-2-(hydroxyimino)acetate with a base such as, but not limited to, triethylamine will provide compounds of formula 56. The reaction may be performed in a solvent such as but limited to toluene and may require the use of heat.

Scheme 16

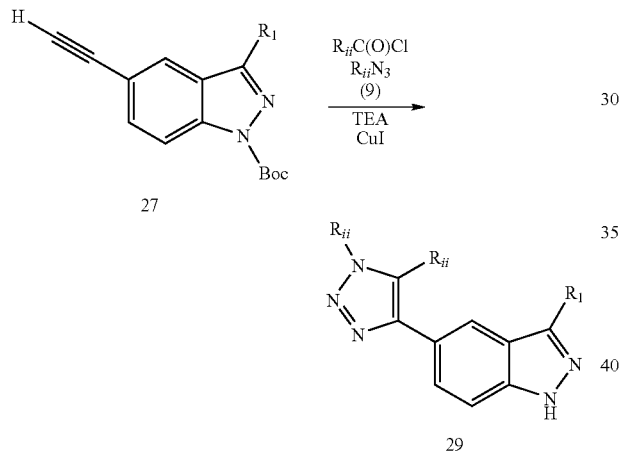

As outlined in Scheme 16, compounds of formula 29 which are representative of compounds of formula (I) wherein A is (ii) may be prepared accordingly. Compounds of formula (27), wherein $R_1$ is defined in formula (I), when treated with a compound of formula 9, $R_{ii}C(O)Cl$ or ICl, CuI, and triethylamine in a solvent such as, but not limited to, tetrahydrofuran will provide compounds of formula 29. The reaction may be performed at ambient temperature or with the use of heat.

Scheme 17

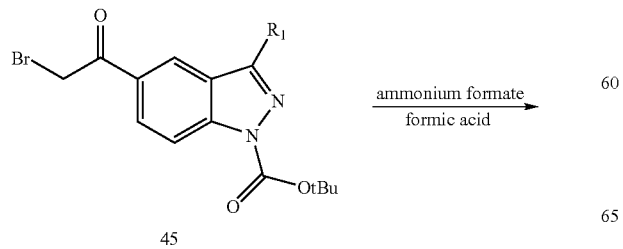

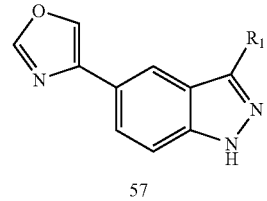

57

As outlined in Scheme 17, compounds of formula 57 which are representative of compound of formula (I), wherein A is (vi), may be prepared accordingly. Compounds of formula 45, wherein $R_1$ is defined in formula (I), when treated with ammonium formate and formic acid will provide compound of formula 57.

Scheme 18

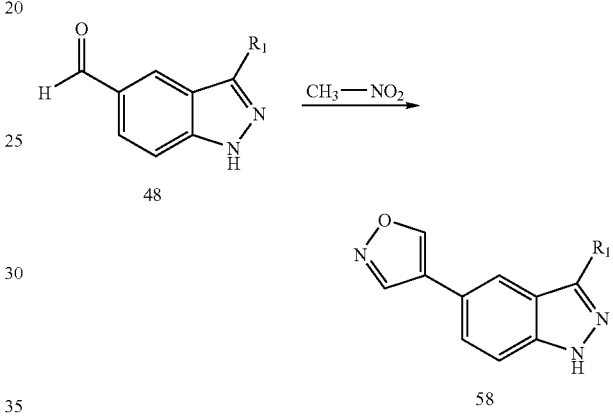

As outlined in Scheme 18, compounds of formula 58 which are representative of compounds of formula (I), wherein A is (vii), may be prepared accordingly. Compounds of formula 48, wherein $R_1$ is defined in formula (I), when treated with nitromethane will provide compounds of formula 58 (Organic Preparations and Procedures International, 2001, 33, 381-386).

Scheme 19

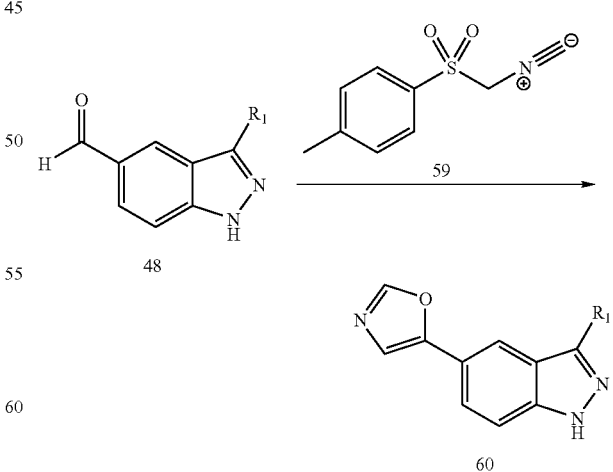

As outlined in Scheme 19, compounds of formula 60 which are representative of compounds of formula (I), wherein A is (vi), may be prepared accordingly. Compounds of formula 48, wherein $R_1$ is defined in formula (I), when treated with 1-(isocyanomethyl sulfonyl)-4-methylbenzene, 59, and a suitable base such as, but not limited to, potassium carbonate in a solvent such as methanol or tetrahydrofuran and subsequently treated with a suitable acid such as hydrochloric acid will provide compounds of formula 60.

Scheme 20

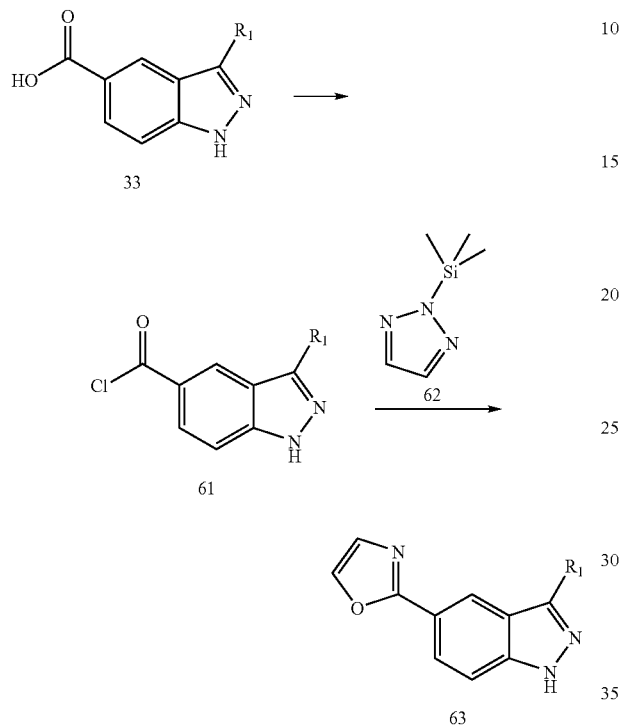

As outlined in Scheme 20, compound of formula 63 which are representative of compounds of formula (I), wherein A is (vi), may be prepared accordingly. Compounds of formula 33, wherein $R_1$ is defined in formula (I), when treated with a suitable chlorinating agent such as thionyl chloride will provide compounds of formula 61. Compounds of formula 61, when treated with 2-(trimethylsilyl)-2H-1,2,3-triazole, 62, in a solvent such as sulfolane will provide compound of formula 63.

Scheme 21

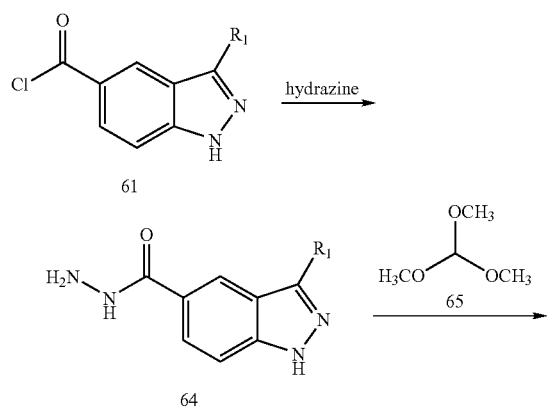

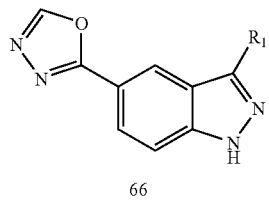

As outlined in Scheme 21, compounds of formula 66 which are representative of compounds of formula (I), wherein A is (ix), may be prepared accordingly. Compounds of formula 61, wherein $R_1$ is defined in formula (I), when treated with hydrazine in a suitable solvent such as tetrahydrofuran will provide compounds of formula 64. Compounds of formula 64, when treated with trimethylorthoformate, 65, in the presence of a catalytic amount of p-toluene sulfonic acid in a solvent such as tetrahydrofuran will provide compounds of formula 66.

Scheme 22

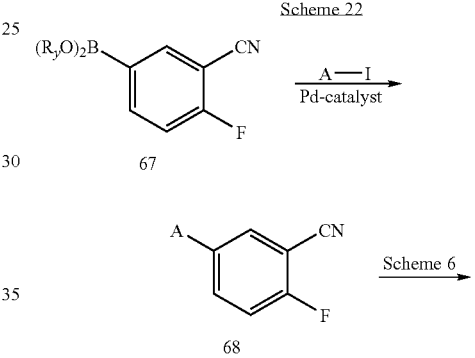

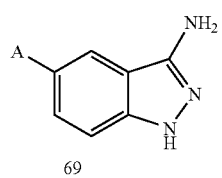

As outlined in Scheme 22, compounds of formula 69 which are representative of compounds of formula (I), wherein A is as defined in formula (I) can be made accordingly. Compounds of formula 67, wherein $R_{y'}$ is hydrogen, alkyl, aryl or the two $R_{y'}$ groups together with the boron atom to which they are attached form a 1,3-dioxoborolane, in the presence of a palladium catalyst using the Suzuki reaction conditions described in Scheme 1 in the presence of a heteroaryl iodide (A-I) provide compounds of formula 68. Compounds of formula 68 are transformed to compounds of formula 69 upon treatment with hydrazine as described in Scheme 6.

Scheme 23

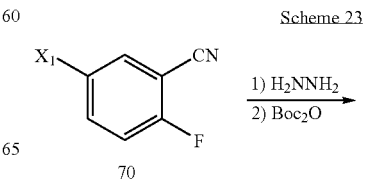

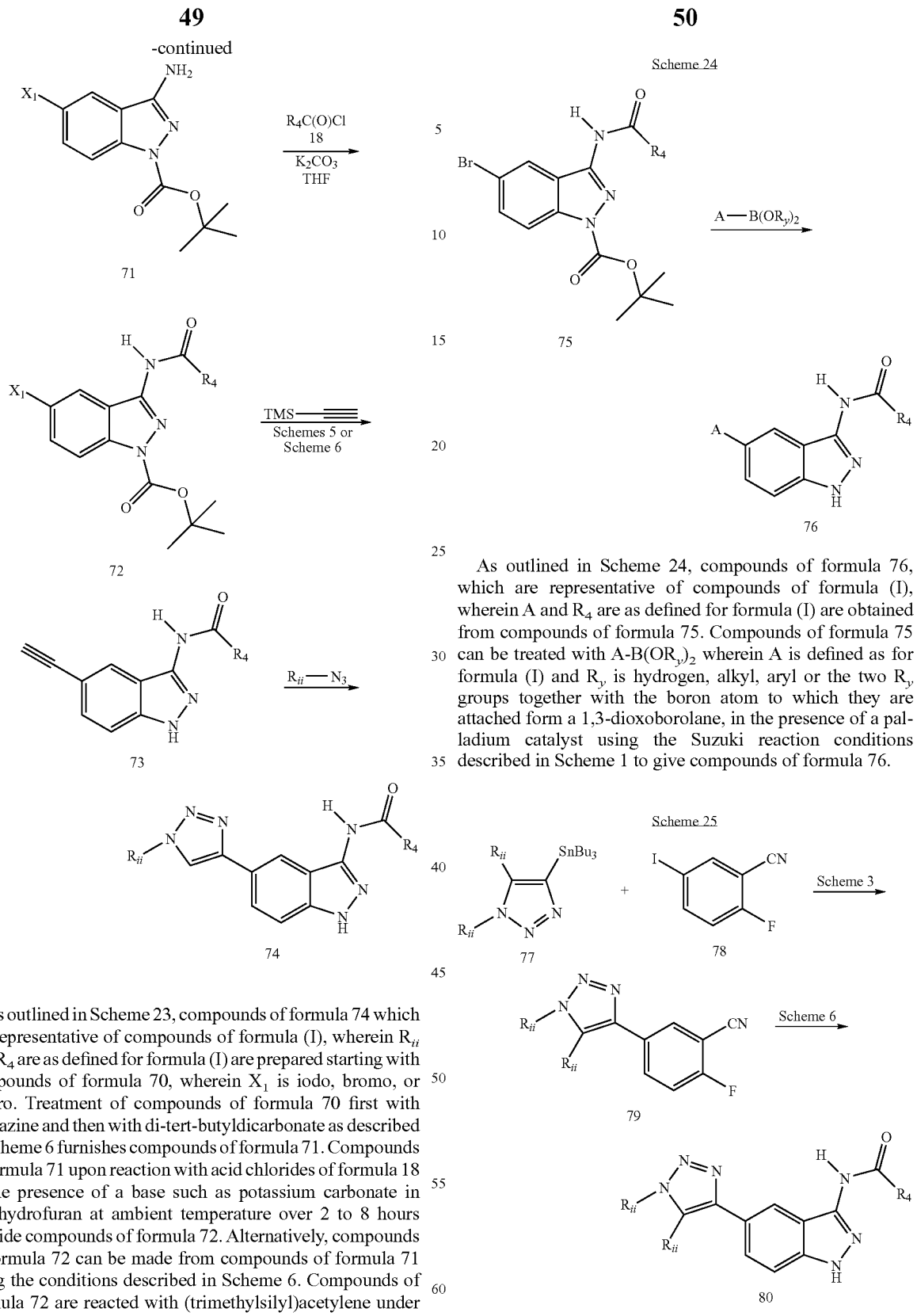

As outlined in Scheme 23, compounds of formula 74 which are representative of compounds of formula (I), wherein $R_{ii}$ and $R_4$ are as defined for formula (I) are prepared starting with compounds of formula 70, wherein $X_1$ is iodo, bromo, or chloro. Treatment of compounds of formula 70 first with hydrazine and then with di-tert-butyldicarbonate as described in Scheme 6 furnishes compounds of formula 71. Compounds of formula 71 upon reaction with acid chlorides of formula 18 in the presence of a base such as potassium carbonate in tetrahydrofuran at ambient temperature over 2 to 8 hours provide compounds of formula 72. Alternatively, compounds of formula 72 can be made from compounds of formula 71 using the conditions described in Scheme 6. Compounds of formula 72 are reacted with (trimethylsilyl)acetylene under the conditions described in Schemes 5 and 6 to give compounds of formula 73. Compounds of formula 74 are obtained from compounds of formula 73 upon treatment with $R_{ii}$—$N_3$ in aqueous t-butanol in the presence of copper(II) sulfate and sodium (R)-2-((S)-1,2-dihydroxyethyl)-4-hydroxy-5-oxo-2,5-dihydrofuran-3-olate at 40-80° C. over 1 to 6 hours.

As outlined in Scheme 24, compounds of formula 76, which are representative of compounds of formula (I), wherein A and $R_4$ are as defined for formula (I) are obtained from compounds of formula 75. Compounds of formula 75 can be treated with A-B(OR$_y$)$_2$ wherein A is defined as for formula (I) and $R_y$ is hydrogen, alkyl, aryl or the two $R_y$ groups together with the boron atom to which they are attached form a 1,3-dioxoborolane, in the presence of a palladium catalyst using the Suzuki reaction conditions described in Scheme 1 to give compounds of formula 76.

As outlined in Scheme 25, compounds of formula 80, which are representative of compounds of formula (I), wherein $R_{ii}$ and $R_4$ are as defined for formula (I) are prepared accordingly. Compounds of formula 77 and 78 reacted under Stille coupling conditions described in Scheme 3 supply compounds of formula 79. Compounds of formula 79 when reacted as described in Scheme 6 provide compounds of formula 80.

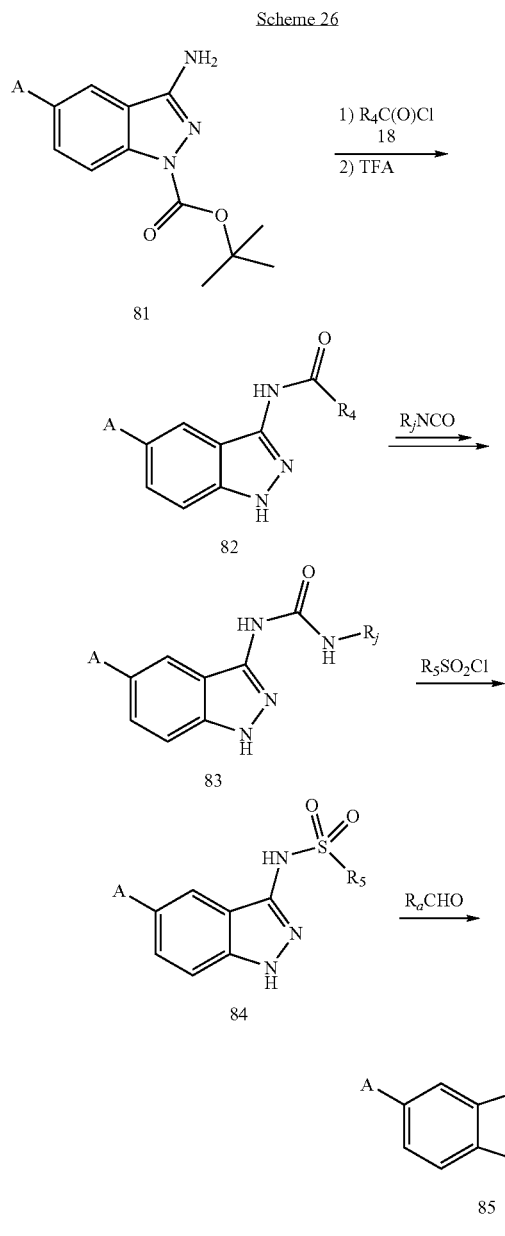

As outlined in Scheme 26, compounds of formulas 82, 83, 84, and 85, which are representative of compounds of formula (I), wherein A, $R_4$, $R_5$, $R_a$ and $R_j$ are as defined for formula (I), are prepared from compounds of formula 81. Compounds of formula 81 can be treated with an acid chloride, 18, in solvent such as tetrahydrofuran in the presence of a base such as potassium carbonate or triethylamine to give compounds of formula 82. An alternative solvent is dichloromethane and an alternative base is pyridine. The acid chlorides can be prepared from the corresponding carboxylic acids by treatment with oxalyl chloride with a catalytic amount of N,N-dimethylformamide. To prepare compounds of formula 83, compounds of formula 81 can be treated with $R_j$NCO in heated pyridine. Compounds of formula 84 are prepared from compounds of formula 81 by treatment with $R_5SO_2Cl$ in pyridine at or near room temperature. Compounds of formula 85 are also prepared from compounds of formula 81 in a reductive amination reaction with $R_aCHO$ in the presence of a reducing agent such as sodium triacetoxyborohydride or sodium cyanoborohydride and acetic acid in a solvent such as 1,2-dichloroethane at or near room temperature and subsequent treatment with trifluoroacetic acid in dichloromethane to remove the t-butoxycarbonyl protecting group.

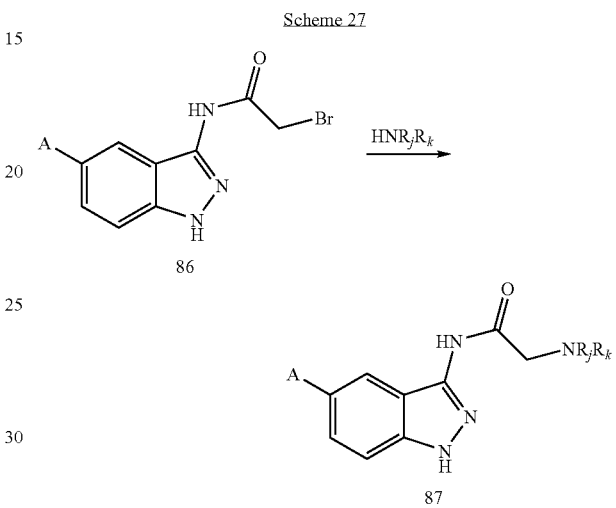

As outlined in Scheme 27, compounds of formula 87, wherein A, $R_j$ and $R_k$ are defined for formula (I), can be prepared from compounds of formula 86. Compounds of formula 86 are prepared as described for compounds of formula 82 in Scheme 26. Compounds of formula 86 can then be heated in the presence of an amine, $HNR_jR_k$, and a base such as triethylamine in a solvent such as acetonitrile to give compounds of formula 87. Alternatively, heterocycles such as pyrrolidine, piperidine, piperazine, and morpholine can be substituted for the amine.

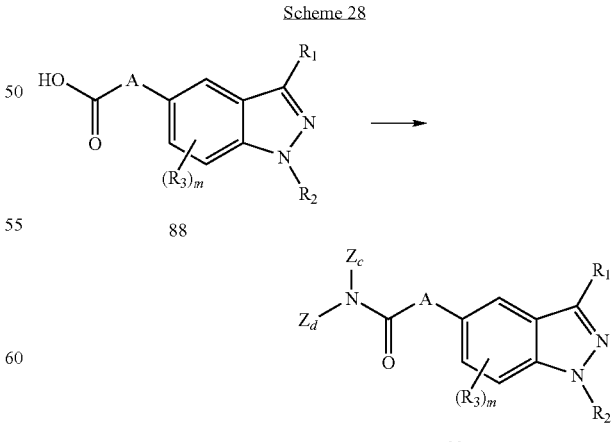

As outlined in Scheme 28, compounds of formula 89, wherein A, $R_1$, $R_2$, $R_3$, m, $Z_c$ and $Z_d$ are as defined for formula (I), can be prepared form compound of formula 88. Compounds of formula 88 can be prepared as described in Schemes 1-4, 7-9, 22, 24, and 26. During the preparation of compounds of formula 88, the carboxylic acid moiety pendant on A can be protected as an ester and subsequently hydrolyzed to expose the carboxylic acid by methods known to one skilled in the art of organic synthesis. Compounds of formula 88 when treated with an amine ($HNZ_cZ_d$) using carboxylic acid-amine coupling conditions known to one skilled in the art will provide compounds of formula 89. Standard carboxylic acid amine coupling conditions include adding a coupling reagent such as, but not limited to, 1-(3-dimethylaminopropyl)-3-ethylcarbodiimide hydrochloride (EDCI), 1,3dicyclohexylcarbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU) or O-benzotriazol-1-yl-N,N,N',N'-tetramethyluronium tetrafluoroborate (TBTU) optionally in the presence of a base such as triethylamine or diisopropylethylamine with or without an auxiliary reagent such as, but not limited to, 1-hydroxy-7-azabenzotriazole (HOAT) or 1-hydroxybenzotriazole hydrate (HOBT) in a solvent such as, but not limited to, dichloromethane or N,N-dimethylformamide.

Scheme 29

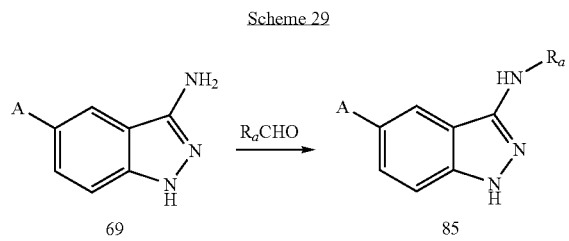

As outlined in Scheme 29, compounds of formula 85, which are representative of compounds of formula (I), wherein A and $R_a$ are as defined for formula (I), are prepared from compounds of formula 69. Compounds of formula 85 are also prepared from compounds of formula 69 in a reductive amination reaction with $R_a$CHO in the presence of a reducing agent such as sodium triacetoxyborohydride or sodium cyanoborohydride and acetic acid in a solvent such as 1,2-dichloroethane, dichloromethane, or N,N-dimethylformamide at or near room temperature.

EXAMPLES

The compounds and processes of the invention will be better understood by reference to the following examples, which are intended as an illustration of and not a limitation upon the scope of the invention.

Example 1

5-(1-benzyl-1H-1,2,3-triazol-5-yl)-1H-indazole
Compound with 5-(1-benzyl-1H-1,2,3-triazol-4-yl)-1H-indazole Example 1A tert-Butyl 5-iodo-1H-indazole-1-carboxylate To an ice bath cooled solution of 4-iodo-2-methylaniline (20 g, 83.24 mmol) in chloroform (250 mL) was added dropwise a solution of acetic anhydride (21.2 g, 208.11 mmol) in chloroform (50 mL). Upon completion of the addition, the mixture was stirred at room temperature for 1 hour. Potassium acetate (2.5 g, 24.97 mmol) and isoamylnitrite (22.3 mL, 166.48 mmol) were added and the mixture was heated at 70° C. for 20 hours. The mixture was cooled and quenched with saturated aqueous $NaHCO_3$ to pH 7. The mixture was extracted with dichloromethane, and the organics were dried over sodium sulfate and filtered. The solvent was evaporated under reduced pressure. The crude solid was washed with methanol, dissolved in tetrahydrofuran (200 mL) and treated with a warm solution of KOH (60 g) in water (200 mL). The mixture was stirred for 15 minutes and was treated with 6 N HCl to pH 1. The layers were separated, the organic layer was dried over sodium sulfate and filtered, and the solvent was evaporated under reduced pressure. The crude solid was dissolved in dichloromethane (500 mL) and triethylamine (23 mL, 166.48 mmol), and di-tert-butyldicarbonate (23.6 g, 108.2 mmol) and a catalytic amount of dimethylaminopyridine (~5 mg) were added. The mixture was stirred at room temperature for 2 hours, diluted with water, extracted with dichloromethane, and dried with sodium sulfate and filtered. The solvent was evaporated under reduced pressure to afford the title compound. MS (ESI+) m/z 344.9 $(M+H)^+$.

Example 1B tert-Butyl 5-((trimethylsilyl)ethynyl)-1H-indazole-1-carboxylate

Example 1A (10.81 g, 31.4 mmol), dichlorobis(triphenylphosphine)palladium(II) (1.1 g, 1.57 mmol), and copper (I) iodide (365 mg, 1.92 mmol) were combined in triethylamine (70 mL) under an inert atmosphere. Trimethylsilyl acetylene (5.0 mL, 36.0 mmol) was added and the mixture was stirred at 60° C. overnight. The solvent was removed under reduced pressure and the resulting residue was dissolved in methylene chloride and washed with 1 N hydrochloric acid. The mixture was absorbed on silica gel and purified by silica gel chromatography eluting with a gradient of 5-40% ethyl acetate in hexanes to afford the title compound. MS (ESI+) m/z 215.0 $(M-99)^+$.

Example 1C

5-Ethynyl-1H-indazole

Example 1B (7.93 g, 25.2 mmol) was dissolved in methanol (150 mL). A solution of 1 N potassium hydroxide (50 mL) was added, and the mixture was stirred at ambient temperature for 1 hour. The solvent was removed under reduced pressure, and the resulting slurry was dissolved in ethyl acetate and washed with water and brine. The organic layer was dried over sodium sulfate and filtered, and the solvent was removed under reduced pressure to afford the title compound. $^1$H NMR (300 MHz, DMSO-$d_6$) δ ppm 13.24 (s, 1H) 8.10 (s, 1H) 7.95 (s, 1H) 7.55 (d, J=8.82 Hz, 1H) 7.39 (dd, J=8.48, 1.36 Hz, 1H) 4.03 (s, 1H).

Example 1D 5-(1-benzyl-1H-1,2,3-triazol-5-yl)-1H-indazole
Compound with 5-(1-benzyl-1H-1,2,3-triazol-4-yl)-1H-indazole Into a microwave vial were added 100.0 mg (0.70 mmol) of Example 1C and 94 mg (0.70 mmol) of benzyl azide. The mixture was heated at 160° C. for 20 minutes using microwave irradiation (CEM-Discover, 100 Watts, 1 minute ramp time). The mixture was dissolved in ethyl acetate and purified by silica gel chromatography eluting with 75% ethyl acetate in hexane to afford the title compounds. $^1$H NMR (300 MHz, DMSO-$d_6$) δ ppm 13.28 (s, 1H) 13.12 (s, 1H) 8.61 (s, 1H) 8.23 (s, 1H) 8.13 (s, 1H) 8.11 (s, 1H) 7.94 (s, 1H) 7.82-7.89 (m, 2H) 7.56-7.70 (m, 2H) 7.20-7.44 (m, 9H) 6.97-7.02 (m, 2H) 5.69 (s, 2H) 5.65 (s, 2H). MS (CI) m/z 276 (M+H)$^+$.

Example 2

5-(1H-1,2,3-triazol-5-yl)-1H-indazole

Into a microwave vial were added 100.0 mg (0.70 mmol) of Example 1C, 81 mg (0.7 mmol) of trimethylsilyl azide, CuI (4 mg), and dimethylformamide/methanol (1 mL, 9:1). The mixture was heated at 160° C. for 20 minutes using microwave irradiation (CEM-Discover, 100 Watts, 1 minute ramp time). The mixture was dissolved in ethyl acetate, and the organic layer was washed with water. The organic layer was dried over anhydrous MgSO$_4$, filtered and concentrated under reduced pressure, and purified by silica gel chromatography eluting with 80% ethyl acetate in hexanes to afford the title compound. $^1$H NMR (300 MHz, DMSO-$d_6$) δ ppm 13.16 (s, 1H) 8.31 (s, 1H) 8.25 (s, 1H) 8.13 (s, 1H) 7.87 (d, J=8.82 Hz, 1H) 7.62 (d, J=8.82 Hz, 1H). MS (CI) m/z 186 (M+H)$^+$.

Example 3

5-(1-benzyl-1H-1,2,3-triazol-4-yl)-1H-indazole

Example 3A tert-Butyl 5-iodo-1H-indazole-1-carboxylate

To an ice bath cooled solution of 4-iodo-2-methylaniline (20 g, 83.24 mmol) in chloroform (250 mL) was added dropwise with an addition funnel a solution of acetic anhydride (21.2 g, 208.11 mmol) in chloroform (50 mL). Upon completion of the addition, the mixture was stirred at room temperature for 1 hour. Potassium acetate (2.5 g, 24.97 mmol) and isoamylnitrite (22.3 mL, 166.48 mmol) were added, and the mixture was heated at 70° C. for 20 hour. The mixture was then cooled and quenched with saturated aqueous NaHCO$_3$ to pH 7. The mixture was extracted with dichloromethane, dried over sodium sulfate, filtered, and the solvent was evaporated under reduced pressure. The crude solid was washed with methanol, dissolved in tetrahydrofuran (200 mL) and treated with a warm solution of KOH (60 g) in water (200 mL). The mixture was stirred for 15 minutes and was treated with 6 N HCl to pH 1. The layers were separated, the organic layer was dried over sodium sulfate and filtered, and the solvent was evaporated under reduced pressure. The crude material was dissolved in dichloromethane (500 mL) and triethylamine (23 mL, 166.48 mmol), and di-tert-butyldicarbonate (23.6 g, 108.2 mmol), and a catalytic amount of dimethylaminopyridine (~5 mg) were added. The mixture was stirred at room temperature for 2 hours, quenched with water, extracted with dichloromethane, and dried over sodium sulfate and filtered. The solvent was evaporated under reduced pressure to afford the title compound. MS (ESI+) m/z 344.9 (M+H)$^+$.

Example 3B tert-Butyl 5-((trimethylsilyl)ethynyl)-1H-indazole-1-carboxylate

Example 3A, (10.81 g, 31.4 mmol), dichlorobis(triphenylphosphine)palladium(II) (1.1 g, 1.57 mmol), and copper (I) iodide (365 mg, 1.92 mmol) were combined in triethylamine (70 mL) under an inert atmosphere. Trimethylsilyl acetylene (5.0 mL, 36.0 mmol) was added and the mixture was stirred at 60° C. overnight. The solvent was removed under reduced pressure and the resulting residue was dissolved in methylene chloride and washed with 1 N hydrochloric acid. The mixture was absorbed on silica gel and purified by silica gel chromatography eluting with a gradient of 5-40% ethyl acetate in hexanes to afford the title compound. MS (ESI+) m/z 215.0 (M−99)$^+$.

Example 3C

5-Ethynyl-1H-indazole

Example 3B (7.93 g, 25.2 mmol) was dissolved in methanol (150 mL). A solution of 1 N potassium hydroxide (50 mL) was added and the mixture was stirred at ambient temperature for 1 hour. The solvent was removed under reduced pressure, and the resulting slurry was dissolved in ethyl acetate and washed with water and brine. The organic layer was dried over sodium sulfate, filtered, and the solvent was removed under reduced pressure to afford the title compound. $^1$H NMR (300 MHz, DMSO-$d_6$) δ ppm 13.24 (s, 1H) 8.10 (s, 1H) 7.95 (s, 1H) 7.55 (d, J=8.82 Hz, 1H) 7.39 (dd, J=8.48, 1.36 Hz, 1H) 4.03 (s, 1H).

Example 3D 5-(1-benzyl-1H-1,2,3-triazol-4-yl)-1H-indazole

Example 3C (40 mg, 0.28 mmol), benzyl azide (37 mg, 0.28 mmol), CuSO$_4$ (14 mg, 0.056 mmol) and Cu wire (14 mg) were combined in tert-butanol (0.5 mL) and water (0.5 mL) and heated in a CEM-Discover microwave for 10 minutes at 125° C. and 100 Watts. To the mixture was added 1M HCl and water, the product was extracted with dichloromethane, and purified by silica gel chromatography (50% ethyl acetate in hexanes) to afford the title compound. $^1$H NMR (400 MHz, DMSO-$d_6$) δ ppm 13.10 (s, 1H) 8.60 (s, 1H) 8.23 (s, 1H) 8.11 (s, 1H) 7.85 (d, J=8.59, 1.53 Hz, 1H) 7.59 (d, J=8.59 Hz, 1H) 7.26-7.49 (m, 5H) 5.65 (s, 2H). MS (ESI+) m/z 276.0 (M+H)$^+$.

Example 4

5-[1-(2-methylbenzyl)-1H-1,2,3-triazol-4-yl]-1H-indazole

Into a 5 mL CEM Microwave reaction tube which contained a Teflon-coated micro-flea stirring bar were added 17.6 mg (0.124 mmol) of Example 3C, 300 µL aqueous solution containing 7.80 mg (0.118 mmol) of sodium azide; followed by 15.79 µL (0.118 mmol; 21.80 mg 0.95 equivalents) of 2-methyl-benzyl bromide (added neat). To the suspension were then added 300 µL of tert-butanol; 25 mg of copper wire; and finally 50 µL of 1 N aqueous copper sulfate pentahydrate solution. The microwave reaction vessel was then capped and heated with stirring for 10 minutes at 125° C. at 100 Watts power on a CEM-Discover microwave. After cooling to ambient temperature, the mixture was diluted with 0.25 N aqueous HCl; and the aqueous suspension was extracted with dichloromethane. The organic layer was washed with distilled water; saturated aqueous NaCl; and then dried over anhydrous sodium sulfate and filtered. The dried solution was diluted with acetonitrile; and the soluble organic material was then filtered thru a glass wool plug which was overlaid with additional anhydrous sodium sulfate. An aliquot of the filtrate was then removed for subsequent LC/MS analysis. Those solutions that contained the desired triazole product were then evaporated in-vacuo and then redissolved in 1.50 mL of 1:1 DMSO/methanol. The solution of the crude triazole product was then purified by reverse-phase HPLC using an acetonitrile/water 0.1% TFA gradient elution method to afford the title compound. $^1$H NMR (500 MHz, DMSO-$d_6$/D$_2$O) δ ppm 2.37 (s, 3H) 5.66 (s, 2H) 7.16-7.34 (m, 4H) 7.63 (d, J=8.54 Hz, 1H) 7.87 (d, J=8.70, 1.37 Hz, 1H) 8.14 (s, 1H) 8.25 (s, 1H) 8.49 (s, 1H). MS (ESI+) m/z 289.9 (M+H)$^+$.

Example 5

5-[1-(3-methylbenzyl)-1H-1,2,3-triazol-4-yl]-1H-indazole

The title compound was prepared according to the procedure outlined in Example 4, substituting 2-methylbenzylbromide with 3-methyl-benzyl bromide. $^1$H NMR (500 MHz, DMSO-$d_6$/D$_2$O) δ ppm 8.58 (s, 1H) 8.25 (s, 1H) 8.14 (s, 1H) 7.87 (d, J=8.85, 1.53 Hz, 1H) 7.64 (d, J=8.54 Hz, 1H) 7.30 (t, J=7.63 Hz, 1H) 7.14-7.24 (m, 3H) 5.60 (s, 2H) 2.31 (s, 3H). MS (ESI+) m/z 289.8 (M+H)$^+$.

Example 6

5-[1-(4-methylbenzyl)-1H-1,2,3-triazol-4-yl]-1H-indazole

The title compound was prepared according to the procedure outlined in Example 4, substituting 2-methylbenzylbromide with 4-methyl-benzyl bromide. $^1$H NMR (500 MHz, DMSO-$d_6$/D$_2$O) δ ppm 8.55 (s, 1H) 8.24 (s, 1H) 8.14 (s, 1H) 7.86 (d, J=8.54, 1.53 Hz, 1H) 7.63 (d, J=8.85 Hz, 1H) 7.25-7.33 (m, 2H) 7.18-7.24 (m, 2H) 5.59 (s, 2H) 2.29 (s, 3H). MS (ESI+) m/z 290.1 (M+H)$^+$.

Example 7

5-[1-(3-methoxybenzyl)-1H-1,2,3-triazol-4-yl]-1H-indazole

The title compound was prepared according to the procedure outlined in Example 4, substituting 2-methyl-benzyl bromide with 3-methoxylbenzylbromide. $^1$H NMR (500 MHz, DMSO-$d_6$/D$_2$O) δ ppm 8.59 (s, 1H) 8.25 (s, 1H) 8.14 (s, 1H) 7.87 (d, J=8.54, 1.53 Hz, 1H) 7.64 (d, J=8.85 Hz, 1H) 7.33 (t, J=7.93 Hz, 1H) 6.89-7.00 (m, 3H) 5.62 (s, 2H) 3.76 (s, 3H). MS (ESI+) m/z 306.1 (M+H)$^+$.

Example 8

5-[1-(2-fluorobenzyl)-1H-1,2,3-triazol-4-yl]-1H-indazole

The title compound was prepared according to the procedure outlined in Example 4, substituting 2-methyl-benzyl bromide with 2-fluorobenzylbromide. $^1$H NMR (500 MHz, DMSO-$d_6$/D$_2$O) δ ppm 8.57 (s, 1H) 8.25 (s, 1H) 8.12-8.17 (m, 1H) 7.87 (d, J=8.54, 1.53 Hz, 1H) 7.64 (d, J=8.54 Hz, 1H) 7.41-7.49 (m, J=7.32, 7.32 Hz, 2H) 7.22-7.33 (m, J=7.02 Hz, 2H) 5.71 (s, 2H). MS (ESI+) m/z 293.9 (M+H)$^+$.

Example 9

5-[1-(3-fluorobenzyl)-1H-1,2,3-triazol-4-yl]-1H-indazole

The title compound was prepared according to the procedure outlined in Example 4, substituting 2-methyl-benzyl bromide with 3-fluorobenzylbromide. $^1$H NMR (500 MHz, DMSO-$d_6$/D$_2$O) δ ppm 8.61 (s, 1H) 8.25 (s, 1H) 8.15 (s, 1H) 7.87 (d, J=8.85, 1.53 Hz, 1H) 7.64 (d, J=8.54 Hz, 1H) 7.41-7.51 (m, 1H) 7.15-7.28 (m, 3H) 5.68 (s, 2H). MS (ESI+) m/z 293.8 (M+H)$^+$.

Example 10

5-[1-(4-fluorobenzyl)-1H-1,2,3-triazol-4-yl]-1H-indazole

The title compound was prepared according to the procedure outlined in Example 4, substituting 2-methyl-benzyl bromide with 4-fluorobenzylbromide. $^1$H NMR (500 MHz, DMSO-$d_6$/D$_2$O) δ ppm 8.58 (s, 1H) 8.24 (s, 1H) 8.14 (s, 1H) 7.86 (d, J=8.85, 1.53 Hz, 1H) 7.64 (d, J=8.85 Hz, 1H) 7.46 (d, J=8.85, 5.49 Hz, 2H) 7.24 (t, J=9.00 Hz, 2H) 5.64 (s, 2H). MS (ESI+) m/z 293.9 (M+H)$^+$.

Example 11

5-[1-(2-chlorobenzyl)-1H-1,2,3-triazol-4-yl]-1H-indazole

The title compound was prepared according to the procedure outlined in Example 4, substituting 2-methyl-benzyl bromide with 2-chlorobenzylbromide. $^1$H NMR (500 MHz, DMSO-$d_6$/D$_2$O) δ ppm 8.56 (s, 1H) 8.26 (s, 1H) 8.14 (s, 1H) 7.88 (d, J=8.54, 1.53 Hz, 1H) 7.64 (d, J=8.54 Hz, 1H) 7.55 (d, J=7.63, 1.53 Hz, 1H) 7.32-7.48 (m, 3H) 5.76 (s, 2H). MS (ESI+) m/z 309.8 (M+H)$^+$.

Example 12

5-[1-(3-chlorobenzyl)-1H-1,2,3-triazol-4-yl]-1H-indazole

The title compound was prepared according to the procedure outlined in Example 4, substituting 2-methyl-benzyl bromide with 3-chlorobenzylbromide. $^1$H NMR (500 MHz, DMSO-$d_6$/D$_2$O) δ ppm 8.62 (s, 1H) 8.26 (s, 1H) 8.15 (s, 1H) 7.87 (d, J=8.54, 1.53 Hz, 1H) 7.64 (d, J=8.54 Hz, 1H) 7.40-7.49 (m, J=7.63 Hz, 3H) 7.35 (d, J=6.41 Hz, 1H) 5.67 (s, 2H). MS (ESI+) m/z 309.8 (M+H)$^+$.

Example 13

5-[1-(4-chlorobenzyl)-1H-1,2,3-triazol-4-yl]-1H-indazole

The title compound was prepared according to the procedure outlined in Example 4, substituting 2-methyl-benzyl bromide with 4-chlorobenzylbromide. $^1$H NMR (500 MHz, DMSO-$d_6$/D$_2$O) δ ppm 8.58 (s, 1H) 8.24 (s, 1H) 8.15 (s, 1H)

7.86 (d, J=8.54, 1.53 Hz, 1H) 7.64 (d, J=8.85 Hz, 1H) 7.45-7.52 (m, 2H) 7.38-7.44 (m, 2H) 5.65 (s, 2H). MS (ESI−) m/z 307.7 (M−H)⁻.

Example 14

5-[1-(2-bromobenzyl)-1H-1,2,3-triazol-4-yl]-1H-indazole

The title compound was prepared according to the procedure outlined in Example 4, substituting 2-methyl-benzyl bromide with 2-bromobenzylbromide. $^1$H NMR (500 MHz, DMSO-d$_6$/D$_2$O) δ ppm 8.55 (s, 1H) 8.26 (s, 1H) 8.14 (s, 1H) 7.88 (d, J=8.54, 1.53 Hz, 1H) 7.72 (d, J=7.93 Hz, 1H) 7.64 (d, J=8.54 Hz, 1H) 7.41-7.50 (m, 1H) 7.27-7.40 (m, 2H) 5.74 (s, 2H). MS (ESI+) m/z 353.5 (M+H)⁺.

Example 15

5-[1-(2-nitrobenzyl)-1H-1,2,3-triazol-4-yl]-1H-indazole

The title compound was prepared according to the procedure outlined in Example 4, substituting 2-methyl-benzyl bromide with 2-nitrobenzylbromide. $^1$H NMR (500 MHz, DMSO-d$_6$/D$_2$O) δ ppm 8.57 (s, 1H) 8.27 (s, 1H) 8.12-8.22 (m, 2H) 7.88 (d, J=8.54, 1.53 Hz, 1H) 7.75-7.83 (m, 1H) 7.60-7.72 (m, 2H) 7.27 (d, J=7.63 Hz, 1H) 6.02 (s, 2H). MS (ESI+) m/z 320.8 (M+H)⁺.

Example 16

5-[1-(3-nitrobenzyl)-1H-1,2,3-triazol-4-yl]-1H-indazole

The title compound was prepared according to the procedure outlined in Example 4, substituting 2-methyl-benzyl bromide with 3-nitrobenzylbromide. $^1$H NMR (500 MHz, DMSO-d$_6$/D$_2$O) δ ppm 8.65 (s, 1H) 8.21-8.28 (m, 3H) 8.15 (s, 1H) 7.80-7.91 (m, 2H) 7.73 (t, J=7.78 Hz, 1H) 7.65 (d, J=8.54 Hz, 1H) 5.83 (s, 2H). MS (ESI+) m/z 320.8 (M+H)⁺.

Example 17

5-[1-(4-nitrobenzyl)-1H-1,2,3-triazol-4-yl]-1H-indazole

The title compound was prepared according to the procedure outlined in Example 4, substituting 2-methyl-benzyl bromide with 4-nitrobenzylbromide. $^1$H NMR (500 MHz, DMSO-d$_6$/D$_2$O) δ ppm 8.64 (s, 1H) 8.22-8.31 (m, 3H) 8.15 (s, 1H) 7.88 (d, J=8.70, 1.37 Hz, 1H) 7.57-7.68 (m, 3H) 5.83 (s, 2H). MS (ESI+) m/z 320.7 (M+H)⁺.

Example 18

2-{[4-(1H-indazol-5-yl)-1H-1,2,3-triazol-1-yl]methyl}benzonitrile

The title compound was prepared according to the procedure outlined in Example 4, substituting 2-methyl-benzyl bromide with 2-cyanobenzylbromide. $^1$H NMR (500 MHz, DMSO-d$_6$/D$_2$O) δ ppm 8.61 (s, 1H) 8.26 (s, 1H) 8.15 (s, 1H) 7.93 (d, J=7.63 Hz, 1H) 7.88 (d, J=8.54, 1.53 Hz, 1H) 7.72-7.80 (m, 1H) 7.57-7.68 (m, 2H) 7.53 (d, J=7.93 Hz, 1H) 5.86 (s, 2H). MS (ESI+) m/z 300.9 (M+H)⁺.

Example 19

3-{[4-(1H-indazol-5-yl)-1H-1,2,3-triazol-1-yl]methyl}benzonitrile

The title compound was prepared according to the procedure outlined in Example 4, substituting 2-methyl-benzyl bromide with 3-cyanobenzylbromide. $^1$H NMR (500 MHz, DMSO-d$_6$/D$_2$O) δ ppm 8.63 (s, 1H) 8.26 (s, 1H) 8.15 (s, 1H) 7.85-7.93 (m, 2H) 7.83 (d, J=7.63 Hz, 1H) 7.72 (d, J=8.24 Hz, 1H) 7.56-7.68 (m, 2H) 5.74 (s, 2H). MS (ESI+) m/z 300.9 (M+H)⁺.

Example 20

4-{[4-(1H-indazol-5-yl)-1H-1,2,3-triazol-1-yl]methyl}benzonitrile

The title compound was prepared according to the procedure outlined in Example 4, substituting 2-methyl-benzyl bromide with 4-cyanobenzylbromide. $^1$H NMR (500 MHz, DMSO-d$_6$/D$_2$O) δ ppm 8.62 (s, 1H) 8.26 (s, 1H) 8.15 (s, 1H) 7.82-7.93 (m, J=8.24 Hz, 3H) 7.65 (d, J=8.54 Hz, 1H) 7.54 (d, J=8.24 Hz, 2H) 5.78 (s, 2H). MS (ESI+) m/z 300.7 (M+H)⁺.

Example 21

5-{1-[2-(trifluoromethyl)benzyl]-1H-1,2,3-triazol-4-yl}-1H-indazole

The title compound was prepared according to the procedure outlined in Example 4, substituting 2-methyl-benzyl bromide with 2-trifluoromethylbenzylbromide. $^1$H NMR (500 MHz, DMSO-d$_6$/D$_2$O) δ ppm 8.56 (s, 1H) 8.27 (s, 1H) 8.15 (s, 1H) 7.89 (d, J=8.85, 1.53 Hz, 1H) 7.85 (d, J=7.93 Hz, 1H) 7.72 (t, J=7.63 Hz, 1H) 7.55-7.68 (m, 2H) 7.33 (d, J=7.93 Hz, 1H) 5.85 (s, 2H). MS (ESI+) m/z 300.7 (M+H)⁺.

Example 22

5-{1-[3-(trifluoromethyl)benzyl]-1H-1,2,3-triazol-4-yl}-1H-indazole

The title compound was prepared according to the procedure outlined in Example 4, substituting 2-methyl-benzyl bromide with 3-trifluoromethylbenzylbromide. $^1$H NMR (500 MHz, DMSO-d$_6$/D$_2$O) δ ppm 8.65 (s, 1H) 8.25 (s, 1H) 8.14 (s, 1H) 7.87 (d, J=8.70, 1.37 Hz, 1H) 7.77 (s, 1H) 7.71-7.76 (m, 1H) 7.61-7.69 (m, 3H) 5.78 (s, 2H). MS (ESI+) m/z 344.0 (M+H)⁺.

Example 23

5-{1-[4-(trifluoromethyl)benzyl]-1H-1,2,3-triazol-4-yl}-1H-indazole

The title compound was prepared according to the procedure outlined in Example 4, substituting 2-methyl-benzyl bromide with 4-trifluoromethylbenzylbromide. $^1$H NMR (500 MHz, DMSO-d$_6$/D$_2$O) δ ppm 8.63 (s, 1H) 8.25 (s, 1H) 8.14 (s, 1H) 7.87 (d, J=8.54 Hz, 1H) 7.78 (d, J=7.93 Hz, 2H)

7.63 (d, J=8.54 Hz, 1H) 7.58 (d, J=7.93 Hz, 2H) 5.78 (s, 2H). MS (ESI+) m/z 344.2 (M+H)+.

Example 24

5-{1-[3-(trifluoromethoxy)benzyl]-1H-1,2,3-triazol-4-yl}-1H-indazole

The title compound was prepared according to the procedure outlined in Example 4, substituting 2-methyl-benzyl bromide with 3-trifluoromethoxybenzylbromide. $^1$H NMR (500 MHz, DMSO-d$_6$/D$_2$O) δ ppm 8.64 (s, 1H) 8.25 (s, 1H) 8.14 (s, 1H) 7.87 (d, J=8.54 Hz, 1H) 7.64 (d, J=8.54 Hz, 1H) 7.56 (t, J=8.24 Hz, 1H) 7.31-7.45 (m, 3H) 5.73 (s, 2H). MS (ESI+) m/z 359.9 (M+H)+.

Example 25

5-{1-[4-(trifluoromethoxy)benzyl]-1H-1,2,3-triazol-4-yl}-1H-indazole

The title compound was prepared according to the procedure outlined in Example 4, substituting 2-methyl-benzyl bromide with 4-trifluoromethoxybenzylbromide. $^1$H NMR (500 MHz, DMSO-d$_6$/D$_2$O) δ ppm 8.61 (s, 1H) 8.25 (s, 1H) 8.14 (s, 1H) 7.87 (d, J=8.70, 1.37 Hz, 1H) 7.63 (d, J=8.54 Hz, 1H) 7.52 (d, J=8.85 Hz, 2H) 7.40 (d, J=8.24 Hz, 2H) 5.70 (s, 2H). MS (ESI+) m/z 359.9 (M+H)+.

Example 26

5-[1-(4-tert-butylbenzyl)-1H-1,2,3-triazol-4-yl]-1H-indazole

The title compound was prepared according to the procedure outlined in Example 4, substituting 2-methyl-benzyl bromide with 4-tert-butylbenzylbromide. $^1$H NMR (500 MHz, DMSO-d$_6$/D$_2$O) δ ppm 8.58 (s, 1H) 8.24 (s, 1H) 8.13 (s, 1H) 7.86 (d, J=8.85, 1.53 Hz, 1H) 7.63 (d, J=8.54 Hz, 1H) 7.42 (d, J=8.24 Hz, 2H) 7.32 (d, J=8.24 Hz, 2H) 5.60 (s, 2H) 1.26 (s, 9H). MS (ESI+) m/z 332.1 (M+H)+.

Example 27

Methyl 3-{[4-(1H-indazol-5-yl)-1H-1,2,3-triazol-1-yl]methyl}benzoate

The title compound was prepared according to the procedure outlined in Example 4, substituting 2-methyl-benzyl bromide with 3-carbomethoxybenzylbromide. $^1$H NMR (500 MHz, DMSO-d$_6$/D$_2$O) δ ppm 8.62 (s, 1H) 8.25 (s, 1H) 8.14 (s, 1H) 7.92-7.99 (m, 2H) 7.87 (d, J=8.54, 1.53 Hz, 1H) 7.68 (d, J=7.63 Hz, 1H) 7.63 (d, J=8.54 Hz, 1H) 7.58 (t, J=7.63 Hz, 1H) 5.75 (s, 2H) 3.86 (s, 3H). MS (ESI+) m/z 333.9 (M+H)+.

Example 28

Methyl 4-{[4-(1H-indazol-5-yl)-1H-1,2,3-triazol-1-yl]methyl}benzoate

The title compound was prepared according to the procedure outlined in Example 4, substituting 2-methyl-benzyl bromide with 4-carbomethoxybenzylbromide. $^1$H NMR (500 MHz, DMSO-d$_6$/D$_2$O) δ ppm 8.62 (s, 1H) 8.25 (s, 1H) 8.14 (s, 1H) 7.99 (d, J=8.24 Hz, 2H) 7.87 (d, J=8.85 Hz, 1H) 7.63 (d, J=8.54 Hz, 1H) 7.49 (d, J=8.24 Hz, 2H) 5.76 (s, 2H) 3.85 (s, 3H). MS (ESI+) m/z 333.9 (M+H)+.

Example 29

5-[1-(2,4-dimethylbenzyl)-1H-1,2,3-triazol-4-yl]-1H-indazole

The title compound was prepared according to the procedure outlined in Example 4, substituting 2-methyl-benzyl bromide with 2,4-dimethylbenzylchloride. $^1$H NMR (500 MHz, DMSO-d$_6$/D$_2$O) δ ppm 8.45 (s, 1H) 8.24 (s, 1H) 8.13 (s, 1H) 7.86 (d, J=8.54 Hz, 1H) 7.62 (d, J=8.54 Hz, 1H) 7.12 (d, J=7.93 Hz, 1H) 7.07 (s, 1H) 7.04 (d, J=7.63 Hz, 1H) 5.60 (s, 2H) 2.32 (s, 3H) 2.26 (s, 3H). MS (ESI+) m/z 304.0 (M+H)+.

Example 30

5-[1-(3,5-dimethylbenzyl)-1H-1,2,3-triazol-4-yl]-1H-indazole

The title compound was prepared according to the procedure outlined in Example 4, substituting 2-methyl-benzyl bromide with 3,5-dimethylbenzylbromide. $^1$H NMR (500 MHz, DMSO-d$_6$/D$_2$O) δ ppm 8.56 (s, 1H) 8.24 (s, 1H) 8.13 (s, 1H) 7.87 (d, J=8.54 Hz, 1H) 7.63 (d, J=8.54 Hz, 1H) 6.95-7.01 (m, 3H) 5.55 (s, 2H) 2.26 (s, 6H). MS (ESI+) m/z 304.2 (M+H)+.

Example 31

5-[1-(2,3-dichlorobenzyl)-1H-1,2,3-triazol-4-yl]-1H-indazole

The title compound was prepared according to the procedure outlined in Example 4, substituting 2-methyl-benzyl bromide with 2,3-dichlorobenzylchloride. $^1$H NMR (500 MHz, DMSO-d$_6$/D$_2$O) δ ppm 8.59 (s, 1H) 8.26 (s, 1H) 8.14 (s, 1H) 7.88 (d, J=8.70, 1.37 Hz, 1H) 7.69 (d, J=8.09, 1.37 Hz, 1H) 7.63 (d, J=8.54 Hz, 1H) 7.44 (t, J=7.78 Hz, 1H) 7.31 (d, J=7.78, 1.07 Hz, 1H) 5.81 (s, 2H). MS (ESI+) m/z 343.8 (M+H)+.

Example 32

5-[1-(2,4-dichlorobenzyl)-1H-1,2,3-triazol-4-yl]-1H-indazole

The title compound was prepared according to the procedure outlined in Example 4, substituting 2-methyl-benzyl bromide with 2,4-dichlorobenzylchloride. $^1$H NMR (500 MHz, DMSO-d$_6$/D$_2$O) δ ppm 8.56 (s, 1H) 8.25 (s, 1H) 8.13 (s, 1H) 7.87 (d, J=8.54 Hz, 1H) 7.72 (d, J=2.14 Hz, 1H) 7.63 (d, J=8.54 Hz, 1H) 7.50 (d, J=8.39, 1.98 Hz, 1H) 7.40 (d, J=8.24 Hz, 1H) 5.74 (s, 2H). MS (ESI−) m/z 341.8 (M−H)−.

Example 33

5-[1-(2,5-dichlorobenzyl)-1H-1,2,3-triazol-4-yl]-1H-indazole

The title compound was prepared according to the procedure outlined in Example 4, substituting 2-methyl-benzyl bromide with 2,5-dichlorobenzylchloride. $^1$H NMR (500 MHz, DMSO-d$_6$/D$_2$O) δ ppm 8.59 (s, 1H) 8.26 (s, 1H) 8.14 (s, 1H) 7.88 (d, J=8.85 Hz, 1H) 7.63 (d, J=8.85 Hz, 1H)

7.56-7.61 (m, 1H) 7.49-7.55 (m, 1H) 7.47 (d, J=2.44 Hz, 1H) 5.75 (s, 2H). MS (ESI+) m/z 343.8 (M+H)$^+$.

Example 34

5-[1-(3,5-dichlorobenzyl)-1H-1,2,3-triazol-4-yl]-1H-indazole

The title compound was prepared according to the procedure outlined in Example 4, substituting 2-methyl-benzyl bromide with 3,5-dichlorobenzylchloride. $^1$H NMR (500 MHz, DMSO-d$_6$/D$_2$O) δ ppm 8.64 (s, 1H) 8.26 (s, 1H) 8.15 (s, 1H) 7.87 (d, J=8.85 Hz, 1H) 7.57-7.71 (m, 2H) 7.44 (d, J=1.53 Hz, 2H) 5.69 (s, 2H). MS (ESI+) m/z 344.1 (M+H)$^+$.

Example 35

5-{1-[2,4-bis(trifluoromethyl)benzyl]-1H-1,2,3-triazol-4-yl}-1H-indazole

The title compound was prepared according to the procedure outlined in Example 4, substituting 2-methyl-benzyl bromide with 2,4-bis(trifluoromethyl)bromide. $^1$H NMR (500 MHz, DMSO-d$_6$/D$_2$O) δ ppm 8.62 (s, 1H) 8.27 (s, 1H) 8.07-8.18 (m, 3H) 7.89 (d, J=8.70, 1.37 Hz, 1H) 7.64 (d, J=8.54 Hz, 1H) 7.49 (d, J=7.93 Hz, 1H) 5.96 (s, 2H). MS (ESI+) m/z 411.7 (M+H)$^+$.

Example 36

N-cyclohexyl-6-(1H-indazol-5-yl)imidazo[2,1-b][1,3]thiazol-5-amine

Example 36A 1H-indazole-5-carbaldehyde

To a solution of 5-bromoindazole (5 g, 25.38 mmol) in tetrahydrofuran (100 mL) cooled at −50° C. under argon was added dropwise a solution of 1.6 M n-butyllithium in hexanes (40 mL, 63.44 mmol). Dimethylformamide (3.9 mL, 50.75 mmol) was added, and the mixture was allowed to warm to room temperature and stirred for 15 minutes. The mixture was then quenched with water, extracted with ethyl acetate, preabsorbed onto silica gel and purified by silica gel chromatography eluting with a gradient of 10-30% ethyl acetate in hexanes to afford the title compound. $^1$H NMR (500 MHz, DMSO-d$_6$) δ ppm 10.03 (s, 1H) 8.45 (s, 1H) 8.35 (s, 1H) 7.85 (dd, J=8.70, 1.37 Hz, 1H) 7.69 (d, J=8.54 Hz, 1H).

Example 36B

N-cyclohexyl-6-(1H-indazol-5-yl)imidazo[2,1-b][1,3]thiazol-5-amine

Example 36A (50 mg, 0.34 mmol) and 2-aminothiazole (28 mg, 0.34 mmol) were combined with scandium triflate (8 mg, 0.017 mmol) in anhydrous methanol (1 mL) in a 4 mL vial. The vial was sealed and shaken at ambient temperature for 30 minutes. Cyclohexyl isocyanide (42 mL, 0.34 mmol) was added, and the mixture was shaken for 2 days at room temperature. The mixture was purified by reverse-phase HPLC using an acetonitrile/water 0.1% TFA gradient elution method to afford the title compound as the TFA salt. $^1$H NMR (500 MHz, DMSO-d$_6$) δ ppm 13.12 (s, 1H) 8.32 (s, 1H) 8.13 (s, 1H) 8.05 (d, J=8.85, 1.22 Hz, 1H) 7.92 (d, J=4.27 Hz, 1H) 7.60 (d, J=8.54 Hz, 1H) 7.37 (d, J=3.66 Hz, 1H) 4.89 (s, 1H) 2.78-2.94 (m, 1H) 1.73-1.83 (m, 2H) 1.58-1.68 (m, 2H) 1.45-1.53 (m, 1H) 1.16-1.29 (m, 2H) 1.04-1.14 (m, 3H). MS (ESI+) m/z 338.1 (M+H)$^+$.

Example 37

N-cyclohexyl-2-(1H-indazol-5-yl)imidazo[1,2-a]pyridin-3-amine

The title compound was prepared according to the procedure outlined in Example 36B, substituting 2-aminothiazole with 2-aminopyridine. $^1$H NMR (500 MHz, DMSO-d$_6$) δ ppm 13.04 (s, 1H) 8.57 (s, 1H) 8.23-8.39 (m, 2H) 8.11 (s, 1H) 7.57 (d, J=8.54 Hz, 1H) 7.46 (d, J=8.85 Hz, 1H) 7.12-7.21 (m, 1H) 6.88 (t, J=6.71 Hz, 1H) 4.78 (d, J=5.80 Hz, 1H) 2.78-2.91 (m, 1H) 1.69-1.77 (m, J=10.98 Hz, 2H) 1.57-1.67 (m, 2H) 1.45-1.53 (m, 1H) 1.21-1.34 (m, 2H) 1.01-1.16 (m, 3H). MS (ESI+) m/z 332.1 (M+H)$^+$.

Example 38

N-cyclohexyl-2-(1H-indazol-5-yl)imidazo[1,2-a]pyrazin-3-amine

The title compound was prepared according to the procedure outlined in Example 36B, substituting 2-aminothiazole with 2-aminopyrazine. $^1$H NMR (500 MHz, DMSO-d$_6$) δ ppm 13.12 (s, 1H) 8.90 (d, J=1.22 Hz, 1H) 8.61 (s, 1H) 8.37 (d, J=4.58, 1.53 Hz, 1H) 8.29 (d, J=8.70, 1.37 Hz, 1H) 8.15 (s, 1H) 7.85 (d, J=4.58 Hz, 1H) 7.62 (d, J=8.85 Hz, 1H) 5.05 (d, J=6.71 Hz, 1H) 2.81-2.99 (m, 1H) 1.70-1.77 (m, J=10.68 Hz, 2H) 1.58-1.67 (m, 2H) 1.47 (s, 1H) 1.24-1.38 (m, 2H) 1.00-1.16 (m, 3H). MS (ESI+) m/z 333.1 (M+H)$^+$.

Example 39

5-[1-benzyl-4-(4-fluorophenyl)-1H-imidazol-5-yl]-1H-indazole

Into a 20 mL scintillation vial was added 50.0 mg (0.34 mmol) of Example 36A. To the solid was added a 2.0 mL dimethylformamide solution containing 0.46 mmol (49 mg) of benzylamine and 50 mg of powdered activated 4 Å molecular sieves. The vial was then capped and heated at 60° C. for 4 hours on an orbital shaker. The vial was allowed to cool to ambient temperature; and was uncapped. To the suspension was added 32 mg (0.23 mmol) of anhydrous potassium carbonate followed by 66 mg (0.23 mmol) α-(p-toluenesulfonyl)-4-fluorobenzylisonitrile. The vial was then capped and heated overnight at 60° C. on a shaker. The vial was removed from the shaker; allowed to cool to ambient temperature; and the resulting suspension was filtered. The filtrate was evaporated under reduced pressure at medium heat on a Savant Speed Vac. The crude residues were redissolved in 1:1 DMSO/methanol and purified by reverse-phase HPLC using an acetonitrile/water TFA gradient elution method to afford the title compound as the TFA salt. $^1$H NMR (300 MHz, DMSO-d$_6$) δ ppm 9.01 (s, 1H) 8.12 (s, 1H) 7.76 (s, 1H) 7.60 (d, J=8.48 Hz, 2H) 7.32-7.45 (m, 2H) 7.09-7.30 (m, 6H) 6.96 (d, J=6.61, 2.88 Hz, 2H) 5.23 (s, 2H). MS (DCI) m/z 369 (M+H)$^+$.

Example 40

N-{3-[4-(4-fluorophenyl)-5-(1H-indazol-5-yl)-1H-imidazol-1-yl]propyl}-N,N-dimethylamine The title compound was prepared as a TFA salt according to the procedure outlined in Example 39 substituting benzylamine with $N^1,N^1$-dimethylpropane-1,3-diamine. $^1$H NMR (300 MHz, DMSO-d$_6$) δ ppm 9.49 (s, 1H) 8.88 (s, 1H) 8.19 (s, 1H) 7.94 (s, 1H) 7.73 (d, J=8.81 Hz, 1H) 7.29-7.44 (m, 3H) 7.17 (t, J=8.98 Hz, 2H) 4.01 (t, J=7.12 Hz, 2H) 2.89-3.04 (m, J=10.51 Hz, 2H) 2.68 (s, 3H) 2.67 (s, 3H) 1.87-2.02 (m, 2H). MS (DCI) m/z 364 (M+H)$^+$.

Example 41

N-cyclohexyl-2-(1H-indazol-5-yl)imidazo[1,2-a]pyrimidin-3-amine

The title compound was prepared as a TFA salt according to the procedure outlined in Example 36B substituting pyrimidin-2-amine for thiazol-2-amine. $^1$H NMR (500 MHz, DMSO-d$_6$) δ ppm 13.21-13.41 (m, 1H) 9.07 (d, J=5.80 Hz, 1H) 8.85 (d, J=3.05 Hz, 1H) 8.51 (s, 1H) 8.24 (s, 1H) 8.14 (d, J=8.70, 1.37 Hz, 1H) 7.73 (d, J=8.85 Hz, 1H) 7.47-7.56 (m, 1H) 5.25-5.41 (m, J=2.75 Hz, 1H) 2.81-2.91 (m, J=10.53, 10.53 Hz, 1H) 1.74-1.83 (m, 2H) 1.56-1.66 (m, 2H) 1.43-1.50 (m, 1H) 1.24 (q, J=11.09 Hz, 2H) 1.00-1.14 (m, 3H). MS (ESI+) m/z 333.1 (M+H)$^+$.

Example 42

5-[4-(4-fluorophenyl)-1-(1-phenylethyl)-1H-imidazol-5-yl]-1H-indazole

The title compound was prepared according to the procedure outlined in Example 39 substituting 1-phenylethanamine for benzylamine. $^1$H NMR (300 MHz, CDCl$_3$) δ ppm 8.04 (s, 1H) 7.75-7.84 (m, 1H) 7.35-7.55 (m, 4H) 7.20-7.31 (m, 5H) 6.76-7.01 (m, 4H) 5.09 (q, J=7.12 Hz, 1H) 1.82 (d, 3H). MS (DCI) m/z 383 (M+H)$^+$.

Example 43

2-(1H-indazol-5-yl)-N-isopropylimidazo[1,2-a]pyrimidin-3-amine

Example 36A (42 mg, 0.287 mmol) and 2-aminopyrimidine (27 mg, 0.284 mmol) were combined with scandium triflate (7 mg, 0.014 mmol) in anhydrous methanol (2 mL) in a 4 mL vial. The vial was sealed and shaken at ambient temperature for 30 minutes. Isopropyl isocyanide (27 mL, 0.286 mmol) was added and the mixture was shaken at ambient temperature overnight, followed by 40° C. for 2 hours. The mixture was absorbed on silica gel and purified using silica gel chromatography eluting using a gradient of 0-5% methanol in dichloromethane to afford the title compound. $^1$H NMR (300 MHz, DMSO-d$_6$) δ ppm 13.08 (s, 1H) 8.75 (d, J=6.95, 1.86 Hz, 1H) 8.60 (s, 1H) 8.31 (d, J=8.82, 1.36 Hz, 1H) 8.20 (d, J=4.75 Hz, 1H) 8.14 (s, 1H) 7.60 (d, J=8.82 Hz, 1H) 7.03 (d, J=6.78, 4.07 Hz, 1H) 6.54 (d, J=4.75 Hz, 1H) 4.86 (d, J=5.09 Hz, 1H) 1.05 (d, J=6.10 Hz, 6H). MS (ESI+) m/z 293.0 (M+H)$^+$.

Example 44

4-(1H-indazol-5-yl)-N-phenyl-1,3-thiazol-2-amine

Example 44A tert-Butyl 5-bromo-1H-indazole-1-carboxylate

5-Bromoindazole (4.40 g, 22.3 mmol) and a catalytic amount of dimethylaminopyridine (~50 mg) were dissolved in dichloromethane (100 mL). Di-tert-butyl dicarbonate (5.43 g, 24.9 mmol) was added, and the mixture was stirred at ambient temperature overnight. The mixture was absorbed on silica gel and purified by silica gel chromatography eluting with a gradient of 0-40% ethyl acetate in hexanes to afford the title compound. MS (ESI+) m/z 297.2 (M+H)$^+$.

Example 44B tert-Butyl 5-acetyl-1H-indazole-1-carboxylate

Example 44A (5.12 g, 17.2 mmol), tributyl (1-ethoxyvinyl) tin (7.0 mL, 20.7 mmol), and dichlorobis(triphenylphosphine)palladium(II) (672 mg, 0.957 mmol) were combined in toluene (85 mL). Nitrogen was bubbled into the mixture for 5 minutes, and the mixture was heated to 100° C. in a sealed tube overnight. The mixture was absorbed on silica gel and purified by silica gel chromatography eluting with a gradient of 0-40% ethyl acetate in hexanes to afford the title compound. MS (ESI+) m/z 283.0 (M+Na)$^+$.

Example 44C tert-Butyl 5-(2-bromoacetyl)-1H-indazole-1-carboxylate

Example 44B (1.60 g, 6.15 mmol) and pyridinium tribromide (1.98 g, 6.19 mmol) were combined in tetrahydrofuran and heated to 40° C. for 2 hours. The mixture was absorbed on silica gel and purified by silica gel chromatography eluting with a gradient of 0-40% ethyl acetate in hexanes to afford the title compound. MS (ESI+) m/z 360.9 (M+Na)$^+$.

Example 44D 4-(1H-indazol-5-yl)-N-phenyl-1,3-thiazol-2-amine

Example 44C (71 mg, 0.208 mmol) and 1-phenyl-2-thiourea (33 mg, 0.217 mmol) were combined in ethanol (300 mL) in a 4 mL vial. The vial was shaken at 80° C. overnight. The mixture was absorbed on silica gel and purified by silica gel chromatography eluting with a gradient of methanol in dichloromethane (0-5%) to afford the title compound. $^1$H NMR (400 MHz, DMSO-d$_6$) δ ppm 13.08 (s, 1H) 10.23 (s, 1H) 8.32 (s, 1H) 8.14 (s, 1H) 7.93 (d, J=8.59, 1.53 Hz, 1H) 7.75 (d, J=8.75, 1.07 Hz, 1H) 7.58 (d, J=8.90 Hz, 1H) 7.36 (d, J=8.59, 7.36 Hz, 1H) 7.25 (s, 1H) 6.92-7.02 (m, 1H). MS (ESI+) m/z 292.9 (M+H)$^+$.

Example 45

5-(2-methyl-1,3-thiazol-4-yl)-1H-indazole

The title compound was prepared according to the procedure outlined in Example 44D substituting 1-phenyl-2-thiourea with thioacetamide. $^1$H NMR (300 MHz, DMSO-d$_6$) δ ppm 13.10 (s, 1H) 8.34 (s, 1H) 8.12 (s, 1H) 7.94 (d, J=8.82, 1.70 Hz, 1H) 7.85 (s, 1H) 7.57 (d, J=8.82 Hz, 1H) 2.73 (s, 3H). MS (ESI+) m/z 215.9 (M+H)$^+$.

Example 46

N-ethyl-4-(1H-indazol-5-yl)-1,3-thiazol-2-amine

The title compound was prepared according to the procedure outlined in Example 44D substituting 1-phenyl-2-thiourea with ethylthiourea. $^1$H NMR (300 MHz, DMSO-d$_6$) δ ppm 13.04 (s, 1H) 8.21 (s, 1H) 8.09 (s, 1H) 7.83 (d, J=8.65, 1.53 Hz, 1H) 7.58 (t, J=5.43 Hz, 1H) 7.51 (d, J=8.82 Hz, 1H) 6.96 (s, 1H) 3.22-3.34 (m, 2H) 1.21 (t, J=7.29 Hz, 3H). MS (ESI+) m/z 244.9 (M+H)$^+$.

Example 47

N-benzyl-4-(1H-indazol-5-yl)-1,3-thiazol-2-amine

The title compound was prepared according to the procedure outlined in Example 44D substituting 1-phenyl-2-thiourea with 1-benzyl-2-thiourea. $^1$H NMR (400 MHz, DMSO-d$_6$) δ ppm 13.02 (s, 1H) 8.21 (s, 1H) 8.12 (t, J=5.83 Hz, 1H) 8.08 (s, 1H) 7.83 (d, J=8.90, 1.53 Hz, 1H) 7.50 (d, J=8.90 Hz, 1H) 7.39-7.45 (m, 2H) 7.35 (t, J=7.52 Hz, 2H) 7.26 (t, J=7.21 Hz, 1H) 6.97 (s, 1H) 4.54 (d, J=5.83 Hz, 1H). MS (ESI+) m/z 306.9 (M+H)$^+$.

Example 48

4-(1H-indazol-5-yl)-1,3-thiazol-2-amine

The title compound was prepared according to the procedure outlined in Example 44D substituting 1-phenyl-2-thiourea with thiourea. $^1$H NMR (300 MHz, DMSO-d$_6$) δ ppm 13.03 (s, 1H) 8.17 (s, 1H) 8.07 (s, 1H) 7.81 (d, J=8.82, 1.36 Hz, 1H) 7.50 (d, J=8.82 Hz, 1H) 7.01 (s, 2H) 6.92 (s, 1H). MS (ESI+) m/z 216.9 (M+H)$^+$.

Example 49

4-(1H-indazol-5-yl)-N-(2-phenylethyl)-1,3-thiazol-2-amine

The title compound was prepared according to the procedure outlined in Example 44D substituting 1-phenyl-2-thiourea with 1-phenethylthiourea. $^1$H NMR (300 MHz, DMSO-d$_6$) δ ppm 13.03 (s, 1H) 8.23 (s, 1H) 8.09 (s, 1H) 7.85 (d, J=8.65, 1.53 Hz, 1H) 7.71 (t, J=5.43 Hz, 1H) 7.51 (d, J=8.82 Hz, 1H) 7.26-7.36 (m, 4H) 7.18-7.26 (m, 1H) 6.97 (s, 1H) 3.47-3.59 (m, 1H) 2.94 (t, J=7.44 Hz, 1H). MS (ESI+) m/z 321.0 (M+H)$^+$.

Example 50

N-benzyl-2-(1H-indazol-5-yl)imidazo[1,2-a]pyrimidin-3-amine

The title compound was prepared according to the procedure outlined in Example 43 substituting benzylisocyanide for isopropyl isocyanide. $^1$H NMR (300 MHz, DMSO-d$_6$) δ ppm 13.10 (s, 1H) 8.50-8.58 (m, 2H) 8.39 (d, J=4.07, 2.03 Hz, 1H) 8.25 (d, J=8.81, 1.36 Hz, 1H) 8.13 (s, 1H) 7.61 (d, J=8.81 Hz, 1H) 7.24 (s, 5H) 6.92 (d, J=6.78, 4.07 Hz, 1H) 5.44 (t, J=6.27 Hz, 1H) 4.13 (d, J=6.10 Hz, 2H). MS (ESI+) m/z 341.0 (M+H)$^+$.

Example 51

N-butyl-2-(1H-indazol-5-yl)imidazo[1,2-a]pyrimidin-3-amine

The title compound was prepared according to the procedure outlined in Example 43 substituting butylisocyanide for isopropyl isocyanide. $^1$H NMR (300 MHz, DMSO-d$_6$) δ ppm 13.09 (s, 1H) 8.70 (d, J=6.78, 2.03 Hz, 1H) 8.55 (s, 1H) 8.44 (d, J=4.07, 2.03 Hz, 1H) 8.25 (d, J=8.82, 1.36 Hz, 1H) 8.14 (s, 1H) 7.61 (d, J=8.82 Hz, 1H) 7.03 (d, J=6.78, 4.07 Hz, 1H) 4.90 (t, J=5.93 Hz, 1H) 2.96 (s, 2H) 1.49 (s, 2H) 1.34 (s, 2H) 0.82 (t, J=7.29 Hz, 3H). MS (ESI+) m/z 307.0 (M+H)$^+$.

Example 52

N-(4-chlorophenyl)-2-(1H-indazol-5-yl)imidazo[1,2-a]pyrimidin-3-amine

The title compound was prepared according to the procedure outlined in Example 43 substituting 4-chlorophenylisocyanide for isopropyl isocyanide. $^1$H NMR (500 MHz, DMSO-d$_6$) δ ppm 13.12 (s, 1H) 8.58 (dd, J=4.12, 1.98 Hz, 1H) 8.46 (d, J=15.87 Hz, 2H) 8.40 (dd, J=6.71, 1.83 Hz, 1H) 8.06-8.16 (m, 2H) 7.58 (d, J=8.85 Hz, 1H) 7.18 (d, J=8.85 Hz, 2H) 7.05 (dd, J=6.71, 3.97 Hz, 1H) 6.57 (d, J=8.85 Hz, 2H). MS (ESI+) m/z 361.0 (M+H)$^+$.

Example 53

2-(1H-indazol-5-yl)-N-(4-methoxyphenyl)imidazo[1,2-a]pyrimidin-3-amine

The title compound was prepared according to the procedure outlined in Example 43 substituting 4-methoxyphenylisocyanide for isopropyl isocyanide. $^1$H NMR (500 MHz, DMSO-d$_6$) δ ppm 13.10 (s, 1H) 8.56 (dd, J=3.97, 2.14 Hz, 1H) 8.47 (s, 1H) 8.36 (dd, J=6.56, 1.98 Hz, 1H) 8.15 (dd, J=8.70, 1.37 Hz, 1H) 8.10 (s, 1H) 7.99 (s, 1H) 7.57 (d, J=8.54 Hz, 1H) 7.03 (dd, J=6.71, 4.27 Hz, 1H) 6.76 (d, J=8.85 Hz, 2H) 6.50 (d, J=8.85 Hz, 2H) 3.63 (s, 3H). MS (ESI+) m/z 357.4 (M+H)$^+$.

Example 54

2-(1H-indazol-5-yl)imidazo[1,2-a]pyrimidine

The title compound was prepared according to the procedure outlined in Example 44D substituting 2-aminopyrimidine for 1-phenyl-2-thiourea. $^1$H NMR (300 MHz, DMSO-d$_6$) δ ppm 13.13 (s, 1H) 8.96 (dd, J=6.78, 2.03 Hz, 1H) 8.51 (dd, J=4.41, 2.03 Hz, 1H) 8.42 (s, 1H) 8.36 (s, 1H) 8.15 (s, 1H) 8.01 (dd, J=8.82, 1.70 Hz, 1H) 7.62 (d, J=8.48 Hz, 1H) 7.04 (dd, J=6.61, 4.24 Hz, 1H). MS (ESI+) m/z 236.1 (M+H)$^+$.

Example 55

Methyl N-[2-(1H-indazol-5-yl)imidazo[1,2-a]pyridin-3-yl]glycinate

The title compound was prepared as a TFA salt according to the procedure outlined in Example 36B substituting 2-aminopyridine for 2-aminothiazole and methyl 2-isocyanoacetate for cyclohexyl isocyanide. $^1$H NMR (400 MHz, DMSO-d$_6$) δ ppm 13.41 (s, 1H) 8.90 (d, J=6.75 Hz, 1H) 8.38 (s, 1H) 8.27 (s, 1H) 7.84-7.98 (m, 3H) 7.77 (d, J=8.90 Hz, 1H) 7.55 (td, J=6.75, 1.23 Hz, 1H) 5.95-6.06 (m, 1H) 3.87 (d, J=4.60 Hz, 2H) 3.51 (s, 3H). MS (ESI+) m/z 340.1 (M+H)$^+$.

Example 56

N-benzyl-2-(1H-indazol-5-yl)imidazo[1,2-a]pyridin-3-amine

The title compound was prepared according to the procedure outlined in Example 36B substituting 2-aminopyridine for 2-aminothiazole and benzyl isocyanide for cyclohexyl isocyanide. The final product precipitated out of solution and was isolated after filtration. $^1$H NMR (400 MHz, DMSO-d$_6$) d ppm 13.04 (s, 1H) 8.49 (s, 1H) 8.16-8.27 (m, 2H) 8.09 (s, 1H) 7.58 (d, J=8.90 Hz, 1H) 7.44 (d, J=8.90 Hz, 1H) 7.19-7.35 (m, 5H) 7.13 (ddd, J=8.98, 6.67, 0.92 Hz, 1H) 6.80 (td, J=6.75, 0.92 Hz, 1H) 5.32 (t, J=6.14 Hz, 1H) 4.12 (d, J=6.14 Hz, 2H). MS (ESI+) m/z 322.1 (M+H)$^+$.

Example 57

N-(4-chlorophenyl)-2-(1H-indazol-5-yl)imidazo[1,2-a]pyridin-3-amine

The title compound was prepared according to the procedure outlined in Example 36B substituting 2-aminopyridine for 2-aminothiazole and 1-chloro-4-isocyanobenzene for cyclohexyl isocyanide. $^1$H NMR (400 MHz, DMSO-d$_6$) δ ppm 13.06 (s, 1H) 8.39 (s, 2H) 8.05-8.14 (m, 2H) 7.94 (d, J=6.75 Hz, 1H) 7.62 (d, J=8.90 Hz, 1H) 7.55 (d, J=8.59 Hz, 1H) 7.28-7.34 (m, 1H) 7.17 (d, J=8.90 Hz, 2H) 6.88-6.96 (m, J=6.75, 6.75 Hz, 1H) 6.53 (d, J=8.59 Hz, 2H). MS (ESI+) m/z 360.0 (M+H)$^+$.

Example 58

2-(1H-indazol-5-yl)-N-(4-methoxyphenyl)imidazo [1,2-a]pyridin-3-amine

The title compound was prepared according to the procedure outlined in Example 36B substituting 2-aminopyridine for 2-aminothiazole and 1-isocyano-4-methoxybenzene for cyclohexyl isocyanide. $^1$H NMR (400 MHz, DMSO-d$_6$) δ ppm 13.04 (s, 1H) 8.44 (s, 1H) 8.14 (d, J=8.90, 1.23 Hz, 1H) 8.06 (s, 1H) 7.87-7.96 (m, 2H) 7.59 (d, J=8.90 Hz, 1H) 7.54 (d, J=8.59 Hz, 1H) 7.24-7.33 (m, 1H) 6.86-6.93 (m, J=6.75, 6.75 Hz, 1H) 6.75 (d, J=9.21 Hz, 2H) 6.47 (d, J=9.21 Hz, 2H) 3.63 (s, 3H). MS (ESI+) m/z 356.1 (M+H)$^+$.

Example 59 tert-butyl 4-[4-(4-fluorophenyl)-5-(1H-indazol-5-yl)-1H-imidazol-1-yl]piperidine-1-carboxylate The title compound was prepared according to the procedure outlined in Example 39 substituting tert-butyl 4-aminopiperidine-1-carboxylate for benzylamine. $^1$H NMR (400 MHz, DMSO-d$_6$) δ ppm 13.32 (s, 1H) 8.14 (s, 1H) 8.01 (s, 1H) 7.79 (s, 1H) 7.68 (d, J=8.59 Hz, 2H) 7.24-7.39 (m, 2H) 6.97 (t, J=8.90 Hz, 2H) 3.91-4.05 (m, 2H) 3.71-3.84 (m, 1H) 2.53-2.69 (m, 2H) 1.76-1.94 (m, 4H) 1.35-1.40 (m, 9H). MS (DCI) m/z 462 (M+H)$^+$.

Example 60

3,5-bis(1-benzyl-1H-1,2,3-triazol-4-yl)-1H-indazole

Example 60A tert-Butyl 5-bromo-3-iodo-1H-indazole-1-carboxylate

To a solution of 5-bromoindazole (10 g, 50.75 mmol) in dimethylformamide (100 mL) was added KOH (10 g, 177.63 mmol). Over a period of 2 hours, iodine (20 g, 78.80 mmol) was added. The mixture was treated with a solution of Na$_2$S$_2$O$_5$ (20 g) in water (200 mL), extracted with ethyl acetate, washed with brine, dried over sodium sulfate and filtered, and the solvent was removed under reduced pressure. The solid was dissolved in dichloromethane (350 mL) and treated with di-tert-butyl dicarbonate (14.4 g, 65.98 mmol) and dimethylaminopyridine (10 mg, 0.08 mmol). The mixture was stirred for 20 minutes at room temperature and passed directly through a bed of silica gel to afford the title compound. MS (DCI/NH$_3$) m/z 422.9 (M+H)$^+$.

Example 60B tert-butyl 5-bromo-3-phenyl-1H-indazole-1-carboxylate and tert-butyl 5-bromo-3-iodo-1H-indazole-1-carboxylate To a solution of Example 60A (2.1 g, 5 mmol) in toluene (10 mL) was added Pd(PPh$_3$)$_4$ (173 mg, 0.15 mmol), a solution of Na$_2$CO$_3$ (1.1 g, 10 mmol) in water (5 mL), and a solution of phenyl boronic acid (671 mg, 5.5 mmol) in methanol (3 mL). The mixture was stirred at room temperature for 5 days, quenched with water, extracted with ethyl acetate and purified by silica gel chromatography eluting with 5% ethyl acetate/hexanes to afford the title compounds as a mixture. $^1$H NMR (500 MHz, DMSO-d$_6$) δ ppm 8.28 (d, J=1.53 Hz, 1H) 8.12 (d, J=8.85 Hz, 1H) 7.97-8.04 (m, 3H) 7.80-7.86 (m, 2H) 7.75 (d, J=1.83 Hz, 1H) 7.54-7.63 (m, 3H) 1.68 (s, 9H) 1.64 (s, 9H). MS (ESI+) m/z 373.9 (M+H)$^+$.

Example 60C tert-Butyl 3,5-bis((trimethylsilyl)ethynyl)-1H-indazole-1-carboxylate and tert-butyl 5-bromo-3-((trimethylsilyl)ethynyl)-1H-indazole-1-carboxylate Example 60B (1 g, 2.55 mmol), dichlorobis(triphenylphosphine)palladium(II) (89 mg, 0.13 mmol), triethylamine (1.78 mL, 12.75 mmol), trimethylsilyl acetylene (0.432 mL, 3.06 mmol), and CuI (24 mg, 0.13 mmol) were combined in dimethylformamide (10 mL) and stirred at room temperature for 20 hours. The mixture was diluted with ethyl acetate, washed with water, and purified by silica gel chromatography to afford the title compounds. $^1$H NMR (500 MHz, DMSO-d$_6$) δ ppm 8.10 (d, J=8.85 Hz, 1H) 8.07 (d, J=8.85 Hz, 1H) 7.97 (d, J=1.83 Hz, 1H) 7.84 (s, 1H) 7.82 (dd, J=8.85, 1.83 Hz, 1H) 7.71 (dd, J=8.54, 1.53 Hz, 1H) 1.65 (s, 18H) 0.33 (d, J=0.92 Hz, 18H).

Example 60D tert-butyl 3,5-diethynyl-1H-indazole-1-carboxylate and tert-butyl 5-bromo-3-ethynyl-1H-indazole-1-carboxylate To a solution of Example 60C (350 mg, 0.85 mmol) in tetrahydrofuran (5 mL) was added a 1M solution of TBAF in tetrahydrofuran (2 mL, 2 mmol). After 10 minutes, the solvent was evaporated under reduced pressure and the crude mixture was purified by silica gel chromatography eluting with 5% ethyl acetate in hexanes to afford the title compounds. $^1$H NMR (500 MHz, DMSO-d$_6$) δ ppm 8.12 (d, J=7.93 Hz, 1H) 8.07 (d, J=8.85 Hz, 1H) 8.01 (d, J=1.53 Hz, 1H) 7.90 (s, 1H) 7.83 (dd, J=8.85, 1.83 Hz, 1H) 7.74 (dd, J=8.85, 1.53 Hz, 1H) 4.91 (s, 1H) 4.90 (s, 1H) 4.29 (s, 1H) 1.66 (s, 9H) 1.65 (s, 9H).

Example 60E 3,5-bis(1-benzyl-1H-1,2,3-triazol-4-yl)-1H-indazole

The title compound was prepared according to the procedure outlined in Example 3D substituting Example 60D for Example 3C. $^1$H NMR (500 MHz, DMSO-d$_6$) δ ppm 13.35 (s, 1H) 8.76 (s, 1H) 8.71 (s, 1H) 8.70 (s, 1H) 7.92 (d, J=8.61, 1.28 Hz, 1H) 7.64 (d, J=8.79 Hz, 1H) 7.38-7.43 (m, 8H) 7.33-7.37 (m, 2H) 5.73 (s, 2H) 5.66 (s, 2H). MS (ESI+) m/z 433.2 (M+H)$^+$.

Example 61

5-(1-benzyl-1H-1,2,3-triazol-4-yl)-3-phenyl-1H-indazole

Example 61A tert-Butyl 3-phenyl-5-((trimethylsilyl)ethynyl)-1H-indazole-1-carboxylate and tert-butyl 5-bromo-3-phenyl-1H-indazole-1-carboxylate Example 60B (1 g, 2.55 mmol), dichlorobis(triphenylphosphine)palladium(II) (89 mg, 0.13 mmol), triethylamine (1.78 mL, 12.75 mmol), trimethylsilyl acetylene (0.432 mL, 3.06 mmol), and CuI (24 mg, 0.13 mmol) were combined in dimethylformamide (10 mL) and stirred at room temperature for 20 hours. The mixture was diluted with ethyl acetate and purified by silica gel chromatography to afford the title compound. $^1$H NMR (500 MHz, DMSO-d$_6$) δ ppm 8.29 (d, J=1.53 Hz, 1H) 8.09-8.19 (m, 3H) 7.96-8.03 (m, 4H) 7.83 (dd, J=8.85, 1.83 Hz, 1H) 7.72 (dd, J=8.85, 1.53 Hz, 1H) 7.50-7.65 (m, 6H) 1.68 (s, 18H) 0.26-0.27 (m, 9H).

Example 61B tert-Butyl 5-ethynyl-3-phenyl-1H-indazole-1-carboxylate and tert-butyl 5-bromo-3-phenyl-1H-indazole-1-carboxylate The title compound was prepared according to the procedure outlined in Example 60D substituting Example 61A for Example 60C. $^1$H NMR (500 MHz, DMSO-d$_6$) δ ppm 8.28 (d, J=1.53 Hz, 1H) 8.21 (s, 1H) 8.16 (d, J=8.54 Hz, 1H) 8.12 (d, J=8.85 Hz, 1H) 7.97-8.05 (m, 4H) 7.83 (dd, J=8.85, 1.83 Hz, 1H) 7.75 (dd, J=8.85, 1.53 Hz, 1H) 7.53-7.64 (m, 6H) 4.27 (s, 1H) 1.68 (s, 9H) 1.68 (s, 9H).

Example 61C 5-(1-benzyl-1H-1,2,3-triazol-4-yl)-3-phenyl-1H-indazole

The title compound was prepared according to the procedure outlined in Example 3D substituting Example 61B for Example 3C. $^1$H NMR (500 MHz, DMSO-d$_6$) δ ppm 13.38 (s, 1H) 8.77 (s, 1H) 8.52 (s, 1H) 8.06 (d, J=7.33 Hz, 2H) 7.98 (d, J=8.79 Hz, 1H) 7.69 (d, J=8.79 Hz, 1H) 7.53-7.61 (m, J=7.51, 7.51 Hz, 2H) 7.33-7.48 (m, 6H) 5.68 (s, 2H). MS (ESI+) m/z 352.0 (M+H)$^+$.

Example 62

5-(1-benzyl-1H-1,2,3-triazol-4-yl)-1H-indazol-3-amine

Example 62A

2-Fluoro-5-((trimethylsilyl)ethynyl)benzonitrile

5-Bromo-2-fluorobenzonitrile (5.01 g, 25.0 mmol), dichlorobis(triphenylphosphine)palladium(II) (652 mg, 0.929 mmol), and copper (J) iodide (413 mg, 2.17 mmol) were combined in triethylamine (15 mL) under an atmosphere of nitrogen. Trimethylsilyl acetylene (4.2 mL, 29.7 mmol) was added and the mixture was heated to 100° C. The mixture solidified and was monitored by LC/MS. After completion, the mixture was diluted with methylene chloride and washed with 1 N HCl. The organic layer was absorbed on silica gel and purified by silica gel chromatography eluting with a gradient of ethyl acetate in hexanes (5-45%) to afford the title compound. $^1$H NMR (300 MHz, DMSO-d$_6$) δ ppm 8.09 (dd, J=6.10, 2.03 Hz, 1H) 7.77-7.97 (m, 1H) 7.54 (t, J=9.15 Hz, 1H) 0.15-0.32 (m, 9H).

Example 62B

5-Ethynyl-2-fluorobenzonitrile

Tetrabutylammonium fluoride (1.0 M solution in tetrahydrofuran, 70 mL) was added to a solution of Example 62A (5.05 g, 23.2 mmol) in tetrahydrofuran (50 mL) and allowed to stir for 20 minutes. The mixture was diluted with methylene chloride and washed with water. The organic layer was absorbed on silica gel and purified by silica gel chromatography eluting with a gradient of 5-40% ethyl acetate in hexanes to afford the title compound. $^1$H NMR (300 MHz, DMSO-d$_6$) δ ppm 8.13 (dd, J=6.27, 2.20 Hz, 1H) 7.82-7.95 (m, 1H) 7.56 (t, J=8.99 Hz, 1H) 4.40 (s, 1H).

Example 62C 5-(1-Benzyl-1H-1,2,3-triazol-4-yl)-2-fluorobenzonitrile

Example 62B (1.68 g, 11.6 mmol) was dissolved in tert-butanol (14 mL). Benzyl azide (2.14 g, 15.8 mmol) was added and the mixture was transferred to 14 microwave vials (1.0 mL each). Water (0.5 mL), a small piece of copper wire, and a 1 M solution of copper (II) sulfate (0.5 mL) were added to each microwave vial and the vials were heated in a CEM-Discover microwave at 125° C. using 100 Watts for 10 minutes each. The vials were recombined, diluted with ethyl acetate, and washed with water and brine. The organic material was absorbed on silica gel and purified by silica gel chromatography eluting with a gradient of 5-50% ethyl acetate in hexanes to afford the title compound. $^1$H NMR (300 MHz, DMSO-d$_6$) δ ppm 8.73 (s, 1H) 8.33-8.44 (m, 1H) 8.19-8.32 (m, 1H) 7.56-7.70 (m, 1H) 7.28-7.47 (m, 5H) 5.68 (s, 2H).

Example 62D 5-(1-benzyl-1H-1,2,3-triazol-4-yl)-1H-indazol-3-amine

Hydrazine hydrate (18 mL) was added to Example 62C (1.93 g, 6.94 mmoL) in ethanol (10 mL). The mixture was heated to 95° C. overnight. The mixture was diluted with ethyl acetate and washed with water. Some of the product precipitated in the separatory funnel and was filtered to afford the title compound. The ethyl acetate layer was concentrated under reduced pressure and the resulting solid was triturated with methanol to afford additional title compound. $^1$H NMR (300 MHz, DMSO-$d_6$) δ ppm 11.43 (s, 1H) 8.42 (s, 1H) 8.21 (s, 1H) 7.67 (d, J=8.82, 1.70 Hz, 1H) 7.38 (s, 5H) 7.26 (d, J=8.48 Hz, 1H) 5.64 (s, 2H) 5.38 (s, 2H). MS (ESI+) m/z 291.0 (M+H)$^+$.

Example 63

5-(1-benzyl-1H-1,2,3-triazol-4-yl)-1-[(1-methylpiperidin-4-yl)carbonyl]-1H-indazol-3-amine Example 62D (44 mg, 0.152 mmol), 1-methylpiperidine-4-carboxylic acid hydrochloride (27 mg, 0.150 mmol), and HATU (61 mg, 0.160 mmol) were combined in tetrahydrofuran (2 mL). Diisopropylethylamine (110 mL, 0.631 mmol) was added and the mixture was heated to 90° C. for 30 minutes. The mixture was diluted with methylene chloride and washed with 1 N sodium hydroxide. The organic layer was absorbed on silica gel and purified by silica gel chromatography eluting with a gradient of 5-15% methanol in dichloromethane to afford the title compound. $^1$H NMR (300 MHz, DMSO-$d_6$) δ ppm 8.58 (s, 1H) 8.47 (s, 1H) 8.26 (d, J=8.48 Hz, 1H) 7.97 (d, J=8.48, 1.70 Hz, 1H) 7.38 (s, 5H) 6.58 (s, 2H) 5.67 (s, 2H) 3.35-3.47 (m, 1H) 2.95 (d, J=11.19 Hz, 2H) 2.28 (s, 3H) 2.03-2.20 (m, 2H) 1.92 (s, 2H) 1.77 (s, 2H). MS (ESI+) m/z 416.2 (M+H)$^+$.

Example 64

N-[5-(1-benzyl-1H-1,2,3-triazol-4-yl)-1H-indazol-3-yl]-2-methoxyacetamide

Example 64A tert-Butyl 3-amino-5-(1-benzyl-1H-1,2,3-triazol-4-yl)-1H-indazole-1-carboxylate Example 62D (1.80 g, 6.20 mmol) was suspended in methylene chloride (100 mL) with a catalytic amount of dimethylaminopyridine. A solution of di-tert-butyl dicarbonate (1.36 g, 6.23 mmol) in methylene chloride (50 mL) was added dropwise over 1 hour. The mixture was absorbed on silica gel and purified by silica gel chromatography eluting with a gradient of 0-5% methanol in dichloromethane to afford the title compound. MS (ESI+) m/z 391.1 (M+H)$^+$.

Example 64B

N-[5-(1-benzyl-1H-1,2,3-triazol-4-yl)-1H-indazol-3-yl]-2-methoxyacetamide

Example 64A (45 mg, 0.115 mmol) was dissolved in methylene chloride (1.5 mL) and pyridine (0.5 mL). Methoxy acetyl chloride (18 μL, 0.197 mmol) was added and the mixture was stirred at ambient temperature for 2 hours. The solvents were removed using a warm stream of nitrogen, the mixture was injected on a silica gel column, and the product was purified by silica gel chromatography eluting with a gradient of 0-5% methanol in dichloromethane to afford tert-butyl 5-(1-benzyl-1H-1,2,3-triazol-4-yl)-3-(2-methoxyacetamido)-1H-indazole-1-carboxylate (58 mg). The intermediate was dissolved in methylene chloride (2 mL) and trifluoroacetic acid (1 mL) and stirred at ambient temperature overnight. The solvents were removed under reduced pressure, and the mixture was purified by preparative HPLC on a C8 column using a gradient of 10% to 100% acetonitrile/water containing 0.1% trifluoroacetic acid to afford the title compound. $^1$H NMR (300 MHz, DMSO-$d_6$) δ ppm 12.79 (s, 1H) 10.16 (s, 1H) 8.59 (s, 1H) 8.20 (s, 1H) 7.83 (d, J=8.65, 1.53 Hz, 1H) 7.51 (d, J=8.82 Hz, 1H) 7.37 (s, 5H) 5.64 (s, 2H) 4.12 (s, 2H) 3.42 (s, 3H). MS (ESI+) m/z 363.0 (M+H)$^+$.

Example 65

$N^1$-[5-(1-benzyl-1H-1,2,3-triazol-4-yl)-1H-indazol-3-yl]-$N^2$,$N^2$-dimethylglycinamide Example 64A (81 mg, 0.207 mmol) was dissolved in methylene chloride (2 mL) and pyridine (0.5 mL). Dimethylaminoacetylchloride hydrochloride, 80% (120 mg, 0.607 mmol) was added in three portions over 2 hours and the mixture was stirred at ambient temperature overnight. Trifluoroacetic acid (2 mL) was added and the mixture was stirred for 3 hours. The mixture was diluted with methylene chloride and washed with 1 N sodium hydroxide. The organic layer was absorbed on silica gel and purified using silica gel chromatography eluting with a gradient of 5-15% methanol in dichloromethane to afford the title compound. $^1$H NMR (300 MHz, DMSO-$d_6$) δ ppm 12.77 (s, 1H) 10.05 (s, 1H) 8.58 (s, 1H) 8.24 (s, 1H) 7.82 (d, J=8.65, 1.53 Hz, 1H) 7.50 (d, J=8.82 Hz, 1H) 7.30-7.44 (m, 5H) 5.64 (s, 2H) 3.16-3.20 (m, 2H) 2.34 (s, 6H). MS (ESI+) m/z 376.1 (M+H)$^+$.

Example 66

N-[5-(1-benzyl-1H-1,2,3-triazol-4-yl)-1H-indazol-3-yl]butanamide

Example 64A (76 mg, 0.195 mmol) was dissolved in methylene chloride (2 mL) and pyridine (0.2 mL). Butyryl chloride (26 μL, 0.250 mmol) was added and the mixture was stirred at ambient temperature for 2 hours. Trifluoroacetic acid (1 mL) was added and the mixture was stirred for 3 hours. The mixture was diluted with methylene chloride and washed with water. The organic layer was absorbed on silica gel and purified using silica gel chromatography eluting with a gradient of 1-8% methanol in dichloromethane to afford the title compound. $^1$H NMR (300 MHz, DMSO-$d_6$) δ ppm 12.70 (s, 1H) 10.30 (s, 1H) 8.57 (s, 1H) 8.23 (s, 1H) 7.81 (d, J=8.82 Hz, 1H) 7.49 (d, J=8.82 Hz, 1H) 7.37 (s, 5H) 5.64 (s, 2H) 2.39 (t, J=7.29 Hz, 2H) 1.67 (s, 2H) 0.97 (t, J=7.46 Hz, 3H). MS (ESI+) m/z 361.1 (M+H)$^+$.

Example 67

5-[4-(4-fluorophenyl)-1-piperidin-4-yl-1H-imidazol-5-yl]-1H-indazole

The title compound was prepared according to the procedure outlined in Example 39 substituting piperidin-4-amine for benzylamine. $^1$H NMR (300 MHz, DMSO-$d_6$) δ ppm 13.28 (s, 1H) 8.14 (s, 1H) 7.94 (s, 1H) 7.78 (s, 1H) 7.63-7.72 (m, 2H) 7.21-7.43 (m, 2H) 6.90-7.04 (m, 2H) 4.14 (d, J=5.59, 1.86 Hz, 1H) 3.53-3.74 (m, J=5.76 Hz, 1H) 2.94 (d, J=12.21 Hz, 2H) 2.21-2.35 (m, 2H) 1.74-1.88 (m, 3H). MS (DCI) m/z 362 (M+H)$^+$.

Example 68

5-{4-(4-fluorophenyl)-1-[2-(1-methylpyrrolidin-2-yl)ethyl]-1H-imidazol-5-yl}-1H-indazole The title compound was prepared according to the procedure outlined in Example 39 substituting 2-(1-methylpyrrolidin-2-yl)ethanamine for benzylamine. $^1$H NMR (300 MHz, DMSO-$d_6$) δ ppm 13.30 (s, 1H) 8.14 (s, 1H) 7.86 (s, 1H) 7.82 (s, 1H) 7.68 (d, J=8.48 Hz, 1H) 7.24-7.47 (m, 3H) 6.92-7.08 (m, 2H) 3.83 (t, J=7.80 Hz, 2H) 2.71-2.93 (m, 1H) 1.88-2.01 (m, 3H) 1.74-1.88 (m, 1H) 1.00-1.83 (m, 7H). MS (DCI) m/z 390 (M+H)$^+$.

Example 69

5-{4-(4-fluorophenyl)-1-[3-(4-methylpiperazin-1-yl)propyl]-1H-imidazol-5-yl}-1H-indazole The title compound was prepared according to the procedure outlined in Example 39 substituting 3-(4-methylpiperazin-1-yl)propan-1-amine for benzylamine. $^1$H NMR (300 MHz, DMSO-$d_6$) δ ppm 13.36 (s, 1H) 8.13 (s, 1H) 7.81 (s, 2H) 7.67 (d, J=8.48 Hz, 1H) 7.32-7.45 (m, 2H) 7.27 (d, J=8.48, 1.36 Hz, 1H) 6.87-7.06 (m, 2H) 3.72-3.91 (m, 2H) 1.92-2.21 (m, 10H) 1.91-2.20 (s, 3H) 1.51-1.66 (m, 2H). MS (ESI+) m/z 419 (M+H)$^+$.

Example 70

Ethyl 5-(1H-indazol-5-yl)isoxazole-3-carboxylate

Example 3C (1.83 g, 12.9 mmol) was dissolved in toluene (60 mL) and triethylamine (2.2 mL) and warmed to 90° C. Ethyl 2-chloro-2-(hydroxyimino)acetate (1.89 g, 12.5 mmol) was dissolved in toluene (15 mL) and was added dropwise over 30 minutes. Following the addition, the mixture was diluted with ethyl acetate and washed with 1 N hydrochloric acid. The organic layer was concentrated under reduced pressure and the resulting residue was triturated with methanol to afford the title compound. $^1$H NMR (300 MHz, DMSO-$d_6$) δ ppm 13.38 (s, 1H) 8.43 (s, 1H) 8.23 (s, 1H) 7.92 (d, J=8.82, 1.36 Hz, 1H) 7.70 (d, J=8.82 Hz, 1H) 7.44 (s, 1H) 4.41 (q, J=7.12 Hz, 2H) 1.35 (t, J=7.12 Hz, 3H). MS (ESI+) m/z 257.9 (M+H)$^+$.

Example 71

5-(1H-indazol-5-yl)-N-methylisoxazole-3-carboxamide

Example 71A

5-(1H-indazol-5-yl)isoxazole-3-carboxylic Acid

Example 70 (1.50 g, 5.83 mmol) was dissolved in tetrahydrofuran (100 mL), methanol (10 mL), and water (10 mL). Potassium hydroxide (680 mg, 12.1 mmol) was added, and the mixture was stirred at ambient temperature for 2 hours. The solvents were removed under reduced pressure, and the resulting residue was triturated with a mixture of 1 N hydrochloric acid and methanol to provide a solid that was filtered to afford the title compound. $^1$H NMR (300 MHz, DMSO-$d_6$) δ ppm 13.37 (s, 1H) 8.39 (s, 1H) 8.22 (s, 1H) 7.90 (dd, J=8.81, 1.36 Hz, 1H) 7.69 (d, J=8.82 Hz, 1H) 7.30 (s, 1H).

Example 71B

5-(1H-indazol-5-yl)-N-methylisoxazole-3-carboxamide

Example 71A (46 mg, 0.201 mmol), HATU (88 mg, 0.231 mmol), and diisopropylethylamine (133 μL, 0.764 mmol) were combined in tetrahydrofuran (2 mL). Monomethylamine (40% solution in water) (50 μL) was added, and the reaction was stirred at 50° C. for 2 hours. The mixture was diluted with methylene chloride and washed with 1 N sodium hydroxide, 1 N hydrochloric acid, and brine. The organic layer was absorbed on silica gel and purified by silica gel chromatography eluting with a gradient of 10-50% ethyl acetate in hexanes to afford the title compound. $^1$H NMR (300 MHz, DMSO-$d_6$) δ ppm 13.36 (s, 1H) 8.72 (q, J=4.30 Hz, 1H) 8.39 (s, 1H) 8.23 (s, 1H) 7.89 (d, J=8.65, 1.53 Hz, 1H) 7.69 (d, J=8.82 Hz, 1H) 7.28 (s, 1H) 2.80 (d, J=4.75 Hz, 3H). MS (ESI+) m/z 243.0 (M+H)$^+$.

Example 72

5-(3-benzylisoxazol-5-yl)-1H-indazole

Phenylacetaldehyde (90+%) (266 mg, 2.38 mmol) was dissolved in tert-butanol (1 mL) and water (1 mL). Hydroxylamine hydrochloride (79 mg, 1.14 mmol) was added followed by a 6 N solution of sodium hydroxide (19 μL, 31.7 mmol). The mixture was stirred for 30 minutes. Chloramine-T trihydrate (308 mg, 1.09 mmol) was added slowly over 5 minutes followed by the addition of copper (II) sulfate and a small piece of copper wire. Example 3C (154 mg, 1.08 mmol) was added and the mixture was stirred at 50° C. for 2 hours then ambient temperature overnight. The mixture was diluted with methylene chloride and washed with water. The organic layer was absorbed on silica gel and purified by silica gel chromatography eluting with a gradient of 10-50% ethyl acetate in hexanes to afford the title compound. $^1$H NMR (300 MHz, DMSO-$d_6$) δ ppm 13.31 (s, 1H) 8.28 (s, 1H) 8.18 (s, 1H) 7.79 (dd, J=8.65, 1.53 Hz, 1H) 7.64 (d, J=8.81 Hz, 1H) 7.13-7.46 (m, 5H) 6.83 (s, 1H) 4.04 (s, 2H). MS (ESI+) m/z 275.7 (M+H)$^+$.

Example 73

N-[5-(1-benzyl-1H-1,2,3-triazol-4-yl)-1H-indazol-3-yl]benzamide

Example 64A (72 mg, 0.184 mmol) was dissolved in methylene chloride (2 mL) and pyridine (0.2 mL). Benzoyl chloride (36 μL, 0.310 mmol) was added, and the mixture was stirred at ambient temperature for 2 hours. Trifluoroacetic acid (1 mL) was added and the mixture was stirred for 3 hours. The mixture was diluted with methylene chloride and washed with water. The organic layer was absorbed on silica gel and purified using silica gel chromatography eluting with a gradient of 1-8% methanol in dichloromethane to afford the title compound. $^1$H NMR (300 MHz, DMSO-$d_6$) δ ppm 12.88 (s, 1H) 10.81 (s, 1H) 8.63 (s, 1H) 8.16 (s, 1H) 8.06-8.13 (m, 2H) 7.88 (d, J=8.82, 1.36 Hz, 1H) 7.59-7.64 (m, J=7.12 Hz, 1H) 7.51-7.59 (m, 3H) 7.31-7.42 (m, 5H) 5.63 (s, 2H). MS (ESI+) m/z 395.1 (M+H)$^+$.

Example 74

5-(3-propylisoxazol-5-yl)-1H-indazole

The title compound was prepared according to the procedure outlined in Example 72 substituting butyraldehyde for phenylacetaldehyde. $^1$H NMR (300 MHz, DMSO-$d_6$) δ ppm 13.31 (s, 1H) 8.28 (s, 1H) 8.20 (s, 1H) 7.76-7.85 (m, 1H) 7.63-7.70 (m, 1H) 6.88 (s, 1H) 2.63 (t, J=7.46 Hz, 2H) 1.61-1.79 (m, 2H) 0.96 (t, J=7.29 Hz, 3H). MS (ESI+) m/z 228.0 (M+H)$^+$.

Example 75

N-benzyl-4-(1H-indazol-5-yl)-5-phenyl-1,3-thiazol-2-amine

Example 75A 1H-indazole-5-carboxylic Acid

The title compound was prepared according to the procedure outlined in Example 3A, substituting methyl 4-amino-3-methylbenzoate for 4-iodo-2-methylaniline. During the final workup, addition of 6 N HCl until pH 6 resulted in the formation of a solid, which was filtered, washed twice with water and dried in vacuo to afford the title compound. $^1$H NMR (300 MHz, DMSO-$d_6$) δ ppm 13.32 (s, 1H) 12.83 (s, 1H) 8.46 (s, 1H) 8.24 (s, 1H) 7.92 (dd, J=8.82, 1.70 Hz, 1H) 7.60 (d, J=8.82 Hz, 1H).

Example 75B

N-Methoxy-N-methyl-1H-indazole-5-carboxamide

To a suspension of Example 75A (1.6 g, 10 mmol) and N,O-dimethylhydroxylamine (1.1 g, 11 mmol) in dichloromethane (40 mL) and dimethylformamide (10 mL) was added triethylamine (1.67 mL, 12 mmol) and EDC (2.1 g, 11 mmol), and the mixture was stirred at room temperature for 24 hours. The solvents were evaporated under reduced pressure, and the resulting residue was diluted with ethyl acetate and washed with water. The organic layer was dried over sodium sulfate and purified by silica gel column chromatography in ethyl acetate to afford the title compound. MS (ESI+) m/z 206.0 (M+H)$^+$.

Example 75C 1-(1H-indazol-5-yl)-2-phenylethanone

A solution of Example 75B (900 mg, 4.39 mmol) in tetrahydrofuran (10 mL) was cooled under argon with an ice bath and treated with a 2M solution of benzyl magnesium chloride in tetrahydrofuran (6.6 mL, 13.16 mmol). The reaction was stirred overnight at room temperature followed by the addition of one more equivalent of benzyl magnesium chloride. The mixture was heated at 70° C. for 9 hours. One more equivalent of benzylmagnesium chloride was added, and the reaction was heated at 70° C. for another 90 minutes and was allowed to cool to room temperature. Aqueous saturated ammonium chloride was added, and the product was extracted with ethyl acetate and purified by silica gel column chromatography using 30% ethyl acetate in hexanes to afford the title compound. MS (ESI+) m/z 237.1 (M+H)$^+$.

Example 75D tert-Butyl 5-(2-phenylacetyl)-1H-indazole-1-carboxylate

To a suspension of Example 75C (236 mg, 1 mmol) in dichloromethane (2 mL) was added di-tert-butyl dicarbonate (327 mg, 1.5 mmol) and a pinch of dimethylaminopyridine (~2 mg). The mixture was stirred for 15 minutes, and passed through a bed of silica gel and eluted with dichloromethane. The solvent was evaporated under reduced pressure to afford the title compound. MS (ESI+) m/z 337.0 (M+H)$^+$.

Example 75E

2-Bromo-1-(1H-indazol-5-yl)-2-phenylethanone

To a solution of Example 75D (336 mg, 1 mmol) in tetrahydrofuran (20 mL) heated at 40° C. with an oil bath was added dropwise with an addition funnel a solution of pyridinium tribromide (352 mg, 1.1 mmol) in tetrahydrofuran (20 mL) over 10 minutes. The reaction mixture was heated for an extra 2 hours, and was cooled, filtered, and the filtrate was evaporated to afford the title compound. MS (ESI−) m/z 212.9 (M−H)$^-$.

Example 75F

N-benzyl-4-(1H-indazol-5-yl)-5-phenyl-1,3-thiazol-2-amine

A vial containing Example 75E (50 mg, 0.16 mmol) and 1-benzylthiourea (26 mg, 0.16 mmol) in ethanol (1 mL) was capped and heated in a heater shaker at 80° C. for 2 hours. The solution of the crude product was purified by reverse-phase HPLC using an acetonitrile/water 0.1% TFA gradient elution method to afford the title compound as a TFA salt. $^1$H NMR (400 MHz, DMSO-$d_6$) δ ppm 12.99 (s, 1H) 8.33-8.37 (m, 1H) 8.01 (s, 1H) 7.92-7.99 (m, 1H) 7.82 (s, 1H) 7.60-7.67 (m, J=7.83, 7.83 Hz, 1H) 7.31-7.45 (m, 5H) 7.17-7.30 (m, 5H) 4.53 (d, J=4.60 Hz, 2H). MS (ESI+) m/z 383.0 (M+H)$^+$.

Example 76

4-(1H-indazol-5-yl)-N,5-diphenyl-1,3-thiazol-2-amine

The title compound was prepared as a TFA salt according to the procedure outlined in Example 75F substituting 1-phenylthiourea for 1-benzylthiourea. $^1$H NMR (400 MHz, DMSO-$d_6$) δ ppm 13.09 (s, 1H) 10.29 (s, 1H) 8.05 (d, J=0.92 Hz, 1H) 7.89 (d, J=1.53, 0.92 Hz, 1H) 7.69 (d, J=8.59, 1.23 Hz, 2H) 7.47 (dt, J=8.59, 0.92 Hz, 1H) 7.40-7.44 (m, 1H) 7.26-7.37 (m, 7H) 6.94-7.02 (m, J=7.36, 7.36 Hz, 1H). MS (ESI+) m/z 369.0 (M+H)$^+$.

Example 77

5-(1-benzyl-5-cyclopropyl-1H-1,2,3-triazol-4-yl)-1H-indazole

Example 77A tert-butyl 5-(cyclopropylethynyl)-1H-indazole-1-carboxylate

Example 44A (2.31 g, 7.77 mmol), cyclopropyl acetylene (620 mg, 9.37 mmol), dichlorobis(triphenylphosphine)palladium(II) (170 mg, 0.242 mmol), and copper (J) iodide (92 mg, 0.483 mmol) were combined in triethylamine (10 mL) under an inert atmosphere of nitrogen. The mixture was heated to 100° C. in a sealed tube for 4 hours. The mixture was diluted with methylene chloride and washed with 1 N hydrochloric acid. The organic layer was absorbed onto silica gel and purified by silica gel chromatography eluting with a gradient of 5-50% ethyl acetate in hexanes to afford the title compound. MS (ESI+) m/z 283.0 (M+H)+.

Example 77B 5-(1-benzyl-5-cyclopropyl-1H-1,2,3-triazol-4-yl)-1H-indazole

Example 77A (145 mg, 0.51 mmol) and benzyl azide (82 mg, 0.62 mmol) were heated neat in a CEM-Discover microwave at 150° C. and 150 Watts, for 10 minutes. The crude mixture was dissolved in dichloromethane and purified by silica gel column chromatography using 50% ethyl acetate in hexanes as the eluent. $^1$H NMR (400 MHz, DMSO-d$_6$) δ ppm 13.12 (s, 1H) 8.11 (d, J=5.52 Hz, 2H) 7.79 (d, J=8.59, 1.53 Hz, 1H) 7.60 (d, J=8.59 Hz, 1H) 7.26-7.45 (m, 5H) 5.69 (s, 2H) 1.78-1.92 (m, 1H) 0.98-1.09 (m, 2H) 0.31-0.45 (m, 2H). MS (ESI+) m/z 316.0 (M+H)+.

Example 78

5-(1-benzyl-4-cyclopropyl-1H-1,2,3-triazol-5-yl)-1H-indazole

The title compound was isolated as a by-product according to the procedure outlined in Example 77B. $^1$H NMR (500 MHz, DMSO-d$_6$) δ ppm 13.29 (s, 1H) 8.14 (s, 1H) 7.80 (s, 1H) 7.65 (d, J=8.85 Hz, 1H) 7.29 (d, J=8.54, 1.53 Hz, 1H) 7.21-7.27 (m, 3H) 6.93 (d, J=7.48, 1.98 Hz, 2H) 5.49 (s, 2H) 1.70-1.80 (m, 1H) 0.81-0.92 (m, 4H). MS (ESI+) m/z 316.0 (M+H)+.

Example 79

2-(1H-indazol-5-yl)-3-phenylimidazo[1,2-a]pyrimidine

A vial containing Example 75E (80 mg, 0.25 mmol) and pyrimidin-2-amine (23 mg, 0.25 mmol) in ethanol (1 mL) was capped and heated in a heater shaker at 80° C. for 21 hours. The solution of the crude product was purified by reverse-phase HPLC using an acetonitrile/water 0.1% TFA gradient elution method to afford the title compound. $^1$H NMR (400 MHz, DMSO-d$_6$) δ ppm 8.69 (dd, J=4.30, 1.84 Hz, 1H) 8.59 (dd, J=6.75, 1.84 Hz, 1H) 8.07 (s, 1H) 8.02 (s, 1H) 7.46-7.65 (m, 7H) 7.16 (dd, J=6.75, 3.99 Hz, 1H). MS (ESI+) m/z 312.0 (M+H)+.

Example 80

5-[1-(tetrahydro-2H-pyran-4-ylmethyl)-1H-1,2,3-triazol-4-yl]-1H-indazole

Example 80A 4-(azidomethyl)tetrahydro-2H-pyran 4-(Iodomethyl)tetrahydro-2H-pyran (4.76 g, 21.1 mmol) was dissolved in dimethyl sulfoxide (25 mL). Sodium azide (2.70 g, 41.5 mmol) was added and the mixture was stirred at ambient temperature overnight. The resulting slurry was diluted with diethyl ether and washed with water. The organic layer was concentrated under reduced pressure to afford the title compound. The product was used directly in subsequent reactions without characterization.

Example 80B

5-[1-(tetrahydro-2H-pyran-4-ylmethyl)-1H-1,2,3-triazol-4-yl]-1H-indazole

Example 80A (122 mg, 0.864 mmol) and Example 3C (150 mg, 0.619 mmol) were combined in a microwave vial with tert-butanol (1 mL) and water (1 mL). A small piece of copper wire followed by copper(II) sulfate (5 mg, 0.02 mmol) was added, and the vial was stirred in a microwave (CEM-Discover) at 125° C. at 100 W for 10 minutes. The mixture was diluted with methylene chloride and washed with 1 N hydrochloric acid. The organic layer was absorbed onto silica gel and purified by silica gel chromatography eluting with a gradient of 0-5% methanol in dichloromethane to afford the title compound. $^1$H NMR (300 MHz, DMSO-d$_6$) δ ppm 13.11 (s, 1H) 8.53 (s, 1H) 8.22 (s, 1H) 8.12 (s, 1H) 7.85 (d, J=8.48, 1.36 Hz, 1H) 7.60 (d, J=8.82 Hz, 1H) 4.32 (d, J=7.12 Hz, 2H) 3.85 (d, J=11.70, 2.54 Hz, 2H) 3.21-3.36 (m, 2H) 2.14 (s, 1H) 1.47 (s, 2H) 1.30 (s, 2H). MS (ESI+) m/z 284.0 (M+H)+.

Example 81

5-[3-(piperidin-1-ylcarbonyl)isoxazol-5-yl]-1H-indazole

Example 81A 5-(1H-indazol-5-yl)isoxazole-3-carboxylic Acid

Example 70 (1.50 g, 5.83 mmol) was dissolved in tetrahydrofuran (100 mL), methanol (10 mL), and water (10 mL). Potassium hydroxide (680 mg, 12.1 mmol) was added and the mixture was stirred at ambient temperature for 2 hours. The solvents were removed under reduced pressure, and the resulting residue was triturated with a mixture of 1 N hydrochloric acid and methanol to provide a solid that was filtered to afford the title compound. $^1$H NMR (300 MHz, DMSO-d$_6$) δ ppm 13.36 (s, 1H) 8.41 (s, 1H) 8.23 (s, 1H) 7.91 (dd, J=8.82, 1.70 Hz, 1H) 7.70 (d, J=8.82 Hz, 1H) 7.36 (s, 1H).

Example 81B

5-[3-(piperidin-1-ylcarbonyl)isoxazol-5-yl]-1H-indazole

Example 81A (110 mg, 0.480 mmol), piperidine (55 µL, 0.556 mmol), and HATU (101 mg, 0.266 mmol) were combined in dimethylformamide (2 mL). Diisopropylethylamine (133 µL, 0.764 mmol) was added and the reaction was stirred at 45° C. for 2 hours. The mixture was diluted with ethyl acetate and washed with 1 N sodium hydroxide, 1 N hydrochloric acid, water (3 times), and brine. The organic layer was absorbed on silica gel and purified by silica gel chromatography eluting with a gradient of 0-5% methanol in dichloromethane to afford the title compound. $^1$H NMR (300 MHz, DMSO-d$_6$) δ ppm 13.37 (s, 1H) 8.34-8.40 (m, 1H) 8.21-8.25 (m, 1H) 7.84-7.91 (m, 1H) 7.66-7.72 (m, 1H) 7.20 (s, 1H) 3.59-3.69 (m, 2H) 3.48-3.58 (m, 2H) 1.47-1.72 (m, 6H). MS (ESI+) m/z 297.0 (M+H)+.

Example 82

5-(1H-indazol-5-yl)-N-phenylisoxazole-3-carboxamide

The title compound was prepared according to the procedure outlined in Example 81B substituting aniline for piperidine. ¹H NMR (500 MHz, DMSO-d₆) δ ppm 13.40 (s, 1H) 10.74 (s, 1H) 8.44 (s, 1H) 8.25 (s, 1H) 7.93 (d, J=8.85, 1.53 Hz, 1H) 7.82 (d, J=7.63 Hz, 2H) 7.72 (d, J=8.85 Hz, 1H) 7.44 (s, 1H) 7.35-7.42 (m, 2H) 7.16 (t, J=7.32 Hz, 1H). MS (ESI+) m/z 304.9 (M+H)⁺.

Example 83

N-cyclohexyl-5-(1H-indazol-5-yl)isoxazole-3-carboxamide

Example 81A (53 mg, 0.231 mmol), cyclohexylamine (29 μL, 0.253 mmol), and HATU (101 mg, 0.266 mmol) were combined in dimethyl formamide (2 mL). Diisopropylethylamine (133 μL, 0.764 mmol) was added, and the reaction was stirred at 45° C. for 2 hours. The mixture was diluted with ethyl acetate and washed with 1 N sodium hydroxide, 1 N hydrochloric acid, water (3 times), and brine. The organic layer was absorbed on silica gel and purified by silica gel chromatography eluting with a gradient of 0-5% methanol in dichloromethane to afford the title compound. ¹H NMR (300 MHz, DMSO-d₆) δ ppm 13.36 (s, 1H) 8.58 (d, J=8.14 Hz, 1H) 8.38 (s, 1H) 8.22 (s, 1H) 7.88 (d, J=8.81, 1.70 Hz, 1H) 7.69 (d, J=8.81 Hz, 1H) 7.28 (s, 1H) 3.69-3.86 (m, 1H) 1.77 (s, 4H) 1.60 (d, J=12.21 Hz, 1H) 1.20-1.46 (m, 4H) 1.06-1.20 (m, 1H). MS (ESI+) m/z 311.0 (M+H)⁺.

Example 84

5-[3-(piperidin-1-ylmethyl)isoxazol-5-yl]-1H-indazole

Example 81B (22 mg, 0.0742 mmol) was dissolved in tetrahydrofuran (2.5 mL) under an inert atmosphere of nitrogen. Lithium aluminum hydride (1.0 M solution in tetrahydrofuran) (250 μL) was added and the mixture was heated to 70° C. for 20 minutes. Methanol was added, and the mixture was absorbed on silica gel and purified by silica gel chromatography eluting with a gradient of methanol in dichloromethane (0-7%) to afford the title compound. ¹H NMR (400 MHz, DMSO-d₆) δ ppm 13.30 (s, 1H) 8.31 (s, 1H) 8.20 (s, 1H) 7.84 (d, J=8.59, 1.53 Hz, 1H) 7.66 (d, J=8.59 Hz, 1H) 6.92 (s, 1H) 3.54 (s, 2H) 2.32-2.46 (m, 2H) 1.47-1.59 (m, 4H) 1.33-1.46 (m, 2H). MS (ESI+) m/z 283.0 (M+H)⁺.

Example 85

[5-(1H-indazol-5-yl)isoxazol-3-yl]methanol

Example 70 (84 mg, 0.366 mmol) was dissolved in tetrahydrofuran (8 mL). Lithium aluminum hydride (1.0 M solution in tetrahydrofuran) (3.0 mL) was added in 1.0 mL portions over 2 hours. After the final addition, the mixture was stirred for an additional 30 minutes. The mixture was diluted with methylene chloride and washed with water and the organic layer was absorbed on silica gel and purified by silica gel chromatography eluting with a gradient of 0-20% methanol in dichloromethane to afford the title compound. ¹H NMR (400 MHz, DMSO-d₆) δ ppm 13.31 (s, 1H) 8.31 (s, 1H) 8.21 (s, 1H) 7.83 (d, J=8.59, 1.53 Hz, 1H) 7.67 (d, J=8.90 Hz, 1H) 6.93 (s, 1H) 5.51 (s, 1H) 4.56 (d, J=2.45 Hz, 1H). MS (ESI+) m/z 215.9 (M+H)⁺.

Example 86

5-(1H-indazol-5-yl)-N-(2-methoxyethyl)isoxazole-3-carboxamide

The title compound was prepared according to the procedure outlined in Example 81B substituting 2-methoxyethyl amine for piperidine. ¹H NMR (300 MHz, DMSO-d₆) δ ppm 13.36 (s, 1H) 8.74 (t, J=4.92 Hz, 1H) 8.39 (s, 1H) 8.23 (s, 1H) 7.89 (d, J=8.65, 1.53 Hz, 1H) 7.69 (d, J=8.82 Hz, 1H) 7.30 (s, 1H) 3.38-3.53 (m, 4H) 3.28 (s, 3H). MS (ESI+) m/z 287.0 (M+H)⁺.

Example 87

5-(1-benzyl-5-phenyl-1H-1,2,3-triazol-4-yl)-1H-indazole

Example 87A 1-(5-Iodo-1H-indazol-1-yl)ethanone

4-Iodo-2-methylaniline (30.2 g, 130 mmol) was dissolved in chloroform (300 mL) and cooled to 5° C. Acetic anhydride (35 mL, 343 mmol) was added dropwise, and the mixture was allowed to warm to ambient temperature. Potassium acetate (4.21 g, 42.9 mmol) and isoamylnitrite (37 mL, 277 mmol) were added, and the mixture was heated to 70° C. overnight. The mixture was neutralized with saturated aqueous sodium bicarbonate and extracted with methylene chloride. The solvents were removed under reduced pressure and the resulting residue was triturated with methanol to afford the title compound. ¹H NMR (300 MHz, DMSO-d₆) δ ppm 8.41 (s, 1H) 8.33 (s, 1H) 8.05-8.21 (m, 1H) 7.90 (dd, J=8.48, 1.70 Hz, 1H) 2.71 (s, 3H).

Example 87B

1-Benzyl-5-phenyl-4-(tributylstannyl)-1H-1,2,3-triazole

Phenylethynyltri-n-butyltin (8.25 g, 21.1 mmol) and benzyl azide (2.3 mL, 18.4 mmol) were combined and heated to 150° C. overnight. The mixture was purified by silica gel chromatography eluting with a gradient of 5-40% ethyl acetate in hexanes to afford the title compound. MS (ESI+) m/z 526.3 (M+H)⁺.

Example 87C 1-(5-(1-Benzyl-5-phenyl-1H-1,2,3-triazol-4-yl)-1H-indazol-1-yl)ethanone Example 87A (139 mg, 0.486 mmol), Example 87B (284 mg, 0.542 mmol), dichlorobis(triphenylphosphine)palladium(II) (40 mg, 0.057 mmol) and copper thiophene-2-carboxylate (167 mg, 0.876 mmol) were combined in toluene (1.5 mL) in a microwave vial under an inert atmosphere of nitrogen. The vial was heated in a microwave (CEM-Discover) to 150° C. at 125 Watts for 20 minutes. The mixture was absorbed on silica gel and purified by silica gel chromatography eluting with a gradient of 5-40% ethyl acetate in hexanes to afford the title compound. MS (ESI+) m/z 394.1 (M+H)⁺.

Example 87D 5-(1-benzyl-5-phenyl-1H-1,2,3-triazol-4-yl)-1H-indazole

Example 87C (95 mg, 0.242 mmol) was dissolved in tetrahydrofuran (2.0 mL), methanol (1.0 mL) and water (1.0 mL), and potassium hydroxide (64 mg, 1.14 mmol) was added. The mixture was stirred for 2 hours, and diluted with ethyl acetate and washed with water. The organic layer was absorbed on silica gel and purified by silica gel chromatography eluting with a gradient of 0-5% methanol in dichloromethane to afford the title compound. $^1$H NMR (300 MHz, DMSO-d$_6$) δ ppm 13.08 (s, 1H) 8.00 (s, 1H) 7.79 (s, 1H) 7.44-7.56 (m, 5H) 7.24-7.36 (m, 5H) 6.95-7.03 (m, 2H) 5.49 (s, 2H). MS (ESI+) m/z 252.1 (M+H)$^+$.

Example 88

5-(4-benzyl-1H-1,2,3-triazol-1-yl)-1H-indazole

Example 87A (969 mg, 3.39 mmol), 3-phenyl-1-propyne (392 mg, 3.37 mmol), sodium azide (278 mg, 4.28 mmol), sodium ascorbate (68 mg, 3.43 mmol), sodium carbonate (75 mg, 0.708 mmol), and L-proline (78 mg, 8.98 mmol) were combined in a 1:1 mixture of dimethyl sulfoxide and water (10 mL). Copper(II) sulfate pentahydrate (46 mg, 0.184 mmol) was added and the mixture was stirred at 65° C. for 3 hours. 6 N Sodium hydroxide (1 mL) was added, and the mixture was stirred for 30 minutes to deprotect the indazole. The mixture was diluted with ethyl acetate and washed with 1 N hydrochloric acid. The organic layer was concentrated under reduced pressure, and the resulting residue was triturated with methanol. The remaining solids were absorbed on silica gel and purified by silica gel chromatography eluting with a gradient of 0-5% methanol in dichloromethane to afford the title compound. $^1$H NMR (300 MHz, DMSO-d$_6$) δ ppm 13.35 (s, 1H) 8.58 (s, 1H) 8.17-8.27 (m, 1H) 7.86 (d, J=8.82, 2.03 Hz, 1H) 7.67-7.77 (m, 1H) 7.27-7.36 (m, 2H) 7.18-7.27 (m, 1H) 4.10 (s, 1H). MS (ESI+) m/z 276.0 (M+H)$^+$.

Example 89

5-(1-benzyl-5-cyclopropyl-1H-1,2,3-triazol-4-yl)-1H-indazol-3-amine

Example 89A

5-(Cyclopropylethynyl)-2-fluorobenzonitrile

5-Bromo-2-fluorobenzonitrile (3.06 g, 15.3 mmol), dichlorobis(triphenylphosphine)palladium(II) (478 mg, 0.681 mmol), and copper(I) iodide (165 mg, 0.866 mmol) were combined in triethylamine (15 mL) under an inert atmosphere of nitrogen. Cyclopropylacetylene (1.8 mL) was added, and the mixture was heated to 60° C. until it turned to a black solid. The mixture was diluted with methylene chloride and washed with 1 N hydrochloric acid. The organic layer was absorbed on silica gel and purified by silica gel chromatography eluting with a gradient of 5-40% ethyl acetate in hexanes to afford the title compound. MS (ESI+) m/z 319.0 (M+H)$^+$.

Example 89B

5-(1-benzyl-5-cyclopropyl-1H-1,2,3-triazol-4-yl)-1H-indazol-3-amine

Example 89A (211 mg, 1.14 mmol) and benzyl azide (143 µL, 1.14 mmol) were combined in a microwave (CEM-Discover) vial and heated to 160° C. using 100 Watts for 26 minutes. The mixture was absorbed on silica gel and purified by silica gel chromatography eluting with a gradient of 20-60% ethyl acetate in hexanes to afford a mixture of inseparable triazole regiomers. The mixture of regiomers were treated with hydrazine hydrate (3.0 mL) and ethanol (3.0 mL) and heated to 90° C. for 1 hour. The mixture was diluted with methylene chloride and washed with water. The organic layer was absorbed on silica gel and purified by silica gel chromatography eluting with a gradient of 1-6% methanol in dichloromethane to afford the title compound. $^1$H NMR (300 MHz, DMSO-d$_6$) δ ppm 11.43 (s, 1H) 8.07 (s, 1H) 7.63 (d, J=8.65, 1.53 Hz, 1H) 7.32-7.45 (m, 3H) 7.24-7.32 (m, 3H) 5.68 (s, 2H) 5.40 (s, 2H) 1.69-1.83 (m, 1H) 0.98-1.08 (m, 2H) 0.32-0.42 (m, 2H). MS (ESI+) m/z 331.1 (M+H)$^+$.

Example 90

5-(1-benzyl-4-cyclopropyl-1H-1,2,3-triazol-5-yl)-1H-indazol-3-amine

The title compound was isolated as a by-product according to the procedure outlined in Example 89B. $^1$H NMR (300 MHz, DMSO-d$_6$) δ ppm 11.62 (s, 1H) 7.79 (s, 1H) 7.32 (d, J=8.48 Hz, 1H) 7.20-7.27 (m, 3H) 7.15 (d, J=8.65, 1.53 Hz, 1H) 6.93 (d, J=7.12, 2.37 Hz, 2H) 5.49 (s, 2H) 5.45 (s, 2H) 1.71-1.82 (m, 1H) 0.80-0.89 (m, 4H). MS (ESI+) m/z 331.1 (M+H)$^+$.

Example 91

5-(3-isobutylisoxazol-5-yl)-1H-indazol-3-amine

Example 91A

2-fluoro-5-(3-isobutylisoxazol-5-yl)benzonitrile

The title compound was prepared according to the procedure outlined in Example 72 substituting isovaleraldehyde for phenylacetaldehyde and Example 62B for Example 3C. $^1$H NMR (300 MHz, DMSO-d$_6$) δ ppm 8.47 (dd, J=6.10, 2.03 Hz, 1H) 8.19-8.29 (m, 1H) 7.71 (t, J=8.99 Hz, 1H) 7.08 (s, 1H) 2.56 (d, J=7.12 Hz, 2H) 1.86-2.10 (m, 1H) 0.94 (d, J=6.78 Hz, 6H).

Example 91B

5-(3-isobutylisoxazol-5-yl)-1H-indazol-3-amine

To Example 91A (75 mg, 0.307 mmol) was added hydrazine hydrate (1.5 mL) in ethanol (1.0 mL). The mixture was heated to 70° C. overnight in a sealed vial. The mixture was diluted with methylene chloride and washed with water. The organic layer was absorbed on silica gel and purified by silica gel chromatography eluting with a gradient of 0-5% methanol in dichloromethane to afford the title compound. $^1$H NMR (300 MHz, DMSO-d$_6$) δ ppm 11.67 (s, 1H) 8.26 (s, 1H) 7.66 (dd, J=8.82, 1.70 Hz, 1H) 7.32 (d, J=8.48 Hz, 1H) 6.67 (s, 1H) 5.56 (s, 2H) 2.51-2.58 (m, 2H) 1.89-2.11 (m, 1H) 0.95 (d, J=6.44 Hz, 6H). MS (ESI+) m/z 257.0 (M+H)$^+$.

Example 92

5-(3-benzylisoxazol-5-yl)-1H-indazol-3-amine

Example 92A

5-(3-benzylisoxazol-5-yl)-2-fluorobenzonitrile

The title compound was prepared according to the procedure outlined in Example 72 substituting Example 62B for Example 3C. The crude product was used in the next step without further purification or characterization.

Example 92B 5-(3-benzylisoxazol-5-yl)-1H-indazol-3-amine

To Example 92A (65 mg, 0.234 mmol) was added hydrazine hydrate (1.5 mL) in ethanol (1.0 mL). The mixture was heated to 70° C. overnight in a sealed vial. The mixture was diluted with methylene chloride and washed with water. The organic layer was absorbed on silica gel and purified by silica gel chromatography eluting with a gradient of 0-20% methanol in dichloromethane to afford the title compound. $^1$H NMR (300 MHz, DMSO-$d_6$) δ ppm 11.67 (s, 1H) 8.26 (s, 1H) 7.66 (d, J=8.82, 1.70 Hz, 1H) 7.32 (d, J=8.48 Hz, 1H) 6.67 (s, 1H) 5.56 (s, 2H) 2.45-2.57 (m, 2H) 1.91-2.08 (m, 1H) 0.95 (d, J=6.44 Hz, 6H). MS (ESI+) m/z 291.0 (M+H)$^+$.

Example 93

N-{2-[4-(4-fluorophenyl)-5-(1H-indazol-5-yl)-1H-imidazol-1-yl]ethyl}-N,N-dimethylamine The title compound was prepared according to the procedure outlined in Example 39 substituting 2-dimethylaminoethylamine for benzylamine. $^1$H NMR (500 MHz, c) δ ppm 13.28 (s, 1H) 8.14 (s, 1H) 7.78-7.87 (m, 2H) 7.68 (d, J=8.54 Hz, 1H) 7.33-7.41 (m, 2H) 7.28 (d, J=8.54, 1.53 Hz, 1H) 6.95-7.05 (m, 2H) 3.86 (t, J=6.56 Hz, 2H) 2.31 (t, J=6.71 Hz, 2H) 2.00 (s, 6H).

Example 94

5-[4-(4-fluorophenyl)-1-(3-morpholin-4-ylpropyl)-1H-imidazol-5-yl]-1H-indazole

The title compound was prepared according to the procedure outlined in Example 39 substituting 3-morpholinopropylamine for benzylamine. $^1$H NMR (500 MHz, DMSO-$d_6$/D$_2$O) δ ppm 13.28 (s, 1H) 8.14 (s, 1H) 7.79-7.87 (m, 2H) 7.68 (d, J=8.24 Hz, 1H) 7.34-7.42 (m, 2H) 7.28 (d, J=8.54, 1.53 Hz, 1H) 6.92-7.03 (m, 2H) 3.77-3.89 (m, 2H) 3.24-3.30 (m, 4H) 2.10 (t, J=6.56 Hz, 2H) 1.96-2.05 (m, 4H) 1.54-1.66 (m, 2H). MS (ESI+) m/z 406.1 (M+H)$^+$.

Example 95

5-[4-(4-fluorophenyl)-1-(3-pyrrolidin-1-ylpropyl)-1H-imidazol-5-yl]-1H-indazole

The title compound was prepared according to the procedure outlined in Example 39 substituting 3-pyrrolidinopropylamine for benzylamine. $^1$H NMR (500 MHz, DMSO-$d_6$/D$_2$O) δ ppm 8.13 (d, J=0.92 Hz, 1H) 7.79-7.85 (m, 2H) 7.68 (d, J=8.54 Hz, 1H) 7.38 (d, J=8.85, 5.49 Hz, 2H) 7.27 (d, J=8.54, 1.53 Hz, 1H) 6.99 (t, J=9.00 Hz, 2H) 3.82-3.90 (m, 2H) 2.21 (t, J=6.71 Hz, 2H) 2.08-2.18 (m, 4H) 1.56-1.65 (m, 2H) 1.44-1.53 (m, 4H). MS (ESI+) m/z 390.2 (M+H)$^+$.

Example 96

5-{4-(4-fluorophenyl)-1-[2-(4-methylpiperidin-1-yl)ethyl]-1H-imidazol-5-yl}-1H-indazole The title compound was prepared according to the procedure outlined in Example 39 substituting 2-(4-methylpiperidin-1-yl)ethanamine for benzylamine. $^1$H NMR (500 MHz, DMSO-$d_6$/D$_2$O) δ ppm 13.29 (s, 1H) 8.14 (s, 1H) 7.83 (s, 1H) 7.81 (s, 1H) 7.67 (d, J=8.54 Hz, 1H) 7.32-7.40 (m, 2H) 7.28 (dd, J=8.54, 1.53 Hz, 1H) 6.93-7.04 (m, 2H) 3.85 (t, J=6.56 Hz, 2H) 2.60 (d, J=11.60 Hz, 2H) 2.37 (t, J=6.56 Hz, 2H) 1.71-1.85 (m, 2H) 1.45 (d, J=11.29 Hz, 2H) 1.15-1.30 (m, 1H) 0.95-1.07 (m, 2H) 0.83 (d, J=6.71 Hz, 3H) MS (ESI+) m/z 404.1 (M+H)$^+$.

Example 97

5-[1-(1-benzylpiperidin-4-yl)-4-(4-fluorophenyl)-1H-imidazol-5-yl]-1H-indazole

The title compound was prepared according to the procedure outlined in Example 39 substituting 4-amino-N-benzylpiperidine for benzylamine. $^1$H NMR (500 MHz, DMSO-$d_6$/D$_2$O) δ ppm 13.32 (s, 1H) 8.14 (s, 1H) 8.02 (s, 1H) 7.78 (s, 1H) 7.69 (d, J=8.54 Hz, 1H) 7.17-7.40 (m, 8H) 6.97 (t, J=8.85 Hz, 2H) 3.50-3.63 (m, 1H) 3.40 (s, 2H) 2.82 (d, J=11.90 Hz, 2H) 1.90-2.05 (m, 2H) 1.72-1.89 (m, 4H). MS (ESI+) m/z 452.2 (M+H)$^+$.

Example 98

5-[4-(4-fluorophenyl)-1-(2-morpholin-4-ylethyl)-1H-imidazol-5-yl]-1H-indazole

The title compound was prepared according to the procedure outlined in Example 39 substituting 2-morpholinoethylamine for benzylamine. $^1$H NMR (500 MHz, DMSO-$d_6$/D$_2$O) δ ppm 13.27 (s, 1H) 8.14 (s, 1H) 7.86 (s, 1H) 7.81 (s, 1H) 7.67 (d, J=8.54 Hz, 1H) 7.33-7.42 (m, 2H) 7.29 (d, J=8.54 Hz, 1H) 6.95-7.06 (m, 2H) 3.87 (t, J=6.41 Hz, 2H) 3.42-3.51 (m, 4H) 2.40 (t, J=6.56 Hz, 2H) 2.21 (d, J=3.97 Hz, 4H). MS (ESI+) m/z 392.1 (M+H)$^+$.

Example 99

5-[1-(1-benzylpyrrolidin-3-yl)-4-(4-fluorophenyl)-1H-imidazol-5-yl]-1H-indazole

The title compound was prepared according to the procedure outlined in Example 39 substituting 3-pyrrlidinobenzylamine for benzylamine. $^1$H NMR (500 MHz, DMSO-$d_6$/D$_2$O) δ ppm 13.29 (s, 1H) 8.13 (s, 1H) 8.03 (s, 1H) 7.76 (s, 1H) 7.67 (d, J=8.54 Hz, 1H) 7.29-7.38 (m, 6H) 7.20-7.28 (m, 2H) 6.98 (t, J=9.00 Hz, 2H) 4.25-4.34 (m, 1H) 3.53-3.69 (m, 2H) 2.89-2.97 (m, 1H) 2.84 (d, J=9.76, 3.05 Hz, 1H) 2.55 (d, J=10.07, 6.71 Hz, 1H) 2.17-2.34 (m, 2H) 1.92-2.03 (m, 1H). MS (ESI+) m/z 438.1 (M+H)$^+$.

Example 100

Example 100 has been removed and is not part of this document.

Example 101

2-{4-[4-(4-fluorophenyl)-5-(1H-indazol-5-yl)-1H-imidazol-1-yl]piperidin-1-yl}-2-oxoethanol The title compound was prepared according to the procedure outlined in Example 39 substituting 1-(4-aminopiperidin-1-yl)-2-hydroxyethanone for benzylamine. $^1$H NMR (300 MHz, DMSO-$d_6$/D$_2$O) δ ppm 13.27 (s, 1H) 8.14 (s, 1H) 7.99 (s, 1H) 7.81 (s, 1H) 7.69 (d, J=8.48 Hz, 1H) 7.25-7.39

(m, 4H) 6.91-7.03 (m, 2H) 4.48 (t, J=5.43 Hz, 1H) 4.34-4.44 (m, 1H) 4.07 (t, J=5.59 Hz, 1H) 3.79-3.91 (m, 1H) 3.64-3.77 (m, 1H) 2.85 (m, 1H) 2.77-2.90 (m, 5H). MS (DCI) m/z 420 (M+H)$^+$.

Example 102

5-(1-benzyl-5-phenyl-1H-1,2,3-triazol-4-yl)-1H-indazol-3-amine

Example 102A 5-(1-Benzyl-5-phenyl-1H-1,2,3-triazol-4-yl)-2-fluorobenzonitrile Example 87B (415 mg, 0.792 mmol), 5-bromo-2-fluorobenzonitrile (158 mg, 0.790 mmol), dichlorobis(triphenylphosphine)palladium(II) (52 mg, 0.074 mmol), and copper thiophene-2-carboxylate (226 mg, 1.19 mmol) were combined in toluene (2 mL) in a microwave vial under an inert atmosphere of nitrogen. The vial was heated in a microwave (CEM-Discover) to 150° C. at 125 Watts for 20 minutes. The mixture was absorbed on silica gel and purified by silica gel chromatography eluting with a gradient of ethyl acetate in hexanes (5-40%) to afford the title compound. MS (ESI+) m/z 355.1 (M+H)$^+$.

Example 102B 5-(1-benzyl-5-phenyl-1H-1,2,3-triazol-4-yl)-1H-indazol-3-amine

Example 102A (120 mg, 0.339 mmol) was treated with hydrazine hydrate (1.0 mL) in ethanol (1.0 mL) and heated to 60° C. overnight. The mixture was diluted with methylene chloride and washed with water. The organic layer was absorbed on silica gel and purified by silica gel chromatography eluting with a gradient of 0-5% methanol in dichloromethane to afford the title compound. $^1$H NMR (300 MHz, DMSO-d$_6$) δ ppm 11.40 (s, 1H) 8.06 (s, 1H) 7.42-7.55 (m, 3H) 7.23-7.33 (m, 5H) 7.02-7.10 (m, 2H) 6.94-7.02 (m, 2H) 5.49 (s, 2H) 5.34 (s, 2H). MS (ESI+) m/z 367.1 (M+H)$^+$.

Example 103

2-[1-(1H-indazol-5-yl)-1H-1,2,3-triazol-4-yl]propan-2-ol

The title compound was prepared according to the procedure outlined in Example 88 substituting 2-methyl-3-butyn-2-ol for 3-phenyl-1-propyne except that the crude reaction mixture was quenched with 2 mL of 1 N aqueous NaOH; and stirred for 1.5 hours at ambient temperature. The suspension was then dried by heated forced nitrogen gas evaporation prior to extraction. $^1$H NMR (500 MHz, DMSO-d$_6$/D$_2$O) δ ppm 8.51 (s, 1H) 8.22-8.29 (m, 2H) 7.88 (d, J=9.00, 1.98 Hz, 1H) 7.77 (d, J=8.85 Hz, 1H) 1.57 (s, 6H). MS (ESI+) m/z 244.0 (M+H)$^+$.

Example 104

5-[4-(methoxymethyl)-1H-1,2,3-triazol-1-yl]-1H-indazole

The title compound was prepared according to the procedure outlined in Example 88 substituting methyl propargyl ether for 3-phenyl-1-propyne. $^1$H NMR (500 MHz, DMSO-d$_6$/D$_2$O) δ ppm 8.73 (s, 1H) 8.23-8.29 (m, J=1.83 Hz, 2H) 7.88 (d, J=8.85, 2.14 Hz, 1H) 7.78 (d, J=9.15 Hz, 1H) 4.57 (s, 2H) 3.35 (s, 3H). MS (ESI+) m/z 230.0 (M+H)$^+$.

Example 105

1-[1-(1H-indazol-5-yl)-1H-1,2,3-triazol-4-yl]-1-phenylethanol

The title compound was prepared according to the procedure outlined in Example 88 substituting 2-phenyl-3-butyn-2-ol for 3-phenyl-1-propyne. $^1$H NMR (500 MHz, DMSO-d$_6$/D$_2$O) δ ppm 8.52 (s, 1H) 8.21-8.28 (m, 2H) 7.87 (d, J=8.85, 2.14 Hz, 1H) 7.76 (d, J=9.15 Hz, 1H) 7.51-7.57 (m, 2H) 7.34 (t, J=7.78 Hz, 2H) 7.24 (t, J=7.32 Hz, 1H) 1.92 (s, 3H). MS (ESI+) m/z 306.0 (M+H)$^+$.

Example 106

5-(4-propyl-1H-1,2,3-triazol-1-yl)-1H-indazole

The title compound was prepared according to the procedure outlined in Example 88 substituting 1-pentyne for 3-phenyl-1-propyne. $^1$H NMR (500 MHz, DMSO-d$_6$/D$_2$O) δ ppm 8.50 (s, 1H) 8.20-8.30 (m, 2H) 7.87 (d, J=9.00, 1.98 Hz, 1H) 7.77 (d, J=8.85 Hz, 1H) 2.71 (t, J=7.48 Hz, 2H) 1.64-1.78 (m, 2H) 0.97 (t, J=7.32 Hz, 3H). MS (ESI+) m/z 228.0 (M+H)$^+$.

Example 107

1-[1-(1H-indazol-5-yl)-1H-1,2,3-triazol-4-yl]propan-2-ol

The title compound was prepared according to the procedure outlined in Example 88 substituting pent-4-yn-2-ol for 3-phenyl-1-propyne. $^1$H NMR (500 MHz, DMSO-d$_6$/D$_2$O) δ ppm 8.49 (s, 1H) 8.20-8.33 (m, 2H) 7.88 (dd, J=9.00, 1.98 Hz, 1H) 7.74-7.82 (m, 1H) 3.95-4.08 (m, 1H) 2.74-2.89 (m, 2H) 1.16 (d, J=6.10 Hz, 3H). MS (ESI+) m/z 244.0 (M+H)$^+$.

Example 108

3-[1-(1H-indazol-5-yl)-1H-1,2,3-triazol-4-yl]propan-1-ol

The title compound was prepared according to the procedure outlined in Example 88 substituting 4-pentyn-1-ol for 3-phenyl-1-propyne. $^1$H NMR (500 MHz, DMSO-d$_6$/D$_2$O) δ ppm 8.50 (s, 1H) 8.28 (s, 1H) 8.23 (d, J=1.83 Hz, 1H) 7.83-7.91 (m, 1H) 7.74-7.82 (m, 1H) 4.50 (t, J=6.41 Hz, 1H) 3.51 (t, J=6.41 Hz, 2H) 2.77 (t, J=7.63 Hz, 2H) 1.80-1.90 (m, 2H)MS (ESI+) m/z 244.0 (M+H)$^+$.

Example 109

1-{[1-(1H-indazol-5-yl)-1H-1,2,3-triazol-4-yl]methyl}-1H-1,2,3-benzotriazole

The title compound was prepared according to the procedure outlined in Example 88 substituting 1-propargyl-1H-benzotriazole for 3-phenyl-1-propyne. $^1$H NMR (500 MHz, DMSO-d$_6$/D$_2$O) δ ppm 8.91 (s, 1H) 8.21-8.29 (m, 2H) 8.07 (d, J=8.54 Hz, 1H) 7.99 (d, J=8.54 Hz, 1H) 7.84 (d, J=9.00, 1.98 Hz, 1H) 7.72-7.81 (m, 1H) 7.57-7.65 (m, 1H) 7.41-7.52 (m, 1H) 6.16 (s, 2H). MS (ESI−) m/z 315.0 (M−H)$^−$.

Example 110

5-{4-[(phenylthio)methyl]-1H-1,2,3-triazol-1-yl}-1H-indazole

The title compound was prepared according to the procedure outlined in Example 88 substituting phenyl propargyl sulfide for 3-phenyl-1-propyne. $^1$H NMR (500 MHz, DMSO-$d_6$/$D_2O$) δ ppm 8.59 (s, 1H) 8.26 (s, 1H) 8.21 (d, J=1.22 Hz, 1H) 7.80-7.86 (m, 1H) 7.72-7.79 (m, 1H) 7.43 (d, J=8.39, 1.37 Hz, 2H) 7.35 (t, J=7.78 Hz, 2H) 7.22 (t, J=7.32 Hz, 1H) 4.38 (s, 2H). MS (ESI+) m/z 308.3 (M+H)$^+$.

Example 111

5-(4-cyclopropyl-1H-1,2,3-triazol-1-yl)-1H-indazole

The title compound was prepared according to the procedure outlined in Example 88 substituting cyclopropylacetylene for 3-phenyl-1-propyne. $^1$H NMR (500 MHz, DMSO-$d_6$/$D_2O$) δ ppm 8.46 (s, 1H) 8.25 (s, 1H) 8.20 (d, J=1.53 Hz, 1H) 7.84 (d, J=9.00, 1.98 Hz, 1H) 7.76 (d, J=8.85 Hz, 1H) 1.97-2.14 (m, 1H) 0.93-1.06 (m, 2H) 0.77-0.91 (m, 2H). MS (ESI+) m/z 226.0 (M+H)$^+$.

Example 112

5-[4-(2-phenylethyl)-1H-1,2,3-triazol-1-yl]-1H-indazole

The title compound was prepared according to the procedure outlined in Example 88 substituting 1-phenyl-1-butyne for 3-phenyl-1-propyne. The product was a 1:1 mixture of starting material and title compound. $^1$H NMR (500 MHz, DMSO-$d_6$/$D_2O$) δ ppm 8.48 (s, 1H) 8.25 (s, 1H) 8.21 (d, J=1.53 Hz, 1H) 8.06 (s, 1H) 7.81-7.89 (m, 1H) 7.73-7.80 (m, 1H) 7.61 (dd, J=8.85, 1.53 Hz, 1H) 7.45 (d, J=8.54 Hz, 1H) 7.25-7.36 (m, 4H) 7.17-7.25 (m, 1H) 3.04 (s, 4H). MS (ESI+) m/z 290.1 (M+H)$^+$.

Example 113

5-[4-(cyclohexylmethyl)-1H-1,2,3-triazol-1-yl]-1H-indazole

The title compound was prepared according to the procedure outlined in Example 88 substituting 3-cyclohexyl-1-propyne for 3-phenyl-1-propyne. $^1$H NMR (500 MHz, DMSO-$d_6$/$D_2O$) δ ppm 8.49 (s, 1H) 8.21-8.29 (m, 2H) 7.88 (d, J=9.00, 1.98 Hz, 1H) 7.77 (d, J=8.85 Hz, 1H) 2.61 (d, J=6.71 Hz, 2H) 1.54-1.77 (m, 6H) 1.08-1.30 (m, 3H) 0.91-1.05 (m, 2H). MS (ESI+) m/z 282.2 (M+H)$^+$.

Example 114

5-(4-cyclopentyl-1H-1,2,3-triazol-1-yl)-1H-indazole

The title compound was prepared according to the procedure outlined in Example 88 substituting cyclopentylacetylene for 3-phenyl-1-propyne. $^1$H NMR (500 MHz, DMSO-$d_6$/$D_2O$) δ ppm 8.52 (s, 1H) 8.19-8.30 (m, 2H) 7.88 (d, J=9.00, 1.98 Hz, 1H) 7.77 (d, J=8.85 Hz, 1H) 3.13-3.27 (m, 1H) 1.98-2.15 (m, 2H) 1.57-1.84 (m, 6H). MS (ESI+) m/z 254.0 (M+H)$^+$.

Example 115

1-[1-(1H-indazol-5-yl)-1H-1,2,3-triazol-4-yl]cyclohexanol

The title compound was prepared according to the procedure outlined in Example 88 substituting 1-ethynyl-1-cyclohexanol for 3-phenyl-1-propyne. $^1$H NMR (500 MHz, DMSO-$d_6$/$D_2O$) δ ppm 8.52 (s, 1H) 8.21-8.30 (m, J=1.53 Hz, 2H) 7.89 (dd, J=9.00, 1.98 Hz, 1H) 7.77 (d, J=8.85 Hz, 1H) 2.16-2.46 (m, 1H) 1.92-2.05 (m, 2H) 1.77-1.86 (m, 2H) 1.61-1.77 (m, 2H) 1.51-1.59 (m, 1H) 1.42-1.51 (m, 2H) 1.28-1.40 (m, J=9.92, 2.90 Hz, 1H) MS (ESI+) m/z 284.0 (M+H)$^+$.

Example 116

5-[4-(phenoxymethyl)-1H-1,2,3-triazol-1-yl]-1H-indazole

The title compound was prepared according to the procedure outlined in Example 88 substituting phenyl propargyl ether for 3-phenyl-1-propyne. $^1$H NMR (500 MHz, DMSO-$d_6$/$D_2O$) δ ppm 8.87 (s, 1H) 8.22-8.34 (m, 2H) 7.89 (d, J=8.85, 1.83 Hz, 1H) 7.79 (d, J=9.15 Hz, 1H) 7.29-7.41 (m, 2H) 7.09 (d, J=7.63 Hz, 2H) 6.99 (t, J=7.32 Hz, 1H) 5.25 (s, 2H). MS (ESI+) m/z 292.0 (M+H)$^+$.

Example 117

5-{4-[(1,1-dioxidothiomorpholin-4-yl)methyl]-1H-1,2,3-triazol-1-yl}-1H-indazole The title compound was prepared according to the procedure outlined in Example 88 substituting N-propargyl thiomorpholine-sulfone for 3-phenyl-1-propyne. $^1$H NMR (500 MHz, DMSO-$d_6$/$D_2O$) δ ppm 8.81 (s, 1H) 8.24-8.36 (m, 2H) 7.89 (d, J=9.00, 1.98 Hz, 1H) 7.80 (d, J=9.15 Hz, 1H) 4.38 (s, 2H) 3.30-3.56 (m, J=39.36 Hz, 8H). MS (ESI+) m/z 332.9 (M+H)$^+$.

Example 118

5-[4-(3-phenylpropyl)-1H-1,2,3-triazol-1-yl]-1H-indazole

The title compound was prepared according to the procedure outlined in Example 88 substituting 1-phenyl-1-pentyne for 3-phenyl-1-propyne. $^1$H NMR (500 MHz, DMSO-$d_6$/$D_2O$) δ ppm 8.52 (s, 1H) 8.26 (s, 1H) 8.23 (d, J=1.53 Hz, 1H) 7.87 (d, J=9.00, 1.98 Hz, 1H) 7.76 (d, J=9.15 Hz, 1H) 7.31 (t, J=7.32 Hz, 2H) 7.23-7.28 (m, 2H) 7.20 (t, J=7.32 Hz, 1H) 2.74 (t, J=7.63 Hz, 2H) 2.65-2.72 (m, 2H) 1.95-2.05 (m, 2H). MS (ESI+) m/z 304.2 (M+H)$^+$.

Example 119

[1-benzyl-4-(1H-indazol-5-yl)-1H-1,2,3-triazol-5-yl](phenyl)methanone

Example 119A tert-Butyl 5-ethynyl-1H-indazole-1-carboxylate

To a solution of Example 3C (230 mg, 1.62 mmol) in dichloromethane (10 mL) was added di-tert-butyl dicarbonate (459 mg, 2.1 mmol) and a pinch of dimethylaminopyridine (~3 mg), and the mixture was stirred for 30 minutes at room temperature. Water was added, and the product was extracted with dichloromethane, dried over sodium sulfate, filtered, and the solvent was evaporated under reduced pressure to afford the title compound. MS (ESI+) m/z 265.0 (M+Na)+.

Example 119B

[1-benzyl-4-(1H-indazol-5-yl)-1H-1,2,3-triazol-5-yl](phenyl)methanone

A vial under argon containing Example 119A (90 mg, 0.37 mmol), benzyl azide (0.047 mL, 0.37 mmol), tetrahydrofuran (3 mL), triethylamine (0.062 mL, 0.44 mmol), CuI (71 mg, 0.37 mmol) and benzoyl chloride (0.059 mL, 0.51 mmol) was capped and shaken for 16 hours. The solvents were evaporated, and the product was purified by silica gel column chromatography in 5-30% ethyl acetate in hexanes. The crude material was treated with TFA (0.5 mL) in dichloromethane (1 mL) and purified by reverse-phase HPLC using an acetonitrile/water 0.1% TFA gradient elution method to afford the title compound. $^1$H NMR (500 MHz, DMSO-$d_6$/$D_2O$) δ ppm 13.08 (s, 1H) 7.98 (s, 1H) 7.77 (s, 1H) 7.54 (d, J=8.24, 1.22 Hz, 2H) 7.43-7.48 (m, 1H) 7.33-7.40 (m, 2H) 7.22-7.30 (m, 5H) 7.17-7.21 (m, 2H) 5.74 (s, 2H). MS (ESI+) m/z 380.1 (M+H)+.

Example 120

N,N-diethyl-N-{[1-(1H-indazol-5-yl)-1H-1,2,3-triazol-4-yl]methyl}amine

The title compound was prepared according to the procedure outlined in Example 88 substituting 1,1-diethylpropargylamine for 3-phenyl-1-propyne. $^1$H NMR (300 MHz, DMSO-$d_6$) δ ppm 8.98 (s, 1H) 8.30 (d, J=1.36 Hz, 1H) 8.27 (s, 1H) 7.85-7.93 (m, 1H) 7.75-7.83 (m, 1H) 4.53 (d, J=4.07 Hz, 2H) 3.11-3.23 (m, 4H) 1.31 (t, J=7.12 Hz, 6H). MS (ESI+) m/z 271.0 (M+H)+.

Example 121

Ethyl N-[2-(1H-indazol-5-yl)imidazo[1,2-a]pyrimidin-3-yl]-beta-alaninate

The title compound was prepared according to the procedure outlined in Example 43 substituting ethyl isocyanopropionate for isopropyl isocyanide. $^1$H NMR (300 MHz, DMSO-$d_6$) δ ppm 13.09 (s, 1H) 8.71 (d, J=6.78, 2.03 Hz, 1H) 8.54 (s, 1H) 8.46 (d, J=4.24, 1.87 Hz, 1H) 8.23 (d, J=8.82, 1.36 Hz, 1H) 8.14 (s, 1H) 7.61 (d, J=8.82 Hz, 1H) 7.05 (d, J=6.78, 4.07 Hz, 1H) 5.03 (t, J=5.93 Hz, 1H) 3.96 (q, J=7.12 Hz, 2H) 3.23 (q, J=6.22 Hz, 2H) 2.47-2.55 (m, 2H) 1.08 (t, J=7.12 Hz, 3H). MS (ESI+) m/z 351.1 (M+H)+.

Example 122

5-(1-benzyl-5-methyl-1H-1,2,3-triazol-4-yl)-1H-indazole

Example 122A

1-Benzyl-5-methyl-4-(tributylstannyl)-1H-1,2,3-triazole

Tributyl(1-propynyl)tin (3.87 g, 11.8 mmol) and benzyl azide (2.2 mL, 17.6 mmol) were combined and heated to 150° C. overnight. The mixture was purified by silica gel chromatography eluting with a gradient of 5-40% ethyl acetate in hexanes to afford the title compound. MS (ESI+) m/z 464.2 (M+H)+.

Example 122B 1-(5-(1-Benzyl-5-methyl-1H-1,2,3-triazol-4-yl)-1H-indazol-1-yl)ethanone Example 87A (235 mg, 0.821 mmol), Example 122A (380 mg, 0.822 mmol), dichlorobis(triphenylphosphine)palladium(II) (60 mg, 0.085 mmol), and copper thiophene-2-carboxylate (325 mg, 1.23 mmol) were combined in toluene (2.0 mL) in a microwave vial under an inert atmosphere of nitrogen. The vial was heated in a microwave (CEM-Discover) to 150° C. at 125 Watts for 20 minutes. The mixture was absorbed on silica gel and purified by silica gel chromatography eluting with a gradient of 5-40% ethyl acetate in hexanes to afford the title compound. MS (ESI+) m/z 332.2 (M+H)+.

Example 122C 5-(1-benzyl-5-methyl-1H-1,2,3-triazol-4-yl)-1H-indazole

Example 122B (109 mg, 0.329 mmol) was dissolved in tetrahydrofuran (3.0 mL) and water (0.5 mL), and potassium hydroxide (53 mg, 0.945 mmol) was added. The mixture was stirred for 2 hours, diluted with ethyl acetate, and washed with water. The organic layer was absorbed on silica gel and purified by silica gel chromatography eluting with a gradient of 0-5% methanol in dichloromethane to afford the title compound. $^1$H NMR (300 MHz, DMSO-$d_6$) δ ppm 13.13 (s, 1H) 8.12 (s, 1H) 8.01 (s, 1H) 7.71-7.78 (m, 1H) 7.59-7.66 (m, 1H) 7.31-7.45 (m, 3H) 7.23-7.29 (m, 2H) 5.65 (s, 2H) 2.43 (s, 3H). MS (ESI+) m/z 290.1 (M+H)+.

Example 123

5-(1-benzyl-5-methyl-1H-1,2,3-triazol-4-yl)-1H-indazol-3-amine

Example 123A 5-(1-Benzyl-5-methyl-1H-1,2,3-triazol-4-yl)-2-fluorobenzonitrile Example 122A (415 mg, 0.792 mmol), 5-bromo-2-fluorobenzonitrile (158 mg, 0.790 mmol), dichlorobis(triphenylphosphine)palladium(II) (52 mg, 0.074 mmol), and copper thiophene-2-carboxylate (226 mg, 1.19 mmol) were combined in toluene (2 mL) in a microwave vial under an inert atmosphere of nitrogen. The vial was heated in a microwave (CEM-Discover) at 150° C. at 125 Watts for 20 minutes. The mixture was absorbed on silica gel and purified by silica gel chromatography eluting with a gradient of 5-40% ethyl acetate in hexanes to afford the title compound. MS (ESI+) m/z 293.0 (M+H)+.

Example 123B 5-(1-benzyl-5-methyl-1H-1,2,3-triazol-4-yl)-1H-indazol-3-amine

Example 123A (120 mg, 0.339 mmol) was treated with hydrazine hydrate (1.0 mL) in ethanol (1.0 mL) and heated to 60° C. overnight. The mixture was diluted with methylene chloride and washed with water. The organic layer was absorbed on silica gel and purified by silica gel chromatography eluting with a gradient of methanol in dichloromethane (0-5%) to afford the title compound. $^1$H NMR (300 MHz, DMSO-$d_6$) δ ppm 11.43 (s, 1H) 7.98 (s, 1H) 7.60 (d, J=8.65, 1.53 Hz, 1H) 7.27-7.44 (m, 4H) 7.21-7.27 (m, 2H) 5.65 (s, 2H) 5.41 (s, 2H) 2.41 (s, 3H). MS (ESI+) m/z 305.1 (M+H)$^+$.

Example 124

$N^3$-[2-(1H-indazol-5-yl)imidazo[1,2-a]pyrimidin-3-yl]-β-alaninamide

Example 121 (42 mg, 0.120 mmol) and a solution of 7 N ammonia in methanol (1.0 mL) were combined and heated to 60° C. overnight. The mixture was absorbed on silica gel and purified by silica gel chromatography eluting with a gradient of methanol in dichloromethane (1-7%) to afford the title compound. $^1$H NMR (300 MHz, DMSO-$d_6$) δ ppm 13.09 (s, 1H) 8.76 (d, J=6.78, 2.03 Hz, 1H) 8.56 (s, 1H) 8.45 (d, J=4.07, 2.03 Hz, 1H) 8.24 (d, J=8.82, 1.36 Hz, 1H) 8.15 (s, 1H) 7.61 (d, J=8.48 Hz, 1H) 7.32 (s, 1H) 7.03 (d, J=6.78, 4.07 Hz, 1H) 6.85 (s, 1H) 4.93 (t, J=6.10 Hz, 1H) 3.11-3.23 (m, 2H) 2.32 (t, J=6.78 Hz, 2H). MS (ESI+) m/z 322.0 (M+H)$^+$.

Example 125

5-(1-benzyl-5-iodo-1H-1,2,3-triazol-4-yl)-1H-indazol-3-amine

Example 125A 5-(1-Benzyl-5-iodo-1H-1,2,3-triazol-4-yl)-2-fluorobenzonitrile

A mixture of Example 62B (200 mg, 1.38 mmol), benzyl azide (0.176 mL, 1.38 mmol), tetrahydrofuran (12 mL), triethylamine (0.230, 1.56 mmol), CuI (263 mg, 1.38 mmol) and ICl (0.069 mL, 1.38 mmol) under argon was stirred at room temperature for 24 hours. The solvent was evaporated and the crude mixture was dissolved in dichloromethane, loaded directly onto a silica gel column and eluted with ethyl acetate/hexanes (10-20%) to afford the title compound. MS (ESI+) m/z 404.9 (M+H)$^+$.

Example 125B 5-(1-benzyl-5-iodo-1H-1,2,3-triazol-4-yl)-1H-indazol-3-amine

Example 125A (50 mg, 0.12 mmol) and hydrazine monohydrate (1 mL) in ethanol (1 mL) were heated at 95° C. for 2 hours. Water was added, and the solid was collected by filtration and further purified by reverse-phase HPLC using an acetonitrile/water 0.1% TFA gradient elution method to afford the title compound as a TFA salt. $^1$H NMR (500 MHz, DMSO-$d_6$) δ ppm 12.07 (s, 1H) 8.30 (s, 1H) 7.83 (d, J=8.85, 1.53 Hz, 1H) 7.44 (d, J=8.54 Hz, 1H) 7.38-7.43 (m, J=7.32, 7.32 Hz, 2H) 7.32-7.37 (m, 1H) 7.23-7.27 (m, J=7.02 Hz, 2H) 5.74 (s, 2H) 4.00 (s, 2H). MS (ESI+) m/z 417.0 (M+H)$^+$.

Example 126

N-{3-[4-(3-amino-1H-indazol-5-yl)-1-benzyl-1H-1,2,3-triazol-5-yl]phenyl}-N'-(3-methylphenyl)urea Example 126A 1-(3-(1-Benzyl-4-(3-cyano-4-fluorophenyl)-1H-1,2,3-triazol-5-yl)phenyl)-3-m-tolylurea A vial under argon containing Example 125A (94 mg, 0.23 mmol), 1-(3-(4,4,5,5-tetramethyl-1,3,2-dioxaborolan-2-yl)phenyl)-3-m-tolylurea (prepared according to a procedure described in WO2004/113304) (990 mg, 0.26 mmol), PdCl$_2$dppf.dichloromethane (19 mg, 0.02 mmol), potassium carbonate (64 mg, 0.46 mmol), DME (2 mL) and water (0.2 mL) was capped and heated in a heater shaker at 80° C. for 90 minutes. The solvents were evaporated and the product was extracted with methanol/dichloromethane. Silica gel column chromatography using 10% ethyl acetate in hexanes afforded the title compound. MS (ESI+) m/z 503.2 (M+H)$^+$.

Example 126B

N-{3-[4-(3-amino-1H-indazol-5-yl)-1-benzyl-1H-1,2,3-triazol-5-yl]phenyl}-N'-(3-methylphenyl)urea Example 126A (25 mg, 0.05 mmol) and hydrazine monohydrate (0.5 mL) in ethanol (2 mL) were heated at 80° C. for 1 hour. The crude mixture was loaded onto a silica gel column and eluted with a gradient of 0-5% methanol in dichloromethane to afford the title compound. $^1$H NMR (500 MHz, DMSO-$d_6$) δ ppm 11.40 (s, 1H) 8.79 (s, 1H) 8.63 (s, 1H) 8.12 (s, 1H) 7.57 (d, J=8.24, 1.22 Hz, 1H) 7.43 (t, J=1.83 Hz, 1H) 7.38 (t, J=7.93 Hz, 1H) 7.23-7.34 (m, 4H) 7.08-7.22 (m, 4H) 7.03 (d, J=6.71 Hz, 2H) 6.88 (d, J=7.63 Hz, 1H) 6.78 (d, J=7.32 Hz, 1H) 5.50 (s, 2H) 5.36 (s, 2H) 2.26 (s, 3H). MS (ESI+) m/z 515.3 (M+H)$^+$.

Example 127

5-(1H-indazol-5-yl)-N-(2-isopropoxyethyl)isoxazole-3-carboxamide

In a 20 mL vial a solution of 81A (37 mg, 0.18 mmol) dissolved in dimethylformamide (0.8 mL) was added, followed by the addition of HATU (61 mg, 0.18 mmol) dissolved in dimethylformamide (0.8 mL). Then a solution of 2-isopropoxyethanamine (20 mg, 0.20 mmol) dissolved in dimethylformamide (0.9 mL) was added followed by diisopropylethylamine (42 mg, 0.36 mmol) dissolved in dimethylformamide (0.8 mL). The mixture was then shaken at 40° C. for three hours. The crude reaction mixture was filtered through a Si-carbonate cartridge (6 mL, 2 g) supplied by Silicycle Chemical Division with methanol, checked with LC/MS, and concentrated to dryness. The residue was dissolved in 1:1 DMSO/methanol and purified by reverse phase HPLC (Agilent, 5%-100% TFA/water gradient, 8 minute run). $^1$H NMR (300 MHz, DMSO-$d_6$/D$_2$O) δ ppm 8.38-8.43 (m, 1H) 8.22-8.30 (m, 1H) 7.90 (d, 1H) 7.73 (d, 1H) 7.21-7.29 (m, 1H) 3.56-3.65 (m, 1H) 3.52 (t, 2H) 3.43 (t, 2H) 1.10 (d, 6H). MS (ESI+) m/z 315 (M+H)$^+$.

Example 128

5-[3-(morpholin-4-ylcarbonyl)isoxazol-5-yl]-1H-indazole

The title compound was prepared according to the procedure outlined in Example 127 substituting morpholine for 2-isopropoxyethanamine. $^1$H NMR (300 MHz, DMSO-$d_6$/$D_2O$) δ ppm 8.36-8.43 (m, 1H) 8.22-8.29 (m, 1H) 7.89 (d, 1H) 7.72 (d, 1H) 7.11-7.22 (m, 1H) 3.68-3.72 (m, 4H) 3.61-3.68 (m, 4H). MS (ESI+) m/z 299 (M+H)$^+$.

Example 129

5-(1H-indazol-5-yl)-N-(3-morpholin-4-ylpropyl)isoxazole-3-carboxamide

The title compound was prepared as a TFA salt according to the procedure outlined in Example 127 substituting 3-morpholinopropan-1-amine for 2-isopropoxyethanamine. $^1$H NMR (300 MHz, DMSO-$d_6$/$D_2O$) δ ppm 8.37-8.46 (m, 1H) 8.20-8.31 (m, 1H) 7.91 (d, 1H) 7.73 (d, 1H) 7.17-7.36 (m, 1H) 3.98-4.08 (m, 2H) 3.57-3.73 (m, 2H) 3.42-3.51 (m, 2H) 3.35-3.41 (m, 2H) 3.14-3.22 (m, 2H) 3.01-3.14 (m, 2H) 1.88-2.06 (m, 2H). MS (ESI+) m/z 356 (M+H)$^+$.

Example 130

N-[2-(1H-imidazol-4-yl)ethyl]-5-(1H-indazol-5-yl)isoxazole-3-carboxamide

The title compound was prepared according to the procedure outlined in Example 127 substituting 2-(1H-imidazol-4-yl)ethanamine for 2-isopropoxyethanamine. $^1$H NMR (300 MHz, DMSO-$d_6$/$D_2O$) δ ppm 8.90-8.97 (m, 1H) 8.34-8.46 (m, 1H) 8.20-8.32 (m, 1H) 7.90 (d, 1H) 7.72 (d, 1H) 7.38-7.49 (m, 1H) 7.14-7.28 (m, 1H) 3.57 (t, 2H) 2.96 (t, 2H). MS (ESI+) m/z 323 (M+H)$^+$.

Example 131

(3R)-1-{[5-(1H-indazol-5-yl)isoxazol-3-yl]carbonyl}piperidin-3-ol

The title compound was prepared according to the procedure outlined in Example 127 substituting (R)-piperidin-3-ol hydrochloride for 2-isopropoxyethanamine. $^1$H NMR (300 MHz, DMSO-$d_6$/$D_2O$) δ ppm 8.34-8.45 (m, 1H) 8.19-8.30 (m, 1H) 7.89 (d, 1H) 7.72 (d, 1H) 7.13 (d, 1H) 4.03-4.19 (m, 1H) 3.64-3.72 (m, 1H) 3.54-3.62 (m, 1H) 3.34-3.44 (m, 1H) 3.20-3.32 (m, 1H) 2.99-3.10 (m, 1H) 1.67-2.03 (m, 2H) 1.36-1.61 (m, 2H). MS (ESI+) m/z 313 (M+H)$^+$.

Example 132

1-{[5-(1H-indazol-5-yl)isoxazol-3-yl]carbonyl}piperidine-3-carboxamide

The title compound was prepared according to the procedure outlined in Example 127 substituting piperidine-3-carboxamide for 2-isopropoxyethanamine. $^1$H NMR (300 MHz, DMSO-$d_6$/$D_2O$) δ ppm 8.36-8.45 (m, 1H) 8.22-8.32 (m, 1H) 7.90 (d, 1H) 7.72 (d, 1H) 7.07-7.23 (m, 1H) 4.27-4.56 (m, 1H) 3.91-4.05 (m, 1H) 3.09-3.37 (m, 1H) 2.85-3.04 (m, 1H) 2.31-2.45 (m, 1H) 1.89-2.05 (m, 1H) 1.73-1.86 (m, 1H) 1.60-1.72 (m, 1H) 1.36-1.55 (m, 1H). MS (ESI−) m/z 338 (M−H)$^−$.

Example 133

2-[2-(4-{[5-(1H-indazol-5-yl)isoxazol-3-yl]carbonyl}piperazin-1-yl)ethoxy]ethanol The title compound was prepared as a TFA salt according to the procedure outlined in Example 127 substituting 2-(2-(piperazin-1-yl)ethoxy)ethanol for 2-isopropoxyethanamine. $^1$H NMR (300 MHz, DMSO-$d_6$/$D_2O$) δ ppm 8.39-8.48 (m, 1H) 8.19-8.32 (m, 1H) 7.92 (d, 1H) 7.74 (d, 1H) 7.17-7.27 (m, 1H) 4.49-4.60 (m, 1H) 3.94-4.01 (m, 1H) 3.76-3.81 (m, 4H) 3.56-3.63 (m, 2H) 3.51-3.56 (m, 2H) 3.33-3.43 (m, 3H) 3.13-3.23 (m, 1H) 2.65-2.75 (m, 2H). MS (ESI+) m/z 386 (M+H)$^+$.

Example 134

5-{3-[(4-methyl-1,4-diazepan-1-yl)carbonyl]isoxazol-5-yl}-1H-indazole

The title compound was prepared as a TFA salt according to the procedure outlined in Example 127 substituting 1-methyl-1,4-diazepane for 2-isopropoxyethanamine. $^1$H NMR (300 MHz, DMSO-$d_6$/$D_2O$) δ ppm 8.38-8.46 (m, 1H) 8.22-8.32 (m, 1H) 7.85-7.98 (m, 1H) 7.75 (d, 1H) 7.22 (d, 1H) 4.07-4.19 (m, 1H) 3.69-3.77 (m, 2H) 3.59-3.67 (m, 1H) 3.44-3.59 (m, 1H) 3.35-3.44 (m, 1H) 3.24-3.35 (m, 2H) 2.84-2.95 (m, 3H) 2.66-2.74 (m, 1H) 2.10-2.26 (m, 2H). MS (ESI+) m/z 326 (M+H)$^+$.

Example 135

N-(3-hydroxypropyl)-5-(1H-indazol-5-yl)isoxazole-3-carboxamide

The title compound was prepared according to the procedure outlined in Example 127 substituting 3-aminopropan-1-ol for 2-isopropoxyethanamine. $^1$H NMR (300 MHz, DMSO-$d_6$/$D_2O$) δ ppm 8.36-8.45 (m, 1H) 8.20-8.30 (m, 1H) 7.84-7.94 (m, 1H) 7.71 (d, 1H) 7.18-7.28 (m, 1H) 3.48 (t, 2H) 3.35 (t, 2H) 1.64-1.78 (m, 2H). MS (ESI+) m/z 387 (M+H)$^+$.

Example 136

N-[(1R)-2-hydroxy-1-phenylethyl]-5-(1H-indazol-5-yl)isoxazole-3-carboxamide

The title compound was prepared according to the procedure outlined in Example 127 substituting (R)-2-amino-2-phenylethanol for 2-isopropoxyethanamine. $^1$H NMR (300 MHz, DMSO-$d_6$/$D_2O$) δ ppm 9.11 (d, 1H) 8.37-8.46 (m, 1H) 8.23-8.28 (m, 1H) 7.91 (d, 1H) 7.73 (d, 1H) 7.40-7.45 (m, 2H) 7.32-7.39 (m, 2H) 7.23-7.32 (m, 2H) 5.05-5.13 (m, 1H) 3.66-3.72 (m, 2H). MS (ESI+) m/z 349 (M+H)$^+$.

Example 137

N-[3-(1H-imidazol-1-yl)propyl]-5-(1H-indazol-5-yl)isoxazole-3-carboxamide

The title compound was prepared according to the procedure outlined in Example 127 substituting 3-(1H-imidazol-1-yl)propan-1-amine for 2-isopropoxyethanamine. $^1$H NMR (300 MHz, DMSO-$d_6$/$D_2O$) δ ppm 9.02-9.10 (m, 1H) 8.40-8.44 (m, 1H) 8.25-8.29 (m, 1H) 7.87-7.95 (m, 1H) 7.71-7.82 (m, 2H) 7.61-7.69 (m, 1H) 7.20-7.29 (m, 1H) 4.28 (t, 2H) 3.33 (t, 2H) 2.06-2.19 (m, 2H). MS (ESI+) m/z 337 (M+H)$^+$.

Example 138

5-(1H-indazol-5-yl)-N-[3-(2-oxopyrrolidin-1-yl) propyl]isoxazole-3-carboxamide

The title compound was prepared according to the procedure outlined in Example 127 substituting 1-(3-aminopropyl) pyrrolidin-2-one for 2-isopropoxyethanamine. $^1$H NMR (300 MHz, DMSO-$d_6$/D$_2$O) δ ppm 8.38-8.43 (m, 1H) 8.24-8.30 (m, 1H) 7.87-7.93 (m, 1H) 7.73 (d, 1H) 7.22-7.26 (m, 1H) 3.39 (t, 2H) 3.21-3.30 (m, 4H) 2.26 (t, 2H) 1.90-2.00 (m, 2H) 1.70-1.79 (m, 2H). MS (ESI+) m/z 354 (M+H)$^+$.

Example 139

N-{2-[4-(aminosulfonyl)phenyl]ethyl}-5-(1H-indazol-5-yl)isoxazole-3-carboxamide

The title compound was prepared according to the procedure outlined in Example 127 substituting 4-(2-aminoethyl) benzenesulfonamide for 2-isopropoxyethanamine. $^1$H NMR (300 MHz, DMSO-$d_6$/D$_2$O) δ ppm 8.37-8.42 (m, 1H) 8.24-8.29 (m, 1H) 7.86-7.93 (m, 1H) 7.70-7.80 (m, 3H) 7.47 (d, 2H) 7.20-7.24 (m, 1H) 3.57 (t, 2H) 2.96 (t, 2H). MS (ESI+) m/z 412 (M+H)$^+$.

Example 140

[1-benzyl-4-(1H-indazol-5-yl)-1H-1,2,3-triazol-5-yl] (3-chlorophenyl)methanone

The title compound was prepared according to the procedure outlined in Example 119B substituting 3-chlorobenzoyl chloride for benzoyl chloride. $^1$H NMR (500 MHz, DMSO-$d_6$) δ ppm 13.09 (s, 1H) 7.99 (s, 1H) 7.77 (s, 1H) 7.38-7.51 (m, 4H) 7.28-7.37 (m, 3H) 7.20-7.27 (m, 4H) 5.78 (s, 2H). MS (ESI+) m/z 414.1 (M+H)$^+$.

Example 141

[1-benzyl-4-(1H-indazol-5-yl)-1H-1,2,3-triazol-5-yl] (cyclopropyl)methanone

The title compound was prepared according to the procedure outlined in Example 119B substituting cyclopropanecarbonyl chloride for benzoyl chloride. $^1$H NMR (500 MHz, DMSO-$d_6$) δ ppm 13.26 (s, 1H) 8.18 (s, 1H) 8.08 (s, 1H) 7.61-7.70 (m, 2H) 7.29-7.40 (m, 3H) 7.24 (d, J=7.02 Hz, 2H) 5.79 (s, 2H) 1.86-2.00 (m, 1H) 0.98-1.12 (m, 2H) 0.77-0.93 (m, 2H). MS (ESI+) m/z 344.1 (M+H)$^+$.

Example 142

5-[5-cyclopropyl-1-(tetrahydro-2H-pyran-4-ylmethyl)-1H-1,2,3-triazol-4-yl]-1H-indazole

Example 142A

5-Cyclopropyl-1-((tetrahydro-2H-pyran-4-yl)methyl)-4-(tributylstannyl)-1H-1,2,3-triazole Cyclopropyl acetylene (142 mg, 2.15 mmol) was added to 1,1,1-tributyl-N,N-dimethylstannanamine (716 mg, 2.14 mmol) in hexane (3.0 mL) and stirred in a sealed vial at 70° C. for 2 hours. The mixture was cooled to ambient temperature, and the vial was stirred unsealed for 10 minutes. Example 80A (455 mg, 3.22 mmol) was added, and the vial was resealed and heated to 130° C. overnight. The mixture was purified by silica gel chromatography eluting with a gradient of ethyl acetate in hexanes (5-50%) to afford the title compound. MS (ESI+) m/z 498.3 (M+H)$^+$.

Example 142B 1-(5-(5-Cyclopropyl-1-((tetrahydro-2H-pyran-4-yl) methyl)-1H-1,2,3-triazol-4-yl)-1H-indazol-1-yl)ethanone Example 142A (220 mg, 0.444 mmol), Example 87A (128 mg, 0.447 mmol), dichlorobis(triphenylphosphine)palladium(II) (33 mg, 0.047 mmol), and copper thiophene-2-carboxylate (127 mg, 0.666 mmol) were combined in toluene (2.0 mL) in a 4 mL vial under an inert atmosphere of nitrogen. The vial was sealed and heated 150° C. for 20 minutes. The mixture was absorbed on silica gel and purified by silica gel chromatography eluting with a gradient of 5-70% ethyl acetate in hexanes to afford the title compound. MS (ESI+) m/z 366.0 (M+H)$^+$.

Example 142C

5-[5-cyclopropyl-1-(tetrahydro-2H-pyran-4-ylmethyl)-1H-1,2,3-triazol-4-yl]-1H-indazole Example 142B (46 mg, 0.126 mmol) was dissolved in tetrahydrofuran (2.0 mL) and water (0.5 mL) and potassium hydroxide (80 mg, 1.43 mmol) was added. The mixture was stirred for 2 hours, and was diluted with methylene chloride and washed with water. The organic layer was absorbed on silica gel and purified by silica gel chromatography eluting with a gradient of 0-8% methanol in dichloromethane to afford the title compound. $^1$H NMR (300 MHz, CDCl$_3$) δ ppm 8.19 (s, 1H) 7.96 (d, J=8.82 Hz, 1H) 7.61 (d, J=7.80 Hz, 1H) 7.25-7.28 (m, 1H) 4.34 (d, J=6.44 Hz, 2H) 4.02 (d, J=11.36, 3.56 Hz, 2H) 3.42 (t, J=11.53 Hz, 2H) 2.33-2.46 (m, 1H) 1.81-1.95 (m, 1H) 1.59-1.70 (m, 2H) 1.43-1.58 (m, 2H) 1.23-1.28 (m, 1H) 1.10-1.20 (m, 2H) 0.47-0.62 (m, 2H). MS (ESI+) m/z 324.1 (M+H)$^+$.

Example 143

N$^1$-{[1-benzyl-4-(1H-indazol-5-yl)-1H-1,2,3-triazol-5-yl]methyl}glycinamide

Example 143A 2-((1-Benzyl-4-(tributylstannyl)-1H-1,2,3-triazol-5-yl)methyl)isoindoline-1,3-dione N-Propargylphthalimide (2.35 g mg, 12.7 mmol) was added to 1,1,1-tributyl-N,N-dimethylstannanamine (4.23 mg, 12.7 mmol) in hexane (3.0 mL) and stirred in a sealed vial at 70° C. for 2 hours. The mixture was cooled to ambient temperature and the vial was stirred unsealed for 10 minutes. Benzyl azide (2.0 mL, 16.0 mmol) was added and the vial was resealed and heated to 130° C. overnight. The mixture was purified by silica gel chromatography eluting with a gradient of 10-50% ethyl acetate in hexanes to afford the title compound. MS (ESI+) m/z 609.3 (M+H)$^+$.

Example 143B 2-((4-(1-Acetyl-1H-indazol-5-yl)-1-benzyl-1H-1,2,3-triazol-5-yl)methyl)isoindoline-1,3-dione Example 143A (567 mg, 0.934 mmol), Example 87A (268 mg, 0.934 mmol), dichlorobis(triphenylphosphine)palladium(II) (67 mg, 0.095 mmol), and copper thiophene-2-carboxylate (268 mg, 1.41 mmol) were combined in toluene (2.5 mL) in a microwave vial under an inert atmosphere of nitrogen. The vial was heated in a microwave (CEM-Discover) to 150° C. at 125 Watts for 20 minutes. The mixture was absorbed on silica gel and purified by silica gel chromatography eluting with a gradient of 10-50% ethyl acetate in hexanes to afford the title compound. MS (ESI+) m/z 477.2 $(M+H)^+$.

Example 143C (1-Benzyl-4-(1H-indazol-5-yl)-1H-1,2,3-triazol-5-yl)methanamine

Example 143B (140 mg, 0.294 mmol) was treated with hydrazine hydrate (0.7 mL) in ethanol (0.7 mL) and stirred at ambient temperature overnight. The mixture was absorbed on silica gel and purified by silica gel chromatography eluting with a gradient of 1-6% methanol in dichloromethane to afford the title compound. MS (ESI+) m/z 305.0 $(M+H)^+$.

Example 143D $N^1$-{[1-benzyl-4-(1H-indazol-5-yl)-1H-1,2,3-triazol-5-yl]methyl}glycinamide Example 143C (66 mg, 0.217 mmol), N-(tert-butoxycarbonyl)-glycine (39 mg, 0.223 mmol), and HATU (85 mg, 0.224 mmol) were combined in methylene chloride (2.5 mL). Diisopropylethylamine (150 μL, 0.865 mmol) was added and the mixture was stirred at ambient temperature overnight. The mixture was absorbed on silica gel and purified by silica gel chromatography eluting with a gradient of 0-6% methanol in dichloromethane to afford tert-butyl 2-((1-benzyl-4-(1H-indazol-5-yl)-1H-1,2,3-triazol-5-yl)methylamino)-2-oxoethylcarbamate. This carbamate was dissolved in tetrahydrofuran (2 mL) and 0.5 mL of a solution of 1 N hydrochloric acid in diethyl ether was added and the mixture was stirred for 20 minutes at room temperature. The solvents were removed under reduced pressure, and diethyl ether was added to the mixture and stirred at room temperature overnight. The solvent was decanted, and the resulting residue was dried under a stream of nitrogen to afford the title compound as a hydrochloride salt. $^1$H NMR (300 MHz, DMSO-$d_6$) δ ppm 13.21 (s, 1H) 9.02 (t, J=5.09 Hz, 1H) 8.11-8.16 (m, 2H) 8.06 (s, 2H) 7.75-7.82 (m, 1H) 7.64 (d, J=8.82 Hz, 1H) 7.30-7.45 (m, 3H) 7.23-7.31 (m, 2H) 5.72 (s, 2H) 4.57 (d, J=5.09 Hz, 2H) 3.41 (q, J=5.76 Hz, 2H). MS (ESI+) m/z 362.1 $(M+H)^+$.

Example 144

(4-fluorophenyl)[4-(1H-indazol-5-yl)-1-(tetrahydro-2H-pyran-4-ylmethyl)-1H-1,2,3-triazol-5-yl]methanone The title compound was prepared according to the procedure outlined in Example 119B substituting 4-fluorobenzoyl chloride for benzoyl chloride and Example 80A for benzyl azide. $^1$H NMR (300 MHz, DMSO-$d_6$) δ ppm 13.10 (s, 1H) 8.00 (s, 1H) 7.72-7.80 (m, 3H) 7.38-7.44 (m, 1H) 7.30-7.36 (m, 1H) 7.09-7.19 (m, 2H) 4.41 (d, J=7.12 Hz, 2H) 3.80 (d, J=11.36, 2.54 Hz, 2H) 3.14-3.26 (m, 2H) 2.04-2.19 (m, 1H) 1.38-1.49 (m, 2H) 1.19-1.35 (m, 2H). MS (ESI+) m/z 406.1 $(M+H)^+$.

Example 145

(4-chlorophenyl)[4-(1H-indazol-5-yl)-1-(tetrahydro-2H-pyran-4-ylmethyl)-1H-1,2,3-triazol-5-yl]methanone The title compound was prepared according to the procedure outlined in Example 119B substituting 4-chlorobenzoyl chloride for benzoyl chloride and Example 80A for benzyl azide. $^1$H NMR (300 MHz, DMSO-$d_6$) δ ppm 13.10 (s, 1H) 8.00 (s, 1H) 7.77 (s, 1H) 7.68 (d, J=8.48 Hz, 2H) 7.29-7.45 (m, 4H) 4.42 (d, J=7.12 Hz, 2H) 3.81 (d, J=11.19, 2.71 Hz, 2H) 3.14-3.27 (m, 2H) 2.03-2.19 (m, 1H) 1.38-1.51 (m, 2H) 1.22-1.36 (m, 2H). MS (ESI+) m/z 422.1 $(M+H)^+$.

Example 146

(3-chlorophenyl)[4-(1H-indazol-5-yl)-1-(tetrahydro-2H-pyran-4-ylmethyl)-1H-1,2,3-triazol-5-yl]methanone The title compound was prepared according to the procedure outlined in Example 119B substituting 3-chlorobenzoyl chloride for benzoyl chloride and Example 80A for benzyl azide. $^1$H NMR (300 MHz, DMSO-$d_6$) δ ppm 13.04 (s, 1H) 7.95 (s, 1H) 7.64 (s, 1H) 7.48-7.54 (m, 1H) 7.29-7.35 (m, 1H) 7.22-7.28 (m, 1H) 7.13-7.22 (m, 3H) 4.58 (d, J=7.12 Hz, 2H) 3.86 (d, J=11.53, 2.37 Hz, 2H) 3.20-3.30 (m, 2H) 2.11-2.24 (m, 1H) 1.45-1.54 (m, 2H) 1.33-1.44 (m, 2H). MS (ESI+) m/z 422.1 $(M+H)^+$.

Example 147

(2-chlorophenyl)[4-(1H-indazol-5-yl)-1-(tetrahydro-2H-pyran-4-ylmethyl)-1H-1,2,3-triazol-5-yl]methanone The title compound was prepared according to the procedure outlined in Example 119B substituting 2-chlorobenzoyl chloride for benzoyl chloride and Example 80A for benzyl azide. $^1$H NMR (300 MHz, DMSO-$d_6$) δ ppm 13.08 (s, 1H) 7.99 (s, 1H) 7.75 (s, 1H) 7.66 (t, J=1.86 Hz, 1H) 7.56 (d, J=7.80 Hz, 1H) 7.47-7.53 (m, 1H) 7.36-7.42 (m, 1H) 7.23-7.34 (m, 2H) 4.45 (d, J=6.78 Hz, 2H) 3.82 (d, J=11.19, 2.37 Hz, 2H) 3.18-3.29 (m, 2H) 2.09-2.23 (m, 1H) 1.41-1.53 (m, 2H) 1.28-1.38 (m, 2H). MS (ESI+) m/z 422.1 $(M+H)^+$.

Example 148 cyclopentyl[4-(1H-indazol-5-yl)-1-(tetrahydro-2H-pyran-4-ylmethyl)-1H-1,2,3-triazol-5-yl]methanone The title compound was prepared according to the procedure outlined in Example 119B substituting cyclopentanecarbonyl chloride for benzoyl chloride and Example 80A for benzyl azide. $^1$H NMR (300 MHz, DMSO-$d_6$) δ ppm 13.27 (s, 1H) 8.18 (s, 1H) 7.95 (s, 1H) 7.68 (d, J=8.48 Hz, 1H) 7.52 (d, J=8.48, 1.70 Hz, 1H) 4.47 (d, J=7.12 Hz, 2H) 3.85 (d, J=11.53, 2.37 Hz, 2H) 3.18-3.30 (m, 2H) 3.02-3.14 (m, 1H) 2.00-2.17 (m, 1H) 1.19-1.76 (m, 12H). MS (ESI+) m/z 380.1 $(M+H)^+$.

Example 149

1-benzyl-4-(1H-indazol-5-yl)-1H-1,2,3-triazole-5-carboxylic Acid

Example 149A

Methyl 1-benzyl-4-(tributylstannyl)-1H-1,2,3-triazole-5-carboxylate

Methyl propiolate (5.75 g, 68.4 mmol) was added to methyl ethyl(tributylstannyl)carbamate (26.9 g, 68.6 mmol) in a large sealed tube. The mixture was heated to 70° C. overnight. The mixture was cooled to ambient temperature and the vial was stirred unsealed for 10 minutes. Benzyl azide (10.2 mL, 81.6 mmol) was added, and the vial was resealed and heated to 130° C. overnight. The mixture was purified by silica gel chromatography eluting with a gradient of 5-40% ethyl acetate in hexanes to afford the title compound. MS (ESI+) m/z 508.3 (M+H)$^+$.

Example 149B

Methyl 4-(1-acetyl-1H-indazol-5-yl)-1-benzyl-1H-1,2,3-triazole-5-carboxylate

Example 149A (7.17 g, 14.1 mmol), Example 87A (4.02 g, 14.1 mmol), dichlorobis(triphenylphosphine)palladium(II) (1.01 mg, 1.44 mmol), and copper thiophene-2-carboxylate (4.07 mg, 21.3 mmol) were combined in toluene (55 mL) in a large sealed tube under an inert atmosphere of nitrogen. The tube was sealed and heated at 150° C. for 30 minutes. The mixture was absorbed on silica gel and purified by silica gel chromatography eluting with a gradient of 10-50% ethyl acetate in hexanes to afford the title compound. MS (ESI+) m/z 376.1 (M+H)$^+$.

Example 149C 1-benzyl-4-(1H-indazol-5-yl)-1H-1,2,3-triazole-5-carboxylic Acid Example 149B (3.40 mg, 9.06 mmol) was dissolved in tetrahydrofuran (100 mL), methanol (10 mL), and water (10 mL), and potassium hydroxide (1.63 g, 29.1 mmol) was added. The mixture was stirred for 3 hours, was diluted with ethyl acetate and washed with 1 N hydrochloric acid, washed with brine, and the combined organic layers were dried over sodium sulfate. After filtration, the solvents were removed under reduced pressure to afford the title compound. $^1$H NMR (300 MHz, DMSO-d$_6$) δ ppm 13.16 (s, 1H) 8.11-8.18 (m, 2H) 7.66-7.76 (m, 1H) 7.54-7.62 (m, 1H) 7.31-7.43 (m, 3H) 7.22-7.29 (m, 2H) 5.93 (s, 2H). MS (ESI+) m/z 320.0 (M+H)$^+$.

Example 150

5-{5-(4-fluorophenyl)-1-[4-(trifluoromethyl)benzyl]-1H-1,2,3-triazol-4-yl}-1H-indazol-3-amine

Example 150A 1-(Azidomethyl)-4-(trifluoromethyl)benzene

Sodium azide (2.30 g, 35.4 mmol) was added to a solution of 4-(trifluoromethyl)benzyl bromide (4.26 g, 17.8 mmol) dissolved in dimethyl sulfoxide (15 mL) and stirred at ambient temperature overnight. The mixture was diluted with ethyl acetate, washed with water and brine, and dried over sodium sulfate. After filtration, the solvent was removed under reduced pressure to afford the title compound. The crude product was used in the next step without further characterization.

Example 150B 5-(4-Fluorophenyl)-4-(tributylstannyl)-1-(4-(trifluoromethyl)benzyl)-1H-1,2,3-triazole 4-Fluorophenyl acetylene (524 mg, 4.36 mmol) was added to 1,1,1-tributyl-N,N-dimethylstannanamine (1.46 g, 4.37 mmol), and the mixture was stirred in a sealed vial at 50° C. for 30 minutes. The mixture was cooled to ambient temperature, and the vial was stirred unsealed for 10 minutes. Example 150A (1.28 g, 6.30 mmol) was added and the vial was resealed and heated to 130° C. overnight. The mixture was purified by silica gel chromatography eluting with a gradient of 5-35% ethyl acetate in hexanes to afford the title compound. MS (ESI+) m/z 612.3 (M+H)$^+$.

Example 150C

2-Fluoro-5-(5-(4-fluorophenyl)-1-(4-(trifluoromethyl)benzyl)-1H-1,2,3-triazol-4-yl)benzonitrile Example 150B (485 mg, 0.795 mmol), 5-bromo-2-fluorobenzonitrile (143 mg, 0.715 mmol), dichlorobis(triphenylphosphine)palladium(II) (49 mg, 0.070 mmol), and copper thiophene-2-carboxylate (205 mg, 1.08 mmol) were combined in toluene (2.0 mL) in a 4 mL vial under an inert atmosphere of nitrogen. The vial was sealed and heated at 150° C. for 30 minutes. The mixture was absorbed onto silica gel and purified by silica gel chromatography eluting with a gradient of 10-50% ethyl acetate in hexanes to afford the title compound. MS (ESI+) m/z 441.2 (M+H)$^+$.

Example 150D

5-{5-(4-fluorophenyl)-1-[4-(trifluoromethyl)benzyl]-1H-1,2,3-triazol-4-yl}-1H-indazol-3-amine Example 150C was treated with hydrazine hydrate (1.0 mL) in ethanol (1.0 mL), and the reaction mixture was stirred and heated to 65° C. for 3 hours. The mixture was diluted with methylene chloride and washed with water. The organic layer was absorbed on silica gel and purified by silica gel chromatography eluting with a gradient of 0-6% methanol in dichloromethane to afford the title compound. $^1$H NMR (300 MHz, DMSO-d$_6$) δ ppm 11.42 (s, 1H) 8.04 (s, 1H) 7.67 (d, J=8.14 Hz, 2H) 7.26-7.41 (m, 4H) 7.22 (d, J=8.48 Hz, 2H) 7.03-7.15 (m, 2H) 5.62 (s, 2H) 5.36 (s, 2H). MS (ESI+) m/z 453.1 (M+H)$^+$.

Example 151

5-[1-benzyl-5-(4-fluorophenyl)-1H-1,2,3-triazol-4-yl]-1H-indazol-3-amine

Example 151A

1-Benzyl-5-(4-fluorophenyl)-4-(tributylstannyl)-1H-1,2,3-triazole

4-Fluorophenyl acetylene (525 mg, 4.37 mmol) was added to 1,1,1-tributyl-N,N-dimethylstannanamine (1.46 g, 4.37 mmol), and the mixture was stirred in a sealed vial at 50° C. for 2 hours. The mixture was cooled to ambient temperature, and the vial was stirred unsealed for 10 minutes. Benzyl azide (850 μL, 6.80 mmol) was added, and the vial was resealed and heated to 130° C. overnight. The mixture was purified by silica gel chromatography eluting with a gradient of 5-35% ethyl acetate in hexanes to afford the title compound. MS (ESI+) m/z 544.4 (M+H)$^+$.

Example 151B 5-(1-Benzyl-5-(4-fluorophenyl)-1H-1,2,3-triazol-4-yl)-2-fluorobenzonitrile Example 151A (361 mg, 0.666 mmol), 5-bromo-2-fluorobenzonitrile (119 mg, 0.595 mmol), dichlorobis(triphenylphosphine)palladium(II) (45 mg, 0.064 mmol), and copper thiophene-2-carboxylate (193 mg, 1.01 mmol) were combined in toluene (2.0 mL) in a 4 mL vial under an inert atmosphere of nitrogen. The vial was sealed and heated 150° C. for 30 minutes. The mixture was absorbed on silica gel and purified by silica gel chromatography eluting with a gradient of 10-50% ethyl acetate in hexanes to afford the title compound. MS (ESI+) m/z 373.0 (M+H)$^+$.

Example 151C

5-[1-benzyl-5-(4-fluorophenyl)-1H-1,2,3-triazol-4-yl]-1H-indazol-3-amine

Example 151B (135 mg, 0.363 mmol) was treated with hydrazine hydrate (1.0 mL) in ethanol (1.0 mL) and stirred and heated to 65° C. for 3 hours. The mixture was diluted with methylene chloride and washed with water. The organic layer was absorbed on silica gel and purified by silica gel chromatography eluting with a gradient of 0-6% methanol in dichloromethane to afford the title compound. $^1$H NMR (300 MHz, DMSO-d$_6$) δ ppm 11.40 (s, 1H) 8.02 (s, 1H) 7.24-7.38 (m, 7H) 7.03-7.14 (m, 2H) 6.98 (d, J=7.29, 2.20 Hz, 2H) 5.50 (s, 2H) 5.35 (s, 2H). MS (ESI+) m/z 385.1 (M+H)$^+$.

Example 152

[4-(1H-indazol-5-yl)-1-(tetrahydro-2H-pyran-4-ylmethyl)-1H-1,2,3-triazol-5-yl](tetrahydro-2H-pyran-4-yl)methanone The title compound was prepared according to the procedure outlined in Example 119B substituting Example 80A for benzyl azide and tetrahydro-2H-pyran-4-carbonyl chloride for benzoyl chloride. $^1$H NMR (300 MHz, DMSO-d$_6$) δ ppm 13.30 (s, 1H) 8.18 (s, 1H) 8.00 (s, 1H) 7.69 (d, J=8.48 Hz, 1H) 7.53 (d, J=8.65, 1.53 Hz, 1H) 4.48 (d, J=7.12 Hz, 2H) 3.79-3.90 (m, 2H) 3.62-3.74 (m, 2H) 3.18-3.30 (m, 2H) 2.76-2.88 (m, 1H) 2.64-2.76 (m, 2H) 2.00-2.17 (m, 1H) 1.20-1.58 (m, 8H). MS (ESI+) m/z 396.0 (M+H)$^+$.

Example 153

5-[1-benzyl-5-(2-methylphenyl)-1H-1,2,3-triazol-4-yl]-1H-indazole

Example 153A

1-Benzyl-5-o-tolyl-4-(tributylstannyl)-1H-1,2,3-triazole

2-Ethynyl toluene (456 μL, 3.62 mmol) was added to 1,1,1-tributyl-N,N-dimethylstannanamine (1.21 g, 3.62 mmol), and the mixture was stirred in a sealed vial at 70° C. for 3 hours. The mixture was cooled to ambient temperature, and the vial was stirred unsealed for 10 minutes. Benzyl azide (678 μL, 5.42 mmol) was added, and the vial was resealed and heated to 130° C. overnight. The mixture was purified by silica gel chromatography eluting with a gradient of 5-45% ethyl acetate in hexanes to afford the title compound. MS (ESI+) m/z 539.8 (M+H)$^+$.

Example 153B 1-(5-(1-Benzyl-5-o-tolyl-1H-1,2,3-triazol-4-yl)-1H-indazol-1-yl)ethanone Example 153A (119 mg, 0.221 mmol), Example 87A (63 mg, 0.221 mmol), dichlorobis(triphenylphosphine)palladium(II) (16 mg, 0.023 mmol), and copper thiophene-2-carboxylate (65 mg, 0.341 mmol) were combined in toluene (2.0 mL) in a 4 mL vial under an inert atmosphere of nitrogen. The vial was sealed and heated at 150° C. for 20 minutes. The mixture was absorbed on silica gel and purified by silica gel chromatography eluting with a gradient 5-45% of ethyl acetate in hexanes to afford the title compound. MS (ESI+) m/z 408.7 (M+H)$^+$.

Example 153C

5-[1-benzyl-5-(2-methylphenyl)-1H-1,2,3-triazol-4-yl]-1H-indazole

Example 153B (42 mg, 0.103 mmol) was dissolved in tetrahydrofuran (2.0 mL) and water (0.3 mL), and potassium hydroxide (48 mg, 0.856 mmol) was added. The mixture was stirred for 1 hour, was diluted with methylene chloride and washed with water. The organic layer was absorbed on silica gel and purified by silica gel chromatography eluting with a gradient of 1-6% methanol in dichloromethane to afford the title compound. $^1$H NMR (300 MHz, DMSO-d$_6$) δ ppm 13.07 (s, 1H) 7.97 (s, 1H) 7.73 (s, 1H) 7.44-7.53 (m, 3H) 7.39 (t, J=6.95 Hz, 1H) 7.28-7.35 (m, 2H) 7.21-7.29 (m, 3H) 6.86-6.95 (m, 2H) 5.28-5.45 (m, 2H) 1.59 (s, 3H). MS (ESI+) m/z 366.1 (M+H)$^+$.

Example 154

5-{1-benzyl-5-[(4-methylpiperazin-1-yl)carbonyl]-1H-1,2,3-triazol-4-yl}-1H-indazole The title compound was prepared according to the procedure outlined in Example 81B substituting Example 149C for Example 81A and 1-methyl piperazine for piperidine and tetrahydrofuran for dimethylformamide. $^1$H NMR (300 MHz, DMSO-d$_6$) δ ppm 13.20 (s, 1H) 8.16 (s, 1H) 7.96 (s, 1H) 7.57-7.69 (m, 2H) 7.31-7.44 (m, 3H) 7.23-7.30 (m, 2H) 5.36-5.83 (m, 2H) 3.40-3.65 (m, J=4.75 Hz, 2H) 2.38-2.49 (m, 2H) 2.10-2.22 (m, 2H) 1.89 (s, 3H) 1.40 (t, J=4.92 Hz, 2H). MS (ESI+) m/z 402.2 (M+H)$^+$.

Example 155

1-{[1-benzyl-4-(1H-indazol-5-yl)-1H-1,2,3-triazol-5-yl]carbonyl}piperidin-4-ol

The title compound was prepared according to the procedure outlined in Example 81B substituting Example 149C for Example 81A and 4-hydroxy piperidine for piperidine and tetrahydrofuran for dimethylformamide. $^1$H NMR (300 MHz, DMSO-d$_6$) δ ppm 13.15-13.24 (m, 1H) 8.16 (s, 1H) 7.97 (s, 1H) 7.55-7.68 (m, 2H) 7.32-7.43 (m, 3H) 7.23-7.30 (m, 2H) 5.41-5.83 (m, J=65.10 Hz, 2H) 4.58 (d, J=3.39 Hz, 1H) 3.74-3.91 (m, 1H) 3.37-3.48 (m, 2H) 2.66-2.79 (m, 1H) 2.25-2.47 (m, 1H) 1.54-1.68 (m, 1H) 1.20-1.36 (m, 1H) 0.74-0.90 (m, 1H) 0.40-0.60 (m, 1H). MS (ESI+) m/z 403.1 (M+H)$^+$.

Example 156

1-acetyl-5-[5-(4-fluorophenyl)-1-(tetrahydro-2H-pyran-4-ylmethyl)-1H-1,2,3-triazol-4-yl]-1H-indazole

Example 156A 5-(4-Fluorophenyl)-1-((tetrahydro-2H-pyran-4-yl)methyl)-4-(tributylstannyl)-1H-1,2,3-triazole 4-Fluorophenyl acetylene (440 µL, 3.88 mmol) was added to 1,1,1-tributyl-N,N-dimethylstannanamine (1.30 g, 3.89 mmol), and the mixture was stirred in a sealed vial at 50° C. for 40 minutes. The mixture was cooled to ambient temperature, and the vial was stirred unsealed for 10 minutes. Example 80A (710 µL, 5.68 mmol) was added and the vial was resealed and heated to 130° C. overnight. The mixture was purified by silica gel chromatography eluting with a gradient of 5-50% ethyl acetate in hexanes to afford the title compound. MS (ESI+) m/z 552.4 (M+H)$^+$.

Example 156B 1-acetyl-5-[5-(4-fluorophenyl)-1-(tetrahydro-2H-pyran-4-ylmethyl)-1H-1,2,3-triazol-4-yl]-1H-indazole Example 156A (433 mg, 0.787 mmol), Example 87A (205 mg, 0.717 mmol), dichlorobis(triphenylphosphine)palladium(II) (55 mg, 0.078 mmol), and copper thiophene-2-carboxylate (224 mg, 1.17 mmol) were combined in toluene (2.0 mL) in a 4 mL vial under an inert atmosphere of nitrogen. The vial was sealed and heated to 150° C. for 20 minutes. The mixture was absorbed on silica gel and purified by silica gel chromatography eluting with a gradient of 5-45% ethyl acetate in hexanes, and was triturated with methanol to afford the title compound. $^1$H NMR (300 MHz, DMSO-d$_6$) δ ppm 8.40-8.48 (m, J=0.68 Hz, 1H) 8.25 (d, J=8.82 Hz, 1H) 7.82-7.91 (m, 1H) 7.73 (d, J=8.48, 1.70 Hz, 1H) 7.50-7.60 (m, 2H) 7.38-7.49 (m, 2H) 4.13 (d, J=7.12 Hz, 2H) 3.76 (d, J=11.36, 2.54 Hz, 2H) 3.10-3.25 (m, 2H) 2.70 (s, 3H) 1.86-2.08 (m, 1H) 1.37 (d, J=12.55, 1.70 Hz, 2H) 1.03-1.23 (m, 2H). MS (ESI+) m/z 420.2 (M+H)$^+$.

Example 157

1-benzyl-4-(1H-indazol-5-yl)-N,N-dimethyl-1H-1,2,3-triazole-5-carboxamide

The title compound was prepared according to the procedure outlined in Example 81B substituting Example 149C for Example 81A and dimethylamine for piperidine and tetrahydrofuran for dimethylformamide. $^1$H NMR (300 MHz, DMSO-d$_6$) δ ppm 13.19 (s, 1H) 8.15 (s, 1H) 7.96 (t, J=1.19 Hz, 1H) 7.62 (d, J=1.36 Hz, 2H) 7.33-7.44 (m, 3H) 7.24-7.33 (m, 2H) 5.59 (s, 2H) 2.92 (s, 3H) 2.21 (s, 3H). MS (ESI+) m/z 347.1 (M+H)$^+$.

Example 158

N,1-dibenzyl-4-(1H-indazol-5-yl)-1H-1,2,3-triazole-5-carboxamide

The title compound was prepared according to the procedure outlined in Example 81B substituting Example 149C for Example 81A and benzyl amine for piperidine and tetrahydrofuran for dimethylformamide. $^1$H NMR (300 MHz, DMSO-d$_6$) δ ppm 13.15 (s, 1H) 9.35 (t, J=6.10 Hz, 1H) 8.01 (d, J=12.55 Hz, 2H) 7.68 (d, J=8.82, 1.36 Hz, 1H) 7.53 (d, J=8.82 Hz, 1H) 7.17-7.41 (m, 10H) 5.66 (s, 2H) 4.41 (d, J=6.10 Hz, 2H). MS (ESI+) m/z 409.1 (M+H)$^+$.

Example 159

N-(2-hydroxy-2-phenylethyl)-5-(1H-indazol-5-yl)-N-methylisoxazole-3-carboxamide

The title compound was prepared according to the procedure outlined in Example 81B substituting DL-alpha-(methylaminomethyl)benzyl alcohol for piperidine. $^1$H NMR (300 MHz, DMSO-d$_6$) δ ppm 13.01 (s, 1H) 8.29 (s, 1H) 8.17 (s, 1H) 7.73-7.85 (m, 1H) 7.62-7.72 (m, 1H) 7.16-7.43 (m, 5H) 6.86 (s, 1H) 5.17 (d, J=4.39 Hz, 1H) 4.89 (s, 1H) 3.71 (d, J=5.49 Hz, 2H) 3.10 (s, 3H). MS (ESI+) m/z 363.1 (M+H)$^+$.

Example 160

N-[(1S)-2-hydroxy-1-phenylethyl]-5-(1H-indazol-5-yl)isoxazole-3-carboxamide

The title compound was prepared according to the procedure outlined in Example 81B substituting (S)-2-amino-2-phenylethanol for piperidine. $^1$H NMR (300 MHz, DMSO-d$_6$) δ ppm 13.37 (s, 1H) 9.05 (d, J=8.14 Hz, 1H) 8.40 (s, 1H) 8.23 (s, 1H) 7.89 (d, J=8.65, 1.53 Hz, 1H) 7.70 (d, J=8.82 Hz, 1H) 7.20-7.46 (m, 6H) 5.02-5.13 (m, 1H) 4.98 (t, J=5.59 Hz, 1H) 3.61-3.82 (m, 2H). MS (ESI+) m/z 349.0 (M+H)$^+$.

Example 161

N-benzyl-N-(2-hydroxyethyl)-5-(1H-indazol-5-yl)isoxazole-3-carboxamide

The title compound was prepared according to the procedure outlined in Example 81B substituting 2-(benzylamino)ethanol for piperidine. $^1$H NMR (300 MHz, DMSO-d$_6$) δ ppm 13.37 (s, 1H) 9.05 (d, J=8.48 Hz, 1H) 8.40 (s, 1H) 8.23 (s, 1H) 7.89 (d, J=8.65, 1.53 Hz, 1H) 7.70 (d, J=8.82 Hz, 1H) 7.22-7.45 (m, 6H) 5.02-5.14 (m, 1H) 4.98 (t, J=5.76 Hz, 1H) 3.61-3.81 (m, 2H). MS (ESI+) m/z 349.0 (M+H)$^+$.

Example 162

5-[1-benzyl-5-(2-methylphenyl)-1H-1,2,3-triazol-4-yl]-3-methyl-1H-indazole

Example 162A 1-(5-Bromo-3-methyl-1H-indazol-1-yl)ethanone

5-Bromo-3-methyl-1H-indazole (838 mg, 3.97 mmol) was dissolved in methylene chloride (15 mL) and diisopropylethylamine (0.7 mL). Acetic anhydride (500 µL, 5.29 mmol) was added and the mixture was stirred at ambient temperature overnight. The mixture was diluted with ethyl acetate, washed with 1 N sodium hydroxide followed by 1 N hydrochloric acid and then brine. The organic layer was dried over sodium sulfate and the solvent was removed under reduced pressure to afford the title compound. MS (ESI+) m/z 252.7 (M+H)$^+$.

Example 162B 1-(5-(1-Benzyl-5-o-tolyl-1H-1,2,3-triazol-4-yl)-3-methyl-1H-indazol-1-yl)ethanone Example 153A (436 mg, 0.808 mmol), Example 162A (205 mg, 0.810 mmol), dichlorobis(triphenylphosphine)palladium(II) (56 mg, 0.080 mmol), and copper thiophene-2-carboxylate (239 mg, 1.25 mmol) were combined in toluene (2.0 mL) in a 4 mL vial under an inert atmosphere of nitrogen. The vial was sealed and heated 150° C. for 30 minutes. The mixture was absorbed on silica gel and purified by silica gel chromatography eluting with a gradient of 10-50% ethyl acetate in hexanes to afford the title compound. MS (ESI+) m/z 422.6 (M+H)$^+$.

Example 162C

5-[1-benzyl-5-(2-methylphenyl)-1H-1,2,3-triazol-4-yl]-3-methyl-1H-indazole

Example 162B (202 mg, 0.548 mmol) was dissolved in tetrahydrofuran (5.0 mL), methanol (0.5 mL) and water (0.5 mL) and potassium hydroxide (133 mg, 2.37 mmol) was added. The mixture was stirred for 1 hour and then was diluted with methylene chloride and washed with water. The organic layer was absorbed on silica gel and purified by silica gel chromatography eluting with a gradient of 30-80% ethyl acetate in hexanes to afford the title compound. $^1$H NMR (300 MHz, DMSO-d$_6$) δ ppm 12.63 (s, 1H) 7.70 (s, 1H) 7.44-7.52 (m, 1H) 7.38-7.43 (m, 1H) 7.29-7.38 (m, 4H) 7.22-7.29 (m, 3H) 6.89-6.96 (m, J=6.44, 3.05 Hz, 2H) 5.30-5.48 (m, 2H) 2.32 (s, 3H) 1.58 (s, 3H). MS (ESI+) m/z 380.1 (M+H)$^+$.

Example 163

5-[1-benzyl-5-(2-methylphenyl)-1H-1,2,3-triazol-4-yl]-1H-indazol-3-amine

Example 163A 5-(1-Benzyl-5-o-tolyl-1H-1,2,3-triazol-4-yl)-2-fluorobenzonitrile

Example 153A (450 mg, 0.834 mmol), 5-bromo-2-fluorobenzonitrile (167 mg, 0.835 mmol), dichlorobis(triphenylphosphine)palladium(II) (56 mg, 0.080 mmol), and copper thiophene-2-carboxylate (242 mg, 1.27 mmol) were combined in toluene (2.0 mL) in a 4 mL vial under an inert atmosphere of nitrogen. The vial was sealed and heated at 150° C. for 30 minutes. The mixture was absorbed on silica gel and purified by silica gel chromatography eluting with a gradient of 10-50% ethyl acetate in hexanes to afford the title compound. MS (ESI+) m/z 369.2 (M+H)$^+$.

Example 163B

5-[1-benzyl-5-(2-methylphenyl)-1H-1,2,3-triazol-4-yl]-1H-indazol-3-amine

Example 163A (202 mg, 0.548 mmol) was treated with hydrazine hydrate (1.0 mL) in ethanol (1.0 mL) and stirred and heated to 60° C. overnight. The mixture was diluted with methylene chloride and washed with water. The organic layer was absorbed on silica gel and purified by silica gel chromatography eluting with a gradient of 35-85% ethyl acetate in hexanes to afford the title compound. $^1$H NMR (300 MHz, DMSO-d$_6$) δ ppm 11.38 (s, 1H) 8.11 (s, 1H) 7.41-7.49 (m, 1H) 7.33-7.40 (m, J=6.95, 6.95 Hz, 1H) 7.28-7.32 (m, 2H) 7.21-7.28 (m, 3H) 7.00-7.06 (m, 1H) 6.86-6.95 (m, 3H) 5.27-5.44 (m, 4H) 1.58 (s, 3H). MS (ESI+) m/z 381.1 (M+H)$^+$.

Example 164

2-{2-[1-(1H-indazol-5-yl)-1H-1,2,3-triazol-4-yl]ethyl}-1H-isoindole-1,3(2H)-dione The title compound was prepared according to the procedure outlined in Example 88 substituting 2-(but-3-ynyl)isoindoline-1,3-dione for 3-phenyl-1-propyne. The crude product was subjected to 25% TFA/dichloromethane and purified by reverse-phase HPLC using an acetonitrile/water 0.1% TFA gradient elution method to afford the title compound. $^1$H NMR (400 MHz, DMSO-d$_6$) δ ppm 13.33 (s, 1H) 8.65 (s, 1H) 8.22 (s, 1H) 8.18 (d, J=1.53 Hz, 1H) 7.78-7.90 (m, 5H) 7.71-7.75 (m, 1H) 3.92 (t, J=7.21 Hz, 2H) 3.08 (t, J=7.21 Hz, 2H). MS (ESI+) m/z 359.0 (M+H)$^+$.

Example 165

5-{4-[(2,4-dichlorophenoxy)methyl]-1H-1,2,3-triazol-1-yl}-1H-indazole

The title compound was prepared according to the procedure outlined in Example 88 substituting 2,4-dichloro-1-(prop-2-ynyloxy)benzene for 3-phenyl-1-propyne. The crude product was subjected to 25% TFA/dichloromethane and was purified by reverse-phase HPLC using an acetonitrile/water 0.1% TFA gradient elution method to afford the title compound. $^1$H NMR (400 MHz, DMSO-d$_6$) δ ppm 13.38 (s, 1H) 8.93 (s, 1H) 8.28 (d, J=1.53 Hz, 1H) 8.23 (s, 1H) 7.88 (d, J=8.90, 1.84 Hz, 1H) 7.76 (d, J=8.90 Hz, 1H) 7.59 (d, J=2.46 Hz, 1H) 7.39-7.49 (m, 2H) 5.37 (s, 2H). MS (ESI+) m/z 359.9 (M+H)$^+$.

Example 166

5-{4-[(2,6-dichlorophenoxy)methyl]-1H-1,2,3-triazol-1-yl}-1H-indazole

The title compound was prepared according to the procedure outlined in Example 88 substituting 1,3-dichloro-2-(prop-2-ynyloxy)benzene for 3-phenyl-1-propyne. The crude product was subjected to 25% TFA/dichloromethane and purified by reverse-phase HPLC using an acetonitrile/water 0.1% TFA gradient elution method to afford the title compound. $^1$H NMR (500 MHz, DMSO-d$_6$) δ ppm 13.39 (s, 1H) 8.97 (s, 1H) 8.29 (d, J=1.53 Hz, 1H) 8.24 (s, 1H) 7.89 (d, J=9.00, 1.98 Hz, 1H) 7.76 (d, J=8.85 Hz, 1H) 7.51-7.55 (m, 2H) 7.19-7.26 (m, J=8.24, 8.24 Hz, 1H) 5.23 (s, 2H). MS (ESI+) m/z 359.9 (M+H)$^+$.

Example 167

5-[5-(4-fluorophenyl)-1-(tetrahydro-2H-pyran-4-ylmethyl)-1H-1,2,3-triazol-4-yl]-1H-indazole Example 156B (168 mg, 0.401 mmol) was dissolved in tetrahydrofuran (5.0 mL), methanol (0.5 mL) and water (0.5 mL) and potassium hydroxide (138 mg, 2.46 mmol) was added. The mixture was stirred for 1 hour, and was diluted with methylene chloride and washed with water. The organic layer was absorbed on silica gel and purified by silica gel chromatography eluting with a gradient of 0-7% methanol in dichloromethane to afford the title compound. $^1$H NMR (300 MHz, DMSO-$d_6$) δ ppm 13.08 (s, 1H) 8.02 (s, 1H) 7.77 (s, 1H) 7.50-7.58 (m, 2H) 7.37-7.49 (m, 4H) 4.11 (d, J=7.12 Hz, 2H) 3.76 (d, J=11.53, 2.71 Hz, 2H) 3.11-3.24 (m, 2H) 1.88-2.03 (m, 1H) 1.30-1.43 (m, J=12.72, 1.86 Hz, 2H) 1.04-1.22 (m, 2H). MS (ESI+) m/z 378.1 (M+H)$^+$.

Example 168

1-{[1-(1H-indazol-5-yl)-1H-1,2,3-triazol-4-yl]methyl}-1H-indazole

Example 168A 1-(Prop-2-ynyl)-1H-indazole

Indazole (530 mg, 4.49 mmol) was dissolved in dimethylformamide (4 mL). Sodium hydride (60% suspension in mineral oil, 231 mg, 5.78 mmol) was added slowly, and the mixture was stirred for 10 minutes. Propargyl bromide (80% wt in toluene, 5.0 mL) was added, and the mixture was stirred at ambient temperature overnight. The mixture was diluted with ethyl acetate, washed excessively with water, absorbed on silica gel, and purified by silica gel chromatography eluting with a gradient of 5-30% ethyl acetate in hexanes to afford the title compound. MS (ESI+) m/z 157.1 (M+H)$^+$.

Example 168B

1-{[1-(1H-indazol-5-yl)-1H-1,2,3-triazol-4-yl]methyl}-1H-indazole

The title compound was prepared according to the procedure outlined in Example 88 substituting Example 168A for 3-phenyl-1-propyne. $^1$H NMR (300 MHz, DMSO-$d_6$) δ ppm 13.36 (s, 1H) 8.78 (s, 1H) 8.22 (d, J=2.03, 0.68 Hz, 1H) 8.20 (s, 1H) 8.10 (d, J=1.02 Hz, 1H) 7.80-7.87 (m, 2H) 7.75-7.80 (m, 1H) 7.68-7.74 (m, 1H) 7.39-7.46 (m, 1H) 7.13-7.19 (m, 1H) 5.81 (s, 2H). MS (ESI+) m/z 316.0 (M+H)$^+$.

Example 169

5-[1-benzyl-5-(piperidin-1-ylcarbonyl)-1H-1,2,3-triazol-4-yl]-1H-indazole

The title compound was prepared according to the procedure outlined in Example 81B substituting Example 149C for Example 81A and tetrahydrofuran for dimethylformamide. $^1$H NMR (300 MHz, DMSO-$d_6$) δ ppm 13.20 (s, 1H) 8.16 (s, 1H) 7.95-8.00 (m, J=1.02 Hz, 1H) 7.62-7.68 (m, 1H) 7.57-7.63 (m, 1H) 7.31-7.44 (m, 3H) 7.24-7.30 (m, 2H) 5.36-5.84 (m, J=69.17 Hz, 2H) 3.43-3.59 (m, 2H) 2.43-2.59 (m, 2H) 1.17-1.46 (m, J=39.67 Hz, 4H) 0.49-0.65 (m, 2H). MS (ESI+) m/z 387.1 (M+H)$^+$.

Example 170

5-[5-(2-methylphenyl)-1-(tetrahydro-2H-pyran-4-ylmethyl)-1H-1,2,3-triazol-4-yl]-1H-indazole Example 170A 1-((Tetrahydro-2H-pyran-4-yl)methyl)-5-o-tolyl-4-(tributylstannyl)-1H-1,2,3-triazole 2-Ethynyl toluene (576 mg, 4.57 mmol) was added to 1,1,1-tributyl-N,N-dimethylstannanamine (1.53 g, 4.58 mmol), and the mixture stirred in a sealed vial at 70° C. for 2 hours. The mixture was cooled to ambient temperature, and the vial was stirred unsealed for 10 minutes. Example 80A (648 mg, 4.59 mmol) was added and the vial was resealed and heated to 130° C. overnight. The mixture was purified by silica gel chromatography eluting with a gradient of 5-50% ethyl acetate in hexanes to afford the title compound. MS (ESI+) m/z 548.4 (M+H)$^+$.

Example 170B 1-(5-(1-((Tetrahydro-2H-pyran-4-yl)methyl)-5-o-tolyl-1H-1,2,3-triazol-4-yl)-1H-indazol-1-yl)ethanone Example 170A (432 mg, 0.791 mmol), Example 87A (222 mg, 0.776 mmol), dichlorobis(triphenylphosphine)palladium(II) (58 mg, 0.083 mmol), and copper thiophene-2-carboxylate (231 mg, 1.21 mmol) were combined in toluene (2.0 mL) in a 4 mL vial under an inert atmosphere of nitrogen. The vial was sealed and heated at 150° C. for 20 minutes. The mixture was absorbed on silica gel and purified by silica gel chromatography eluting with a gradient of 20-70% ethyl acetate in hexanes to afford the title compound. MS (ESI+) m/z 416.2 (M+H)$^+$.

Example 170C

5-[5-(2-methylphenyl)-1-(tetrahydro-2H-pyran-4-ylmethyl)-1H-1,2,3-triazol-4-yl]-1H-indazole Example 170B (184 mg, 0.443 mmol) was dissolved in tetrahydrofuran (3.0 mL), methanol (0.3 mL), and water (0.3 mL) and potassium hydroxide (140 mg, 2.50 mmol) was added. The mixture was stirred for 3 hours, and was diluted with methylene chloride and washed with water. The organic layer was absorbed on silica gel and purified by silica gel chromatography eluting with a gradient of 35-100% ethyl acetate in hexanes to afford the title compound. $^1$H NMR (300 MHz, DMSO-$d_6$) δ ppm 13.08 (s, 1H) 7.98 (s, 1H) 7.68-7.74 (m, J=1.02, 1.02 Hz, 1H) 7.49-7.56 (m, 1H) 7.45-7.49 (m, 3H) 7.41-7.45 (m, J=7.46 Hz, 2H) 4.10 (d, J=13.73, 6.95 Hz, 1H) 3.89 (d, J=13.90, 7.80 Hz, 1H) 3.77 (d, J=10.51, 2.71 Hz, 2H) 3.10-3.24 (m, 2H) 1.92 (s, 3H) 1.88-1.98 (m, 1H) 1.26-1.43 (m, 2H) 1.04-1.21 (m, 2H). MS (ESI+) m/z 374.1 (M+H)$^+$.

Example 171

5-[5-(2-methylphenyl)-1-(tetrahydro-2H-pyran-4-ylmethyl)-1H-1,2,3-triazol-4-yl]-1H-indazol-3-amine Example 171A 2-Fluoro-5-(1-((tetrahydro-2H-pyran-4-yl)methyl)-5-o-tolyl-1H-1,2,3-triazol-4-yl)benzonitrile Example 170A (411 mg, 0.752 mmol), 5-bromo-2-fluorobenzonitrile (151 mg, 0.755 mmol), dichlorobis(triphenylphosphine)palladium(II) (52 mg, 0.074 mmol), and copper thiophene-2-carboxylate (223 mg, 1.17 mmol) were combined in toluene (2.0 mL) in a 4 mL vial under an inert atmosphere of nitrogen. The vial was sealed and heated 150° C. for 30 minutes. The mixture was absorbed on silica gel and purified by silica gel chromatography eluting with a gradient of 10-50% ethyl acetate in hexanes to afford the title compound. MS (ESI+) m/z 377.6 (M+H)+.

Example 171B

5-[5-(2-methylphenyl)-1-(tetrahydro-2H-pyran-4-ylmethyl)-1H-1,2,3-triazol-4-yl]-1H-indazol-3-amine Example 171A (175 mg, 0.465 mmol) was treated with hydrazine hydrate (2.0 mL) in ethanol (2.0 mL), and the mixture was stirred and heated to 65° C. for 2 hours. The mixture was diluted with methylene chloride and washed with water. The organic layer was absorbed on silica gel and purified by silica gel chromatography eluting with a gradient of 1-8% methanol in dichloromethane to afford the title compound. $^1$H NMR (300 MHz, DMSO-$d_6$) δ ppm 11.39 (s, 1H) 8.08 (s, 1H) 7.45-7.55 (m, 1H) 7.37-7.45 (m, 3H) 7.01-7.08 (m, J=8.48 Hz, 1H) 6.89-6.97 (m, 1H) 5.34 (s, 2H) 4.09 (d, J=13.73, 6.95 Hz, 1H) 3.89 (d, J=13.73, 7.63 Hz, 1H) 3.70-3.81 (m, 2H) 3.08-3.24 (m, 2H) 1.91 (s, 3H) 1.84-1.99 (m, 1H) 1.22-1.41 (m, 2H) 1.04-1.20 (m, 2H). MS (ESI+) m/z 389.1 (M+H)+.

Example 172

5-[1-benzyl-5-(morpholin-4-ylcarbonyl)-1H-1,2,3-triazol-4-yl]-1H-indazole

The title compound was prepared according to the procedure outlined in Example 81B substituting Example 149C for Example 81A, morpholine for piperidine, and tetrahydrofuran for dimethylformamide. $^1$H NMR (300 MHz, DMSO-$d_6$) δ ppm 13.22 (s, 1H) 8.18 (s, 1H) 7.95-8.03 (m, 1H) 7.64-7.70 (m, 1H) 7.57-7.64 (m, 1H) 7.33-7.45 (m, 3H) 7.24-7.31 (m, 2H) 5.76 (s, 1H) 5.52 (s, 1H) 3.33-3.59 (m, 4H) 2.61-2.74 (m, 2H) 2.45-2.59 (m, 2H). MS (ESI+) m/z 389.1 (M+H)+.

Example 173

5-[1-benzyl-5-(4-methoxyphenyl)-1H-1,2,3-triazol-4-yl]-1H-indazol-3-amine

A vial under argon containing Example 125B (50 mg, 0.12 mmol), 4-methoxyphenylboronic acid (20 mg, 0.13 mmol), PdCl$_2$(dppf) dichloromethane (10 mg, 0.01 mmol) and potassium carbonate (33 mg, 0.24 mmol) in DME (2 mL) and water (0.2 mL) was capped and heated at 80° C. in a heater shaker for 48 hours. The solvent was evaporated under reduced pressure, and the product was purified by reverse-phase HPLC using an acetonitrile/water 0.1% TFA gradient elution method to afford the title compound. $^1$H NMR (400 MHz, DMSO-$d_6$) δ ppm 11.85 (s, 1H) 8.18 (s, 1H) 7.26-7.34 (m, 3H) 7.19-7.25 (m, 2H) 7.16-7.19 (m, 2H) 7.02 (t, J=8.13 Hz, 4H) 5.47 (s, 2H) 3.80 (s, 3H). MS (ESI+) m/z 397.1 (M+H)+.

Example 174

N-[(1S)-1-benzyl-2-hydroxyethyl]-5-(1H-indazol-5-yl)isoxazole-3-carboxamide

The title compound was prepared according to the procedure outlined in Example 81B substituting (S)-(−)-2-amino-3-phenyl-1-propanol for piperidine. $^1$H NMR (300 MHz, DMSO-$d_6$) δ ppm 13.36 (s, 1H) 8.47 (d, J=8.82 Hz, 1H) 8.38 (s, 1H) 8.22 (s, 1H) 7.87 (m, J=8.82, 1.70 Hz, 1H) 7.69 (d, J=8.82 Hz, 1H) 7.23-7.31 (m, 3H) 7.22 (s, 1H) 7.12-7.21 (m, 1H) 4.90 (t, J=5.59 Hz, 1H) 4.07-4.28 (m, 1H) 3.40-3.58 (m, 2H) 2.89-3.00 (m, 1H) 2.75-2.86 (m, 1H). MS (ESI+) m/z 363.0 (M+H)+.

Example 175

N-[(1S,2R)-2-hydroxy-2,3-dihydro-1H-inden-1-yl]-5-(1H-indazol-5-yl)isoxazole-3-carboxamide The title compound was prepared according to the procedure outlined in Example 81B substituting (1S,2R)-(−)-cis-1-amino-2-indanol for piperidine. $^1$H NMR (300 MHz, DMSO-$d_6$) δ ppm 13.38 (s, 1H) 8.42 (s, 1H) 8.24 (s, 1H) 8.16 (d, J=8.48 Hz, 1H) 7.91 (d, J=8.82, 1.70 Hz, 1H) 7.71 (d, J=8.48 Hz, 1H) 7.45 (s, 1H) 7.16-7.32 (m, 4H) 5.36-5.47 (m, 2H) 4.50-4.61 (m, 1H) 3.14 (d, J=15.43, 5.26 Hz, 1H) 2.90 (d, J=16.28, 1.70 Hz, 1H). MS (ESI+) m/z 361.0 (M+H)+.

Example 176

5-{3-[(3-phenylmorpholin-4-yl)carbonyl]isoxazol-5-yl}-1H-indazole

The title compound was prepared according to the procedure outlined in Example 81B substituting 3-phenylmorpholine hydrochloride for piperidine. $^1$H NMR (300 MHz, DMSO-$d_6$) δ ppm 13.38 (s, 1H) 8.32-8.46 (m, 1H) 8.24 (s, 1H) 7.81-7.96 (m, 1H) 7.70 (d, J=8.82 Hz, 1H) 7.37-7.55 (m, 4H) 7.26-7.37 (m, 2H) 5.34-5.71 (m, 1H) 4.51 (d, J=13.22 Hz, 1H) 3.78-4.39 (m, 3H) 3.59 (t, J=11.36 Hz, 1H) 3.33-3.41 (m, 1H). MS (ESI+) m/z 375.0 (M+H)+.

Example 177

N-benzyl-5-(1H-indazol-5-yl)isoxazole-3-carboxamide

The title compound was prepared according to the procedure outlined in Example 81B substituting benzylamine for piperidine. $^1$H NMR (300 MHz, DMSO-$d_6$) δ ppm 13.36 (s, 1H) 9.35 (t, J=6.27 Hz, 1H) 8.40 (s, 1H) 8.23 (s, 1H) 7.89 (d, J=8.82, 1.70 Hz, 1H) 7.69 (d, J=8.82 Hz, 1H) 7.33-7.40 (m, 4H) 7.32 (s, 1H) 7.22-7.30 (m, 1H) 4.48 (d, J=6.10 Hz, 2H). MS (ESI+) m/z 319.0 (M+H)+.

Example 178

((1S)-2-{[5-(1H-indazol-5-yl)isoxazol-3-yl]carbonyl}-6,7-dimethoxy-1,2,3,4-tetrahydroisoquinolin-1-yl)methanol The title compound was prepared according to the procedure outlined in Example 81B substituting (S)-(6,7-dimethoxy-1,2,3,4-tetrahydroisoquinolin-1-yl)methanol for piperidine. MS (ESI+) m/z 435.1 (M+H)+.

Example 179

N-[(1R)-3-hydroxy-1-phenylpropyl]-5-(1H-indazol-5-yl)isoxazole-3-carboxamide

The title compound was prepared according to the procedure outlined in Example 81B substituting (R)-3-amino-3-phenylpropanol for piperidine. $^1$H NMR (300 MHz, DMSO-$d_6$) δ ppm 13.37 (s, 1H) 9.24 (d, J=8.48 Hz, 1H) 8.39 (s, 1H) 8.23 (s, 1H) 7.88 (d, J=8.82, 1.70 Hz, 1H) 7.69 (d, J=8.82 Hz, 1H) 7.38-7.46 (m, 2H) 7.34 (t, J=7.46 Hz, 2H) 7.19-7.30 (m, 2H) 5.09-5.27 (m, 1H) 4.62 (t, J=4.92 Hz, 1H) 3.37-3.52 (m, 2H) 2.00-2.16 (m, 1H) 1.84-2.00 (m, 1H). MS (ESI+) m/z 363.1 (M+H)$^+$.

Example 180

N-[(1S)-3-hydroxy-1-phenylpropyl]-5-(1H-indazol-5-yl)isoxazole-3-carboxamide

The title compound was prepared according to the procedure outlined in Example 81B substituting (S)-3-amino-3-phenylpropanol for piperidine. $^1$H NMR (300 MHz, DMSO-d$_6$) δ ppm 13.36 (s, 1H) 9.24 (d, J=8.14 Hz, 1H) 8.39 (s, 1H) 8.22 (s, 1H) 7.88 (d, J=8.65, 1.53 Hz, 1H) 7.69 (d, J=8.81 Hz, 1H) 7.37-7.45 (m, 2H) 7.29-7.37 (m, 2H) 7.19-7.29 (m, 2H) 5.08-5.30 (m, 1H) 4.55-4.68 (m, 1H) 3.37-3.51 (m, 2H) 2.00-2.14 (m, 1H) 1.83-1.99 (m, 1H). MS (ESI+) m/z 363.0 (M+H)$^+$.

Example 181

N-2,3-dihydro-1H-inden-1-yl-5-(1H-indazol-5-yl)isoxazole-3-carboxamide

The title compound was prepared according to the procedure outlined in Example 81B substituting 1-aminoindane for piperidine. $^1$H NMR (300 MHz, DMSO-d$_6$) δ ppm 13.37 (s, 1H) 9.13 (d, J=8.14 Hz, 1H) 8.39 (s, 1H) 8.23 (s, 1H) 7.89 (d, J=8.82, 1.36 Hz, 1H) 7.70 (d, J=8.82 Hz, 1H) 7.35 (s, 1H) 7.15-7.32 (m, 4H) 5.55 (q, J=7.91 Hz, 1H) 2.95-3.08 (m, 1H) 2.76-2.94 (m, 1H) 2.37-2.49 (m, 1H) 2.01-2.15 (m, 1H). MS (ESI+) m/z 345.0 (M+H)$^+$.

Example 182

N-2,3-dihydro-1H-inden-2-yl-5-(1H-indazol-5-yl)isoxazole-3-carboxamide

The title compound was prepared according to the procedure outlined in Example 81B substituting 2-aminoindane for piperidine. $^1$H NMR (300 MHz, DMSO-d$_6$) δ ppm 13.37 (s, 1H) 9.08 (d, J=7.46 Hz, 1H) 8.39 (s, 1H) 8.23 (s, 1H) 7.89 (d, J=8.82, 1.70 Hz, 1H) 7.69 (d, J=8.82 Hz, 1H) 7.31 (s, 1H) 7.10-7.28 (m, 4H) 4.63-4.79 (m, 1H) 3.24 (d, J=15.77, 7.63 Hz, 2H) 2.96-3.08 (m, 2H). MS (ESI+) m/z 345.0 (M+H)$^+$.

Example 183

5-(1H-indazol-5-yl)-N-(1-phenylpropyl)isoxazole-3-carboxamide

The title compound was prepared according to the procedure outlined in Example 81B substituting alpha-ethylbenzylamine for piperidine. $^1$H NMR (300 MHz, DMSO-d$_6$) δ ppm 13.36 (s, 1H) 9.18 (d, J=8.82 Hz, 1H) 8.38 (s, 1H) 8.22 (s, 1H) 7.88 (d, J=8.82, 1.36 Hz, 1H) 7.69 (d, J=8.48 Hz, 1H) 7.39-7.48 (m, 2H) 7.34 (t, J=7.29 Hz, 2H) 7.19-7.29 (m, 2H) 4.84-5.00 (m, 1H) 1.69-2.04 (m, 2H) 0.91 (t, J=7.29 Hz, 3H). MS (ESI+) m/z 347.1 (M+H)$^+$.

Example 184

5-{1-benzyl-5-[3-(dimethylamino)phenyl]-1H-1,2,3-triazol-4-yl}-1H-indazol-3-amine The title compound was prepared as a TFA salt according to the procedure outlined in Example 173 substituting 3-(dimethylamino)phenylboronic acid for 4-methoxyphenylboronic acid. $^1$H NMR (500 MHz, DMSO-d$_6$) δ ppm 11.52 (s, 1H) 8.17 (s, 1H) 7.22-7.35 (m, 4H) 7.08-7.15 (m, 2H) 7.03 (d, J=6.71 Hz, 2H) 6.82 (d, J=8.39, 2.29 Hz, 1H) 6.48-6.54 (m, 2H) 5.47 (s, 2H) 2.78 (s, 6H). MS (ESI+) m/z 410.2 (M+H)$^+$.

Example 185

5-{1-benzyl-5-[4-(dimethylamino)phenyl]-1H-1,2,3-triazol-4-yl}-1H-indazol-3-amine The title compound was prepared as a TFA salt according to the procedure outlined in Example 173 substituting 4-(dimethylamino)phenylboronic acid for 4-methoxyphenylboronic acid. $^1$H NMR (500 MHz, DMSO-d$_6$) δ ppm 11.65 (s, 1H) 8.17 (s, 1H) 7.23-7.38 (m, 3H) 7.12-7.16 (m, 2H) 7.01-7.09 (m, 4H) 6.74-6.78 (m, 2H) 5.45 (s, 2H) 2.95 (s, 6H). MS (ESI+) m/z 410.2 (M+H)$^+$.

Example 186

N-{3-[4-(3-amino-1H-indazol-5-yl)-1-benzyl-1H-1,2,3-triazol-5-yl]phenyl}acetamide The title compound was prepared according to the procedure outlined in Example 173 substituting 3-acetamidophenylboronic acid for 4-methoxyphenylboronic acid. $^1$H NMR (500 MHz, DMSO-d$_6$) δ ppm 10.05 (s, 1H) 8.14 (s, 1H) 7.69 (d, J=8.54 Hz, 1H) 7.54 (s, 1H) 7.41 (t, J=7.93 Hz, 1H) 7.24-7.32 (m, 3H) 7.08-7.16 (m, 2H) 6.93-7.04 (m, 3H) 5.48 (s, 2H) 2.01 (s, 3H). MS (ESI+) m/z 424.2 (M+H)$^+$.

Example 187

N-{4-[4-(3-amino-1H-indazol-5-yl)-1-benzyl-1H-1,2,3-triazol-5-yl]phenyl}acetamide The title compound was prepared according to the procedure outlined in Example 173 substituting 4-acetamidophenylboronic acid for 4-methoxyphenylboronic acid. $^1$H NMR (500 MHz, DMSO-d$_6$) δ ppm 10.14 (s, 1H) 8.07 (s, 1H) 7.66 (d, J=8.85 Hz, 2H) 7.24-7.32 (m, 3H) 7.18-7.22 (m, 2H) 7.04-7.11 (m, 2H) 6.98-7.02 (m, 2H) 5.48 (s, 2H) 5.35 (s, 2H) 2.04-2.10 (m, 3H). MS (ESI+) m/z 424.1 (M+H)$^+$.

Example 188

5-{1-benzyl-5-[3-(1H-pyrazol-1-yl)phenyl]-1H-1,2,3-triazol-4-yl}-1H-indazol-3-amine The title compound was prepared according to the procedure outlined in Example 173 substituting 3-(1H-pyrazol-1-yl)phenylboronic acid for 4-methoxyphenylboronic acid. $^1$H NMR (500 MHz, DMSO-d$_6$) δ ppm 11.40 (s, 1H) 8.45 (d, J=2.75 Hz, 1H) 8.09 (s, 1H) 7.99 (d, J=8.24, 1.53 Hz, 1H) 7.80-7.85 (m, 1H) 7.74 (d, J=1.83 Hz, 1H) 7.56 (t, J=7.93 Hz, 1H) 7.20-7.30 (m, 3H) 7.06-7.16 (m, 3H) 6.98-7.04 (m, 2H) 6.53-6.54 (m, 1H) 5.55 (s, 2H) 5.35 (s, 2H). MS (ESI+) m/z 433.2 (M+H)$^+$.

Example 189

5-[1-benzyl-5-(1-methyl-1H-pyrazol-4-yl)-1H-1,2,3-triazol-4-yl]-1H-indazol-3-amine The title compound was prepared according to the procedure outlined in Example 173 substituting 1-methyl-1H- pyrazol-4-ylboronic acid for 4-methoxyphenylboronic acid. $^1$H NMR (500 MHz, DMSO-d$_6$) δ ppm 11.78 (s, 1H) 8.11 (s, 1H) 7.87 (s, 1H) 7.43 (s, 1H) 7.27-7.41 (m, 4H) 7.24 (d, J=8.54 Hz, 1H) 7.05-7.11 (m, J=7.02 Hz, 2H) 5.54 (s, 2H) 3.86 (s, 3H). MS (ESI+) m/z 370.9 (M+H)$^+$.

Example 190

3-[4-(3-amino-1H-indazol-5-yl)-1-benzyl-1H-1,2,3-triazol-5-yl]-N-phenylbenzamide The title compound was prepared according to the procedure outlined in Example 173 substituting 3-(phenylcarbamoyl)phenylboronic acid for 4-methoxyphenylboronic acid. $^1$H NMR (500 MHz, DMSO-d$_6$) δ ppm 11.41 (s, 1H) 10.22 (s, 1H) 8.07-8.12 (m, 2H) 7.95 (s, 1H) 7.73 (d, J=7.63 Hz, 2H) 7.60 (t, J=7.78 Hz, 1H) 7.43 (d, J=7.63 Hz, 1H) 7.32-7.39 (m, 2H) 7.21-7.30 (m, 3H) 7.05-7.15 (m, 3H) 7.00 (d, J=6.71 Hz, 2H) 5.54 (s, 2H) 5.36 (s, 2H). MS (ESI+) m/z 486.2 (M+H)$^+$.

Example 191

3-[4-(3-amino-1H-indazol-5-yl)-1-benzyl-1H-1,2,3-triazol-5-yl]-N-benzylbenzamide The title compound was prepared according to the procedure outlined in Example 173 substituting 3-(benzylcarbamoyl)phenylboronic acid for 4-methoxyphenylboronic acid. $^1$H NMR (500 MHz, DMSO-d$_6$) δ ppm 11.41 (s, 1H) 9.04 (t, J=5.95 Hz, 1H) 8.07 (s, 1H) 8.01 (d, J=7.93 Hz, 1H) 7.85 (s, 1H) 7.56 (t, J=7.78 Hz, 1H) 7.41 (d, J=7.63 Hz, 1H) 7.21-7.35 (m, 8H) 7.01-7.11 (m, 2H) 6.96 (d, J=7.32, 2.14 Hz, 2H) 5.52 (s, 2H) 5.35 (s, 2H) 4.45 (d, J=5.80 Hz, 2H). MS (ESI+) m/z 500.2 (M+H)$^+$.

Example 192

5-[1-benzyl-5-(1-methyl-1H-indol-5-yl)-1H-1,2,3-triazol-4-yl]-1H-indazol-3-amine The title compound was prepared as a TFA salt according to the procedure outlined in Example 173 substituting 1-methyl-1H-indol-5-ylboronic acid for 4-methoxyphenylboronic acid. $^1$H NMR (500 MHz, DMSO-d$_6$) δ ppm 11.35 (s, 1H) 8.14 (s, 1H) 7.54 (d, J=8.54 Hz, 1H) 7.50 (d, J=1.53 Hz, 1H) 7.42 (d, J=3.05 Hz, 1H) 7.24-7.33 (m, 3H) 6.97-7.05 (m, 5H) 6.44 (d, J=2.75 Hz, 1H) 5.46 (s, 2H) 5.33 (s, 2H) 3.83 (s, 3H). MS (ESI+) m/z 420.1 (M+H)$^+$.

Example 193

5-[1-benzyl-5-(3-methoxyphenyl)-1H-1,2,3-triazol-4-yl]-1H-indazol-3-amine

The title compound was prepared according to the procedure outlined in Example 173 substituting 3-methoxyphenylboronic acid for 4-methoxyphenylboronic acid. $^1$H NMR (500 MHz, DMSO-d$_6$) δ ppm 11.40 (s, 1H) 8.08 (s, 1H) 7.34-7.40 (m, 1H) 7.24-7.32 (m, 3H) 7.03-7.11 (m, 3H) 6.98-7.02 (m, 2H) 6.80-6.85 (m, 2H) 5.49 (s, 2H) 5.35 (s, 2H) 3.66 (s, 3H). MS (ESI+) m/z 397.1 (M+H)$^+$.

Example 194

5-[1-benzyl-5-(3-morpholin-4-ylphenyl)-1H-1,2,3-triazol-4-yl]-1H-indazol-3-amine A vial under argon containing Example 125B (35 mg, 0.09 mmol), 3-morpholinophenylboronic acid (21 mg, 0.09 mmol), PdCl$_2$(dppf)-dichloromethane (7 mg, 0.009 mmol) and potassium carbonate (24 mg, 0.18 mmol) in DME (1 mL) and water (0.1 mL) was capped and heated at 80° C. in a heater shaker for 3 days. The solvent was evaporated under reduced pressure, and the product was purified by reverse-phase HPLC using an acetonitrile/water 0.1% TFA gradient elution method to afford the title compound as a TFA salt. $^1$H NMR (500 MHz, DMSO-d$_6$) δ ppm 11.52 (s, 1H) 8.14 (s, 1H) 7.26-7.34 (m, 4H) 6.98-7.12 (m, 5H) 6.67-6.75 (m, 2H) 5.47 (s, 2H) 3.57-3.73 (m, 4H) 2.91-3.03 (m, 4H). MS (ESI+) m/z 452.2 (M+H)$^+$.

Example 195

5-[3-(1,3-dihydro-2H-isoindol-2-ylcarbonyl)isoxazol-5-yl]-1H-indazole

The title compound was prepared according to the procedure outlined in Example 81B substituting isoindoline for piperidine. $^1$H NMR (300 MHz, DMSO-d$_6$) δ ppm 13.38 (s, 1H) 8.43 (s, 1H) 8.25 (s, 1H) 7.93 (d, J=8.82, 1.36 Hz, 1H) 7.71 (d, J=8.48 Hz, 1H) 7.30-7.47 (m, 5H) 5.18 (s, 2H) 4.92 (s, 2H). MS (ESI+) m/z 331.0 (M+H)$^+$.

Example 196

5-{3-[(4-methyl-2-phenylpiperazin-1-yl)carbonyl]isoxazol-5-yl}-1H-indazole

The title compound was prepared according to the procedure outlined in Example 81B substituting 1-methyl-3-phenylpiperazine for piperidine. $^1$H NMR (300 MHz, DMSO-d$_6$) δ ppm 13.12 (s, 1H) 8.28-8.36 (m, 1H) 8.18 (s, 1H) 7.83 (d, J=8.79, 1.46 Hz, 1H) 7.67 (d, J=8.79 Hz, 1H) 7.48 (d, J=7.69 Hz, 2H) 7.30-7.40 (m, 2H) 7.21-7.29 (m, 1H) 7.14 (s, 1H) 5.56-5.73 (m, J=5.86 Hz, 1H) 3.99-4.19 (m, J=8.42 Hz, 1H) 3.38-3.47 (m, 1H) 3.05-3.21 (m, J=7.69 Hz, 1H) 2.80 (d, J=11.72 Hz, 1H) 2.41 (d, J=12.08, 4.39 Hz, 1H) 2.24 (s, 3H) 2.02-2.16 (m, 1H). MS (ESI+) m/z 388.1 (M+H)$^+$.

Example 197

1-{[1-benzyl-4-(1H-indazol-5-yl)-1H-1,2,3-triazol-5-yl]carbonyl}piperidin-4-amine Example 197A tert-Butyl 1-(1-benzyl-4-(1H-indazol-5-yl)-1H-1,2,3-triazole-5-carbonyl)piperidin-4-ylcarbamate The title compound was prepared according to the procedure outlined in Example 81B substituting Example 149C for Example 81B and 4-Boc-aminopiperidine for piperidine. MS (ESI+) m/z 502.3 (M+H)$^+$.

Example 197B

1-{[1-benzyl-4-(1H-indazol-5-yl)-1H-1,2,3-triazol-5-yl]carbonyl}piperidin-4-amine Example 197A (101 mg, 0.201 mmol) was dissolved in 4 M hydrochloric acid in dioxane (4 mL) and methanol (1 mL) and stirred at ambient temperature for 2 hours. The solvents were removed under reduced pressure to afford the title compound as an HCl salt. $^1$H NMR (300 MHz, DMSO-d$_6$) δ ppm 8.18 (s, 1H) 7.92-8.08 (m, J=1.36 Hz, 3H) 7.53-7.70 (m, 2H) 7.24-7.47 (m, 5H) 5.40-5.73 (m, J=3.39 Hz, 2H) 4.34-4.63

(m, 1H) 3.44-3.53 (m, J=3.39 Hz, 1H) 2.95-3.17 (m, 2H) 2.76-2.94 (m, J=11.02, 11.02 Hz, 1H) 1.87-2.03 (m, J=11.87 Hz, 1H) 1.30-1.52 (m, J=10.85 Hz, 2H) 0.66-0.91 (m, J=10.17 Hz, 1H). MS (ESI+) m/z 402.2 (M+H)$^+$.

Example 198

N-[5-(1-benzyl-5-phenyl-1H-1,2,3-triazol-4-yl)-1H-indazol-3-yl]benzamide

Example 198A tert-butyl 3-amino-5-(1-benzyl-5-phenyl-1H-1,2,3-triazol-4-yl)-1H-indazole-1-carboxylate Example 102B (200 mg, 0.55 mmol) and N,N-dimethylpyridin-4-amine (5 mg, 0.04 mmol) were dissolved in methylene chloride. The mixture was stirred at room temperature while a solution of di-tert-butyl dicarbonate (120 mg, 0.55 mmol) in 5 mL methylene chloride was added dropwise. The reaction mixture was allowed to stir at room temperature for 8 hours, was concentrated under vacuum, dissolved in methylene chloride (10 mL) and washed with dilute aqueous HCl solution (1 N, 10 mL) and saturated NaHCO$_3$ aqueous solution (10 mL). The organic layer was concentrated and purified by reverse phase-HPLC (CH$_3$CN/H$_2$O/NH$_4$OAc) to afford the title compound. $^1$H NMR (300 MHz, DMSO-d$_6$) δ ppm 8.29 (s, 2H), 7.43-7.59 (m, 3H), 7.23-7.38 (m, 6H), 6.98 (d, J=7.17, 2.39 Hz, 2H), 6.38 (s, 2H), 5.52 (s, 2H), 1.55 (s, 9H). MS (ESI+) m/z 467 (M+H)$^+$.

Example 198B

N-[5-(1-benzyl-5-phenyl-1H-1,2,3-triazol-4-yl)-1H-indazol-3-yl]benzamide

Example 198A (37.5 mg, 0.08 mmol) and pyridine (12.7 mg, 0.16 mmol) were dissolved in methylene chloride (2 mL). The mixture was allowed to stir at room temperature. Benzoyl chloride (14 mg, 0.1 mmol) was added to the mixture. The reaction mixture was allowed to stir at room temperature overnight, concentrated under vacuum and purified by reverse phase-HPLC(CH$_3$CN/H$_2$O/NH$_4$OAc) to afford the Boc-protected precursor. The precursor was treated with 1:1 TFA/dichloromethane (2 mL) for 1 hour and was concentrated under vacuum to afford the title compound as a TFA salt. $^1$H NMR (300 MHz, DMSO-d$_6$) δ ppm 12.84 (s, 1H), 10.70 (s, 1H), 8.01 (d, J=6.99 Hz, 2H), 7.87 (s, 1H), 7.50-7.69 (m, 3H), 7.36-7.48 (m, 5H), 7.18-7.35 (m, 5H), 6.92-7.03 (m, 2H), 5.48 (s, 2H). MS (ESI+) m/z 471 (M+H)$^+$.

Example 199

N-[5-(1-benzyl-5-phenyl-1H-1,2,3-triazol-4-yl)-1H-indazol-3-yl]benzenesulfonamide The title compound was prepared according to the procedure outlined in Example 198B substituting benzenesulfonyl chloride for benzoyl chloride. $^1$H NMR (300 MHz, DMSO-d$_6$) δ ppm 12.69 (s, 1H), 10.61 (s, 1H), 7.99 (s, 1H), 7.70-7.76 (m, 2H), 7.45-7.62 (m, 6H), 7.24-7.36 (m, 7H), 6.99 (d, J=6.99, 2.21 Hz, 2H), 5.50 (s, 2H). MS (ESI+) m/z 507 (M+H)$^+$.

Example 200

N-[5-(1-benzyl-5-phenyl-1H-1,2,3-triazol-4-yl)-1H-indazol-3-yl]-N'-(4-methoxyphenyl)urea Example 198A (25 mg, 0.54 mmol) was dissolved in dioxane (2 mL) and 1-isocyanato-4-methoxybenzene (24 mg, 0.16 mmol) was added to the solution. The reaction mixture was stirred at 80° C. for 12 hours, concentrated, and purified by reverse phase-HPLC (CH$_3$CN/H$_2$O/NH$_4$OAc) to afford the Boc-protected precursor. The precursor was treated with 1:1 TFA/dichloromethane (2 mL) for 1 hour and concentrated under vacuum to afford the title compound as a TFA salt. $^1$H NMR (300 MHz, DMSO-d$_6$) δ ppm 12.54 (s, 1H), 9.51 (s, 1H), 9.42 (s, 1H), 8.28 (s, 1H), 7.45-7.51 (m, 3H), 7.36-7.42 (m, 2H), 7.24-7.35 (m, 7H), 6.98 (d, J=7.17, 2.39 Hz, 2H), 6.87-6.94 (m, 2H), 5.50 (s, 2H), 3.74 (s, 3H). MS (ESI+) m/z 516 (M+H)$^+$.

Example 201

N-[5-(1-benzyl-5-phenyl-1H-1,2,3-triazol-4-yl)-1H-indazol-3-yl]butanamide

The title compound was prepared as a TFA salt according to the procedure outlined in Example 198B substituting butyryl chloride for benzoyl chloride. $^1$H NMR (300 MHz, DMSO-d$_6$) δ ppm 10.77-10.84 (m, 1H), 8.07 (s, 1H), 7.97 (d, J=8.82 Hz, 1H), 7.64 (d, J=8.82, 1.47 Hz, 1H), 7.43-7.57 (m, 3H), 7.22-7.38 (m, 5H), 6.91-7.06 (m, 2H), 5.50 (s, 2H), 2.33 (t, J=7.17 Hz, 2H), 1.54-1.60 (m, 2H), 0.91 (t, J=7.35 Hz, 3H). MS (ESI+) m/z 437 (M+H)$^+$.

Example 202

N-[5-(1-benzyl-5-phenyl-1H-1,2,3-triazol-4-yl)-1H-indazol-3-yl]-2-methylpropanamide The title compound was prepared according to the procedure outlined in Example 198B substituting isobutyryl chloride for benzoyl chloride. $^1$H NMR (300 MHz, DMSO-d$_6$) δ ppm 12.66 (s, 1H), 10.12 (s, 1H), 7.80 (s, 1H), 7.42-7.55 (m, 4H), 7.33-7.39 (m, 1H), 7.22-7.32 (m, 5H), 6.97 (d, J=6.99, 2.57 Hz, 2H), 5.48 (s, 1H), 2.59-2.69 (m, 1H), 1.07 (d, J=6.99 Hz, 6H). MS (ESI+) m/z 437 (M+H)$^+$.

Example 203

N-[5-(1-benzyl-5-phenyl-1H-1,2,3-triazol-4-yl)-1H-indazol-3-yl]cyclopropanecarboxamide The title compound was prepared according to the procedure outlined in Example 198B substituting cyclopropanecarbonyl chloride for benzoyl chloride. $^1$H NMR (300 MHz, DMSO-d$_6$) δ ppm 10.45-10.64 (s, 1H), 7.91 (s, 1H), 7.43-7.55 (m, 3H), 7.31-7.43 (m, 2H), 7.23-7.30 (m, 5H), 6.97 (d, J=7.17, 2.39 Hz, 2H), 5.48 (s, 2H), 1.77-1.91 (m, 1H), 0.69-0.87 (m, 4H). MS (ESI+) m/z 435 (M+H)$^+$.

Example 204

N-[1-benzoyl-5-(1-benzyl-5-cyclopropyl-1H-1,2,3-triazol-4-yl)-1H-indazol-3-yl]benzamide Example 89B (33 mg, 0.1 mmol) was dissolved in tetrahydrofuran (0.6 mL) in a CEM microwave tube. Benzoyl chloride (28 mg, 0.2 mmol) was added and the mixture was heated at 120° C. for 15 minutes in the CEM-Discover microwave. The reaction mixture was cooled to room temperature, and concentrated. The residue was purified by reverse phase-HPLC(CH$_3$CN/H$_2$O/NH$_4$OAc) to afford the title compound. $^1$H NMR (300 MHz, DMSO-d$_6$) δ ppm 11.35 (s, 1H), 8.55 (d, J=8.82 Hz, 1H), 8.36 (s, 1H), 8.17 (d, J=8.64, 1.65 Hz, 1H), 8.06 (d, J=7.54, 2.39 Hz, 4H), 7.51-7.72 (m, 6H), 7.26-7.45 (m, 5H), 5.71 (s, 2H), 1.76-1.87 (m, 1H), 1.11 (d, J=6.62 Hz, 2H), 0.44 (d, J=4.41 Hz, 2H). MS (ESI+) m/z 539 (M+H)$^+$.

Example 205

N-[5-(1-benzyl-5-cyclopropyl-1H-1,2,3-triazol-4-yl)-1H-indazol-3-yl]-3-fluorobenzamide Example 205A tert-Butyl 3-amino-5-(1-benzyl-5-cyclopropyl-1H-1,2,3-triazol-4-yl)-1H-indazole-1-carboxylate The title compound was prepared according to the procedure outlined in Example 198A substituting Example 89B for Example 102A. $^1$H NMR (300 MHz, DMSO-d$_6$) δ ppm 8.26 (s, 1H), 7.96-8.07 (m, 1H), 7.86-7.95 (m, 1H), 7.35-7.46 (m, 3H), 7.28-7.35 (m, 2H), 6.35-6.47 (m, 2H), 5.70 (s, 2H), 1.72-1.84 (m, 1H), 1.60 (s, 9H), 0.99-1.10 (d, J=1.84 Hz, 2H), 0.38 (d, J=3.68 Hz, 2H). MS (ESI+) m/z 431 (M+H)$^+$.

Example 205B

N-[5-(1-benzyl-5-cyclopropyl-1H-1,2,3-triazol-4-yl)-1H-indazol-3-yl]-3-fluorobenzamide Example 205A (25 mg, 0.058 mmol) and pyridine (9.2 mg, 0.116 mmol) were dissolved in methylene chloride (1 mL). The mixture was allowed to stir at room temperature, and 3-fluorobenzoyl chloride (11.1 mg, 0.58 mmol) was added to the mixture. The reaction mixture was allowed to stir at room temperature overnight, and was concentrated and purified by reverse phase-HPLC(CH$_3$CN/H$_2$O/NH$_4$OAc) to afford the Boc-protected precursor. The precursor was treated with 1:1 TFA/dichloromethane (2 mL) for 1 hour and concentrated under vacuum to afford the title compound as a TFA salt. $^1$H NMR (300 MHz, DMSO-d$_6$) δ ppm 10.58 (s, 1H), 7.75 (s, 1H), 7.51-7.60 (m, 1H), 7.46 (d, J=8.82, 1.47 Hz, 1H), 7.15-7.28 (m, 2H), 7.10 (d, J=2.21 Hz, 1H), 6.88-7.05 (m, 6H), 5.31 (s, 2H), 1.35-1.47 (m, J=5.15 Hz, 1H), 0.68 (d, J=8.27, 1.65 Hz, 2H), 0.03 (d, J=5.52 Hz, 2H). MS (ESI+) m/z 453 (M+H)$^+$.

Example 206

N-[5-(1-benzyl-5-cyclopropyl-1H-1,2,3-triazol-4-yl)-1H-indazol-3-yl]benzamide

The title compound was prepared according to the procedure outlined in Example 205B substituting benzoyl chloride for 3-fluorobenzoyl chloride. $^1$H NMR (300 MHz, DMSO-d$_6$) δ ppm 12.89 (s, 1H), 10.83 (s, 1H), 8.02-8.15 (m, 3H), 7.83 (d, J=8.82, 1.47 Hz, 1H), 7.50-7.66 (m, 4H), 7.24-7.43 (m, 5H), 5.67 (s, 2H), 1.77 (m, 1H), 0.99-1.10 (m, 2H), 0.39 (m, 2H). MS (ESI+) m/z 435 (M+H)$^+$.

Example 207

N-benzyl-5-(1-benzyl-5-cyclopropyl-1H-1,2,3-triazol-4-yl)-1H-indazol-3-amine

To a solution of Example 89B (18.3 mg, 0.05 mmol) in dimethylformamide (2 mL) was added acetic acid (15 mg, 0.25 mmol) and benzaldehyde (6.4 mg, 0.06 mmol). The reaction mixture was stirred at room temperature overnight. Sodium triacetoxyborohydride (NaBH(OAc)$_3$, 32 mg, 0.15 mmol) was added to the mixture. The reaction was stirred at room temperature for 3 hours, concentrated and purified by reverse phase-HPLC (CH$_3$CN/H$_2$O/NH$_4$OAc) to afford the title compound. $^1$H NMR (300 MHz, DMSO-d$_6$) δ ppm 13.09 (s, 1H), 9.24 (s, 1H), 8.02-8.10 (m, 3H), 7.84-7.90 (m, 1H), 7.49-7.67 (m, 4H), 7.25-7.45 (m, 5H), 5.70 (s, 2H), 3.30 (s, 2H), 1.88-1.95 (m, 1H), 1.01-1.09 (m, 2H), 0.43 (d, J=4.04 Hz, 2H). MS (ESI+) m/z 421 (M+H)$^+$.

Example 208

N-[(1R)-1-benzyl-2-hydroxyethyl]-5-(1H-indazol-5-yl)isoxazole-3-carboxamide

The title compound was prepared according to the procedure outlined in Example 81B substituting (R)-(+)-2-amino-3-phenyl-1-propanol (37 mg, 0.245 mmol) for piperidine. $^1$H NMR (300 MHz, DMSO-d$_6$) δ ppm 13.36 (s, 1H) 8.46 (d, J=8.82 Hz, 1H) 8.37 (s, 1H) 8.22 (s, 1H) 7.87 (dd, J=8.82, 1.36 Hz, 1H) 7.69 (d, J=8.82 Hz, 1H) 7.12-7.35 (m, 6H) 4.89 (t, J=5.59 Hz, 1H) 4.13-4.25 (m, 1H) 3.40-3.58 (m, 2H) 2.90-2.99 (m, 1H) 2.74-2.87 (m, 1H). MS (ESI+) m/z 363.0 (M+H)$^+$.

Example 209

5-(1-benzyl-1H-pyrazol-4-yl)-1H-indazole

Example 209A 1-(5-Bromo-1H-indazol-1-yl)ethanone

4-Bromo-2-methylaniline (25.0 g, 134 mmol) was dissolved in chloroform (250 mL), and the mixture was cooled to 5° C. Acetic anhydride (35 mL, 343 mmol) was added dropwise, and the mixture was allowed to warm to ambient temperature. Potassium acetate (3.97 g, 40.4 mmol) and isoamylnitrite (35 mL, 262 mmol) were added, and the mixture was heated at 70° C. overnight. The mixture was neutralized with saturated sodium bicarbonate and extracted with methylene chloride. The combined organic layers were concentrated under reduced pressure, and the resulting residue was triturated with methanol to afford the title compound. $^1$H NMR (300 MHz, DMSO-d$_6$) δ ppm 8.45 (s, 1H) 8.26 (d, J=8.82 Hz, 1H) 8.17 (d, J=1.70 Hz, 1H) 7.77 (dd, J=8.82, 2.03 Hz, 1H) 2.72 (s, 3H).

Example 209B 5-(1-benzyl-1H-pyrazol-4-yl)-1H-indazole

Example 209A (425 mg, 1.78 mmol), 1-benzyl-4-(4,4,5,5-tetramethyl-1,3,2-dioxaborolan-2-yl)-1H-pyrazole (508 mg, 1.79 mmol), dichlorobis(triphenylphosphine)palladium(II) (133 mg, 0.189 mmol), and potassium carbonate (742 mg, 5.37 mmol) were combined in a sealed vial with dioxane (10 mL) and water (1 mL) under and inert atmosphere of nitrogen, and the mixture was heated to 110° C. overnight. The mixture was diluted with methylene chloride and washed with water. The organic layer was absorbed on silica gel and purified by silica gel chromatography eluting with a gradient of 45-90% ethyl acetate in hexanes to afford the title compound. $^1$H NMR (300 MHz, DMSO-d$_6$) δ ppm 13.00 (s, 1H)

8.25 (s, 1H) 8.02 (s, 1H) 7.92 (s, 2H) 7.55-7.61 (m, 1H) 7.48-7.54 (m, 1H) 7.25-7.40 (m, 5H) 5.35 (s, 2H). MS (ESI+) m/z 274.9 (M+H)+.

Example 210

N-[(1R)-3-hydroxy-1-phenylpropyl]-5-(3-methyl-1H-indazol-5-yl)isoxazole-3-carboxamide

Example 210A tert-Butyl 5-bromo-3-methyl-1H-indazole-1-carboxylate

5-Bromo-3-methyl-1H-indazole (5.11 g, 24.2 mmol) and catalytic dimethylaminopyridine (~30 mg) were dissolved in methylene chloride (100 mL). Di-tert-butyl dicarbonate (5.9 g, 27.0 mmol) was added, and the mixture was stirred at ambient temperature for 3 hours. The solvent was removed under reduced pressure, and the resulting residue was diluted with ethyl acetate and washed with 1 N sodium hydroxide (twice), 0.1 N hydrochloric acid, and brine. The organic layer was dried over sodium sulfate and filtered. The filtrate was concentrated under reduced pressure to afford the title compound. MS (ESI+) m/z 210.8 (M−Boc)+.

Example 210B tert-Butyl 3-methyl-5-((trimethylsilyl)ethynyl)-1H-indazole-1-carboxylate Example 210A (7.55 g, 24.3 mmol), dichlorobis(triphenylphosphine)palladium(II) (870 mg, 1.24 mmol), and copper(I) iodide (250 mg, 1.31 mmol) were combined in triethylamine (60 mL) under an inert atmosphere of nitrogen. Trimethylsilyl acetylene (4.0 mL, 28.9 mmol) was added, and the mixture was heated at 60° C. overnight. The mixture was diluted with methylene chloride and washed with 0.1 M hydrochloric acid. The organic layer was absorbed onto silica gel and purified by silica gel chromatography eluting with a gradient of 10-40% ethyl acetate in hexanes to afford the title compound. MS (ESI+) m/z 228.9 (M−Boc)+.

Example 210C

5-Ethynyl-3-methyl-1H-indazole

Example 210B (7.26 g, 22.1 mmol) was dissolved in methanol (170 mL). A solution of 1 N potassium hydroxide (45 mL) was added, and the mixture was stirred at ambient temperature overnight. The solvent was removed under reduced pressure, and the resulting residue was diluted with ethyl acetate and washed with water and brine. The organic layer was dried over sodium sulfate and concentrated under reduced pressure to afford the title compound. MS (ESI+) m/z 157.1 (M+H)+.

Example 210D

Ethyl 5-(3-methyl-1H-indazol-5-yl)isoxazole-3-carboxylate

Example 210C (411 mg, 2.63 mmol) was dissolved in toluene (15 mL) and triethylamine (478 µL) and warmed to 90° C. Ethyl chlorooximidoacetate (480 mg, 3.17 mmol) dissolved in toluene (15 mL) was added slowly dropwise over 30 minutes. Following the addition, the mixture was diluted with ethyl acetate and washed with 1 N hydrochloric acid. The organic layer was concentrated under reduced pressure and the resulting residue was triturated with methanol to afford the title compound. MS (ESI+) m/z 271.9 (M+H)+.

Example 210E 5-(3-methyl-1H-indazol-5-yl)isoxazole-3-carboxylic Acid

Example 210D (325 mg, 1.20 mmol) was dissolved in tetrahydrofuran (10 mL), methanol (1 mL), and water (1 mL) and potassium hydroxide (150 mg, 2.67 mmol) was added. The mixture was stirred at ambient temperature for 3 hours. The mixture was diluted with ethyl acetate and washed with 1 N hydrochloric acid. The product precipitated in the separatory funnel and was filtered to afford the title compound. MS (ESI+) m/z 243.9 (M+H)+.

Example 210F

N-[(1R)-3-hydroxy-1-phenylpropyl]-5-(3-methyl-1H-indazol-5-yl)isoxazole-3-carboxamide The title compound was prepared according to the procedure outlined in Example 81B substituting Example 210E for Example 81A and (R)-3-amino-3-phenylpropan-1-ol for piperidine. $^1$H NMR (300 MHz, DMSO-$d_6$) δ ppm 12.93 (s, 1H) 8.45 (d, J=8.82 Hz, 1H) 8.33 (s, 1H) 7.84 (d, J=8.82, 1.70 Hz, 1H) 7.59 (d, J=9.16 Hz, 1H) 7.21-7.29 (m, 5H) 7.13-7.21 (m, 1H) 4.89 (t, J=5.59 Hz, 1H) 4.10-4.26 (m, 1H) 3.42-3.56 (m, 2H) 2.88-3.00 (m, 1H) 2.75-2.87 (m, 1H) 2.55 (s, 3H). MS (ESI+) m/z 377.1 (M+H)+.

Example 211

3-[4-(3-amino-1H-indazol-5-yl)-1-benzyl-1H-1,2,3-triazol-5-yl]phenol

A vial under argon containing Example 125B (35 mg, 0.09 mmol), 3-hydroxyphenylboronic acid (12 mg, 0.09 mmol), PdCl$_2$(dppf)-dichloromethane (7 mg, 0.009 mmol) and potassium carbonate (24 mg, 0.18 mmol) in DME (1 mL) and water (0.1 mL) was capped and heated at 80° C. in a heater shaker for 3 days. The solvent was evaporated and the product was purified by reverse-phase HPLC using an acetonitrile/water 0.1% TFA gradient elution method to afford the title compound. $^1$H NMR (500 MHz, DMSO-$d_6$) δ ppm 11.40 (s, 1H) 9.68 (s, 1H) 8.09 (s, 1H) 7.24-7.35 (m, 5H) 6.98-7.13 (m, 3H) 6.88 (d, J=8.09, 1.98 Hz, 1H) 6.73 (s, 1H) 6.60-6.66 (m, 1H) 5.47 (s, 2H) 5.35 (s, 2H). MS (ESI+) m/z 383.1 (M+H)+.

Example 212

3-[4-(3-amino-1H-indazol-5-yl)-1-benzyl-1H-1,2,3-triazol-5-yl]benzamide

The title compound was prepared according to the procedure outlined in Example 173 substituting 3-carbamoylphenylboronic acid for 4-methoxyphenylboronic acid. $^1$H NMR (500 MHz, DMSO-$d_6$) δ ppm 11.41 (s, 1H) 8.07 (s, 1H) 7.97-8.03 (m, 2H) 7.83-7.87 (m, 1H) 7.53 (t, J=7.78 Hz, 1H) 7.45 (s, 1H) 7.38 (d, J=7.63 Hz, 1H) 7.23-7.30 (m, 3H) 7.00-7.10 (m, 2H) 6.96 (d, J=7.48, 1.98 Hz, 2H) 5.51 (s, 2H) 5.35 (s, 2H). MS (ESI+) m/z 410.1 (M+H)+.

Example 213

5-{1-benzyl-5-[4-(methylsulfonyl)phenyl]-1H-1,2,3-triazol-4-yl}-1H-indazol-3-amine The title compound was prepared according to the procedure outlined in Example 173 substituting 4-(methylsulfonyl)phenylboronic acid for 4-methoxyphenylboronic acid. $^1$H NMR (500 MHz, DMSO-d$_6$) δ ppm 11.44 (s, 1H) 7.94-8.01 (m, 3H) 7.58 (d, J=8.54 Hz, 2H) 7.22-7.30 (m, 3H) 7.04-7.13 (m, 2H) 6.98 (d, J=7.48, 1.98 Hz, 2H) 5.56 (s, 2H) 5.37 (s, 2H) 3.28 (s, 3H). MS (ESI+) m/z 445.2 (M+H)$^+$.

Example 214

N-[5-(1-benzyl-5-cyclopropyl-1H-1,2,3-triazol-4-yl)-1H-indazol-3-yl]-2-chlorobenzamide The title compound was prepared according to the procedure outlined in Example 205B substituting 2-chlorobenzoyl chloride for 3-fluorobenzoyl chloride. $^1$H NMR (300 MHz, DMSO-d$_6$) δ ppm 10.94 (s, 1H), 8.24 (s, 1H), 7.85 (d, J=8.82, 1.47 Hz, 1H), 7.65 (d, J=6.99, 1.84 Hz, 1H), 7.43-7.61 (m, 4H), 7.26-7.42 (m, 5H), 5.68 (s, 2H), 1.71-1.83 (m, 1H), 1.04-1.12 (m, 2H), 0.37-0.45 (m, 2H). MS (ESI+) m/z 469 (M+H)$^+$.

Example 215

N-[5-(1-benzyl-5-cyclopropyl-1H-1,2,3-triazol-4-yl)-1H-indazol-3-yl]-4-chlorobenzamide The title compound was prepared according to the procedure outlined in Example 205B substituting 4-chlorobenzoyl chloride for 3-fluorobenzoyl chloride. $^1$H NMR (300 MHz, DMSO-d$_6$) δ ppm 10.53 (s, 1H), 7.65-7.71 (m, 3H), 7.42 (d, J=8.82, 1.47 Hz, 1H), 7.18-7.24 (m, 2H), 7.12-7.18 (m, 1H), 6.93-7.02 (m, 3H), 6.83-6.92 (m, 3H), 5.27 (s, 2H), 1.30-1.44 (m, 1H), 0.59-0.67 (m, 2H), −0.07-0.04 (m, 2H). MS (ESI+) m/z 469 (M+H)$^+$.

Example 216

N-[5-(1-benzyl-5-cyclopropyl-1H-1,2,3-triazol-4-yl)-1H-indazol-3-yl]ethanesulfonamide The title compound was prepared according to the procedure outlined in Example 205B substituting ethanesulfonyl chloride for 3-fluorobenzoyl chloride. $^1$H NMR (300 MHz, DMSO-d$_6$) δ ppm 10.19 (s, 1H), 8.15 (s, 1H), 7.82 (d, J=8.64, 1.65 Hz, 1H), 7.53 (d, J=8.82 Hz, 1H), 7.35-7.45 (m, 3H), 7.27-7.35 (m, 2H), 5.69 (s, 2H), 3.30 (q, J=7.35 Hz, 2H), 1.74-1.87 (m, 1H), 1.27-1.36 (m, 3H), 1.02-1.12 (m, 2H), 0.34-0.44 (m, 2H). MS (ESI+) m/z 423 (M+H)$^+$.

Example 217

N-[5-(1-benzyl-5-cyclopropyl-1H-1,2,3-triazol-4-yl)-1H-indazol-3-yl]benzenesulfonamide The title compound was prepared according to the procedure outlined in Example 205B substituting benzenesulfonyl chloride for 3-fluorobenzoyl chloride. $^1$H NMR (300 MHz, DMSO-d$_6$) δ ppm 12.75 (s, 1H), 10.69 (s, 1H), 8.02 (s, 1H), 7.71-7.83 (m, 3H), 7.43-7.60 (m, 4H), 7.34-7.43 (m, 3H), 7.27-7.34 (m, 2H), 5.69 (s, 2H), 1.69-1.83 (m, 1H), 0.99-1.11 (m, 2H), 0.31-0.45 (m, 2H). MS (ESI+) m/z 471 (M+H)$^+$.

Example 218

N-[5-(1-benzyl-5-cyclopropyl-1H-1,2,3-triazol-4-yl)-1H-indazol-3-yl]-2-chlorobenzenesulfonamide The title compound was prepared according to the procedure outlined in Example 205B substituting 2-chlorobenzene-1-sulfonyl chloride for 3-fluorobenzoyl chloride. $^1$H NMR (300 MHz, DMSO-d$_6$) δ ppm 12.36 (s, 1H), 10.60 (s, 1H), 7.67 (s, 1H), 7.62 (d, J=7.91, 1.65 Hz, 1H), 7.40 (d, J=8.82, 1.47 Hz, 1H), 7.14-7.27 (m, 2H), 7.00-7.12 (m, 4H), 6.96-7.00 (m, 1H), 6.90-6.95 (m, 2H), 5.31 (s, 2H), 1.29-1.44 (m, 1H), 0.61-0.74 (m, 2H), −0.05-0.05 (m, 2H). MS (ESI+) m/z 505 (M+H)$^+$.

Example 219

N-[5-(1-benzyl-5-cyclopropyl-1H-1,2,3-triazol-4-yl)-1H-indazol-3-yl]-3-chlorobenzenesulfonamide The title compound was prepared as an HCl salt according to the procedure outlined in Example 205B substituting 3-chlorobenzene-1-sulfonyl chloride for 3-fluorobenzoyl chloride. $^1$H NMR (300 MHz, DMSO-d$_6$) δ ppm 12.84 (s, 1H), 10.86 (s, 1H), 8.00 (s, 1H), 7.82 (s, 1H), 7.72 (d, J=7.72 Hz, 1H), 7.64 (d, J=1.84 Hz, 1H), 7.57 (d, J=7.72 Hz, 1H), 7.50 (d, J=8.82 Hz, 1H), 7.34-7.45 (m, 3H), 7.28-7.34 (m, 2H), 5.69 (s, 2H), 1.71-1.83 (m, 1H), 1.06 (m, 2H), 0.37 (m, 2H). MS (ESI+) m/z 505 (M+H)$^+$.

Example 220

N-[5-(1-benzyl-5-cyclopropyl-1H-1,2,3-triazol-4-yl)-1H-indazol-3-yl]-4-chlorobenzenesulfonamide The title compound was prepared as an HCl salt according to the procedure outlined in Example 205B substituting 4-chlorobenzene-1-sulfonyl chloride for 3-fluorobenzoyl chloride. $^1$H NMR (300 MHz, DMSO-d$_6$) δ ppm 12.80 (s, 1H), 10.79 (s, 1H), 8.00 (s, 1H), 7.73-7.83 (m, 3H), 7.56-7.64 (m, 2H), 7.49 (d, J=8.82 Hz, 1H), 7.34-7.45 (m, 3H), 7.28-7.34 (m, 2H), 5.69 (s, 2H), 1.71-1.86 (m, 1H), 0.99-1.12 (m, 2H), 0.31-0.43 (m, 2H). MS (ESI+) m/z 505 (M+H)$^+$.

Example 221

N-[5-(1-benzyl-5-cyclopropyl-1H-1,2,3-triazol-4-yl)-1H-indazol-3-yl]-2,5-dimethylfuran-3-sulfonamide The title compound was prepared as an HCl salt according to the procedure outlined in Example 205B substituting 2,5-dimethylfuran-3-sulfonyl chloride for 3-fluorobenzoyl chloride. $^1$H NMR (300 MHz, DMSO-d$_6$) δ ppm 12.82 (s, 1H), 10.48 (s, 1H), 8.00 (s, 1H), 7.78 (d, J=8.64, 1.65 Hz, 1H), 7.50 (d, J=9.19 Hz, 1H), 7.34-7.45 (m, 3H), 7.28-7.33 (m, 2H), 6.20 (s, 1H), 5.69 (s, 2H), 2.11 (s, 6H), 1.71-1.84 (m, 1H), 1.01-1.11 (m, 2H), 0.32-0.41 (m, 2H). MS (ESI+) m/z 489 (M+H)$^+$.

Example 222

5-(1-benzyl-5-cyclopropyl-1H-1,2,3-triazol-4-yl)-N-(2-chlorobenzyl)-1H-indazol-3-amine The title compound was prepared according to the procedure outlined in Example 207 substituting 2-chlorobenzaldehyde for benzaldehyde. ¹H NMR (300 MHz, DMSO-d₆) δ ppm 11.55 (s, 1H), 8.20 (s, 1H), 7.69 (d, J=8.46, 1.47 Hz, 1H), 7.49 (d, J=8.82 Hz, 1H), 7.34-7.46 (m, 4H), 7.23-7.33 (m, 5H), 5.69 (s, 2H), 4.56 (s, 2H), 1.72-1.83 (m, 1H), 0.99-1.09 (m, 2H), 0.35-0.42 (m, 2H). MS (ESI+) m/z 455 (M+H)⁺.

Example 223

5-(1-benzyl-5-cyclopropyl-1H-1,2,3-triazol-4-yl)-N-(3-chlorobenzyl)-1H-indazol-3-amine The title compound was prepared according to the procedure outlined in Example 207 substituting 3-chlorobenzaldehyde for benzaldehyde. ¹H NMR (300 MHz, DMSO-d₆) δ ppm 11.53 (s, 1H), 8.15 (s, 1H), 7.59-7.77 (m, 1H), 7.25-7.48 (m, 10H), 5.68 (s, 2H), 4.49 (s, 2H), 1.71-1.80 (m, 1H), 1.04 (s, 2H), 0.38 (s, 2H).

Example 224

N-[5-(1-benzyl-5-cyclopropyl-1H-1,2,3-triazol-4-yl)-1H-indazol-3-yl]-3-chlorobenzamide The title compound was prepared according to the procedure outlined in Example 205B substituting 3-chlorobenzoyl chloride for 3-fluorobenzoyl chloride. ¹H NMR (300 MHz, DMSO-d₆) δ ppm 10.99 (s, 1H), 8.12 (s, 2H), 8.03 (d, J=7.72 Hz, 1H), 7.83 (d, J=8.46 Hz, 1H), 7.68 (s, 1H), 7.58 (t, J=8.09 Hz, 2H), 7.33-7.44 (m, 3H), 7.25-7.33 (m, 2H), 5.68 (s, 2H), 1.72-1.86 (m, 1H), 0.99-1.12 (m, 2H), 0.34-0.45 (m, 2H). MS (ESI+) m/z 470 (M+H)⁺.

Example 225

N-[5-(1-benzyl-5-cyclopropyl-1H-1,2,3-triazol-4-yl)-1H-indazol-3-yl]-2-furamide

The title compound was prepared according to the procedure outlined in Example 205B substituting furan-2-carbonyl chloride for 3-fluorobenzoyl chloride. ¹H NMR (300 MHz, DMSO-d₆) δ ppm 10.36 (s, 1H), 7.71 (s, 1H), 7.42 (d, J=8.82, 1.47 Hz, 1H), 7.15 (d, J=8.82 Hz, 1H), 7.06 (d, J=3.31 Hz, 1H), 6.93-7.03 (m, 3H), 6.86-6.93 (m, 2H), 6.31 (d, J=3.49, 1.65 Hz, 1H), 5.28 (s, 1H), 1.31-1.45 (m, 1H), 0.59-0.71 (m, 2H), −0.05-0.05 (m, 2H). MS (ESI+) m/z 425 (M+H)⁺.

Example 226

5-(1-benzyl-5-cyclopropyl-1H-1,2,3-triazol-4-yl)-N-ethyl-1H-indazol-3-amine

The title compound was prepared according to the procedure outlined in Example 207 substituting acetaldehyde for benzaldehyde. ¹H NMR (300 MHz, DMSO-d₆) δ ppm 8.56 (s, 1H), 8.30-8.42 (m, 1H), 7.90-8.17 (m, 2H), 7.20-7.45 (m, 5H), 5.70 (s, 2H), 1.78-1.93 (m, 2H), 1.67 (s, 1H), 1.06 (m, 3H), 0.95 (m, 2H), 0.29-0.48 (m, 2H). MS (ESI+) m/z 359 (M+H)⁺.

Example 227

5-(1-benzyl-5-cyclopropyl-1H-1,2,3-triazol-4-yl)-N-(4-chlorobenzyl)-1H-indazol-3-amine The title compound was prepared according to the procedure outlined in Example 207 substituting 4-chlorobenzaldehyde for benzaldehyde. ¹H NMR (300 MHz, DMSO-d₆) δ ppm 10.01 (s, 1H), 9.25 (s, 1H), 8.25-8.33 (m, 1H), 8.09 (d, J=8.46 Hz, 1H), 7.84-7.97 (m, 2H), 7.57-7.73 (m, 2H), 7.26-7.51 (m, 6H), 5.70 (s, 2H), 1.71-1.84 (m, 1H), 0.97-1.15 (m, 2H), 0.36-0.47 (m, 2H). MS (ESI+) m/z 455 (M+H)⁺.

Example 228

5-(1-benzyl-5-cyclopropyl-1H-1,2,3-triazol-4-yl)-N-(3-furylmethyl)-1H-indazol-3-amine The title compound was prepared according to the procedure outlined in Example 207 substituting furan-3-carbaldehyde for benzaldehyde. ¹H NMR (300 MHz, DMSO-d₆) δ ppm 8.21 (s, 1H), 7.90 (s, 1H), 7.71-7.82 (m, 1H), 7.55-7.68 (m, 2H), 7.24-7.51 (m, 6H), 5.68 (s, 2H), 4.33 (s, 2H), 1.67-1.85 (m, 1H), 0.95-1.13 (m, 2H), 0.30-0.42 (m, 2H). MS (ESI+) m/z 411 (M+H)⁺.

Example 229

N-[5-(1-benzyl-5-cyclopropyl-1H-1,2,3-triazol-4-yl)-1H-indazol-3-yl]-N'-[5-methyl-2-(trifluoromethyl)-3-furyl]urea Example 205A (30 mg, 0.07 mmol) was dissolved in dioxane (2 mL) and 3-isocyanato-5-methyl-2-(trifluoromethyl) furan (40 mg, 0.21 mmol) was added to the solution. The reaction mixture was stirred at 80° C. for 12 hours, concentrated and purified by reverse phase-HPLC(CH₃CN/H₂O/NH₄OAc) to afford the Boc-protected precursor. The precursor was dissolved in methanol and treated with excess HCl in dioxane (4 M, 0.5 mmol). The reaction was allowed to stir for 5 hours and concentrated under vacuum to afford the title compound as an HCl salt. ¹H NMR (300 MHz, DMSO-d₆) δ ppm 12.73 (s, 1H), 10.19 (s, 1H), 8.40 (s, 1H), 7.83 (d, J=8.82, 1.47 Hz, 1H), 7.64-7.75 (m, 1H), 7.49 (d, J=8.82 Hz, 1H), 7.35-7.45 (m, 3H), 7.27-7.35 (m, 2H), 5.69 (s, 2H), 2.33 (s, 3H), 1.73-1.84 (m, 1H), 1.02-1.11 (m, 2H), 0.35-0.43 (m, 2H). MS (ESI+) m/z 522 (M+H)⁺.

Example 230

N-[5-(1-benzyl-5-cyclopropyl-1H-1,2,3-triazol-4-yl)-1H-indazol-3-yl]-3-furamide

The title compound was prepared as an HCl salt according to the procedure outlined in Example 205B substituting furan-3-carbonyl chloride for 3-fluorobenzoyl chloride. ¹H NMR (300 MHz, DMSO-d₆) δ ppm 10.64 (s, 1H), 8.46 (s, 1H), 8.13 (s, 1H), 7.74-7.84 (m, 2H), 7.52-7.58 (m, 1H), 7.33-7.46 (m, 3H), 7.24-7.33 (m, 3H), 7.06 (s, 1H), 5.68 (s, 2H), 1.70-1.86 (m, 1H), 0.99-1.09 (m, 2H), 0.33-0.44 (m, 2H). MS (ESI+) m/z 425 (M+H)⁺.

Example 231

5-(1H-indazol-5-yl)-N-[(1S)-1-phenylpropyl]isoxazole-3-carboxamide

The title compound was prepared according to the procedure outlined in Example 81B substituting (S)-(−)-1-phenylpropyl amine for piperidine. ¹H NMR (300 MHz, DMSO-d₆) δ ppm 13.37 (s, 1H) 9.20 (d, J=8.48 Hz, 1H) 8.39 (s, 1H) 8.23 (s, 1H) 7.88 (d, J=8.81, 1.70 Hz, 1H) 7.69 (d, J=8.81 Hz, 1H) 7.38-7.49 (m, 2H) 7.18-7.38 (m, 4H) 4.83-5.02 (m, 1H) 1.73-1.97 (m, 2H) 0.86-0.97 (m, 3H). MS (ESI+) m/z 347.0 (M+H)⁺.

Example 232

5-(1H-indazol-5-yl)-N-[(1R)-1-phenylpropyl]isoxazole-3-carboxamide

The title compound was prepared according to the procedure outlined in Example 81B substituting (R)-(−)-1-phenylpropyl amine for piperidine. $^1$H NMR (300 MHz, DMSO-d$_6$) δ ppm 13.37 (s, 1H) 9.20 (d, J=8.48 Hz, 1H) 8.39 (s, 1H) 8.23 (s, 1H) 7.88 (d, J=8.65, 1.53 Hz, 1H) 7.69 (d, J=8.81 Hz, 1H) 7.39-7.48 (m, 2H) 7.18-7.38 (m, 4H) 4.85-4.99 (m, 1H) 1.74-1.97 (m, 2H) 0.91 (t, J=7.29 Hz, 3H). MS (ESI+) m/z 347.0 (M+H)$^+$.

Example 233

5-(1-benzyl-1H-pyrazol-4-yl)-1H-indazol-3-amine

Example 233A 5-(1-Benzyl-1H-pyrazol-4-yl)-2-fluorobenzonitrile

5-Bromo-2-fluorobenzonitrile (484 mg, 2.42 mmol), 1-benzyl-4-(4,4,5,5-tetramethyl-1,3,2-dioxaborolan-2-yl)-1H-pyrazole (736 mg, 2.59 mmol), dichlorobis(triphenylphosphine)palladium(II) (174 mg, 0.248 mmol), and potassium carbonate (1.36 g, 9.84 mmol) were combined in a sealed vial with dioxane (10 mL) and water (1 mL) under an inert atmosphere of nitrogen, and the mixture was heated to 110° C. overnight. The mixture was diluted with methylene chloride and washed with water. The organic layer was absorbed on silica gel and purified by silica gel chromatography eluting with a gradient of 10-50% ethyl acetate in hexanes to afford the title compound. MS (ESI+) m/z 290.0 (M+H)$^+$.

Example 233B 5-(1-benzyl-1H-pyrazol-4-yl)-1H-indazol-3-amine

Example 233A (591 mg, 2.13 mmol) was treated with hydrazine hydrate (4.0 mL) in ethanol (3.0 mL) and was stirred and heated to 70° C. overnight. The mixture was diluted with methylene chloride and washed with water. The organic layer was concentrated under reduced pressure, and the resulting residue was triturated with methanol to afford the title compound. $^1$H NMR (300 MHz, DMSO-d$_6$) δ ppm 11.32 (s, 1H) 8.10 (s, 1H) 7.85 (s, 1H) 7.80 (s, 1H) 7.44 (d, J=8.48, 1.70 Hz, 1H) 7.25-7.41 (m, 5H) 7.21 (d, J=8.82 Hz, 1H) 5.35 (s, 2H) 5.24-5.30 (m, 2H). MS (ESI+) m/z 290.0 (M+H)$^+$.

Example 234

1-benzyl-4-(1H-indazol-5-yl)-N-[(2S)-tetrahydrofuran-2-ylmethyl]-1H-1,2,3-triazole-5-carboxamide Into a 20 mL vial, a solution of Example 149C (51 mg, 0.16 mmol) dissolved in dimethylformamide (0.5 mL) was added, followed by the addition of (S)-(+)-tetrahydrofurfurylamine (18.2 mg, 0.18 mmol) dissolved in dimethylformamide (0.9 mL). A solution of HATU (68 mg, 0.18 mmol) dissolved in dimethylformamide (0.5 mL) was added followed by a solution of diisopropylethylamine (0.087 mL, 0.5 mmol) dissolved in dimethylformamide (0.5 mL). The mixture was shaken at 50° C. overnight. The reaction was filtered through a Si-Carbonate cartridge (6 mL-1 g) supplied by Silicycle Chemical Division, and the filtrate was transferred to 20 mL vials. The reaction was checked by LC/MS and concentrated to dryness. The residue was dissolved in 1:1 DMSO/methanol and purified by reverse phase HPLC (Agilent, 5%-100% TFA/water gradient, 8 minute run). $^1$H NMR (300 MHz, DMSO-d$_6$/D$_2$O) δ ppm 1.35-1.54 (m, 1H) 1.64-1.96 (m, 3H) 3.17-3.26 (m, 1H) 3.32-3.38 (m, 1H) 3.50-3.77 (m, 2H) 3.81-4.00 (m, 1H) 5.58-5.74 (m, 2H) 7.21-7.41 (m, 5H) 7.54-7.66 (m, 1H) 7.68-7.84 (m, 1H) 8.01-8.19 (m, 2H). MS (ESI−) m/z 401 (M−H)$^-$.

Example 235

1-benzyl-4-(1H-indazol-5-yl)-N-(2-isopropoxyethyl)-1H-1,2,3-triazole-5-carboxamide The title compound was prepared according to the procedure outlined in Example 234 substituting 2-aminoethylisopropyl ether for (S)-(+)-tetrahydrofurfurylamine. $^1$H NMR (300 MHz, DMSO-d$_6$/D$_2$O) δ ppm 0.98 (d, 6H) 3.31-3.45 (m, 4H) 3.45-3.57 (m, 1H) 5.61-5.74 (m, 2H) 7.25-7.46 (m, 5H) 7.57-7.65 (m, 1H) 7.68-7.80 (m, 1H) 8.04-8.13 (m, 2H). MS (ESI+) m/z 405 (M+H)$^+$.

Example 236

1-benzyl-4-(1H-indazol-5-yl)-N-[(2R)-tetrahydrofuran-2-ylmethyl]-1H-1,2,3-triazole-5-carboxamide The title compound was prepared according to the procedure outlined in Example 234 substituting (R)-(−)-tetrahydrofurfurylamine for (S)-(+)-tetrahydrofurfurylamine. $^1$H NMR (300 MHz, DMSO-d$_6$/D$_2$O) δ ppm 1.34-1.60 (m, 1H) 1.65-1.94 (m, 3H) 3.16-3.26 (m, 1H) 3.33-3.39 (m, 1H) 3.51-3.77 (m, 2H) 3.78-4.00 (m, 1H) 5.60-5.73 (m, 2H) 7.26-7.45 (m, 5H) 7.56-7.68 (m, 1H) 7.71-7.79 (m, 1H) 8.01-8.15 (m, 2H). MS (ESI−) m/z 401 (M−H)$^-$.

Example 237

1-benzyl-4-(1H-indazol-5-yl)-N-(tetrahydrofuran-3-ylmethyl)-1H-1,2,3-triazole-5-carboxamide The title compound was prepared according to the procedure outlined in Example 234 substituting 3-aminomethyltetrahydrofuran for (S)-(+)-tetrahydrofurfurylamine. $^1$H NMR (300 MHz, DMSO-d$_6$/D$_2$O) δ ppm 1.36-1.59 (m, 1H) 1.67-2.00 (m, 1H) 2.19-2.45 (m, 1H) 3.11-3.23 (m, 2H) 3.45-3.77 (m, 2H) 5.45-6.14 (m, 2H) 7.16-7.44 (m, 5H) 7.50-7.84 (m, 2H) 7.96-8.25 (m, 2H). MS (ESI+) m/z 403 (M+H)$^+$.

Example 238

1-benzyl-N-cyclopentyl-4-(1H-indazol-5-yl)-1H-1,2,3-triazole-5-carboxamide

The title compound was prepared according to the procedure outlined in Example 234 substituting cyclopentylamine for (S)-(+)-tetrahydrofurfurylamine. $^1$H NMR (300 MHz, DMSO-d$_6$/D$_2$O) δ ppm 1.19-1.63 (m, 6H) 1.71-1.99 (m, 2H) 3.99-4.37 (m, 1H) 5.52-5.77 (m, 2H) 7.22-7.45 (m, 5H) 7.55-7.83 (m, 2H) 7.95-8.20 (m, 2H). MS (ESI−) m/z 385 (M−H)$^-$.

Example 239

1-benzyl-N-(cyclopentylmethyl)-4-(1H-indazol-5-yl)-1H-1,2,3-triazole-5-carboxamide The title compound was prepared according to the procedure outlined in Example 234 substituting aminomethylcyclopentane for (S)-(+)-tetrahydrofurfurylamine. $^1$H NMR (300 MHz, DMSO-d$_6$/D$_2$O) δ ppm 1.02-1.28 (m, 2H) 1.34-1.73 (m, 6H) 1.83-2.17 (m, 1H) 3.03-3.17 (m, 2H) 5.51-5.80 (m, 2H) 7.20-7.42 (m, 5H) 7.52-7.81 (m, 2H) 7.93-8.19 (m, 2H). MS (ESI+) m/z 401 (M+H)$^+$.

Example 240

1-benzyl-N-ethyl-4-(1H-indazol-5-yl)-N-methyl-1H-1,2,3-triazole-5-carboxamide

The title compound was prepared according to the procedure outlined in Example 234 substituting N-methylethylamine hydrochloride for (S)-(+)-tetrahydrofurfurylamine. $^1$H NMR (300 MHz, DMSO-d$_6$/D$_2$O) δ ppm 0.33-0.56 (m, 1H) 0.90-1.14 (m, 2H) 2.15-2.25 (m, 2H) 2.58-2.69 (m, 1H) 2.82-3.01 (m, 1H) 3.35-3.52 (m, 1H) 5.40-5.67 (m, 2H) 7.14-7.48 (m, 5H) 7.56-7.79 (m, 2H) 7.90-8.24 (m, 2H). MS (ESI+) m/z 361 (M+H)$^+$.

Example 241

1-benzyl-4-(1H-indazol-5-yl)-N-isopropyl-N-methyl-1H-1,2,3-triazole-5-carboxamide The title compound was prepared according to the procedure outlined in Example 234 substituting methylisopropylamine for (S)-(+)-tetrahydrofurfurylamine. $^1$H NMR (300 MHz, DMSO-d$_6$/D$_2$O) δ ppm 0.22-0.51 (m, 2H) 0.84-1.09 (m, 4H) 1.96-2.13 (m, 2H) 2.74-2.87 (m, 1H) 4.44-4.92 (m, 1H) 5.43-5.67 (m, 2H) 7.20-7.44 (m, 5H) 7.51-7.73 (m, 2H) 7.84-8.14 (m, 2H). MS (ESI+) m/z 375 (M+H)$^+$.

Example 242

1-benzyl-4-(1H-indazol-5-yl)-N-(2-methoxyethyl)-N-methyl-1H-1,2,3-triazole-5-carboxamide The title compound was prepared according to the procedure outlined in Example 234 substituting N-(2-methoxyethyl)methylamine for (S)-(+)-tetrahydrofurfurylamine. $^1$H NMR (300 MHz, DMSO-d$_6$/D$_2$O) δ ppm 2.25-2.42 (m, 2H) 2.74-3.06 (m, 4H) 3.40-3.75 (m, 3H) 5.38-5.73 (m, 2H) 7.18-7.45 (m, 5H) 7.53-7.74 (m, 2H) 7.85-8.19 (m, 2H). MS (ESI+) m/z 391 (M+H)$^+$.

Example 243

1-benzyl-4-(1H-indazol-5-yl)-N-phenyl-1H-1,2,3-triazole-5-carboxamide

The title compound was prepared according to the procedure outlined in Example 234 substituting aniline for (S)-(+)-tetrahydrofurfurylamine. $^1$H NMR (300 MHz, DMSO-d$_6$/D$_2$O) δ ppm 5.65-5.79 (m, 2H) 7.04-7.55 (m, 10H) 7.54-7.84 (m, 2H) 7.95-8.21 (m, 2H). MS (ESI+) m/z 395 (M+H)$^+$.

Example 244

1-benzyl-N-(4-chlorophenyl)-4-(1H-indazol-5-yl)-1H-1,2,3-triazole-5-carboxamide

The title compound was prepared according to the procedure outlined in Example 234 substituting 4-chloroaniline for (S)-(+)-tetrahydrofurfurylamine. $^1$H NMR (300 MHz, DMSO-d$_6$/D$_2$O) δ ppm 5.70-5.74 (m, 2H) 7.25-7.42 (m, 7H) 7.43-7.52 (m, 2H) 7.54-7.66 (m, 1H) 7.68-7.77 (m, 1H) 8.03-8.15 (m, 2H). MS (ESI−) m/z 427 (M−H)$^-$.

Example 245

1-benzyl-4-(1H-indazol-5-yl)-N-(2-morpholin-4-ylethyl)-1H-1,2,3-triazole-5-carboxamide The title compound was prepared according to the procedure outlined in Example 234 substituting N-(3-aminopropyl)morpholine for (S)-(+)-tetrahydrofurfurylamine. $^1$H NMR (300 MHz, DMSO-d$_6$/D$_2$O) δ ppm 2.94-3.13 (m, 6H) 3.46-3.61 (m, 2H) 3.63-3.79 (m, 4H) 5.61-5.88 (m, 2H) 7.19-7.46 (m, 5H) 7.56-7.88 (m, 2H) 7.88-8.30 (m, 2H). MS (ESI−) m/z 430 (M−H)$^-$.

Example 246

1-benzyl-N-[2-(dimethylamino)ethyl]-4-(1H-indazol-5-yl)-N-methyl-1H-1,2,3-triazole-5-carboxamide The title compound was prepared as a TFA salt according to the procedure outlined in Example 234 substituting N,N,N-trimethylethylenediamine for (S)-(+)-tetrahydrofurfurylamine. $^1$H NMR (300 MHz, DMSO-d$_6$/D$_2$O) δ ppm 2.28-2.42 (m, 3H) 2.73-3.00 (m, 6H) 3.07-3.19 (m, 2H) 3.56-3.80 (m, 2H) 5.55-5.68 (m, 2H) 7.24-7.47 (m, 5H) 7.56-7.78 (m, 2H) 7.91-8.02 (m, 1H) 8.10-8.17 (m, 1H). MS (ESI+) m/z 404 (M+H)$^+$.

Example 247

1-benzyl-N-(2-hydroxyethyl)-4-(1H-indazol-5-yl)-N-propyl-1H-1,2,3-triazole-5-carboxamide The title compound was prepared according to the procedure outlined in Example 234 substituting 2-(propylamino)ethanol for (S)-(+)-tetrahydrofurfurylamine. $^1$H NMR (300 MHz, DMSO-d$_6$/D$_2$O) δ ppm 0.22-0.39 (m, 1H) 0.80-1.06 (m, 3H) 1.50-1.75 (m, 1H) 2.65-2.78 (m, 1H) 2.80-2.94 (m, 1H) 2.97-3.09 (m, 1H) 3.37-3.50 (m, 1H) 3.51-3.63 (m, 1H) 3.61-3.73 (m, 1H) 5.39-5.74 (m, 2H) 7.20-7.44 (m, 5H) 7.50-7.85 (m, 2H) 7.86-8.25 (m, 2H). MS (ESI+) m/z 405 (M+H)$^+$.

Example 248

1-benzyl-N-[3-(dimethylamino)propyl]-4-(1H-indazol-5-yl)-N-methyl-1H-1,2,3-triazole-5-carboxamide The title compound was prepared as a TFA salt according to the procedure outlined in Example 234 substituting N,N,N-trimethyl-1,3-propanediamine for (s)-(+)-tetrahydrofurfurylamine. $^1$H NMR (300 MHz, DMSO-d$_6$/D$_2$O) δ ppm 8.06-8.23 (m, 1H) 7.85-8.05 (m, 1H) 7.57-7.73 (m, 2H) 7.19-7.48 (m, 5H) 5.41-5.74 (m, 2H) 3.36-3.45 (m, 2H) 2.88-3.10 (m, 3H) 2.60-2.86 (m, 5H) 2.24-2.42 (m, 4H) 1.73-1.91 (m, 1H). MS (ESI+) m/z 418 (M+H)$^+$.

Example 249

1-benzyl-N-[2-(diethylamino)ethyl]-4-(1H-indazol-5-yl)-N-methyl-1H-1,2,3-triazole-5-carboxamide The title compound was prepared as a TFA salt according to the procedure outlined in Example 234 substituting N,N-diethyl-N-methylethylenediamine for (s)-(+)-tetrahydrofurfurylamine. $^1$H NMR (300 MHz, DMSO-d$_6$/D$_2$O) δ ppm 7.82-8.24 (m, 2H) 7.56-7.76 (m, 2H) 7.15-7.49 (m, 5H) 5.54-5.71 (m, 2H) 3.60-3.77 (m, 2H) 3.20-3.24 (m, 2H) 3.13-3.18 (m, 2H) 3.03-3.11 (m, 2H) 2.32-2.44 (m, 3H) 0.63-1.41 (m, 6H). MS (ESI+) m/z 432 (M+H)+.

Example 250

N,1-dibenzyl-N-ethyl-4-(1H-indazol-5-yl)-1H-1,2,3-triazole-5-carboxamide

The title compound was prepared according to the procedure outlined in Example 234 substituting N-ethylbenzylamine for (S)-(+)-tetrahydrofurfurylamine. $^1$H NMR (300 MHz, DMSO-d$_6$/D$_2$O) δ ppm 7.81-8.20 (m, 2H) 7.49-7.71 (m, 2H) 7.24-7.51 (m, 9H) 6.39-7.18 (m, 2H) 5.41-5.74 (m, 2H) 4.53-4.84 (m, 1H) 3.82-4.00 (m, 1H) 3.37-3.54 (m, 1H) 2.61-2.78 (m, 1H) 0.91-1.08 (m, 1H) 0.27-0.45 (m, 2H). MS (ESI+) m/z 437 (M+H)+.

Example 251

N,1-dibenzyl-N-(2-hydroxyethyl)-4-(1H-indazol-5-yl)-1H-1,2,3-triazole-5-carboxamide The title compound was prepared according to the procedure outlined in Example 234 substituting N-benzylethanolamine for (S)-(+)-tetrahydrofurfurylamine. MS (ESI+) m/z 453 (M+H)+.

Example 252

(3R)-1-{[1-benzyl-4-(1H-indazol-5-yl)-1H-1,2,3-triazol-5-yl]carbonyl}piperidin-3-ol The title compound was prepared according to the procedure outlined in Example 234 substituting (R)-(+)-3-hydroxypiperidine hydrochloride for (S)-(+)-tetrahydrofurfurylamine. $^1$H NMR (300 MHz, DMSO-d$_6$/D$_2$O) δ ppm 7.83-8.22 (m, 2H) 7.51-7.78 (m, 2H) 7.23-7.45 (m, 5H) 5.46-5.75 (m, 2H) 3.80-4.31 (m, 1H) 3.40-3.68 (m, 1H) 2.58-3.15 (m, 2H) 2.19-2.49 (m, 1H) 0.31-2.14 (m, 4H). MS (ESI+) m/z 403 (M+H)+.

Example 253

1-{[1-benzyl-4-(1H-indazol-5-yl)-1H-1,2,3-triazol-5-yl]carbonyl}piperidine-4-carboxamide The title compound was prepared according to the procedure outlined in Example 234 substituting isonipecotamide for (S)-(+)-tetrahydrofurfurylamine. $^1$H NMR (300 MHz, DMSO-d$_6$/D$_2$O) δ ppm 7.86-8.24 (m, 2H) 7.53-7.70 (m, 2H) 7.22-7.46 (m, 5H) 5.42-5.77 (m, 2H) 4.19-4.48 (m, 1H) 2.65-3.10 (m, 2H) 2.27-2.47 (m, 1H) 2.05-2.24 (m, 1H) 1.65-1.89 (m, 1H) 1.29-1.55 (m, 1H) 0.98-1.27 (m, 1H) 0.52-0.87 (m, 1H). MS (ESI+) m/z 430 (M+H)+.

Example 254

5-{1-benzyl-5-[(2,6-dimethylmorpholin-4-yl)carbonyl]-1H-1,2,3-triazol-4-yl}-1H-indazole The title compound was prepared according to the procedure outlined in Example 234 substituting 2,6-dimethylmorpholine for (S)-(+)-tetrahydrofurfurylamine. $^1$H NMR (300 MHz, DMSO-d$_6$/D$_2$O) δ ppm 7.87-8.27 (m, 2H) 7.50-7.76 (m, 2H) 7.12-7.45 (m, 5H) 5.46-5.68 (m, 2H) 4.16-4.43 (m, 1H) 2.61-2.98 (m, 1H) 2.16-2.41 (m, 2H) 1.77-2.13 (m, 1H) 0.86-1.39 (m, 3H) 0.38-0.83 (m, 3H). MS (ESI+) m/z 417 (M+H)+.

Example 255

5-{5-[(4-acetylpiperazin-1-yl)carbonyl]-1-benzyl-1H-1,2,3-triazol-4-yl}-1H-indazole The title compound was prepared according to the procedure outlined in Example 234 substituting 1-acetylpiperazine for (S)-(+)-tetrahydrofurfurylamine. $^1$H NMR (300 MHz, DMSO-d$_6$/D$_2$O) δ ppm 7.89-8.41 (m, 2H) 7.55-7.86 (m, 2H) 7.07-7.51 (m, 5H) 5.44-5.82 (m, 2H) 3.46-3.70 (m, 3H) 3.35-3.49 (m, 2H) 2.57-2.93 (m, 3H) 1.61-2.03 (m, 3H). MS (ESI+) m/z 430 (M+H)+.

Example 256

5-{1-benzyl-5-[(4-phenylpiperazin-1-yl)carbonyl]-1H-1,2,3-triazol-4-yl}-1H-indazole The title compound was prepared according to the procedure outlined in Example 234 substituting 1-phenylpiperazine for (S)-(+)-tetrahydrofurfurylamine. $^1$H NMR (300 MHz, DMSO-d$_6$/D$_2$O) δ ppm 7.79-8.38 (m, 2H) 7.53-7.73 (m, 2H) 7.22-7.46 (m, 5H) 7.05-7.19 (m, 2H) 6.64-6.79 (m, 3H) 5.54-5.68 (m, 2H) 3.50-3.90 (m, 2H) 2.93-3.15 (m, 2H) 2.62-2.89 (m, 2H) 2.19-2.43 (m, 2H). MS (ESI−) m/z 462 (M−H)−.

Example 257

1-benzyl-N-[(1R)-1-(hydroxymethyl)-2-methylpropyl]-4-(1H-indazol-5-yl)-1H-1,2,3-triazole-5-carboxamide The title compound was prepared according to the procedure outlined in Example 234 substituting (R)-(+)-2-amino-3-methyl-1-butanol for (S)-(+)-tetrahydrofurfurylamine. $^1$H NMR (300 MHz, DMSO-d$_6$/D$_2$O) δ ppm 7.95-8.31 (m, 2H) 7.52-7.96 (m, 2H) 7.18-7.46 (m, 5H) 5.42-5.86 (m, 2H) 3.68-3.94 (m, 1H) 3.38-3.59 (m, 2H) 1.49-2.08 (m, 1H) 0.50-1.20 (m, 6H). MS (ESI+) m/z 405 (M+H)+.

Example 258

1-benzyl-N-[(1S)-1-(hydroxymethyl)-2-methylpropyl]-4-(1H-indazol-5-yl)-1H-1,2,3-triazole-5-carboxamide The title compound was prepared according to the procedure outlined in Example 234 substituting (S)-(−)-2-amino-3-methyl-1-butanol for (S)-(+)-tetrahydrofurfurylamine. $^1$H NMR (300 MHz, DMSO-d$_6$/D$_2$O) δ ppm 7.94-8.36 (m, 2H) 7.52-7.84 (m, 2H) 7.18-7.51 (m, 5H) 5.57-5.76 (m, 2H) 3.75-3.94 (m, 1H) 3.35-3.54 (m, 2H) 1.70-1.94 (m, 1H) 0.54-1.09 (m, 6H). MS (ESI+) m/z 405 (M+H)+.

Example 259

1-benzyl-N-[3-(1H-imidazol-1-yl)propyl]-4-(1H-indazol-5-yl)-1H-1,2,3-triazole-5-carboxamide The title compound was prepared according to the procedure outlined in Example 234 substituting 1-(3-aminopropyl)imidazole for (S)-(+)-tetrahydrofurfurylamine. $^1$H NMR (300 MHz, DMSO-d$_6$/D$_2$O) δ ppm 8.57-8.85 (m, 1H) 7.92-8.16 (m, 2H) 7.60-7.80 (m, 2H) 7.47-7.55 (m, 2H) 7.19-7.40 (m, 5H) 5.54-5.75 (m, 2H) 3.83-4.21 (m, 2H) 3.19-3.26 (m, 2H) 1.79-2.06 (m, 2H). MS (ESI+) m/z 427 (M+H)$^+$.

Example 260

N-[5-(1-benzyl-5-cyclopropyl-1H-1,2,3-triazol-4-yl)-1H-indazol-3-yl]-N'-ethylurea The title compound was prepared as a hydrochloric acid salt according to the procedure outlined in Example 229 substituting isocyanatoethane for 3-isocyanato-5-methyl-2-(trifluoromethyl)furan. $^1$H NMR (300 MHz, DMSO-d$_6$) δ ppm 12.38 (s, 1H), 9.47 (s, 1H), 8.38 (s, 1H), 7.85-7.97 (m, 1H), 7.78 (d, J=8.82, 1.47 Hz, 1H), 7.34-7.50 (m, 4H), 7.24-7.33 (m, 2H), 5.69 (s, 2H), 3.17-3.29 (m, 2H), 1.70-1.83 (m, 1H), 1.12 (t, J=7.17 Hz, 3H), 1.00-1.08 (m, 2H), 0.37 (d, J=3.68 Hz, 2H). MS (ESI+) m/z 402 (M+H)$^+$.

Example 261

N-[5-(1-benzyl-5-cyclopropyl-1H-1,2,3-triazol-4-yl)-1H-indazol-3-yl]-N'-phenylurea The title compound was prepared as a hydrochloric acid salt according to the procedure outlined in Example 229 substituting isocyanatobenzene for 3-isocyanato-5-methyl-2-(trifluoromethyl)furan. $^1$H NMR (300 MHz, DMSO-d$_6$) δ ppm 12.47-12.78 (m, 1H), 9.64 (s, 1H), 8.39 (s, 1H), 7.70-7.95 (m, 1H), 7.45-7.60 (m, 3H), 7.27-7.45 (m, 7H), 7.02 (m, 1H), 5.69 (s, 2H), 1.79 (m, 1H), 1.07 (m, 2H), 0.40 (m, 2H). MS (ESI+) m/z 450 (M+H)$^+$.

Example 262

N-benzyl-N'-[5-(1-benzyl-5-cyclopropyl-1H-1,2,3-triazol-4-yl)-1H-indazol-3-yl]urea The title compound was prepared as a hydrochloric acid salt according to the procedure outlined in Example 229 substituting (isocyanatomethyl)benzene for 3-isocyanato-5-methyl-2-(trifluoromethyl)furan. $^1$H NMR (300 MHz, DMSO-d$_6$) δ ppm 12.42 (s, 1H), 9.61 (s, 1H), 8.37 (s, 1H), 8.23-8.33 (m, 1H), 7.79 (d, J=8.82, 1.47 Hz, 1H), 7.36-7.50 (m, 4H), 7.28-7.36 (m, 6H), 7.21-7.27 (m, 1H), 5.69 (s, 2H), 4.45 (d, J=5.88 Hz, 2H), 1.65-1.79 (t, J=8.27, 8.27 Hz, 1H), 0.99-1.08 (m, 2H), 0.30-0.43 (m, 2H). MS (ESI+) m/z 464 (M+H)$^+$.

Example 263

N-[5-(1-benzyl-5-cyclopropyl-1H-1,2,3-triazol-4-yl)-1H-indazol-3-yl]-N'-(2-chlorophenyl)urea The title compound was prepared as a hydrochloric acid salt according to the procedure outlined in Example 229 substituting 1-chloro-2-isocyanatobenzene for 3-isocyanato-5-methyl-2-(trifluoromethyl)furan. $^1$H NMR (300 MHz, DMSO-d$_6$) δ ppm 12.74 (s, 1H), 10.23 (s, 1H), 8.44 (s, 1H), 8.34 (d, J=8.09 Hz, 1H), 7.83 (d, J=8.82, 1.47 Hz, 1H), 7.46-7.55 (m, 2H), 7.35-7.45 (m, 3H), 7.28-7.35 (m, 3H), 7.03-7.12 (m, 1H), 5.70 (s, 2H), 1.70-1.86 (m, 1H), 1.00-1.12 (m, 2H), 0.33-0.45 (m, 2H). MS (ESI+) m/z 484 (M+H)$^+$.

Example 264

N-[5-(1-benzyl-5-cyclopropyl-1H-1,2,3-triazol-4-yl)-1H-indazol-3-yl]-N'-(3-chlorophenyl)urea The title compound was prepared as a hydrochloric acid salt according to the procedure outlined in Example 229 substituting 1-chloro-3-isocyanatobenzene for 3-isocyanato-5-methyl-2-(trifluoromethyl)furan. $^1$H NMR (300 MHz, DMSO-d$_6$) δ ppm 12.66 (s, 1H), 10.02 (s, 1H), 9.71 (s, 1H), 8.22-8.48 (m, 1H), 7.71-7.91 (m, 2H), 7.51 (d, J=8.46 Hz, 1H), 7.37-7.46 (m, 2H), 7.26-7.37 (m, 5H), 7.02-7.11 (m, 1H), 5.69 (s, 2H), 1.73-1.89 (m, 1H), 0.99-1.11 (m, 2H), 0.33-0.48 (m, 2H). MS (ESI+) m/z 484 (M+H)$^+$.

Example 265

N-[5-(1-benzyl-5-cyclopropyl-1H-1,2,3-triazol-4-yl)-1H-indazol-3-yl]-N'-(4-chlorophenyl)urea The title compound was prepared as a hydrochloric acid salt according to the procedure outlined in Example 229 substituting 1-chloro-4-isocyanatobenzene for 3-isocyanato-5-methyl-2-(trifluoromethyl)furan. $^1$H NMR (300 MHz, DMSO-d$_6$) δ ppm 12.65 (s, 1H), 9.96 (s, 1H), 9.68 (s, 1H), 8.37 (s, 1H), 7.81 (d, J=8.82, 1.47 Hz, 1H), 7.53-7.60 (m, 2H), 7.50 (d, J=8.82 Hz, 1H), 7.39-7.44 (m, 1H), 7.33-7.40 (m, 4H), 7.27-7.32 (m, 2H), 5.69 (s, 2H), 1.71-1.87 (m, 1H), 1.00-1.12 (m, 2H), 0.34-0.44 (m, 2H). MS (ESI+) m/z 484 (M+H)$^+$.

Example 266

N-[5-(1-benzyl-5-iodo-1H-1,2,3-triazol-4-yl)-1H-indazol-3-yl]benzamide

Example 266A tert-butyl 3-amino-5-(1-benzyl-5-iodo-1H-1,2,3-triazol-4-yl)-1H-indazole-1-carboxylate The title compound was prepared according to the procedure outlined in Example 198A substituting Example 125B for Example 102B. The product was used directly in subsequent reactions without characterization.

Example 266B

N-[5-(1-benzyl-5-iodo-1H-1,2,3-triazol-4-yl)-1H-indazol-3-yl]benzamide

The title compound was prepared as a TFA salt according to the procedure outlined in Example 205B substituting Example 266A for Example 205A. $^1$H NMR (300 MHz, DMSO-d$_6$) δ ppm 12.97 (s, 1H), 10.89 (s, 1H), 8.28 (s, 1H), 8.05-8.14 (m, 2H), 7.88 (d, J=8.82, 1.47 Hz, 1H), 7.58-7.67 (m, 2H), 7.54 (t, J=7.35 Hz, 2H), 7.29-7.45 (m, 3H), 7.23 (d, J=6.99 Hz, 2H), 5.73 (s, 2H). MS (ESI+) m/z 521 (M+H)$^+$.

Example 267

3-[4-(3-amino-1H-indazol-5-yl)-1H-pyrazol-1-yl]
propanenitrile

Example 267A 3-(4-(4,4,5,5-tetramethyl-1,3,2-dioxaborolan-2-yl)-
1H-pyrazol-1-yl)propanenitrile To a solution of 4-(4,4,5,5-tetramethyl-1,3,2-dioxaborolan-2-yl)-1H-pyrazole (5.00 g, 25.8 mmol) in acetonitrile (50 mL) was added acrylonitrile (3.4 mL, 52 mmol) followed by 1,8-diazabicyclo[5.4.0]undec-7-ene (1.94 mL, 12.9 mmol). After about 2 hours, the reaction mixture was concentrated under reduced pressure. The crude material was then dissolved in a minimal amount of dichloromethane and purified via silica gel chromatography eluting with a gradient of 10-50% ethyl acetate in heptane to afford the title compound. $^1$H NMR (400 MHz, DMSO-$d_6$) δ ppm 8.03 (s, 1H), 7.64 (s, 1H), 4.40 (t, J=6.4 Hz, 2H), 3.06 (t, J=6.4 Hz, 2H), 1.26 (s, 12H). MS (ESI+) m/z 247.3 (M+H)$^+$.

Example 267B

3-[4-(3-amino-1H-indazol-5-yl)-1H-pyrazol-1-yl]
propanenitrile

To a microwave vial was added 5-bromo-1H-indazol-3-amine (0.14 g, 0.66 mmol), tetrakis(triphenylphosphine)palladium(0) (0.076 g, 0.066 mmol), and sodium carbonate (0.147 g, 1.39 mmol) followed by a solution of Example 267A (0.212 g, 0.858 mmol) in 1,2-dimethoxyethane (2.50 mL) and then water (1.25 mL). The mixture was heated in a CEM microwave at about 150° C. for about 20 minutes (275 psi maximum pressure, about 2 minutes ramp, 200 maximum watts) and then the mixture was concentrated under reduced pressure. Methanol (20 mL) was added and the resulting mixture was stirred for about 1 hour. The insoluble material was removed by filtration. The filtrate was concentrated under reduced pressure onto silica gel and purified via silica gel chromatography eluting with a stepwise gradient of dichloromethane/methanol/ammonium hydroxide (990:9:1 to 985:13.5:1.5 to 980:18:2) to afford a solid. This solid was dissolved in a minimum amount of hot acetonitrile (~2 mL), filtered to remove minor amount of insolubles, while washing with methanol (<0.5 mL), and left to sit at ambient temperature. The resulting solid that formed overnight was collected by filtration, while washing with additional acetonitrile, and dried in a vacuum oven at about 60° C. for about 2 hours to afford the title compound. $^1$H NMR (400 MHz, DMSO-$d_6$) δ ppm 11.35 (s, 1H), 8.10 (s, 1H), 7.86 (s, 1H), 7.84 (s, 1H), 7.44 (dd, J=8.54, 1.26 Hz, 1H), 7.23 (d, J=8.62 Hz, 1H), 5.32 (s, 2H), 4.42 (t, J=6.36 Hz, 2H), 3.10 (t, J=6.43 Hz, 2H). MS (ESI+) m/z 253.2 (M+H)$^+$.

Example 268

2-[4-(3-amino-1H-indazol-5-yl)-1H-pyrazol-1-yl]
acetamide

Example 268A 2-(4-(4,4,5,5-tetramethyl-1,3,2-dioxaborolan-2-yl)-
1H-pyrazol-1-yl)acetamide A suspension of 4-(4,4,5,5-tetramethyl-1,3,2-dioxaborolan-2-yl)-1H-pyrazole (2.00 g, 10.3 mmol), 2-bromoacetamide (2.14 g, 15.5 mmol), and potassium carbonate (2.14 g, 15.5 mmol) in acetone (60 mL) was heated at about 50° C. for about 3.5 days. The reaction mixture was then cooled to ambient temperature, filtered through diatomaceous earth, while washing with additional acetone, and then concentrated under reduced pressure. The crude material was then dissolved in a minimal amount of dichloromethane and purified via silica gel chromatography eluting with a gradient of 80-100% ethyl acetate in heptane to afford the title compound. $^1$H NMR (400 MHz, DMSO-$d_6$) δ ppm 7.88 (s, 1H), 7.57 (s, 1H), 7.46 (s, 1H), 7.24 (s, 1H), 4.77 (s, 2H), 1.26 (s, 12H). MS (ESI+) m/z 252.2 (M+H)$^+$.

Example 268B

2-[4-(3-amino-1H-indazol-5-yl)-1H-pyrazol-1-yl]
acetamide

The title compound was prepared according to the procedure outlined in Example 267B substituting Example 268A for Example 267A and heating at about 120° C. for about 10 minutes. $^1$H NMR (400 MHz, DMSO-$d_6$) δ ppm 11.32 (s, 1H), 7.98 (s, 1H), 7.87 (s, 1H), 7.77 (s, 1H), 7.48 (s, 1H), 7.45 (d, J=8.6 Hz, 1H), 7.26 (s, 1H), 7.22 (d, J=8.7 Hz, 1H), 5.28 (s, 2H), 4.78 (s, 2H). MS (ESI+) m/z 257.2 (M+H)$^+$.

Example 269

Methyl 3-[4-(3-amino-1H-indazol-5-yl)-1H-pyrazol-
1-yl]propanoate

Example 269A

Methyl 3-(4-(4,4,5,5-tetramethyl-1,3,2-dioxaborolan-2-yl)-1H-pyrazol-1-yl)propanoate The title compound was prepared according to the procedure outlined in Example 267A substituting methyl acrylate for acrylonitrile. $^1$H NMR (400 MHz, DMSO-$d_6$) δ ppm 7.91 (s, 1H), 7.57 (s, 1H), 4.35 (t, J=6.73 Hz, 2H), 2.87 (t, J=6.75 Hz, 2H), 3.59 (s, 3H), 1.24 (s, 12H). MS (ESI+) m/z 281.2 (M+H)$^+$.

Example 269B

Methyl 3-[4-(3-amino-1H-indazol-5-yl)-1H-pyrazol-
1-yl]propanoate

The title compound was prepared according to the procedure outlined in Example 267B substituting Example 269A for Example 267A and heating at about 120° C. for about 20 minutes. $^1$H NMR (400 MHz, DMSO-$d_6$) δ ppm 11.32 (s, 1H), 8.00 (s, 1H), 7.85 (s, 1H), 7.76 (s, 1H), 7.42 (d, J=8.50 Hz, 1H), 7.21 (d, J=8.61 Hz, 1H), 5.28 (s, 2H), 4.37 (t, J=6.71 Hz, 2H), 3.61 (s, 3H), 2.92 (t, J=6.69 Hz, 2H). MS (ESI+) m/z 286.2 (M+H)$^+$.

Example 270

3-[4-(3-amino-1H-indazol-5-yl)-1H-pyrazol-1-yl]
propanamide

Example 270A 3-(4-(4,4,5,5-tetramethyl-1,3,2-dioxaborolan-2-yl)-
1H-pyrazol-1-yl)propanamide The title compound was prepared according to the procedure outlined in Example 267A substituting acrylamide for acrylonitrile (0.72 g, 53%). $^1$H NMR (400 MHz, DMSO-d$_6$) δ ppm 7.84 (s, 1H), 7.56 (s, 1H), 7.37 (s, 1H), 6.88 (s, 1H), 4.30 (t, J=6.80 Hz, 2H), 2.60 (t, J=6.79 Hz, 2H), 1.24 (s, 12H). MS (ESI+) m/z 266.2 (M+H)$^+$.

Example 270B

3-[4-(3-amino-1H-indazol-5-yl)-1H-pyrazol-1-yl] propanamide

The title compound was prepared according to the procedure outlined in Example 267B substituting Example 270A for Example 267A and heating at about 120° C. for about 15 minutes (0.056 g, 22%). $^1$H NMR (400 MHz, DMSO-d$_6$) δ ppm 11.32 (s, 1H), 7.94 (d, J=0.53 Hz, 1H), 7.84 (s, 1H), 7.75 (d, J=0.54 Hz, 1H), 7.42 (m, 2H), 7.20 (d, J=8.26 Hz, 1H), 6.89 (s, 1H), 5.27 (s, 2H), 4.32 (t, J=6.89 Hz, 2H), 2.65 (t, J=6.89 Hz, 2H). MS (ESI+) m/z 271.0 (M+H)$^+$.

Example 271

[4-(3-amino-1H-indazol-5-yl)-1H-pyrazol-1-yl]acetonitrile

Example 271A 2-(4-(4,4,5,5-tetramethyl-1,3,2-dioxaborolan-2-yl)-1H-pyrazol-1-yl)acetonitrile The title compound was prepared according to the procedure outlined in Example 268A substituting 2-bromoacetonitrile for 2-bromoacetamide. $^1$H NMR (400 MHz, DMSO-d$_6$) δ ppm 7.99 (s, 1H), 7.66 (s, 1H), 5.45 (s, 2H), 1.25 (s, 12H).

Example 271B tert-butyl 3-(bis(tert-butoxycarbonyl)amino)-5-bromo-1H-indazole-1-carboxylate To 5-bromo-1H-indazol-3-amine (2.00 g, 9.43 mmol) in tetrahydrofuran (20 mL) was added 4-(dimethylamino)pyridine (0.230 g, 1.886 mmol) and di-tert-butyl dicarbonate (6.18 g, 28.3 mmol). The reaction was heated at 50° C. for about 2 hours, cooled to ambient temperature, and concentrated under reduced pressure. The residue was dissolved in diethyl ether (100 mL) and then washed sequentially with 1 N hydrochloric acid (2×25 mL), 1 N sodium hydroxide (2×25 mL) and brine (25 mL). The organic layer was then dried over sodium sulfate, filtered, concentrated under reduced pressure, and dried in a vacuum oven at about 60° C. to afford the title compound. $^1$H NMR (400 MHz, DMSO-d$_6$) 8.05 (d, J=8.95 Hz, 1H), 7.99 (d, J=1.90 Hz, 1H), 7.81 (dd, J=8.94, 1.89 Hz, 1H), 1.65 (s, 9H), 1.40 (s, 18H). MS (ESI+) m/z 512.2 (M+H)$^+$.

Example 271C tert-butyl 3-(bis(tert-butoxycarbonyl)amino)-5-(1-(cyanomethyl)-1H-pyrazol-4-yl)-1H-indazole-1-carboxylate A vial was charged with Example 271A (0.682 g, 2.93 mmol), Example 271B (1.25 g, 2.44 mmol), cesium carbonate (1.99 g, 6.10 mmol), 1,4-dioxane (12.5 mL) and water (2.50 mL). After a vacuum/nitrogen purge through a septa, tris(dibenzylideneacetone)dipalladium(0) (0.112 g, 0.122 mmol) and tri-t-butylphosphonium tetrafluoroborate (0.085 g, 0.29 mmol) were added and a cap was put on the vial after flushing with nitrogen. After about 6 hours at ambient temperature, the reaction was partitioned between saturated aqueous sodium bicarbonate and dichloromethane (50 mL each). The layers were separated and the aqueous layer was extracted with additional dichloromethane (2×50 mL). The combined organic layers were washed with brine, dried over magnesium sulfate, filtered, and concentrated under reduced pressure. The crude oil was dissolved in a minimal amount of dichloromethane and purified via silica gel chromatography eluting with a gradient of 20-60% ethyl acetate in heptane to afford the title compound. $^1$H NMR (400 MHz, DMSO-d$_6$) δ ppm 8.43 (s, 1H), 8.19 (s, 1H), 8.08 (d, J=9.22 Hz, 1H), 7.93 (m, 2H), 5.53 (s, 2H), 1.67 (s, 9H), 1.39 (s, 18H). MS (ESI+) m/z 539.3 (M+H)$^+$.

Example 271D

[4-(3-amino-1H-indazol-5-yl)-1H-pyrazol-1-yl]acetonitrile

To a solution of tert-butyl 3-(bis(tert-butoxycarbonyl) amino)-5-(1-(cyanomethyl)-1H-pyrazol-4-yl)-1H-indazole-1-carboxylate (0.30 g, 0.557 mmol) in dichloromethane (4.0 mL) was added trifluoroacetic acid (2.0 mL). After about 45 minutes, the reaction was slowly quenched with saturated aqueous sodium bicarbonate. The resulting mixture was extracted with dichloromethane (3×25 mL). The combined organic layers were washed with brine, dried over magnesium sulfate, filtered, and concentrated under reduced pressure to give a crude solid. A white precipitate that was suspended in both the initial aqueous layer and the brine layer was filtered and added to the crude solid. The resulting solid was triturated with dichloromethane/methanol (19:1). The remaining solid was collected by vacuum filtration and dried in a vacuum oven at about 70° C. to afford the title compound. $^1$H NMR (400 MHz, DMSO-d$_6$) δ ppm 11.37 (s, 1H), 8.12 (s, 1H), 7.92 (s, 1H), 7.89 (s, 1H) 7.49-7.41 (m, 1H), 7.24 (d, J=8.71 Hz, 1H), 5.52 (s, 2H), 5.31 (s, 2H). MS (ESI+) m/z 239.1 (M+H)$^+$.

Example 272

4-(3-amino-1H-indazol-5-yl)-N,N-dimethyl-1H-imidazole-1-sulfonamide

3-Cyano-4-fluorophenylboronic acid (0.083 g, 0.503 mmol), 4-iodo-N,N-dimethyl-1H-imidazole-1-sulfonamide (0.167 g, 0.554 mmol), sodium carbonate (0.128 g, 1.208 mmol) and tetrakis(triphenylphosphine)palladium(0) (0.035 g, 0.030 mmol) were combined in dimethoxyethane (4 mL) and water (1.5 mL). The reaction mixture was heated in a microwave (CEM-Discover) at about 150° C. for about 25 minutes. The organic layer was separated and the solvent was removed under reduced pressure. To the residue was added ethanol (0.7 mL) and hydrazine monohydrate (1 mL). The reaction mixture was heated at about 80° C. for about 20 hours. The reaction mixture was partitioned between water (5 mL) and dichloromethane (100 mL). The organic layer was separated and concentrated under reduced pressure. The residue was purified by reverse phase HPLC using acetonitrile/water (0.05 M ammonium acetate) gradient elution method to afford the title compound. $^1$H NMR (400 MHz, DMSO-d$_6$) δ ppm 11.42 (s, 1H), 8.25 (s, 1H), 8.21 (d, J=1.36 Hz, 1H), 7.92 (d, J=1.37 Hz, 1H), 7.74 (dd, J=8.66, 1.58 Hz, 1H), 7.23 (d, J=8.68 Hz, 1H), 5.35 (s, 2H), 2.87 (s, 6H). MS (ESI+) m/z 307.2 (M+H)$^+$.

Example 273

5-pyrazin-2-yl-1H-indazol-3-amine

The title compound was prepared according to the procedure outlined in Example 272 substituting 2-iodopyrazine for 4-iodo-N,N-dimethyl-1H-imidazole-1-sulfonamide. $^1$H NMR (400 MHz, DMSO-$d_6$) δ ppm 11.61 (s, 1H), 9.18 (d, 1H, J=1.6), 8.66 (dd, 1H, J=1.7, 2.4), 8.59 (d, 1H, J=1.0), 8.51 (d, 1H, J=2.5), 8.04 (dd, 1H, J=1.8, 8.8), 7.35 (d, 1H, J=9.2), 5.54 (s, 2H). MS (ESI+) m/z 212.2 (M+H)$^+$.

Example 274

5-thien-2-yl-1H-indazol-3-amine

The title compound was prepared according to the procedure outlined in Example 272 substituting 2-iodothiophene for 4-iodo-N,N-dimethyl-1H-imidazole-1-sulfonamide. $^1$H NMR (400 MHz, DMSO-$d_6$) δ ppm 11.47 (s, 1H), 7.99 (d, 1H, J=1.4), 7.55 (dd, 1H, J=1.8, 8.8), 7.43 (dd, 1H, J=1.0, 5.1), 7.35 (dd, 1H, J=1.1, 3.6), 7.26 (d, 1H, J=8.6), 7.10 (dd, 1H, J=3.5, 5.1), 5.42 (d, 2H, J=8.8). MS (ESI+) m/z 216.1 (M+H)$^+$.

Example 275

5-(2-aminopyrimidin-4-yl)-1H-indazol-3-amine

The title compound was prepared according to the procedure outlined in Example 272 substituting 5-iodopyrimidin-2-amine for 4-iodo-N,N-dimethyl-1H-imidazole-1-sulfonamide. $^1$H NMR (400 MHz, DMSO-$d_6$) δ ppm 11.40 (s, 1H), 8.53 (s, 2H), 7.91 (dd, 1H, J=0.7, 1.5), 7.47 (dd, 1H, J=1.8, 8.6), 7.28 (dd, 1H, J=0.7, 8.7), 6.64 (s, 2H), 5.36 (s, 2H). MS (ESI+) m/z 227.2 (M+H)$^+$.

Example 276

5-(2-methoxypyridin-3-yl)-1H-indazol-3-amine

The title compound was prepared according to the procedure outlined in Example 272 substituting 3-iodo-2-methoxypyridine for 4-iodo-N,N-dimethyl-1H-imidazole-1-sulfonamide. $^1$H NMR (400 MHz, DMSO-$d_6$) δ ppm 11.43 (s, 1H), 8.14 (dd, 1H, J=1.9, 5.0), 7.86 (s, 1H), 7.71 (dd, 1H, J=2.0, 7.2), 7.42 (dd, 1H, J=1.7, 8.7), 7.26 (d, 1H, J=8.6), 7.09 (dd, 1H, J=5.0, 7.3), 5.38 (s, 2H), 3.89 (s, 3H). MS (ESI+) m/z 241.2 (M+H)$^+$.

Example 277

5-imidazo[1,2-a]pyridin-3-yl-1H-indazol-3-amine

The title compound was prepared according to the procedure outlined in Example 272 substituting 3-bromoimidazo[1,2-a]pyridine for 4-iodo-N,N-dimethyl-1H-imidazole-1-sulfonamide. $^1$H NMR (400 MHz, DMSO-$d_6$) δ ppm 8.52 (dt, 1H, J=1.2, 7.0), 7.99 (dd, 1H, J=0.7, 1.7), 7.68 (s, 1H), 7.65 (dt, 2H, J=1.2, 9.0), 7.46 (dd, 1H, J=1.8, 8.6), 7.39 (dd, 1H, J=0.8, 8.6), 7.28 (ddd, 1H, J=1.2, 6.6, 9.2), 6.96 (td, 1H, J=1.3, 6.7), 5.47 (s, 2H). MS (ESI+) m/z 250.2 (M+H)$^+$.

Example 278

N$^2$,N$^2$-dimethyl-N$^1$-[5-(1H-1,2,3-triazol-4-yl)-1H-indazol-3-yl]glycinamide Example 65 (257 mg, 0.685 mmol) was dissolved in ethanol (15 mL). The reaction mixture was hydrogenated in an H-Cube apparatus with palladium hydroxide (20%) on carbon at about 80° C. and about 60 psi for about 8 hours. The solvent was removed under reduced pressure and the residue was purified by reverse phase HPLC using acetonitrile/water (0.05 M ammonium acetate) gradient elution method to afford the title compound. $^1$H NMR (400 MHz, DMSO-$d_6$) δ ppm 8.16-8.37 (m, 1H), 7.10-7.46 (bs, 2H), 7.00-7.34 (bs, 2H), 6.87-7.24 (bs, 2H), 3.33-3.34 (m, 2H). MS (ESI+) m/z 286.2 (M+H)$^+$.

Example 279

5-(1H-pyrazol-5-yl)-1H-indazol-3-amine

The title compound was prepared according to the procedure outlined in Example 272 substituting 5-iodo-1H-pyrazole for 4-iodo-N,N-dimethyl-1H-imidazole-1-sulfonamide. $^1$H NMR (400 MHz, DMSO-$d_6$) δ ppm 7.87-7.94 (m, 3H), 7.60-7.63 (m, 1H), 7.48 (dd, J=8.55, 1.62 Hz, 1H), 7.19-7.32 (m, 2H), 5.25-5.28 (m, 2H). MS (ESI+) m/z 200.1 (M+H)$^+$.

Example 280

5-(4-methyl-1H-imidazol-5-yl)-1H-indazol-3-amine

The title compound was prepared according to the procedure outlined in Example 272 substituting 5-iodo-4-methyl-1H-imidazole for 4-iodo-N,N-dimethyl-1H-imidazole-1-sulfonamide. $^1$H NMR (400 MHz, DMSO-$d_6$) δ ppm 7.85 (s, 1H), 7.52 (d, 2H, J=6.6), 7.22 (m, 1H), 5.32 (bs, 2H). 2.37 (s, 3H). MS (ESI+) m/z 214.1 (M+H)$^+$.

Example 281

5-(1H-imidazol-4-yl)-1H-indazol-3-amine

The title compound was prepared according to the procedure outlined in Example 272 substituting 4-iodo-1H-imidazole for 4-iodo-N,N-dimethyl-1H-imidazole-1-sulfonamide. $^1$H NMR (400 MHz, DMSO-$d_6$) δ ppm 8.07 (s, 1H), 7.66 (s, 1H), 7.63 (d, 1H, J=8.6), 7.37 (s, 1H), 7.20 (d, 1H, J=8.8), 5.28 (s, 2H). MS (ESI+) m/z 200.1 (M+H)$^+$.

Example 282

N$^2$,N$^2$-dimethyl-N$^1$-{5-[1-(3-methylbenzyl)-1H-1,2,3-triazol-4-yl]-1H-indazol-3-yl}glycinamide

Example 282A 5-bromo-1H-indazol-3-amine

The title compound was prepared according to the procedure outlined in Example 62D substituting 5-bromo-2-fluorobenzonitrile for Example 62C. $^1$H NMR (400 MHz, DMSO-$d_6$) δ ppm 11.55 (s, 1H), 7.92 (d, J=1.87 Hz, 1H), 7.30 (dd, J=8.79, 1.89 Hz, 1H), 7.19 (d, J=8.78 Hz, 1H), 5.41 (s, 2H).

Example 282B tert-butyl 3-amino-5-bromo-1H-indazole-1-carboxylate

The title compound was prepared according to the procedure outlined in Example 64A substituting Example 282A for Example 62D. $^1$H NMR (400 MHz, DMSO-$d_6$) δ ppm 8.12

(d, J=1.93 Hz, 1H), 7.95-7.81 (m, 1H), 7.65 (dd, J=8.85, 1.96 Hz, 1H), 6.39 (d, J=4.44 Hz, 1H), 1.58 (m, 9H).

Example 282C tert-butyl 5-bromo-3-(2-(dimethylamino)acetamido)-1H-indazole-1-carboxylate To a mixture of Example 282B (24.43 g, 78 mmol), potassium carbonate (81 g, 587 mmol) and 2-(dimethylamino) acetyl chloride hydrochloride (43.3 g, 274 mmol) was added tetrahydrofuran (200 mL). The reaction mixture was stirred at room temperature for about 2 hours. The reaction mixture was filtered and the filtrate was washed with water (50 mL). The organic layer was separated and the aqueous layer was extracted with dichloromethane (3×100 mL). The combined organic extracts were dried over magnesium sulfate, filtered and concentrated under reduced pressure. The residue was purified by silica gel chromatography eluting with methanol in dichloromethane (5%) to afford the title compound. $^1$H NMR (400 MHz, DMSO-$d_6$) δ ppm 10.72 (s, 1H), 8.19 (d, 1H, J=1.6), 8.03 (d, 1H, J=9.0), 7.76 (dd, 1H, J=2.0, 9.0), 3.22 (s, 2H), 2.32 (s, 6H), 1.63 (s, 9H).

Example 282D tert-butyl 3-(2-(dimethylamino)acetamido)-5-((trimethylsilyl)ethynyl)-1H-indazole-1-carboxylate To a mixture of Example 282C (2.56 g, 6.44 mmol), bis(triphenylphosphine)palladium(II) chloride (0.225 g, 0.321 mmol), and copper(I) iodide (0.073 g, 0.383 mmol) was added triethylamine (20 mL, 144 mmol) followed by ethynyltrimethylsilane (0.760 g, 7.73 mmol). The reaction mixture was heated at about 60° C. for about 3 hours. The reaction mixture was diluted with dichloromethane (100 mL), washed with water (20 mL) and brine (20 mL), dried over magnesium sulfate, filtered and concentrated under reduced pressure. The residue was purified by silica gel chromatography eluting with ethyl acetate in dichloromethane (10%) to give the title compound. $^1$H NMR (400 MHz, DMSO-$d_6$) δ ppm 10.69 (s, 1H), 8.08 (s, 1H), 8.04 (d, 1H, J=9.0), 7.62 (d, 1H, J=8.8), 3.21 (s, 2H), 2.30 (s, 6H), 1.61 (s, 9H), 0.23 (s, 9H).

Example 282E 2-(dimethylamino)-N-(5-ethynyl-1H-indazol-3-yl)acetamide

To Example 282D (0.303 g, 0.731 mmol) in methanol (5 mL) was added aqueous potassium hydroxide (1.46 mL, 1.46 mmol, 1.0 N solution). The reaction mixture was stirred at room temperature for about 1 hour. The solvent was removed under reduced pressure and the residue was dissolved in ethyl acetate (80 mL). The organic layer was separated and washed with water (10 mL) and brine (10 mL), dried over magnesium sulfate, filtered and concentrated under reduced pressure to afford the title compound. $^1$H NMR (400 MHz, DMSO-$d_6$) δ ppm 12.89 (s, 1H), 10.14 (s, 1H), 8.00 (d, 1H, J=12.1), 7.44 (s, 2H), 7.38 (d, 1H, J=8.6), 4.02 (s, 1H), 3.17 (s, 2H), 2.33 (s, 6H).

Example 282F $N^2$,$N^2$-dimethyl-$N^1$-{5-[1-(3-methylbenzyl)-1H-1,2,3-triazol-4-yl]-1H-indazol-3-yl}glycinamide To a suspension of Example 282E (0.16 g, 0.660 mmol) in tert-butanol (1.2 mL) was added 1-(azidomethyl)-3-methylbenzene (0.098 g, 0.667 mmol), then water (1.2 mL). A solution of sodium (R)-2-((S)-1,2-dihydroxyethyl)-4-hydroxy-5-oxo-2,5-dihydrofuran-3-olate (0.057 mL, 0.066 mmol, 1.6 M in water) and an aqueous solution of copper (II) sulfate pentahydrate (0.019 mL, 6.6 μmol, 0.34M) was added. The reaction mixture was heated at about 60° C. for about 2 hours. The solvent was removed under reduced pressure and the residue was purified by reverse phase HPLC using acetonitrile/water (0.05 M ammonium acetate) gradient elution method to afford the title compound. $^1$H NMR (400 MHz, DMSO-$d_6$) δ ppm 12.77 (s, 1H), 10.05 (s, 1H), 8.56 (s, 1H), 8.24 (s, 1H), 7.82 (d, 1H, J=8.6), 7.50 (d, 1H, J=8.8), 7.28 (t, 1H, J=7.6), 7.16 (m, 4H), 5.59 (s, 2H), 3.18 (s, 2H), 2.34 (s, 6H), 2.30 (s, 3H). MS (ESI+) m/z 390.3 (M+H)$^+$.

Example 283

5-(1-benzyl-1H-imidazol-4-yl)-1H-indazol-3-amine

The title compound was prepared according to the procedure outlined in Example 272 substituting 1-benzyl-4-iodo-1H-imidazole for 4-iodo-N,N-dimethyl-1H-imidazole-1-sulfonamide. $^1$H NMR (400 MHz, DMSO-$d_6$) δ ppm 11.29 (s, 1H), 8.07 (s, 1H), 7.79 (s, 1H), 7.61 (d, 1H, J=8.6), 7.46 (s, 1H), 7.36 (m, 5H), 7.17 (d, 1H, J=8.8), 5.28 (s, 2H), 5.22 (s, 2H). MS (ESI+) m/z 290.2 (M+H)$^+$.

Example 284

$N^1$-{5-[1-(4-tert-butylbenzyl)-1H-1,2,3-triazol-4-yl]-1H-indazol-3-yl}-$N^2$,$N^2$-dimethylglycinamide The title compound was prepared according to the procedure outlined in Example 282F substituting 1-(azidomethyl)-4-tert-butylbenzene for 1-(azidomethyl)-3-methylbenzene. $^1$H NMR (400 MHz, DMSO-$d_6$) δ ppm 12.88 (s, 1H), 10.05 (s, 1H), 8.57 (s, 1H), 8.23 (s, 1H), 7.81 (d, 1H, J=8.8), 7.50 (d, 1H, J=8.8), 7.41 (d, 2H, J=8.2), 7.30 (d, 2H, J=8.2), 3.18 (s, 2H), 2.34 (s, 6H), 1.26 (s, 9H). MS (ESI+) m/z 432.2 (M+H)$^+$.

Example 285

$N^2$,$N^2$-dimethyl-$N^1$-{5-[1-(2-piperidin-1-ylethyl)-1H-1,2,3-triazol-4-yl]-1H-indazol-3-yl}glycinamide The title compound was prepared according to the procedure outlined in Example 282F substituting 1-(2-azidoethyl)piperidine for 1-(azidomethyl)-3-methylbenzene. $^1$H NMR (400 MHz, DMSO-$d_6$) δ ppm 12.91 (s, 1H), 10.07 (s, 1H), 8.47 (s, 1H), 8.22 (s, 1H), 7.80 (dd, 1H, J=1.2, 8.7), 7.52 (d, 1H, J=8.8), 4.49 (t, 2H, J=6.4), 3.19 (s, 2H), 2.76 (t, 2H, J=6.4), 2.41 (s, 4H), 2.35 (s, 6H), 1.69 (s, 3H), 1.47 (m, 4H), 1.37 (dd, 2H, J=5.2, 10.2). MS (ESI−) m/z 395.3 (M−H)$^-$.

Example 286

$N^2$$N^2$-dimethyl-$N^1$-{5-[1-(2-morpholin-4-ylethyl)-1H-1,2,3-triazol-4-yl]-1H-indazol-3-yl}glycinamide The title compound was prepared according to the procedure outlined in Example 282F substituting 4-(2-azidoethyl)morpholine for 1-(azidomethyl)-3-methylbenzene. $^1$H NMR (400 MHz, DMSO-$d_6$) δ ppm 12.83 (s, 1H), 10.07 (s, 1H), 8.49 (s, 1H), 8.23 (s, 1H), 7.81 (dd, 1H, J=1.3, 8.7), 7.52 (d, 1H, J=8.8), 4.53 (t, 2H, J=6.3), 3.55 (m, 4H), 3.19 (s, 2H), 2.80 (t, 2H, J=6.3), 2.45 (m, 4H), 2.35 (s, 6H). MS (ESI−) m/z 397.3 (M−H)$^-$.

Example 287

N$^1$-(5-{1-[2-(3,5-dimethylisoxazol-4-yl)ethyl]-1H-1,2,3-triazol-4-yl}-1H-indazol-3-yl)-N$^2$,N$^2$-dimethylglycinamide The title compound was prepared according to the procedure outlined in Example 282F substituting 4-(2-azidoethyl)-3,5-dimethylisoxazole for 1-(azidomethyl)-3-methylbenzene. $^1$H NMR (400 MHz, DMSO-d$_6$) δ ppm 12.90 (s, 1H), 10.07 (s, 1H), 8.44 (s, 1H), 8.21 (s, 1H), 7.78 (dd, 1H, J=1.3, 8.7), 7.52 (d, 1H, J=8.8), 4.51 (t, 2H, J=6.7), 3.19 (s, 2H), 2.93 (t, 2H, J=6.7), 2.35 (s, 6H), 2.08 (d, 6H, J=4.3). MS (ESI−) m/z 407.2 (M−H)$^-$.

Example 288

N$^1$-(5-{1-[2-(3,5-dimethyl-1H-pyrazol-4-yl)ethyl]-1H-1,2,3-triazol-4-yl}-1H-indazol-3-yl)-N$^2$,N$^2$-dimethylglycinamide The title compound was prepared according to the procedure outlined in Example 282F substituting 4-(2-azidoethyl)-3,5-dimethyl-1H-pyrazole for 1-(azidomethyl)-3-methylbenzene. $^1$H NMR (400 MHz, DMSO-d$_6$) δ ppm 12.85 (s, 1H), 10.06 (s, 1H), 8.37 (s, 1H), 8.21 (s, 1H), 7.78 (d, 1H, J=8.8), 7.51 (d, 1H, J=8.8), 4.42 (t, 2H, J=6.9), 3.19 (s, 2H), 2.89 (t, 2H, J=7.0), 2.35 (s, 6H), 1.97 (s, 6H). MS (ESI−) m/z 406.2 (M−H)$^-$.

Example 289

2-(4-{3-[(N,N-dimethylglycyl)amino]-1H-indazol-5-yl}-1H-1,2,3-triazol-1-yl)-2-methylpropanoic Acid The title compound was prepared according to the procedure outlined in Example 282F substituting 2-azido-2-methylpropanoic acid for 1-(azidomethyl)-3-methylbenzene. $^1$H NMR (400 MHz, DMSO-d$_6$) δ ppm 12.77 (s, 1H), 10.03 (s, 1H), 8.47 (s, 1H), 8.22 (s, 1H), 7.85 (dd, 1H, J=0.9, 8.7), 7.49 (d, 1H, J=8.6), 3.21 (s, 2H), 2.36 (s, 6H), 1.77 (s, 6H). MS (ESI−) m/z 370.2 (M−H)$^-$.

Example 290

Ethyl (4-{3-[(N,N-dimethylglycyl)amino]-1H-indazol-5-yl}-1H-1,2,3-triazol-1-yl)acetate The title compound was prepared according to the procedure outlined in Example 282F substituting ethyl 2-azidoacetate for 1-(azidomethyl)-3-methylbenzene. $^1$H NMR (400 MHz, DMSO-d$_6$) δ ppm 12.87 (s, 1H), 10.08 (s, 1H), 8.51 (s, 1H), 8.26 (s, 1H), 7.82 (dd, 1H, J=1.4, 8.7), 7.53 (d, 1H, J=8.8), 5.44 (s, 2H), 4.21 (q, 2H, J=7.0), 3.19 (s, 2H), 2.35 (s, 6H), 1.24 (t, 3H, J=7.1). MS (ESI+) m/z 372.2 (M+H)$^+$.

Example 291

N$^2$,N$^2$-dimethyl-N$^1$-(5-{1-[(trimethylsilyl)methyl]-1H-1,2,3-triazol-4-yl}-1H-indazol-3-yl)glycinamide The title compound was prepared according to the procedure outlined in Example 282F substituting (azidomethyl)trimethylsilane for 1-(azidomethyl)-3-methylbenzene. $^1$H NMR (400 MHz, DMSO-d$_6$) δ ppm 13.04 (s, 1H), 10.20 (s, 1H), 8.46 (s, 1H), 8.36 (s, 1H), 7.94 (dd, 1H, J=1.3, 8.7), 7.65 (d, 1H, J=8.8), 4.18 (s, 2H), 3.33 (s, 2H), 2.49 (s, 6H), 0.25 (m, 9H). MS (ESI+) m/z 372.2 (M+H)$^+$.

Example 292

N$^1$-[5-(3-furyl)-1H-indazol-3-yl]-N$^2$,N$^2$-dimethylglycinamide

The title compound was prepared according to the procedure outlined in Example 233A substituting Example 282C for 5-bromo-2-fluorobenzonitrile and furan-3-ylboronic acid for 1-benzyl-4-(4,4,5,5-tetramethyl-1,3,2-dioxaborolan-2-yl)-1H-pyrazole. $^1$H NMR (600 MHz, DMSO-d$_6$) δ ppm 12.70 (s, 1H), 9.98 (s, 1H), 8.08 (s, 1H), 7.90 (s, 1H), 7.72 (t, 1H, J=1.6), 7.59 (dd, 1H, J=1.4, 8.7), 7.45 (d, 1H, J=8.8), 6.87 (s, 1H), 3.17 (s, 2H), 2.33 (s, 6H). MS (ESI+) m/z 285.2 (M+H)$^+$.

Example 293

N$^2$,N$^2$-dimethyl-N$^1$-[5-(1H-pyrazol-5-yl)-1H-indazol-3-yl]glycinamide

The title compound was prepared according to the procedure outlined in Example 233A substituting Example 282C for 5-bromo-2-fluorobenzonitrile and 1H-pyrazol-5-ylboronic acid for 1-benzyl-4-(4,4,5,5-tetramethyl-1,3,2-dioxaborolan-2-yl)-1H-pyrazole. $^1$H NMR (400 MHz, DMSO-d$_6$) δ ppm 12.68 (s, 1H), 10.01 (s, 1H), 8.12 (s, 1H), 7.80 (d, 1H, J=9.0), 7.69 (s, 1H), 7.46 (d, 1H, J=8.6), 6.60 (d, 1H, J=2.0), 3.17 (d, 2H, J=6.4), 2.34 (s, 6H). MS (ESI+) m/z 285.2 (M+H)$^+$.

Example 294

N$^2$,N$^2$-dimethyl-N$^1$-(5-pyrimidin-5-yl-1H-indazol-3-yl)glycinamide

The title compound was prepared according to the procedure outlined in Example 233A substituting Example 282C for 5-bromo-2-fluorobenzonitrile and pyrimidin-5-ylboronic acid for 1-benzyl-4-(4,4,5,5-tetramethyl-1,3,2-dioxaborolan-2-yl)-1H-pyrazole. $^1$H NMR (600 MHz, DMSO-d$_6$) δ ppm 12.87 (s, 1H), 10.11 (s, 1H), 9.16 (s, 1H), 9.09 (s, 2H), 8.16 (s, 1H), 7.75 (dd, 1H, J=1.5, 8.8), 7.60 (d, 1H, J=8.8), 3.18 (s, 2H), 2.33 (s, 6H). MS (ESI+) m/z 297.2 (M+H)$^+$.

Example 295

N$^1$-[5-(2,1,3-benzoxadiazol-5-yl)-1H-indazol-3-yl]-N$^2$,N$^2$-dimethylglycinamide The title compound was prepared according to the procedure outlined in Example 233A substituting Example 282C for 5-bromo-2-fluorobenzonitrile and benzo[c][1,2,5]oxadiazol-5-ylboronic acid for 1-benzyl-4-(4,4,5,5-tetramethyl-1,3,2-dioxaborolan-2-yl)-1H-pyrazole. $^1$H NMR (600 MHz, DMSO-d$_6$) δ ppm 12.87 (s, 1H), 10.15 (s, 1H), 8.29 (s, 1H), 8.21 (s, 1H), 8.16 (d, 1H, J=9.4), 7.99 (dd, 1H, J=1.1, 9.4), 7.85 (m, 1H), 7.59 (d, 1H, J=8.8), 3.19 (s, 2H), 2.34 (s, 6H). MS (ESI+) m/z 337.2 (M+H)$^+$.

Example 296

N$^2$,N$^2$-dimethyl-N$^1$-[5-(1H-pyrazol-4-yl)-1H-indazol-3-yl]glycinamide

The title compound was prepared according to the procedure outlined in Example 233A substituting Example 282C for 5-bromo-2-fluorobenzonitrile and 4-(4,4,5,5-tetramethyl-1,3,2-dioxaborolan-2-yl)-1H-pyrazole for 1-benzyl-4-(4,4,5,5-tetramethyl-1,3,2-dioxaborolan-2-yl)-1H-pyrazole. $^1$H NMR (600 MHz, DMSO-$d_6$) δ ppm 12.62 (s, 1H), 9.94 (s, 1H), 7.95 (s, 2H), 7.87 (s, 1H), 7.58 (d, 1H, J=8.8), 7.42 (d, 1H, J=8.8), 3.16 (s, 2H), 2.34 (s, 6H). MS (ESI+) m/z 285.2 (M+H)$^+$.

Example 297

$N^2,N^2$-dimethyl-$N^1$-[5-(1-methyl-1H-pyrazol-4-yl)-1H-indazol-3-yl]glycinamide The title compound was prepared according to the procedure outlined in Example 233A substituting Example 282C for 5-bromo-2-fluorobenzonitrile and 1-methyl-4-(4,4,5,5-tetramethyl-1,3,2-dioxaborolan-2-yl)-1H-pyrazole or 1-benzyl-4-(4,4,5,5-tetramethyl-1,3,2-dioxaborolan-2-yl)-1H-pyrazole. $^1$H NMR (600 MHz, DMSO-$d_6$) δ ppm 12.64 (s, 1H), 9.98 (s, 1H), 8.04 (s, 1H), 7.86 (s, 1H), 7.76 (s, 1H), 7.55 (dd, 1H, J=1.6, 8.6), 7.43 (d, 1H, J=8.8), 3.87 (s, 3H), 3.17 (s, 2H), 2.35 (s, 6H). MS (ESI+) m/z 299.2 (M+H)$^+$.

Example 298

$N^1$-[5-(3,5-dimethyl-1H-pyrazol-4-yl)-1H-indazol-3-yl]-$N^2,N^2$-dimethylglycinamide The title compound was prepared according to the procedure outlined in Example 233A substituting Example 282C for 5-bromo-2-fluorobenzonitrile and 3,5-dimethyl-4-(4,4,5,5-tetramethyl-1,3,2-dioxaborolan-2-yl)-1H-pyrazole for 1-benzyl-4-(4,4,5,5-tetramethyl-1,3,2-dioxaborolan-2-yl)-1H-pyrazole. $^1$H NMR (600 MHz, DMSO-$d_6$) δ ppm 12.63 (s, 1H), 10.02 (s, 1H), 7.63 (s, 1H), 7.46 (m, 1H), 7.27 (dd, 1H, J=1.6, 8.6), 3.16 (s, 2H), 2.32 (s, 6H), 2.18 (s, 6H). MS (ESI+) m/z 323.2 (M+H)$^+$.

Example 299

$N^1$-{5-[2-(dimethylamino)pyrimidin-5-yl]-1H-indazol-3-yl}-$N^2,N^2$-dimethylglycinamide The title compound was prepared according to the procedure outlined in Example 233A substituting Example 282C for 5-bromo-2-fluorobenzonitrile and N,N-dimethyl-5-(4,4,5,5-tetramethyl-1,3,2-dioxaborolan-2-yl)pyrimidin-2-amine for 1-benzyl-4-(4,4,5,5-tetramethyl-1,3,2-dioxaborolan-2-yl)-1H-pyrazole. $^1$H NMR (600 MHz, DMSO-$d_6$) δ ppm 12.72 (s, 1H), 10.03 (s, 1H), 8.62 (s, 2H), 7.91 (s, 1H), 7.58 (dd, 1H, J=1.6, 8.6), 7.51 (d, 1H, J=8.5), 3.16 (s, 8H), 2.33 (s, 6H). MS (ESI+) m/z 340.2 (M+H)$^+$.

Example 300

$N^2,N^2$-dimethyl-$N^1$-[5-(2-morpholin-4-ylpyrimidin-5-yl)-1H-indazol-3-yl]glycinamide The title compound was prepared according to the procedure outlined in Example 233A substituting Example 282C for 5-bromo-2-fluorobenzonitrile and 4-(5-(4,4,5,5-tetramethyl-1,3,2-dioxaborolan-2-yl)pyrimidin-2-yl)morpholine for 1-benzyl-4-(4,4,5,5-tetramethyl-1,3,2-dioxaborolan-2-yl)-1H-pyrazole. $^1$H NMR (600 MHz, DMSO-$d_6$) δ ppm 12.74 (s, 1H), 10.03 (s, 1H), 8.67 (s, 2H), 7.94 (s, 1H), 7.60 (dd, 1H, J=1.8, 8.8), 7.52 (d, 1H, J=8.5), 3.74 (m, 4H), 3.67 (m, 4H), 3.17 (s, 2H), 2.33 (s, 6H). MS (ESI+) m/z 382.2 (M+H)$^+$.

Example 301

$N^2,N^2$-dimethyl-$N^1$-{5-[1-(2-morpholin-4-ylethyl)-1H-pyrazol-4-yl]-1H-indazol-3-yl}glycinamide The title compound was prepared according to the procedure outlined in Example 233A substituting Example 282C for 5-bromo-2-fluorobenzonitrile and 4-(2-(4-(4,4,5,5-tetramethyl-1,3,2-dioxaborolan-2-yl)-1H-pyrazol-1-yl)ethyl)morpholine for 1-benzyl-4-(4,4,5,5-tetramethyl-1,3,2-dioxaborolan-2-yl)-1H-pyrazole. $^1$H NMR (600 MHz, DMSO-$d_6$) δ ppm 12.63 (s, 1H), 9.96 (s, 1H), 8.09 (s, 1H), 7.85 (s, 1H), 7.77 (s, 1H), 7.54 (dd, 1H, J=1.5, 8.8), 7.43 (d, 1H, J=8.5), 4.24 (t, 2H, J=6.6), 3.54 (m, 4H), 3.16 (s, 2H), 2.73 (t, 2H, J=6.6), 2.41 (s, 4H), 2.34 (s, 6H). MS (ESI+) m/z 398.3 (M+H)$^+$.

Example 302

$N^1$-[5-(1-benzyl-5-cyclopropyl-1H-1,2,3-triazol-4-yl)-1H-indazol-3-yl]-$N^2,N^2$-dimethylglycinamide

Example 302A 1-benzyl-5-cyclopropyl-4-(tributylstannyl)-1H-1,2,3-triazole

The title compound was prepared according to the procedure outlined in Example 142A substituting toluene for hexane and (azidomethyl)benzene for Example 80A. The crude product was used in the next step without purification.

Example 302B 5-(1-benzyl-5-cyclopropyl-1H-1,2,3-triazol-4-yl)-2-fluorobenzonitrile The title compound was prepared according to the procedure outlined in Example 142B substituting Example 302A for Example 142A and 2-fluoro-5-iodobenzonitrile for 87A. MS (ESI+) m/z 319.2 (M+H)$^+$.

Example 302C 5-(1-benzyl-5-cyclopropyl-1H-1,2,3-triazol-4-yl)-1H-indazol-3-amine The title compound was prepared according to the procedure outlined in Example 62D substituting Example 302B for Example 62C. MS (ESI−) m/z 299.2 (M−H)$^-$.

Example 302D tert-butyl 3-amino-5-(1-benzyl-5-cyclopropyl-1H-1,2,3-triazol-4-yl)-1H-indazole-1-carboxylate The title compound was prepared according to the procedure outlined in Example 64A substituting Example 302C for Example 62D.

Example 302E

N¹-[5-(1-benzyl-5-cyclopropyl-1H-1,2,3-triazol-4-yl)-1H-indazol-3-yl]-N²,N²-dimethylglycinamide The title compound was prepared according to the procedure outlined in Example 64B substituting Example 302D for Example 64A and dimethylaminoacetylchloride hydrochloride for methoxy acetyl chloride. ¹H NMR (400 MHz, DMSO-d₆) δ ppm 12.76 (s, 1H), 10.06 (s, 1H), 8.18 (s, 1H), 7.79 (d, 1H, J=8.8), 7.50 (d, 1H, J=8.8), 7.34 (m, 5H), 5.68 (s, 2H), 3.16 (s, 2H), 2.32 (s, 6H), 1.76 (m, 1H), 1.05 (q, 2H, J=6.1), 0.39 (q, 2H, J=5.4). MS (ESI+) m/z 416.3 (M+H)⁺. MS (ESI+) m/z 416.3 (M+H)⁺.

Example 303

N¹-[5-(1-benzyl-1H-pyrazol-4-yl)-1H-indazol-3-yl]-N²,N²-dimethylglycinamide

Example 303A 3-amino-5-(1-benzyl-1H-pyrazol-4-yl)-indazole-1-carboxylic Acid tert-butyl Ester The title compound was prepared according to the procedure outlined in Example 64A substituting Example 233B for Example 62D (0.925 g, 100%). ¹H NMR (400 MHz, DMSO-d₆) δ ppm 8.19 (s, 1H), 8.04 (s, 1H), 7.90-7.95 (m, 1H), 7.87 (s, 1H), 7.74 (d, J=1.6 Hz, 1H), 7.28-7.36 (m, 5H), 6.27 (s, 2H), 5.37 (s, 2H), 1.58 (s, 9H). MS (ESI+) m/z 390 (M+H)⁺.

Example 303B

N¹-[5-(1-benzyl-1H-pyrazol-4-yl)-1H-indazol-3-yl]-N²,N²-dimethylglycinamide

A suspension of 2-(dimethylamino)acetic acid (32 mg, 0.308 mmol) and oxalyl chloride (0.31 mL, 0.61 mmol) in dichloromethane (5 mL) and dimethylformamide (2 drops) was stirred at ambient temperature for about 1 hour then concentrated under reduced pressure. The residue was suspended in tetrahydrofuran (3 mL) and added to a suspension of Example 303A (40 mg, 0.103 mmol) and potassium carbonate (43 mg, 0.308 mmol) in tetrahydrofuran (5 mL). The reaction mixture was stirred at ambient temperature for about 30 minutes then trifluoroacetic acid (4 mL) was added and the reaction mixture was heated at about 60° C. for about 20 hours. The reaction mixture was cooled to ambient temperature and concentrated under reduced pressure, diluted with dichloromethane (20 mL) and washed with 15% aqueous sodium hydroxide solution (20 mL). The organic extract was separated, dried over magnesium sulfate, filtered and concentrated under reduced pressure. The crude material was purified by reverse-phase HPLC using acetonitrile/water (0.05 M ammonium acetate) gradient elution method to afford the title compound as the acetate salt. ¹H NMR (400 MHz, DMSO-d₆) δ ppm 9.97 (s, 1H), 8.21 (s, 1H), 7.83 (s, 1H), 7.82 (s, 1H), 7.56 (d, J=8.7 Hz, 1H), 7.43 (d, J=8.6 Hz, 1H), 7.32-7.40 (m, 2H), 7.25-7.32 (m, 3H), 5.35 (s, 2H), 3.16 (s, 2H), 2.33 (s, 6H), 1.91 (s, 3H). MS (ESI+) m/z 375 (M+H)⁺.

Example 304

N¹-[5-(1-benzyl-1H-1,2,3-triazol-4-yl)-1H-indazol-3-yl]-N²-methylglycinamide

The title compound was prepared according to the procedure outlined in Example 303B substituting 2-(tert-butoxycarbonyl(methyl)amino)acetic acid for 2-(dimethylamino)acetic acid and Example 64A for Example 303A. ¹H NMR (400 MHz, DMSO-d₆) δ ppm 8.56 (s, 1H), 8.28 (s, 1H), 7.78-7.88 (m, 1H), 7.45-7.56 (m, 1H), 7.28-7.45 (5H, m), 5.64 (2H, s), 2.37 (s, 2H), 1.89 (s, 3H). MS (ESI+) m/z 362 (M+H)⁺.

Example 305

N-[5-(1-benzyl-1H-1,2,3-triazol-4-yl)-1H-indazol-3-yl]-2-pyrrolidin-1-ylacetamide

Example 305A tert-butyl 5-(1-benzyl-1H-1,2,3-triazol-4-yl)-3-(2-bromoacetamido)-1H-indazole-1-carboxylate To a suspension of Example 64A (500 mg, 1.28 mmol) in tetrahydrofuran (12 mL) was added diisopropylethylamine (0.22 mL, 1.28 mmol). The reaction mixture was stirred at ambient temperature for about 15 minutes then 2-bromoacetyl chloride (0.11 mL, 1.2 mmol) was added. The reaction mixture was stirred at ambient temperature for about 16 hours then additional 2-bromoacetyl chloride (0.11 mL, 1.2 mmol) was added. The reaction mixture was stirred for an additional 15 minutes then concentrated under reduced pressure to provide the title compound as a brown solid. This material was used without further purification.

Example 305B

N-[5-(1-benzyl-1H-1,2,3-triazol-4-yl)-1H-indazol-3-yl]-2-pyrrolidin-1-ylacetamide To a solution of Example 305A (44 mg, 0.086 mmol) and diisopropylethylamine (0.015 mL, 0.086 mmol) in acetonitrile (1 mL) was added pyrrolidine (0.021 mL, 0.25 mmol) and the reaction mixture was heated at about 60° C. for about 15 minutes. The reaction mixture was cooled to ambient temperature and trifluoroacetic acid (1 mL) was added. The reaction mixture was heated at about 60° C. for about 48 hours. The reaction mixture was concentrated under reduced pressure, diluted with dichloromethane (20 mL) and washed with 15% aqueous sodium hydroxide solution (20 mL). The organic layer was separated, dried over magnesium sulfate, filtered and concentrated under reduced pressure. The crude material was purified by reverse-phase HPLC using acetonitrile/water (0.05 M ammonium acetate) gradient elution method to afford the title compound. ¹H NMR (400 MHz, DMSO-d₆) δ ppm 8.58 (s, 1H), 8.24 (s, 1H), 7.81 (d, J=8.7 Hz, 1H), 7.50 (d, J=8.7 Hz, 1H), 7.27-7.45 (m, 5H), 5.64 (s, 2H), 3.35 (s, 2H), 2.65 (s, 4H), 1.76 (s, 4H). MS (ESI+) m/z 402 (M+H)⁺.

Example 306

N¹-[5-(1-benzyl-1H-1,2,3-triazol-4-yl)-1H-indazol-3-yl]-N²-cyclopentylglycinamide The title compound was prepared according to the procedure outlined in Example 305B substituting cyclopentanamine for pyrrolidine (0.004 g, 12%). ¹H NMR (400 MHz, DMSO-d₆) δ ppm 8.56 (s, 1H), 8.31 (s, 1H), 7.73-7.86 (d, J=8.8 Hz, 1H), 7.49 (d, J=8.7 Hz, 1H), 7.29-7.45 (m, 5H), 5.64 (s, 2H), 3.37 (s, 2H), 2.99-3.14 (m, 1H), 1.60-1.80 (m, 4H), 1.30-1.50 (m, 4H). MS (ESI+) m/z 416 (M+H)⁺.

Example 307

N$^1$-[5-(1-benzyl-1H-1,2,3-triazol-4-yl)-1H-indazol-3-yl]-N$^2$-cyclopropylglycinamide To a solution of Example 305A (100 mg, 0.196 mmol) and diisopropylethylamine (0.034 mL, 0.19 mmol) in acetonitrile (1 mL) was added cyclopropanamine (11 mg, 0.19 mmol) and the reaction mixture was heated at about 60° C. for about 1 hour. The reaction mixture was cooled to ambient temperature and hydrochloric acid (4 N in dioxane, 1 mL) was added. The reaction mixture was stirred at ambient temperature for about 16 hours. The reaction mixture was concentrated under reduced pressure and the crude material was purified by reverse-phase HPLC using acetonitrile/water (0.05 M ammonium acetate) gradient elution method to afford the title compound as the acetate salt. $^1$H NMR (400 MHz, DMSO-d$_6$) δ ppm 10.18 (s, 1H), 8.28 (s, 1H), 8.56 (s, 1H), 7.81 (d, J=8.6 Hz, 1H), 7.49 (d, J=8.7 Hz, 1H), 7.30-7.45 (m, 5H), 5.64 (s, 2H), 3.45 (s, 2H), 2.18-2.26 (m, 1H), 1.89 (s, 3H), 0.37-0.45 (m, 2H), 0.29-0.37 (m, 2H). MS (ESI+) m/z 388 (M+H)$^+$.

Example 308

N$^1$-[5-(1-benzyl-1H-1,2,3-triazol-4-yl)-1H-indazol-3-yl]-N$^2$-tetrahydro-2H-pyran-4-ylglycinamide The title compound was prepared as the acetate salt according to the procedure outlined in Example 307 substituting tetrahydro-2H-pyran-4-amine for cyclopropanamine. $^1$H NMR (400 MHz, DMSO-d$_6$) δ ppm 8.56 (s, 1H), 8.31 (s, 1H), 7.81 (d, J=8.7 Hz, 1H), 7.50 (d, J=8.7 Hz, 1H), 7.31-7.45 (m, 5H), 5.64 (s, 2H), 3.84 (d, J=11.2 Hz, 2H), 3.43 (s, 2H), 3.30 (t, J=10.8 Hz, 2H), 2.62-2.74 (m, 1H), 1.88 (s, 3H), 1.75-1.85 (m, 2H), 1.24-1.39 (m, 2H). MS (ESI+) m/z 432 (M+H)$^+$.

Example 309

N-[5-(1-benzyl-1H-1,2,3-triazol-4-yl)-1H-indazol-3-yl]-2-(3-hydroxypyrrolidin-1-yl)acetamide The title compound was prepared as the diacetate salt according to the procedure outlined in Example 307 substituting pyrrolidin-3-ol for cyclopropanamine. $^1$H NMR (400 MHz, DMSO-d$_6$) δ ppm 10.09 (s, 1H), 8.22 (s, 1H), 8.58 (s, 1H), 7.82 (d, J=8.7 Hz, 1H), 7.50 (d, J=8.7 Hz, 1H), 7.28-7.45 (m, 5H), 5.64 (s, 2H), 4.16-4.26 (m, 1H), 3.34 (s, 2H), 2.77-2.93 (m, 2H), 2.52-2.65 (m, 2H), 1.98-2.13 (m, 1H), 1.87 (s, 6H), 1.56-1.69 (m, 1H). MS (ESI+) m/z 418 (M+H)$^+$.

Example 310

N-[5-(1-benzyl-1H-1,2,3-triazol-4-yl)-1H-indazol-3-yl]-2-(3-hydroxypiperidin-1-yl)acetamide The title compound was prepared as the acetate salt according to the procedure outlined in Example 307 substituting piperidin-3-ol for cyclopropanamine. $^1$H NMR (400 MHz, DMSO-d$_6$) δ ppm 10.05 (s, 1H), 8.56 (s, 1H), 8.23 (s, 1H), 7.82 (d, J=8.7 Hz, 1H), 7.50 (d, J=8.7 Hz, 1H), 7.29-7.44 (m, 5H), 5.64 (s, 2H), 3.55-3.67 (m, 1H), 3.20 (s, 2H), 2.77-2.88 (m, 1H), 2.60-2.70 (m, 1H), 2.22-2.35 (m, 1H), 2.12-2.23 (m, 1H), 1.88 (s, 3H), 1.66-1.78 (m, 2H), 1.43-1.59 (m, 1H), 1.13-1.27 (m, 1H). MS (ESI+) m/z 432 (M+H)$^+$.

Example 311

N$^1$-[5-(1-benzyl-1H-1,2,3-triazol-4-yl)-1H-indazol-3-yl]-N$^3$,N$^3$-dimethyl-beta-alaninamide The title compound was prepared as the acetate salt according to the procedure outlined in Example 307 substituting dimethylamine for cyclopropanamine. $^1$H NMR (400 MHz, DMSO-d$_6$) δ ppm 10.48 (s, 1H), 8.54 (s, 1H), 8.26 (s, 1H), 7.80 (d, J=8.7 Hz, 1H), 7.48 (d, J=8.7 Hz, 1H), 7.30-7.44 (m, 5H), 5.64 (s, 2H), 2.60 (d, J=6.1 Hz, 2H), 2.54 (d, J=6.3 Hz, 2H), 2.21 (s, 6H), 1.90 (s, 3H). MS (ESI+) m/z 390 (M+H)$^+$.

Example 312

N-[5-(1-benzyl-1H-1,2,3-triazol-4-yl)-1H-indazol-3-yl]-2-morpholin-4-ylacetamide The title compound was prepared according to the procedure outlined in Example 307 substituting morpholine for cyclopropanamine. $^1$H NMR (400 MHz, DMSO-d$_6$) δ ppm 10.10 (s, 1H), 8.57 (s, 1H), 8.23 (s, 1H), 7.81 (d, J=8.7 Hz, 1H), 7.50 (d, J=8.7 Hz, 1H), 7.29-7.46 (m, 5H), 5.64 (s, 2H), 3.59-3.71 (m, 4H), 3.22-3.28 (m, 2H), 2.54-2.64 (m, 4H). MS (ESI+) m/z 418 (M+H)$^+$.

Example 313

N-[5-(1-benzyl-1H-1,2,3-triazol-4-yl)-1H-indazol-3-yl]-2-(4-methylpiperazin-1-yl)acetamide The title compound was prepared as the diacetate salt according to the procedure outlined in Example 307 substituting 1-methylpiperazine for cyclopropanamine. $^1$H NMR (400 MHz, DMSO-d$_6$) δ ppm 8.57 (s, 1H), 8.25 (s, 1H), 7.81 (d, J=8.7 Hz, 1H), 7.50 (d, J=8.7 Hz, 1H), 7.32-7.43 (m, 5H), 5.64 (s, 2H), 3.22 (s, 2H), 2.53-2.65 (m, 4H), 2.31-2.45 (m, 4H), 2.17 (s, 3H), 1.85 (s, 6H). MS (ESI+) m/z 431 (M+H)$^+$.

Example 314

N-[5-(1-benzyl-1H-1,2,3-triazol-4-yl)-1H-indazol-3-yl]-2-(3-oxopiperazin-1-yl)acetamide The title compound was prepared according to the procedure outlined in Example 307 substituting piperazine-2-one for cyclopropanamine. $^1$H NMR (400 MHz, DMSO-d$_6$) δ ppm 10.21 (s, 1H), 8.57 (s, 1H), 8.22 (s, 1H), 7.81 (d, J=8.7 Hz, 1H), 7.50 (d, J=8.7 Hz, 1H), 7.31-7.46 (m, 5H), 5.64 (s, 2H), 3.36 (s, 2H), 3.24 (s, 2H), 3.17 (s, 2H), 2.78 (s, 2H). MS (ESI+) m/z 431 (M+H)$^+$.

Example 315

N$^1$-[5-(1-benzyl-1H-1,2,3-triazol-4-yl)-1H-indazol-3-yl]-N$^2$-isopropylglycinamide The title compound was prepared as the acetate salt according to the procedure outlined in Example 307 substituting propan-2-amine for cyclopropanamine. $^1$H NMR (400 MHz, DMSO-d$_6$) δ ppm 8.56 (s 1H), 8.31 (s, 1H), 7.81 (d, J=8.7 Hz, 1H), 7.49 (d, J=8.7 Hz, 1H), 7.31-7.44 (m, 5H), 5.64 (s, 2H), 3.39 (s, 2H), 2.73-2.86 (m, 1H), 1.90 (s, 3H), 1.04 (d, J=6.1 Hz, 6H). MS (ESI+) m/z 390 (M+H)$^+$.

Example 316

N$^1$-[5-(1-benzyl-1H-1,2,3-triazol-4-yl)-1H-indazol-3-yl]-N$^2$-cyclohexylglycinamide The title compound was prepared as the acetate salt according to the procedure outlined in Example 307 substituting cyclohexanamine for cyclopropanamine. $^1$H NMR (400 MHz, DMSO-d$_6$) δ ppm 8.55 (s, 1H), 8.31 (s, 1H), 7.81 (d, J=8.7 Hz, 1H), 7.49 (d, J=8.7 Hz, 1H), 7.30-7.44 (m, 5H), 5.64 (s, 2H), 3.40 (s, 2H), 1.90 (s, 3H), 1.80-1.88 (m, 2H), 1.63-1.73 (m, 2H), 1.50-1.60 (m, 1H), 1.02-1.29 (m, 5H). MS (ESI+) m/z 430 (M+H)$^+$.

Example 317

N-[5-(1-benzyl-1H-1,2,3-triazol-4-yl)-1H-indazol-3-yl]acetamide

To a mixture of Example 64A (20 mg, 0.051 mmol) and diisopropylethylamine (0.063 mL, 0.35 mmol) in tetrahydrofuran (1.5 mL) was added acetyl chloride (0.013 mL, 0.17 mmol) and the reaction mixture was stirred at ambient temperature for about 1.5 hours. Hydrochloric acid (4 N in dioxane, 1.5 mL) was added and the mixture stirred at ambient temperature for about 16 hours. The solvent was removed under reduced pressure and the crude material was purified by reverse-phase HPLC using acetonitrile/water (0.05 M ammonium acetate) gradient elution method to afford the title compound as the acetate salt. $^1$H NMR (400 MHz, DMSO-d$_6$) δ ppm 10.35 (s, 1H), 8.57 (s, 1H), 8.22 (s, 1H), 7.81 (d, J=8.7 Hz, 1H), 7.48 (d, J=8.7 Hz, 1H), 7.33-7.42 (m, 5H), 5.64 (s, 2H), 2.13 (s, 3H). MS (ESI−) m/z 331 (M−H)$^−$.

Example 318

N$^1$-[5-(1-benzyl-1H-1,2,3-triazol-4-yl)-1H-indazol-3-yl]-N$^2$-cyclobutylglycinamide The title compound was prepared according to the procedure outlined in Example 307 substituting cyclobutanamine for cyclopropanamine. $^1$H NMR (400 MHz, DMSO-d$_6$) δ ppm 8.56 (s, 1H), 8.29 (s, 1H), 7.81 (d, J=8.7 Hz, 1H), 7.49 (d, J=8.7 Hz, 1H), 7.31-7.45 (m, 5H), 5.64 (s, 2H), 3.31 (s, 2H), 2.01-2.20 (m, 2H), 1.48-1.83 (m, 5H). MS (ESI+) m/z 402 (M+H)$^+$.

Example 319

N-[5-(1-benzyl-1H-1,2,3-triazol-4-yl)-1H-indazol-3-yl]-N'-propylurea

To a solution of Example 64A (75 mg, 0.19 mmol) in pyridine (2 mL) was added 1-isocyanatopropane (16 mg, 0.19 mmol) and the reaction mixture was stirred at ambient temperature for about 3 hours. Additional isocyanate (0.1 mL) was added and the mixture was heated at about 80° C. for about 16 hours. The reaction mixture was cooled to ambient temperature and water (5 mL) was added. The resulting precipitate was collected by filtration then treated with hydrochloric acid (4 N solution in dioxane, 3 mL) and stirred at room temperature for about 4.5 hours. Diethyl ether (5 mL) was added and the precipitate collected by filtration. The crude material was purified by reverse-phase HPLC using acetonitrile/water (0.05 M ammonium acetate) gradient elution method to afford the title compound as the acetate salt. $^1$H NMR (400 MHz, DMSO-d$_6$) δ ppm 9.34 (s, 1H), 8.50 (s, 1H), 8.42 (s, 1H), 7.80 (d, J=8.7 Hz, 1H), 7.38 (d, J=8.7 Hz, 1H), 7.31-7.48 (m, 5H), 5.65 (s, 2H), 3.18 (dd, J=6.6, 12.7 Hz, 2H), 1.51 (dd, J=7.1, 14.3 Hz, 2H), 0.91 (t, J=7.3 Hz, 3H). MS (ESI+) m/z 376 (M+H)$^+$.

Example 320

N-[5-(1-benzyl-1H-1,2,3-triazol-4-yl)-1H-indazol-3-yl]ethanesulfonamide

To a solution of Example 64A (75 mg, 0.19 mmol) in pyridine (2 mL) was added ethanesulfonyl chloride (25 mg, 0.19 mmol) and the reaction mixture was stirred at room temperature for about 3 hours. Additional sulfonyl chloride (25 mg, 0.19 mmol) was added and the reaction mixture was stirred for about 48 hours. The reaction mixture was concentrated under reduced pressure and the residue dissolved in dichloromethane (10 mL) and washed with 1 N aqueous hydrochloric acid (10 mL). The organic portion was separated, dried under reduced pressure, and treated with hydrochloric acid (4 N in dioxane, 5 mL) and stirred at room temperature for about 12 hours. The reaction mixture was concentrated under reduced pressure and the crude material was purified by reverse-phase HPLC using acetonitrile/water (0.05 M ammonium acetate) gradient elution method to afford the title compound as the acetate salt. $^1$H NMR (400 MHz, DMSO-d$_6$) δ ppm 10.12 (s, 1H), 8.61 (s, 1H), 8.24 (s, 1H), 7.83 (d, J=8.7 Hz, 1H), 7.52 (d, J=8.7 Hz, 1H), 7.29-7.48 (m, 5H), 5.64 (s, 2H), 3.29 (d, J=9.2 Hz, 2H), 1.31 (t, J=7.3 Hz, 3H). MS (ESI+) m/z 383 (M+H)$^+$.

Example 321

5-(1-benzyl-1H-1,2,3-triazol-4-yl)-N-(cyclopropylmethyl)-1H-indazol-3-amine

A mixture of Example 64A (100 mg, 0.256 mmol), cyclopropanecarbaldehyde (0.057 mL, 0.76 mmol), sodium triacetoxyborohydride (163 mg, 0.76 mmol) and acetic acid (0.044 mL, 0.76 mmol) in 1,2-dichloroethane (5 mL) was stirred at ambient temperature for about 2.5 hours. Hydrochloric acid (4 N in dioxane, 4 mL) was added and the reaction mixture was stirred for about 16 hours. The precipitate was collected by filtration, rinsing with ether (10 mL). The solid was dissolved in dichloromethane (10 mL) and treated with trifluoroacetic acid (0.1 mL) and the reaction mixture was stirred at room temperature for about 2 hours. The reaction mixture was neutralized by the addition of 15% aqueous sodium hydroxide solution (about 15 mL) and the organic layer was separated, dried over magnesium sulfate, filtered and concentrated under reduced pressure. The crude material was purified by reverse-phase HPLC using acetonitrile/water (0.05 M ammonium acetate) gradient elution method to afford the title compound as the acetate salt. $^1$H NMR (400 MHz, DMSO-d$_6$) δ ppm 11.43 (s, 1H), 8.41 (s, 1H), 8.28 (s, 1H), 7.68 (d, J=8.7 Hz, 1H), 7.32-7.45 (m, 5H), 7.26 (d, J=8.6 Hz, 1H), 6.08 (t, J=5.7 Hz, 1H), 5.64 (s, 2H), 3.12 (t, J=6.2 Hz, 2H), 1.04-1.22 (m, 1H), 0.35-0.53 (m, 2H), 0.17-0.32 (m, 2H). MS (ESI+) m/z 345 (M+H)$^+$.

Example 322

N-[5-(1-benzyl-1H-1,2,3-triazol-4-yl)-1H-indazol-3-yl]-N'-ethylurea

The title compound was prepared according to the procedure outlined in Example 319 substituting isocyanatoethane for 1-isocyanatopropane. $^1$H NMR (400 MHz, DMSO-$d_6$) δ ppm 9.32 (s, 1H), 8.49 (s, 1H), 8.42 (s, 1H), 7.81 (d, J=8.7 Hz, 1H), 7.70 (d, J=8.7 Hz, 1H), 7.31-7.49 (m, 5H), 5.65 (s, 2H), 3.23 (d, J=6.9 Hz, 2H), 1.12 (t, J=7.1 Hz, 3H). MS (ESI+) m/z 362 (M+H)$^+$.

Example 323

1-[5-(1-benzyl-1H-1,2,3-triazol-4-yl)-1H-indazol-3-yl]pyrrolidin-2-one

A suspension of Example 64A (200 mg, 0.51 mmol) and diisopropylethylamine (0.089 mL, 0.51 mmol) in tetrahydrofuran (5 mL) was stirred for about 15 minutes at ambient temperature then 4-bromobutanoyl chloride (0.059 mL, 0.51 mmol) was added. The reaction mixture was stirred for about 16 hours. The precipitate was removed by filtration and the filtrate concentrated under reduced pressure. The residue was taken up in acetonitrile (5 mL) and treated with diisopropylethylamine (0.089 mL, 0.51 mmol) and heated at about 60° C. for about 16 hours. The reaction mixture was cooled to room temperature and concentrated under reduced pressure. The residue was treated with hydrochloric acid (4 N in dioxane, 5 mL) and the reaction mixture stirred at room temperature for about 2 hours. The reaction mixture was concentrated under reduced pressure and the crude material was purified by reverse-phase HPLC using acetonitrile/water (0.05 M ammonium acetate) gradient elution method to afford the title compound as the acetate salt. $^1$H NMR (400 MHz, DMSO-$d_6$) δ ppm 12.84 (s, 1H), 8.56 (s, 1H), 8.49 (s, 1H), 7.84 (d, J=8.6 Hz, 1H), 7.51 (d, J=8.7 Hz, 1H), 7.29-7.46 (m, 5H), 5.64 (s, 2H), 3.96 (t, J=6.9 Hz, 2H), 2.56 (t, J=7.9 Hz, 2H), 2.25-2.12 (m, 2H). MS (ESI+) m/z 359 (M+H)$^+$.

Example 324

N-[5-(1-benzyl-1H-1,2,3-triazol-4-yl)-1H-indazol-3-yl]-4-(dimethylamino)butanamide The title compound was prepared as the diacetate salt according to the procedure outlined in Example 303B substituting 4-(dimethylamino)butanoic acid for 2-(dimethylamino)acetic acid and substituting Example 64A for Example 303A. $^1$H NMR (400 MHz, DMSO-$d_6$) δ ppm 10.34 (s, 1H), 8.53 (s, 1H), 8.22 (s, 1H), 7.78 (d, J=8.7 Hz, 1H), 7.47 (d, J=8.7 Hz, 1H), 7.30-7.41 (m, 5H), 5.62 (s, 2H), 2.41 (t, J=7.2 Hz, 2H), 2.28 (t, J=6.8 Hz, 2H), 2.14 (s, 6H), 1.84 (s, 6H), 1.74-1.77 (m, 2H). MS (ESI−) m/z 462 (M−H)$^−$.

Example 325

N-3,4-dihydro-1H-isochromen-4-yl-5-(1H-indazol-5-yl)isoxazole-3-carboxamide

The title compound was prepared according to the procedure outlined in Example 81B substituting 3,4-dihydro-1H-isochromen-4-amine for piperidine. $^1$H NMR (300 MHz, DMSO-$d_6$) δ ppm 13.4 (br s, 1H), 9.02 (d, 1H), 8.4 (m, 1H), 8.22 (m, 1H), 7.75 (m, 1H), 7.2-7.4 (m, 5H), 5.24 (m, 1H), 4.75 (m, 2H), 4.02 (m, 1H), 3.8 (m, 1H). MS m/z (ESI+) 361 (M+H)$^+$.

Example 326

N-(cyclohexylmethyl)-5-(1H-indazol-5-yl)isoxazole-3-carboxamide 5-(1H-Indazol-5-yl)isoxazole-3-carboxylic acid (35 mg, 0.15 mmol, Example 71A), was dissolved in N,N-dimethylformamide (0.8 mL) followed by the addition of HATU (60 mg, 0.15 mmol) dissolved in N,N-dimethylformamide (0.8 mL). Then a solution of 1-cyclohexylmethanamine (17 mg, 0.17 mmol), dissolved in N,N-dimethylformamide (0.8 mL) was added, followed by diisopropylethylamine (56 μL, 0.31 mmol) dissolved in N,N-dimethylformamide (0.8 mL). The resulting mixture was shaken for 3 hours at 40° C. The reaction was filtered, checked by LC/MS and concentrated to dryness. The residues were dissolved in 1:1 dimethyl sulfoxide/methanol and purified by reverse phase HPLC (Phenomenex® Luna® C8(2) 5 μm 100 Å AXIA™ column (30 mm×75 mm), 50 mL/min, 10-100% acetonitrile/0.1% trifluoroacetic acid in water) to provide the title product. $^1$H NMR (500 MHz, DMSO-$d_6$/D$_2$O) δ ppm 0.91-0.97 (m, 2H), 1.12-1.27 (m, 4H), 1.61-1.75 (m, 5H), 3.08-3.16 (m, 2H), 7.22-7.24 (m, 1H), 7.71-7.75 (m, 1H), 7.87-7.92 (m, 1H), 8.23-8.27 (m, 1H), 8.38-8.41 (m, 1H). MS (ESI+) m/z 325 (M+H)$^+$; (ESI−) m/z 323 (M−H)$^−$.

Example 327

N-(3-chlorobenzyl)-5-(1H-indazol-5-yl)isoxazole-3-carboxamide

The title compound was prepared using the procedure described in Example 326 except 1-(3-chlorophenyl)methanamine was substituted for 1-cyclohexylmethanamine. $^1$H NMR (500 MHz, DMSO-$d_6$/D$_2$O) δ ppm 4.47-4.52 (m, 2H), 7.27-7.29 (m, 1H), 7.30-7.42 (m, 4H), 7.72-7.75 (m, 1H), 7.89-7.93 (m, 1H), 8.25-8.28 (m, 1H), 8.41-8.42 (m, 1H). MS (ESI+) m/z 353 (M+H)$^+$; (ESI−) m/z 351 (M−H)$^−$.

Example 328

5-(1H-indazol-5-yl)-N-(2-methoxybenzyl)isoxazole-3-carboxamide

The title compound was prepared using the procedure described in Example 326 except 1-(2-methoxyphenyl)methanamine was substituted for 1-cyclohexylmethanamine. $^1$H NMR (500 MHz, DMSO-$d_6$/D$_2$O) δ ppm 3.82-3.86 (m, 3H), 4.45-4.50 (m, 2H), 6.92-6.97 (m, 1H), 7.01-7.04 (m, 1H), 7.19-7.24 (m, 1H), 7.26-7.31 (m, 2H), 7.69-7.77 (m, 1H), 7.88-7.93 (m, 1H), 8.24-8.28 (m, 1H), 8.38-8.44 (m, 1H). MS (ESI+) m/z 349 (M+H)$^+$; (ESI−) m/z 347 (M−H)$^−$.

Example 329

5-(1H-indazol-5-yl)-N-[2-(trifluoromethyl)benzyl]isoxazole-3-carboxamide

The title compound was prepared using the procedure described in Example 326 except 1-[2-(trifluoromethyl)phenyl]methanamine was substituted for 1-cyclohexylmethanamine. $^1$H NMR (500 MHz, DMSO-$d_6$/D$_2$O) δ ppm 4.66-4.73 (m, 2H), 7.29-7.33 (m, 1H), 7.49-7.60 (m, 2H), 7.67-7.79 (m, 3H), 7.91-7.94 (m, 1H), 8.26-8.28 (m, 1H), 8.41-8.45 (m, 1H). MS (ESI+) m/z 387 (M+H)$^+$; (ESI−) m/z 385 (M−H)$^−$.

Example 330

5-(1H-indazol-5-yl)-N-[3-(trifluoromethyl)benzyl]isoxazole-3-carboxamide

The title compound was prepared using the procedure described in Example 326 except 1-[3-(trifluoromethyl)phenyl]methanamine was substituted for 1-cyclohexylmethanamine. $^1$H NMR (500 MHz, DMSO-d$_6$/D$_2$O) δ ppm 4.57-4.61 (m, 2H), 7.28-7.31 (m, 1H), 7.59-7.77 (m, 5H), 7.90-7.94 (m, 1H), 8.27-8.28 (m, 1H), 8.40-8.43 (m, 1H). MS (ESI−) m/z 385 (M−H)$^−$.

Example 331

5-(1H-indazol-5-yl)-N-[4-(trifluoromethyl)benzyl]isoxazole-3-carboxamide

The title compound was prepared using the procedure described in Example 326 except 1-[4-(trifluoromethyl)phenyl]methanamine was substituted for 1-cyclohexylmethanamine. $^1$H NMR (500 MHz, DMSO-d$_6$/D$_2$O) δ ppm 4.55-4.60 (s, 2H), 7.27-7.30 (m, 1H), 7.54-7.59 (m, 2H), 7.70-7.76 (m, 3H), 7.88-7.94 (m, 1H), 8.24-8.28 (m, 1H), 8.40-8.44 (m, 1H). MS (ESI+) m/z 387 (M+H)$^+$; (ESI−) m/z 385 (M−H)$^−$.

Example 332

5-(1H-indazol-5-yl)-N-(pyridin-2-ylmethyl)isoxazole-3-carboxamide

The title compound was prepared using the procedure described in Example 326 except 1-pyridin-2-ylmethanamine was substituted for 1-cyclohexylmethanamine. $^1$H NMR (500 MHz, DMSO-d$_6$/D$_2$O) δ ppm 4.74-4.84 (s, 2H), 7.30-7.34 (m, 1H), 7.68-7.81 (m, 3H), 7.89-7.97 (m, 1H), 8.22-8.33 (m, 2H), 8.40-8.45 (m, 1H), 8.67-8.76 (m, 1H). MS (ESI+) m/z 320 (M+H)$^+$; (ESI−) m/z 318 (M−H)$^−$.

Example 333

5-(1H-indazol-5-yl)-N-(pyridin-3-ylmethyl)isoxazole-3-carboxamide

The title compound was prepared using the procedure described in Example 326 except 1-pyridin-3-ylmethanamine was substituted for 1-cyclohexylmethanamine. $^1$H NMR (500 MHz, DMSO-d$_6$/D$_2$O) δ ppm 4.61-4.68 (s, 2H), 7.27-7.31 (m, 1H), 7.70-7.75 (m, 1H), 7.83-7.94 (m, 2H), 8.24-8.28 (m, 1H), 8.31-8.37 (m, 1H), 8.40-8.44 (m, 1H), 8.69-8.74 (m, 1H), 8.77-8.82 (m, 1H). MS (ESI+) m/z 320 (M+H)$^+$; (ESI−) m/z 318 (M−H)$^−$.

Example 334

5-(1H-indazol-5-yl)-N-(pyridin-4-ylmethyl)isoxazole-3-carboxamide

The title compound was prepared using the procedure described in Example 326 except 1-pyridin-4-ylmethanamine was substituted for 1-cyclohexylmethanamine. $^1$H NMR (500 MHz, DMSO-d$_6$/D$_2$O) δ ppm 4.73-4.80 (s, 2H), 7.30-7.33 (m, 1H), 7.73-7.78 (m, 1H), 7.89-7.97 (m, 3H), 8.25-8.30 (m, 1H), 8.40-8.46 (m, 1H), 8.76-8.83 (m, 2H). MS (ESI−) m/z 318 (M−H)$^−$.

Example 335

N-(2-chlorobenzyl)-5-(1H-indazol-5-yl)isoxazole-3-carboxamide

The title compound was prepared using the procedure described in Example 326 except 1-(2-chlorophenyl)methanamine was substituted for 1-cyclohexylmethanamine. $^1$H NMR (500 MHz, DMSO-d$_6$/D$_2$O) δ ppm 4.54-4.58 (s, 2H), 7.27-7.32 (m, 1H), 7.33-7.42 (m, 3H), 7.47-7.49 (m, 1H), 7.71-7.77 (m, 1H), 7.88-7.98 (m, 1H), 8.24-8.27 (m, 1H), 8.41-8.44 (m, 1H). MS (ESI+) m/z 353 (M+H)$^+$; (ESI−) m/z 351 (M−H)$^−$.

Example 336

N-(4-chlorobenzyl)-5-(1H-indazol-5-yl)isoxazole-3-carboxamide

The title compound was prepared using the procedure described in Example 326 except 1-(4-chlorophenyl)methanamine was substituted for 1-cyclohexylmethanamine. $^1$H NMR (500 MHz, DMSO-d$_6$/D$_2$O) δ ppm 4.42-4.49 (m, 2H), 7.22-7.31 (m, 1H), 7.34-7.49 (m, 4H), 7.70-7.76 (m, 1H), 7.84-7.92 (m, 1H), 8.17-8.30 (m, 1H), 8.35-8.47 (m, 1H). MS (ESI−) m/z 351 (M−H)$^−$.

Example 337

5-(1H-indazol-5-yl)-N-(1-phenyl-2-piperidin-1-yl-ethyl)isoxazole-3-carboxamide

The title compound was prepared according to the procedure outlined in Example 81B substituting 1-phenyl-2-piperidin-1-ylethanamine for piperidine. $^1$H NMR (300 MHz, DMSO-d$_6$) δ ppm 13.4 (br s, 1H), 9.12 (d, 1H), 8.4 (s, 1H), 8.22 (s, 1H), 7.9 (d, 1H), 7.7 (d, 1H), 7.2-7.4 (m, 6H), 5.2 (m, 1H), 3.2 (m, 2H), 2.3 (m, 4H), 1.2-1.4 (m, 6H). MS (ESI+) m/z 416 (M+H)$^+$.

Example 338

N-[2-(1H-imidazol-1-yl)-1-phenylethyl]-5-(1H-indazol-5-yl)isoxazole-3-carboxamide The title compound was prepared according to the procedure outlined in Example 81B substituting 2-(1H-imidazol-1-yl)-1-phenylethanamine for piperidine. $^1$H NMR (300 MHz, DMSO-d$_6$) δ ppm 13.4 (br s, 1H), 9.5 (d, 1H), 8.4 (s, 1H), 8.22 (s, 1H), 7.78 (m, 1H), 7.52 (d, 2H), 7.72 (d, 2H), 7.2-7.4 (m, 5H), 6.85 (s, 1H), 5.44 (m, 1H), 4.44 (m, 2H). MS (ESI+) m/z 399 (M+H)$^+$.

Example 339

5-(1H-indazol-5-yl)-N-(2-morpholin-4-yl-1-phenylethyl)isoxazole-3-carboxamide

The title compound was prepared according to the procedure outlined in Example 81B substituting 2-morpholin-4-yl-1-phenylethanamine for piperidine. $^1$H NMR (300 MHz, DMSO-d$_6$) δ ppm 13.4 (br s, 1H), 9.2 (d, 1H), 8.4 (s, 1H), 8.22 (s, 1H), 7.9 (d, 1H), 7.7 (d, 1H), 7.2-7.4 (m, 6H), 5.2 (m, 1H), 3.6 (m, 4H), 3.4 (m, 2H), 2.4 (m, 4H). MS (ESI+) m/z 418 (M+H)$^+$.

Example 340

5-(1H-indazol-5-yl)-N-[2-(4-methylpiperazin-1-yl)-1-phenylethyl]isoxazole-3-carboxamide The title compound was prepared according to the procedure outlined in Example 81B substituting 2-(4-methylpiperazin-1-yl)-1-phenylethanamine for piperidine. $^1$H NMR (300 MHz, DMSO-d$_6$) δ ppm 13.6 (br s, 1H), 9.14 (d, 1H), 8.4 (s, 1H), 8.22 (s, 1H), 7.9 (d, 1H), 7.7 (d, 1H), 7.2-7.4 (m, 6H), 5.2 (m, 1H), 3.2 (m, 2H), 2.4 (m, 4H), 2.2 (m, 4H), 2.1 (m, 3H). MS (ESI+) m/z 432 (M+H)+.

Example 341

5-(1H-indazol-5-yl)-N-(1-phenyl-2-pyrrolidin-1-ylethyl)isoxazole-3-carboxamide

The title compound was prepared according to the procedure outlined in Example 81B substituting 1-phenyl-2-pyrrolidin-1-ylethanamine for piperidine. $^1$H NMR (300 MHz, DMSO-d$_6$) δ ppm 13.4 (br s, 1H), 9.14 (d, 1H), 8.4 (s, 1H), 8.22 (s, 1H), 7.9 (d, 1H), 7.7 (d, 1H), 7.2-7.4 (m, 6H), 5.18 (m, 1H), 3.2 (m, 2H), 2.4 (m, 4H), 1.8 (m, 3H). MS (ESI+) m/z 402.5 (M+H)+.

Example 342 tert-butyl 2-({[5-(1H-indazol-5-yl)isoxazol-3-yl]carbonyl}amino)-2-phenylethylcarbamate The title compound was prepared according to the procedure outlined in Example 81B substituting tert-butyl 2-amino-2-phenylethylcarbamate for piperidine. $^1$H NMR (300 MHz, DMSO-d$_6$) δ ppm 13.4 (br s, 1H), 9.14 (d, 1H), 8.4 (s, 1H), 8.22 (s, 1H), 7.9 (d, 1H), 7.7 (d, 1H), 7.2-7.4 (m, 6H), 7.00 (t, 1H), 5.18 (m, 1H), 3.2 (m, 2H), 1.4 (s, 9H). MS (ESI+) m/z 449 (M+H)+.

Example 343

5-(1H-indazol-5-yl)-N-(1-naphthylmethyl)isoxazole-3-carboxamide

The title compound was prepared using the procedure described in Example 326 except 1-(1-naphthyl)methanamine was substituted for 1-cyclohexylmethanamine. $^1$H NMR (500 MHz, DMSO-d$_6$/D$_2$O) δ ppm 4.93-4.99 (m, 2H), 7.28-7.32 (m, 1H), 7.48-7.66 (m, 4H), 7.70-7.76 (m, 1H), 7.86-7.92 (m, 2H), 7.96-8.00 (m, 1H), 8.18-8.23 (m, 1H), 8.24-8.27 (m, 1H), 8.38-8.44 (m, 1H);). MS (ESI-) m/z 367 (M-H)-.

Example 344

5-(1H-indazol-5-yl)-N-(2-phenylethyl)isoxazole-3-carboxamide

The title compound was prepared using the procedure described in Example 326 except 2-phenylethanamine was substituted for 1-cyclohexylmethanamine. $^1$H NMR (500 MHz, DMSO-d$_6$/D$_2$O) δ ppm 2.84-2.92 (t, 2H), 3.47-3.57 (t, 2H), 7.18-7.35 (m, 6H), 7.69-7.77 (m, 1H), 7.86-7.91 (m, 1H), 8.22-8.29 (m, 1H), 8.37-8.44 (m, 1H). MS (ESI+) m/z 333 (M+H)+; (ESI-) m/z 331 (M-H)-.

Example 345

5-(1H-indazol-5-yl)-N-(2-pyridin-2-ylethyl)isoxazole-3-carboxamide

The title compound was prepared using the procedure described in Example 326 except 2-pyridin-2-ylethanamine was substituted for 1-cyclohexylmethanamine. $^1$H NMR (500 MHz, DMSO-d$_6$/D$_2$O) δ ppm 3.22-3.29 (t, 2H), 3.71-3.75 (t, 2H), 7.14-7.26 (m, 1H), 7.70-7.75 (m, 1H), 7.81-7.94 (m, 3H), 8.23-8.29 (m, 1H), 8.35-8.44 (m, 2H), 8.71-8.83 (m, 1H). MS (ESI+) m/z 334 (M+H)+; (ESI-) m/z 332 (M-H)-.

Example 346

5-(1H-indazol-5-yl)-N-(2-pyridin-3-ylethyl)isoxazole-3-carboxamide

The title compound was prepared using the procedure described in Example 326 except 2-pyridin-3-ylethanamine was substituted for 1-cyclohexylmethanamine. $^1$H NMR (500 MHz, DMSO-d$_6$/D$_2$O) δ ppm 3.01-3.13 (t, 2H), 3.55-3.70 (t, 2H), 7.14-7.26 (m, 1H), 7.70-7.77 (m, 1H), 7.84-7.95 (m, 2H), 8.25-8.29 (m, 1H), 8.36-8.45 (m, 2H), 8.69-8.75 (m, 1H), 8.77-8.84 (m, 1H). MS (ESI+) m/z 334 (M+H)+; (ESI-) m/z 332 (M-H)-.

Example 347

5-(1H-indazol-5-yl)-N-(2-pyridin-4-ylethyl)isoxazole-3-carboxamide

The title compound was prepared using the procedure described in Example 326 except 2-pyridin-4-ylethanamine was substituted for 1-cyclohexylmethanamine. $^1$H NMR (500 MHz, DMSO-d$_6$/D$_2$O) δ ppm 3.12-3.23 (t, 2H), 3.67-3.71 (t, 2H), 7.20-7.21 (m, 1H), 7.69-7.76 (m, 1H), 7.86-7.91 (m, 3H), 8.25-8.27 (m, 1H), 8.38-8.41 (m, 1H), 8.70-8.77 (m, 2H). MS (ESI+) m/z 334 (M+H)+; (ESI-) m/z 332 (M-H)-.

Example 348

N-[2-(2-chlorophenyl)ethyl]-5-(1H-indazol-5-yl)isoxazole-3-carboxamide

The title compound was prepared using the procedure described in Example 326 except 2-(2-chlorophenyl)ethanamine was substituted for 1-cyclohexylmethanamine. $^1$H NMR (500 MHz, DMSO-d$_6$/D$_2$O) δ ppm 2.99-3.05 (t, 2H), 3.54-3.61 (t, 2H), 7.21-7.23 (m, 1H), 7.26-7.33 (m, 2H), 7.35-7.40 (m, 1H), 7.41-7.47 (m, 1H), 7.70-7.75 (m, 1H), 7.87-7.93 (m, 1H), 8.23-8.31 (m, 1H), 8.37-8.44 (m, 1H). MS (ESI+) m/z 367 (M+H)+; (ESI-) m/z 365 (M-H)-.

Example 349

N-[2-(3-chlorophenyl)ethyl]-5-(1H-indazol-5-yl)isoxazole-3-carboxamide

The title compound was prepared using the procedure described in Example 326 except 2-(3-chlorophenyl)ethanamine was substituted for 1-cyclohexylmethanamine. $^1$H NMR (500 MHz, DMSO-d$_6$/D$_2$O) δ ppm 2.89 (t, 2H), 3.54 (t, 2H), 7.19-7.42 (m, 5H), 7.69-7.77 (m, 1H), 7.86-7.94 (m, 1H), 8.22-8.29 (m, 1H), 8.38-8.42 (m, 1H). MS (ESI-) m/z 365 (M-H)-.

Example 350

N-[2-(4-chlorophenyl)ethyl]-5-(1H-indazol-5-yl)isoxazole-3-carboxamide

The title compound was prepared using the procedure described in Example 326 except 2-(4-chlorophenyl)ethanamine was substituted for 1-cyclohexylmethanamine. $^1$H NMR (500 MHz, DMSO-d$_6$/D$_2$O) δ ppm 2.86 (t, 2H), 3.50 (t, 2H), 7.17-7.24 (m, 1H), 7.27-7.41 (m, 4H), 7.71-7.76 (m, 1H), 7.85-7.91 (m, 1H), 8.21-8.29 (m, 1H), 8.34-8.44 (m, 1H). MS (ESI−) m/z 365 (M−H)⁻.

Example 351

N-benzyl-N-ethyl-5-(1H-indazol-5-yl)isoxazole-3-carboxamide

The title compound was prepared using the procedure described in Example 326 except N-benzyl-N-ethylamine was substituted for 1-cyclohexylmethanamine. ¹H NMR (500 MHz, DMSO-d₆/D₂O) δ ppm 1.06-1.19 (m, 3H), 3.37-3.49 (m, 2H), 4.69-4.76 (m, 2H), 7.21-7.28 (m, 1H), 7.28-7.49 (m, 5H), 7.69-7.78 (m, 1H), 7.83-7.97 (m, 1H), 8.24-8.32 (m, 1H), 8.36-8.46 (m, 1H). MS (ESI+) m/z 347 (M+H)⁺; (ESI−) m/z 345 (M−H)⁻.

Example 352

5-(1H-indazol-5-yl)-N-methyl-N-(1-naphthylmethyl)isoxazole-3-carboxamide

The title compound was prepared using the procedure described in Example 326 except N-methyl-N-(1-naphthylmethyl)amine was substituted for 1-cyclohexylmethanamine. ¹H NMR (500 MHz, DMSO-d₆/D₂O) δ ppm 3.04-3.11 (m, 3H), 5.20-5.35 (m, 2H), 7.20-7.31 (m, 1H), 7.33-7.66 (m, 4H), 7.66-7.77 (m, 1H), 7.81-8.18 (m, 4H), 8.20-8.28 (m, 1H), 8.31-8.45 (m, 1H). MS (ESI+) m/z 383 (M+H)⁺; (ESI−) m/z 381 (M−H)⁻.

Example 353

5-(1H-indazol-5-yl)-N-methyl-N-(2-phenylethyl)isoxazole-3-carboxamide

The title compound was prepared using the procedure described in Example 326 except N-methyl-N-(2-phenylethyl)amine was substituted for 1-cyclohexylmethanamine. ¹H NMR (500 MHz, DMSO-d₆/D₂O) δ ppm 2.86-2.97 (m, 2H), 3.06-3.13 (m, 3H), 3.70-3.74 (m, 2H), 6.64-7.39 (m, 6H), 7.69-7.92 (m, 2H), 8.24-8.44 (m, 2H). MS (ESI+) m/z 347 (M+H)⁺; (ESI−) m/z 345 (M−H)⁻.

Example 354

5-(1H-indazol-5-yl)-N-methyl-N-(2-pyridin-2-yl-ethyl)isoxazole-3-carboxamide The title compound was prepared using the procedure described in Example 326 except N-methyl-N-(2-pyridin-2-ylethyl)amine was substituted for 1-cyclohexylmethanamine. ¹H NMR (500 MHz, DMSO-d₆/D₂O) δ ppm 3.07-3.22 (m, 3H), 3.26-3.39 (m, 2H), 3.92-4.04 (m, 2H), 6.85-7.14 (m, 1H), 7.65-8.05 (m, 4H), 8.23-8.56 (m, 3H), 8.65-8.86 (m, 1H). MS (ESI+) m/z 348 (M+H)⁺; (ESI−) m/z 346 (M−H)⁻.

Example 355

5-(1H-indazol-5-yl)-N-[(1R)-1-phenylethyl]isoxazole-3-carboxamide

The title compound was prepared using the procedure described in Example 326 except (1R)-1-phenylethanamine was substituted for 1-cyclohexylmethanamine. ¹H NMR (500 MHz, DMSO-d₆/D₂O) δ ppm 1.49-1.54 (m, 3H), 5.12-5.20 (m, 1H), 7.23-7.29 (m, 2H), 7.33-7.46 (m, 4H), 7.71-7.75 (m, 1H), 7.87-7.91 (m, 1H), 8.22-8.28 (m, 1H), 8.37-8.42 (m, 1H). MS (ESI+) m/z 333 (M+H)⁺; (ESI−) m/z 331 (M−H)⁻.

Example 356

5-(1H-indazol-5-yl)-N-1,2,3,4-tetrahydronaphthalen-1-ylisoxazole-3-carboxamide The title compound was prepared using the procedure described in Example 326 except 1,2,3,4-tetrahydronaphthalen-1-amine was substituted for 1-cyclohexylmethanamine. ¹H NMR (500 MHz, DMSO-d₆/D₂O) δ ppm 1.72-2.09 (m, 4H), 2.68-2.85 (m, 2H), 5.19-5.26 (m, 1H), 7.12-7.24 (m, 4H), 7.29-7.35 (m, 1H), 7.69-7.77 (m, 1H), 7.86-7.93 (m, 1H), 8.25-8.30 (m, 1H), 8.38-8.43 (m, 1H). MS (ESI−) m/z 357 (M−H)⁻.

Example 357

5-(1H-indazol-5-yl)-N-[(1S)-1-(1-naphthyl)ethyl]isoxazole-3-carboxamide

The title compound was prepared according to the procedure outlined in Example 81B substituting (1S)-1-(1-naphthyl)ethanamine for piperidine. ¹H NMR (300 MHz, DMSO-d₆) δ ppm 13.4 (br s, 1H), 9.4 (d, 1H), 8.4 (s, 1H), 8.25 (s, 1H), 8.22 (br s, 1H), 7.95 (d, 1H), 7.85 (m, 2H), 7.65 (m, 2H), 7.5 (m, 3H), 7.3 (s, 1H), 5.9 (m, 1H), 1.65 (d, 3H). MS (ESI+) m/z 382.9 (M+H)⁺.

Example 358

5-(1H-indazol-5-yl)-N-[(1R)-1-(1-naphthyl)ethyl]isoxazole-3-carboxamide

The title compound was prepared according to the procedure outlined in Example 81B substituting (1R)-1-(1-naphthyl)ethanamine for piperidine. ¹H NMR (300 MHz, DMSO-d₆) δ ppm 13.4 (br s, 1H), 9.4 (d, 1H), 8.4 (s, 1H), 8.25 (s, 1H), 8.22 (br s, 1H), 7.95 (d, 1H), 7.85 (m, 2H), 7.65 (m, 2H), 7.5 (m, 3H), 7.3 (s, 1H), 5.9 (m, 1H), 1.65 (d, 3H). MS (ESI+) m/z 382.9 (M+H)⁺.

Example 359

N-[3-(dimethylamino)-1-phenylpropyl]-5-(1H-indazol-5-yl)isoxazole-3-carboxamide The title compound was prepared according to the procedure outlined in Example 81B substituting N³,N³-dimethyl-1-phenylpropane-1,3-diamine for piperidine. ¹H NMR (300 MHz, DMSO-d₆) δ ppm 13.4 (br s, 1H), 9.4 (d, 1H), 8.4 (s, 1H), 8.25 (s, 1H), 7.92 (m, 1H), 7.7 (m, 1H), 7.3-7.5 (m, 6H), 5.15 (m, 1H), 3.2 (m, 2H), 7.75 (s, 6H), 2.35 (m, 1H), 2.15 (m, 1H). MS (ESI+) m/z 390 (M+H)⁺.

Example 360

N-(2,3-dihydro-1,4-benzodioxin-5-ylmethyl)-5-(1H-indazol-5-yl)isoxazole-3-carboxamide The title compound was prepared according to the procedure outlined in Example 81B substituting 1-(2,3-dihydro-1,4-benzodioxin-5-yl)methanamine for piperidine. ¹H NMR (300 MHz, DMSO-d₆) δ ppm 13.4 (br s, 1H), 9.24 (t, 1H), 8.4

(s, 1H), 8.25 (s, 1H), 7.92 (d, 1H), 7.7 (d, 1H), 7.24 (s, 1H), 6.9 (m, 3H), 4.4 (d, 2H), 4.3 (d, 2H), 4.25 (d, 2H). MS (ESI+) m/z 377 (M+H)+.

Example 361

N-(3,4-dihydro-2H-1,5-benzodioxepin-6-ylmethyl)-5-(1H-indazol-5-yl)isoxazole-3-carboxamide The title compound was prepared according to the procedure outlined in Example 81B substituting 1-(3,4-dihydro-2H-1,5-benzodioxepin-6-yl)methanamine for piperidine. $^1$H NMR (300 MHz, DMSO-$d_6$) δ ppm 13.4 (br s, 1H), 9.2 (t, 1H), 8.4 (s, 1H), 8.25 (s, 1H), 7.92 (d, 1H), 7.7 (d, 1H), 7.24 (s, 1H), 6.9 (m, 3H), 4.42 (d, 2H), 4.15 (m, 4H), 2.2 (m, 2H). MS (ESI+) m/z 391 (M+H)+.

Example 362

5-(1H-indazol-5-yl)-N-[(1-methyl-1H-indol-4-yl)methyl]isoxazole-3-carboxamide

The title compound was prepared according to the procedure outlined in Example 81B substituting (1-methyl-1H-indol-4-yl)methylamine for piperidine. $^1$H NMR (300 MHz, DMSO-$d_6$) δ ppm 13.4 (br s, 1H), 9.24 (t, 1H), 8.4 (s, 1H), 8.25 (s, 1H), 7.92 (d, 1H), 7.7 (d, 1H), 7.38 (m, 3H), 7.18 (m, 1H), 7.0 (d, 1H), 6.6 (s, 1H), 4.7 (d, 2H), 3.8 (s, 3H). MS (ESI+) m/z 372 (M+H)+.

Example 363

5-{3-[(3-phenylpyrrolidin-1-yl)carbonyl]isoxazol-5-yl}-1H-indazole

The title compound was prepared according to the procedure outlined in Example 81B substituting 3-phenylpyrrolidine for piperidine. $^1$H NMR (300 MHz, DMSO-$d_6$) δ ppm 13.4 (br s, 1H), 8.4 (m, 1H), 8.25 (s, 1H), 7.92 (d, 1H), 7.8 (d, 1H), 7.24 (m, 6H), 4.4 (m, 1H), 3.4 (m, 2H), 2.4 (m, 2H), 2.0 (m, 2H). MS (ESI+) m/z 359 (M+H)+.

Example 364

5-{3-[(2-phenylpyrrolidin-1-yl)carbonyl]isoxazol-5-yl}-1H-indazole

The title compound was prepared according to the procedure outlined in Example 81B substituting 2-phenylpyrrolidine for piperidine. $^1$H NMR (300 MHz, DMSO-$d_6$) δ ppm 13.4 (br s, 1H), 8.4 (m, 1H), 8.25 (s, 1H), 7.92 (d, 1H), 7.8 (d, 1H), 7.24 (m, 6H), 5.6 (m, 0.3H), 5.2 (m, 0.7H), 4.0 (m, 2H), 1.8-2.0 (m, 4H). MS (ESI+) m/z 390 (M+H)+.

Example 365

5-{3-[(2-phenylpiperidin-1-yl)carbonyl]isoxazol-5-yl}-1H-indazole

The title compound was prepared according to the procedure outlined in Example 81B substituting 2-phenylpiperidine for piperidine. $^1$H NMR (300 MHz, DMSO-$d_6$) δ ppm 13.4 (br s, 1H), 8.4 (m, 1H), 8.25 (s, 1H), 7.92 (d, 1H), 7.8 (d, 1H), 7.24 (m, 6H), 5.6 (m, 0.3H), 5.2 (m, 0.7H), 4.0 (m, 2H), 1.8-2.0 (m, 6H). MS (ESI+) m/z 373 (M+H)+.

Example 366

5-(1H-indazol-5-yl)-N-[(1S)-1-phenylethyl]isoxazole-3-carboxamide 5-(1H-Indazol-5-yl)isoxazole-3-carboxylic acid (36 mg, 0.16 mmol, Example 71A), was dissolved in N,N-dimethylformamide (1.0 mL) followed by the addition of HATU (60 mg, 0.16 mmol) dissolved in N,N-dimethylformamide (0.5 mL). Then a solution of (S)-1-phenylethanamine (22 mg, 0.18 mmol), dissolved in N,N-dimethylformamide (0.6 mL) was added, followed by diisopropylethylamine (56 μL, 0.32 mmol) dissolved in N,N-dimethylformamide (0.2 mL). The resulting mixture was shaken for 3 hours at 40° C. The reaction was filtered, checked by LC/MS and concentrated to dryness. The residues were dissolved in 1:1 dimethyl sulfoxide/methanol and purified by reverse phase HPLC (Phenomenex® Luna® C8(2) 5 μm 100 Å AXIA™ column (30 mm×75 mm), 50 mL/min, 10-100% acetonitrile/0.1% trifluoroacetic acid in water) to provide the title product. $^1$H NMR (500 MHz, DMSO-$d_6$/D$_2$O) δ ppm 1.50 (d, 3H), 5.06-5.22 (m, 1H), 7.23-7.29 (m, 2H), 7.34-7.38 (m, 2H), 7.40-7.45 (m, 2H), 7.70-7.75 (m, 1H), 7.87-7.92 (m, 1H), 8.25-8.27 (m, 1H), 8.39-8.41 (m, 1H), 9.28 (d, 1H). MS (ESI+) m/z 333 (M+H)+; (ESI−) m/z 331 (M−H)−.

Example 367

5-(1H-indazol-5-yl)-N-[(1R)-1-(4-methylphenyl)ethyl]isoxazole-3-carboxamide

The title compound was prepared using the procedure described in Example 366 except (1R)-1-(4-methylphenyl)ethanamine was substituted for (S)-1-phenylethanamine. $^1$H NMR (500 MHz, DMSO-$d_6$/D2O) δ ppm 1.49 (d, 3H), 2.25-2.31 (m, 3H), 5.09-5.18 (m, 1H), 7.14-7.18 (m, 2H), 7.23-7.24 (m, 1H), 7.28-7.32 (m, 2H), 7.70-7.75 (m, 1H), 7.86-7.92 (m, 1H), 8.22-8.29 (m, 1H), 8.37-8.42 (m, 1H), 9.19 (d, 1H). MS (ESI+) m/z 347 (M+H)+; (ESI−) 345 (M−H)−.

Example 368

5-(1H-indazol-5-yl)-N-[(1S)-1-(4-methylphenyl)ethyl]isoxazole-3-carboxamide

The title compound was prepared using the procedure described in Example 366 except (1S)-1-(4-methylphenyl)ethanamine was substituted for (S)-1-phenylethanamine. $^1$H NMR (500 MHz, DMSO-$d_6$/D2O) δ ppm 1.48 (d, 3H), 2.26-2.30 (m, 3H), 5.05-5.23 (m, 1H), 7.15-7.17 (m, 2H), 7.22-7.25 (m, 1H), 7.28-7.32 (m, 2H), 7.67-7.79 (m, 1H), 7.86-7.93 (m, 1H), 8.22-8.30 (m, 1H), 8.38-8.41 (m, 1H), 9.21 (d, 1H). MS (ESI−) m/z 345 (M−H)−.

Example 369

N-[(1R,2S)-2-hydroxy-2,3-dihydro-1H-inden-1-yl]-5-(1H-indazol-5-yl)isoxazole-3-carboxamide The title compound was prepared using the procedure described in Example 366 except (1R,2S)-1-aminoindan-2-ol was substituted for (S)-1-phenylethanamine. $^1$H NMR (500 MHz, DMSO-$d_6$/D2O) δ ppm 2.89-2.96 (m, 1H), 3.13-3.21 (m, 1H), 4.55-4.61 (m, 1H), 5.40-5.47 (m, 1H), 7.21-7.34 (m, 4H), 7.39-7.42 (m, 1H), 7.72-7.77 (m, 1H), 7.91-7.95 (m, 1H), 8.25-8.29 (m, 1H), 8.42-8.45 (m, 1H). MS (ESI−) m/z 359 (M−H)−.

Example 370

N-[(1R,2R)-2-hydroxy-2,3-dihydro-1H-inden-1-yl]-5-(1H-indazol-5-yl)isoxazole-3-carboxamide The title compound was prepared using the procedure described in Example 366 except (1R,2R)-1-aminoindan-2-ol was substituted for (S)-1-phenylethanamine. $^1$H NMR (500 MHz, DMSO-d$_6$/D2O) δ ppm 2.72-2.83 (m, 1H), 3.13-3.30 (m, 1H), 4.44-4.53 (m, 1H), 5.24-5.32 (m, 1H), 7.10-7.18 (m, 1H), 7.20-7.27 (m, 3H), 7.30-7.33 (m, 1H), 7.72-7.78 (m, 1H), 7.91-7.93 (m, 1H), 8.24-8.29 (m, 1H), 8.41-8.45 (m, 1H), 9.17 (d, 1H). MS (ESI–) m/z 359 (M–H)$^-$.

Example 371

N-[(1R)-1-(4-bromophenyl)ethyl]-5-(1H-indazol-5-yl)isoxazole-3-carboxamide

The title compound was prepared using the procedure described in Example 366 except (1R)-1-(4-bromophenyl)ethanamine was substituted for (S)-1-phenylethanamine. $^1$H NMR (500 MHz, DMSO-d$_6$/D2O) δ ppm 1.50 (d, 3H), 5.08-5.18 (m, 1H), 7.21-7.27 (m, 1H), 7.36-7.41 (m, 2H), 7.50-7.59 (m, 2H), 7.70-7.76 (m, 1H), 7.86-7.93 (m, 1H), 8.23-8.29 (m, 1H), 8.38-8.41 (m, 1H), 9.32 (d, 1H). MS (ESI+) m/z 411 (M+H)$^+$.

Example 372

N-[(1S)-1-(4-bromophenyl)ethyl]-5-(1H-indazol-5-yl)isoxazole-3-carboxamide

The title compound was prepared using the procedure described in Example 366 except (1S)-1-(4-bromophenyl)ethanamine was substituted for (S)-1-phenylethanamine. $^1$H NMR (500 MHz, DMSO-d$_6$/D2O) δ ppm 1.49 (d, 3H), 5.09-5.19 (m, 1H), 7.23-7.25 (m, 1H), 7.37-7.40 (m, 2H), 7.53-7.57 (m, 2H), 7.71-7.75 (m, 1H), 7.87-7.92 (m, 1H), 8.25-8.27 (m, 1H), 8.38-8.41 (m, 1H), 9.32 (d, 1H). MS (ESI) negative ion 409 (M–H)$^-$.

Example 373

N-[(1R)-1-(4-chlorophenyl)ethyl]-5-(1H-indazol-5-yl)isoxazole-3-carboxamide

The title compound was prepared using the procedure described in Example 366 except (1R)-1-(4-chlorophenyl)ethanamine was substituted for (S)-1-phenylethanamine. $^1$H NMR (500 MHz, DMSO-d$_6$/D2O) δ ppm 1.50 (d, 3H), 5.10-5.21 (m, 1H), 7.22-7.26 (m, 1H), 7.38-7.47 (m, 4H), 7.70-7.75 (m, 1H), 7.87-7.92 (m, 1H), 8.20-8.28 (m, 1H), 8.38-8.41 (m, 1H), 9.33 (d, 1H). MS (ESI–) m/z 365 (M–H)$^-$.

Example 374

N-[(1S)-1-(4-chlorophenyl)ethyl]-5-(1H-indazol-5-yl)isoxazole-3-carboxamide

The title compound was prepared using the procedure described in Example 366 except (1S)-1-(4-chlorophenyl)ethanamine was substituted for (S)-1-phenylethanamine. $^1$H NMR (500 MHz, DMSO-d$_6$/D2O) δ ppm 1.49 (d, 3H), 5.12-5.19 (m, 1H), 7.23-7.25 (m, 1H), 7.39-7.47 (m, 4H), 7.71-7.74 (m, 1H), 7.87-7.91 (m, 1H), 8.25-8.27 (m, 1H), 8.37-8.43 (m, 1H), 9.32 (d, 1H). MS (ESI–) m/z 365 (M–H)$^-$.

Example 375

5-(1H-indazol-5-yl)-N-[(1S)-1-(2-naphthyl)ethyl]isoxazole-3-carboxamide

The title compound was prepared using the procedure described in Example 366 except (1S)-1-(2-naphthyl)ethanamine was substituted for (S)-1-phenylethanamine. $^1$H NMR (500 MHz, DMSO-d$_6$/D2O) δ ppm 1.61 (d, 3H), 5.30-5.38 (m, 1H), 7.25-7.26 (m, 1H), 7.48-7.55 (m, 2H), 7.60-7.63 (m, 1H), 7.72-7.75 (m, 1H), 7.88-7.95 (m, 5H), 8.25-8.28 (m, 1H), 8.39-8.43 (m, 1H), 9.39 (d, 1H). MS (ESI–) m/z 381 (M–H)$^-$.

Example 376

N-[1-(4-ethoxyphenyl)-2-hydroxyethyl]-5-(1H-indazol-5-yl)isoxazole-3-carboxamide The title compound was prepared using the procedure described in Example 366 except 2-amino-2-(4-ethoxyphenyl)ethanol was substituted for (S)-1-phenylethanamine. $^1$H NMR (500 MHz, DMSO-d$_6$/D2O) δ ppm 1.32 (t, 3H), 3.62-3.67 (m, 1H), 3.70-3.73 (m, 1H), 3.96-4.06 (m, 2H), 4.98-5.06 (m, 1H), 6.87-6.91 (m, 2H), 7.23-7.36 (m, 3H), 7.70-7.75 (m, 1H), 7.88-7.91 (m, 1H), 8.25-8.27 (m, 1H), 8.39-8.42 (m, 1H). MS (ESI–) m/z 391 (M–H)$^-$.

Example 377

N-[2-hydroxy-1-(4-isopropylphenyl)ethyl]-5-(1H-indazol-5-yl)isoxazole-3-carboxamide The title compound was prepared using the procedure described in Example 366 except 2-amino-2-(4-isopropylphenyl)ethanol was substituted for (S)-1-phenylethanamine. $^1$H NMR (500 MHz, DMSO-d$_6$/D2O) δ ppm 1.18 (d, 6H), 2.81-2.91 (m, 1H), 3.65-3.70 (m, 1H), 3.72-3.74 (m, 1H), 5.01-5.09 (m, 1H), 7.20-7.28 (m, 3H), 7.29-7.35 (m, 2H), 7.72-7.80 (m, 1H), 7.87-7.95 (m, 1H), 8.24-8.29 (m, 1H), 8.38-8.44 (m, 1H). MS (ESI–) m/z 389 (M–H)$^-$.

Example 378

N-[1-(3,4-dimethylphenyl)-2-hydroxyethyl]-5-(1H-indazol-5-yl)isoxazole-3-carboxamide The title compound was prepared using the procedure described in Example 366 except 2-amino-2-(3,4-dimethylphenyl)ethanol was substituted for (S)-1-phenylethanamine. $^1$H NMR (500 MHz, DMSO-d$_6$/D2O) δ ppm 2.30 (d, 6H), 3.56-3.63 (m, 1H), 3.65-3.73 (m, 1H), 5.32-5.42 (m, 1H), 7.06-7.08 (m, 2H), 7.23-7.28 (m, 2H), 7.69-7.76 (m, 1H), 7.87-7.95 (m, 1H), 8.25-8.28 (m, 1H), 8.39-8.43 (m, 1H). MS (ESI–) m/z 375 (M–H)$^-$.

Example 379

N-[2-hydroxy-1-(2-methoxyphenyl)ethyl]-5-(1H-indazol-5-yl)isoxazole-3-carboxamide The title compound was prepared using the procedure described in Example 366 except 2-amino-2-(2-methoxyphenyl)ethanol was substituted for (S)-1-phenylethanamine. $^1$H NMR (500 MHz, DMSO-d$_6$/D2O) δ ppm 3.60-3.66 (m, 2H), 3.84-3.88 (m, 3H), 5.37-5.48 (m, 1H), 6.95 (t, 1H), 7.00-7.06 (m, 1H), 7.24-7.31 (m, 2H), 7.32-7.36 (m, 1H), 7.71-7.77 (m, 1H), 7.85-7.97 (m, 1H), 8.24-8.28 (m, 1H), 8.40-8.45 (m, 1H). MS (ESI+) m/z 379 (M+H)$^+$; negative ion 377 (M−H)$^-$.

Example 380

N-[2-hydroxy-1-(4-methylphenyl)ethyl]-5-(1H-indazol-5-yl)isoxazole-3-carboxamide The title compound was prepared using the procedure described in Example 366 except 2-amino-2-(4-methylphenyl)ethanol was substituted for (S)-1-phenylethanamine. $^1$H NMR (500 MHz, DMSO-d$_6$/D2O) δ ppm 2.26-2.32 (m, 3H), 3.65-3.70 (m, 1H), 3.72-3.75 (m, 1H), 5.01-5.08 (m, 1H), 7.10-7.21 (m, 2H), 7.25-7.35 (m, 3H), 7.70-7.77 (m, 1H), 7.86-7.95 (m, 1H), 8.26-8.28 (m, 1H), 8.39-8.46 (m, 1H). MS (ESI+) m/z 363 (M+H)$^+$; (ESI−) m/z 361 (M−H)$^-$.

Example 381

5-(1H-indazol-5-yl)-N-[(1R)-1-(2-methoxyphenyl)ethyl]isoxazole-3-carboxamide

The title compound was prepared using the procedure described in Example 366 except (1R)-1-(2-methoxyphenyl)ethanamine was substituted for (S)-1-phenylethanamine. $^1$H NMR (500 MHz, DMSO-d$_6$/D2O) δ ppm 1.43 (d, 3H), 3.82-3.86 (m, 3H), 5.41-5.50 (m, 1H), 6.95 (t, 1H), 7.00-7.05 (m, 1H), 7.23-7.29 (m, 2H), 7.35-7.39 (m, 1H), 7.71-7.76 (m, 1H), 7.88-7.92 (m, 1H), 8.25-8.27 (m, 1H), 8.37-8.43 (m, 1H). MS (ESI+) m/z 363 (M+H)$^+$; (ESI−) m/z 361 (M−H)$^-$.

Example 382

N-[(1S)-1-(3,4-difluorophenyl)ethyl]-5-(1H-indazol-5-yl)isoxazole-3-carboxamide

The title compound was prepared using the procedure described in Example 366 except (1S)-1-(3,4-difluorophenyl)ethanamine was substituted for (S)-1-phenylethanamine. $^1$H NMR (500 MHz, DMSO-d$_6$/D2O) δ ppm 1.50 (d, 3H), 5.09-5.24 (m, 1H), 7.21-7.30 (m, 2H), 7.35-7.44 (m, 1H), 7.44-7.53 (m, 1H), 7.68-7.82 (m, 1H), 7.86-7.94 (m, 1H), 8.26-8.27 (m, 1H), 8.39-8.42 (m, 1H). MS (ESI−) m/z 367 (M−H)$^-$.

Example 383

5-(1H-indazol-5-yl)-N-[(1R)-1-(3-methoxyphenyl)ethyl]isoxazole-3-carboxamide

The title compound was prepared using the procedure described in Example 366 except (1R)-1-(3-methoxyphenyl)ethanamine was substituted for (S)-1-phenylethanamine. $^1$H NMR (500 MHz, DMSO-d$_6$/D2O) δ ppm 1.50 (d, 3H), 3.75-3.77 (m, 3H), 5.01-5.19 (m, 1H), 6.80-6.87 (m, 1H), 6.97-7.02 (m, 2H), 7.21-7.32 (m, 2H), 7.70-7.75 (m, 1H), 7.87-7.95 (m, 1H), 8.22-8.31 (m, 1H), 8.37-8.43 (m, 1H). MS (ESI−) m/z 361 (M−H)$^-$.

Example 384

5-(1H-indazol-5-yl)-N-{(1R)-1-[3-(trifluoromethyl)phenyl]ethyl} isoxazole-3-carboxamide The title compound was prepared using the procedure described in Example 366 except (1R)-1-[3-(trifluoromethyl)phenyl]ethanamine was substituted for (S)-1-phenylethanamine. $^1$H NMR (500 MHz, DMSO-d$_6$/D2O) δ ppm 1.54 (d, 3H), 5.22-5.29 (m, 1H), 7.23-7.27 (m, 1H), 7.58-7.69 (m, 2H), 7.71-7.75 (m, 2H), 7.77-7.83 (m, 1H), 7.87-7.92 (m, 1H), 8.24-8.29 (m, 1H), 8.38-8.42 (m, 1H). MS (ESI−) m/z 399 (M−H)$^-$.

Example 385

N-[1-(2,3-dihydro-1,4-benzodioxin-6-yl)ethyl]-5-(1H-indazol-5-yl)isoxazole-3-carboxamide The title compound was prepared using the procedure described in Example 366 except 1-(2,3-dihydro-1,4-benzodioxin-6-yl)ethanamine was substituted for (S)-1-phenylethanamine. $^1$H NMR (500 MHz, DMSO-d$_6$/D2O) δ ppm 1.46 (d, 3H), 4.18-4.25 (m, 4H), 5.01-5.10 (m, 1H), 6.80-6.95 (m, 3H), 7.22-7.24 (m, 1H), 7.70-7.74 (m, 1H), 7.87-7.91 (m, 1H), 8.26-8.27 (m, 1H), 8.39-8.41 (m, 1H). MS (ESI−) m/z 389 (M−H)$^-$.

Example 386

N-[1-(3,5-dichlorophenyl)-2-hydroxyethyl]-5-(1H-indazol-5-yl)isoxazole-3-carboxamide The title compound was prepared using the procedure described in Example 366 except 2-amino-2-(3,5-dichlorophenyl)ethanol was substituted for (S)-1-phenylethanamine. $^1$H NMR (500 MHz, DMSO-d$_6$/D2O) δ ppm 3.68-3.72 (m, 1H), 3.76-3.78 (m, 1H), 5.02-5.10 (m, 1H), 7.26-7.29 (m, 1H), 7.47-7.52 (m, 3H), 7.72-7.75 (m, 1H), 7.89-7.93 (m, 1H), 8.25-8.28 (m, 1H), 8.39-8.44 (m, 1H). MS (ESI−) m/z 415 (M−H)$^-$.

Example 387 tert-butyl 5-(1-benzyl-1H-1,2,3-triazol-4-yl)-3-[({[6-(trifluoromethyl)pyridin-2-yl]amino}carbonyl)amino]-1H-indazole-1-carboxylate A solution of triphosgene (0.384 mmol, 114 mg, 98%) in dichloromethane (2 mL) was cooled to 0° C. under nitrogen. Then a mixture of triethylamine (0.426 mL, 3.07 mmol) and Example 64A (150 mg, 0.384 mmol) in dichloromethane (2 mL) was slowly added dropwise. The resultant mixture was stirred at room temperature for 1 hour. Then 6-(trifluoromethyl)pyridin-2-amine (62.3 mg, 0.384 mmol) was added followed by stirring overnight at room temperature. The precipitate was filtered off and washed with dichloromethane and water. The product was dried under vacuum to provide the title compound. MS m/z 579.3 (M+H)$^+$.

Example 388

5-(1-benzyl-1H-1,2,3-triazol-4-yl)-1-[(1-methylpiperidin-2-yl)carbonyl]-1H-indazol-3-amine 1-Methylpiperidine-3-carboxylic acid hydrochloride (495 mg, 2.756 mmol) was combined with a mixture of dimethylformamide (3 mL) and pyridine (3 mL) under nitrogen and stirred for 15 minutes. Then carbonyldiimidazole (446 mg) was added portionwise. The resultant solution was stirred at room temperature for 1 hour. Then Example 62 (200 mg, 0.689 mmol) was added followed by stirring at 60° C. for 2 hours and then at room temperature overnight. The reaction mixture was poured into ice water and brine was added. The cold solution was decanted, and the residue was taken into dichloromethane and washed with water (2×). The organic layer was dried with magnesium sulfate, and the volatiles were removed under reduced pressure. The decanted solution was extracted with ethyl acetate (3×). The combined organic layers were washed with brine (2×), dried with magnesium sulfate, and concentrated. The residue was taken into a small amount of acetone and then dropped into distilled water. A precipitate was collected by filtration, washed with water, and dried to provide the title compound. MS m/z 579.3 (M+H)$^+$.

Example 389

5-(1-benzyl-1H-1,2,3-triazol-4-yl)-1-[(dimethylamino)acetyl]-1H-indazol-3-amine 2-(Dimethylamino)acetic acid (710 mg, 6.889 mmol) was dissolved in dimethylformamide (6 mL) and pyridine (6 mL) under nitrogen at room temperature over 15 minutes. Carbonyldiimidazole (1.11 g) was added portionwise. The resultant mixture was stirred at room temperature for 1 hour. Then Example 62 (500 mg, 1.72 mmol) was added, and the mixture was stirred overnight at room temperature. The volatile material was removed under reduced pressure, and the remainder was added to ice water. Sodium chloride was added and thick oil came out of the cool solution. The solution was decanted. The residue was washed with water (3×) and then dried. From the decanted solution, a precipitate came out overnight of the water/dimethylformamide mixture. This proved to be starting material which was filtered off and discarded. The product residue was crystallized in dichloromethane, collected by filtration, rinsed with a small quantity of dichloromethane and ether. The product was dried to provide the title compound. MS m/z 376.3 (M+H)$^+$.

Example 390 tert-butyl 3-amino-5-(1-benzyl-1H-1,2,3-triazol-4-yl)-1H-indazole-1-carboxylate

Example 62 (6.0 g, 20.66 mmol) was suspended in dichloromethane (340 mL) along with a catalytic amount of dimethylaminopyridine. A solution of di-tert-butyl dicarbonate (4.74 g, 21.7 mmol) in dichloromethane (160 mL) was added over 1 hour. The reaction mixture was stirred for approximately 40 hours. Silica gel was added, and the mixture was concentrated. This silica mixture was added to a silica gel column and the material was eluted first with dichloromethane and then with 1% methanol/dichloromethane and lastly with 2% methanol/dichloromethane. The fractions containing the desired product were combined and concentrated to provide the title compound. MS m/z 391.3 (M+H)$^+$.

Example 391

N-[5-(1-benzyl-1H-1,2,3-triazol-4-yl)-1H-indazol-3-yl]-2-piperidin-1-ylacetamide 2-(Piperidin-1-yl)acetic acid (293 mg, 2.05 mmol) was combined with dimethylformamide (3 mL) and pyridine (3 mL). The mixture was stirred for 15 minutes at room temperature, and then carbonyldiimidazole (332 mg) was added portionwise. Stirring was continued at room temperature for 1 hour, and then Example 64A (200 mg, 0.512 mmol) was added followed by continued stirring for 24 hours. The reaction mixture was warmed to 60° C. for 14 hours. A small amount of the title compound was obtained. MS m/z 416.3 (M+H)$^+$.

Example 392

N-[5-(1-benzyl-1H-1,2,3-triazol-4-yl)-1H-indazol-3-yl]-2-morpholin-4-ylacetamide 2-Morpholinoacetic acid (297 mg, 2.05 mmol) was combined with dimethylformamide (3 mL) and pyridine (3 mL). The mixture was stirred for 15 minutes at room temperature, and then carbonyldiimidazole (332 mg) was added portionwise. Stirring was continued at room temperature for 1 hour, and then Example 64A (200 mg, 0.512 mmol) was added followed by continued stirring for 28 hours. The reaction mixture was warmed to 60° C. for 4 hours and then stirring was continued overnight at room temperature. The reaction mixture was warmed again to 60° C. for 7 hours. A small amount of the title compound was obtained. MS m/z 418.3 (M+H)$^+$.

Example 393

N-[5-(1-benzyl-1H-1,2,3-triazol-4-yl)-1H-indazol-3-yl]-1-methylpiperidine-2-carboxamide 1-Methylpiperidine-3-carboxylic acid hydrochloride (375 mg, 2.05 mmol) was combined with dimethylformamide (3 mL) and pyridine (3 mL). The mixture was stirred for 15 minutes at room temperature, and then carbonyldiimidazole (332 mg) was added portionwise. Stirring was continued at room temperature for 1 hour, and then Example 64A (200 mg, 0.512 mmol) was added followed by continued stirring for 28 hours. The reaction mixture was warmed to 60° C. for 4.25 hours and then stirring was continued overnight at room temperature. The reaction mixture was warmed again to 60° C. for 7 hours. A small amount of the title compound was obtained. MS m/z 416.3 (M+H)$^+$.

Example 394

2-(1H-indazol-5-yl)-N-[(1R)-1-(3-methoxyphenyl)ethyl]-1,3-thiazole-5-carboxamide Example 394A (R)-2-bromo-N-(1-(3-methoxyphenyl)ethyl)thiazole-5-carboxamide To a stirring solution of 2-bromothiazole-5-carboxylic acid (0.3 g, 1.442 mmol), diisopropyl ethylamine (0.205 g, 1.586 mmol) and HATU (0.603 g, 1.586 mmol) in dimethylformamide (7.21 mL, 1.442 mmol) was added (R)-1-(3-methoxyphenyl)ethanamine (0.218 g, 1.442 mmol) dropwise. After stirring for 12 hours at 50° C., the reaction was poured into water (50 mL). The precipitated solid was then collected by filtration washing successively with water (2×50 mL) and hexanes (2×50 mL). The recovered product was used without further purification in the next step.

Example 394B (R)-2-(1H-indazol-5-yl)-N-(1-(3-methoxyphenyl)ethyl)thiazole-5-carboxamide A solution of aqueous cesium carbonate (0.391 g, 1.202 mmol) was added to a reaction flask containing (R)-2-bromo- N-(1-(3-methoxyphenyl)ethyl)thiazole-5-carboxamide (0.41 g, 1.202 mmol), tert-butyl 5-(4,4,5,5-tetramethyl-1,3,2-dioxaborolan-2-yl)-1H-indazole-1-carboxylate (0.496 g, 1.442 mmol) and Pd(dppf)$_2$ (1 g, 0.122 mmol) in 1,4-dioxane (6.01 mL, 1.202 mmol). The reaction was heated to 95° C. for 8 hours under a steady stream of nitrogen.

The reaction was then cooled and filtered directly through a 3 cm pad of diatomaceous earth and concentrated. The residue was dissolved in dichloromethane (3 mL) and treated with trifluoroacetic acid (0.093 mL, 1.202 mmol). After 1 hour, the trifluoroacetic acid was removed in vacuo and the residue was purified using HPLC (Phenomenex® Luna® C8(2) 5 μm 100 Å AXIA™ column (30 mm×75 mm), 70 mL/min, 10-95% acetonitrile/0.1% trifluoroacetic acid in water) to supply the title compound. $^1$H NMR (300 MHz, methanol-d$_4$) δ ppm 1.57 (d, 3H) 3.79 (s, 3H) 5.12-5.27 (m, 1H) 6.78-6.86 (m, 1H) 6.93-7.02 (m, 2H) 7.26 (t, J=7.80 Hz, 1H) 7.65 (d, J=8.81 Hz, 1H) 8.03 (dd, J=8.82, 1.70 Hz, 1H) 8.18 (s, 1H) 8.40 (s, 1H) 8.46 (s, 1H) 8.94 (d, J=7.80 Hz, 1H).

Example 395

N-[5-(1-benzyl-1H-1,2,3-triazol-4-yl)-1H-indazol-3-yl]-3-fluorobenzamide

The title compound was prepared according to the procedure outlined in Example 64B substituting 3-fluorobenzoyl chloride for methoxy acetyl chloride. The title compound was eluted from an ion exchange column (SCX, Varian, 10 g) eluting with 2 M ammonia in methanol. $^1$H NMR (400 MHz, DMSO-d$_6$) δ ppm 12.89 (s, 1H), 10.89 (s, 1H), 8.60 (s, 1H), 8.16 (s, 1H), 7.93 (br d, 1H), 7.86 (m, 2H), 7.54 (m, 3H), 7.35 (m, 5H), 5.62 (s, 2H). MS (ESI+) m/z 413.0 (M+H)$^+$.

Example 396

5-(1-benzyl-1H-1,2,3-triazol-4-yl)-N,N-dimethyl-1H-indazole-3-carboxamide

Example 396A 1-benzyl-4-(tributylstannyl)-1H-1,2,3-triazole

Ethynyltributylstannane (1 mL, 3.4 mmol) and benzyl azide (0.65 mL, 5.2 mmol) were heated to 130° C. for 24 hours. The mixture was adsorbed onto silica gel, and purified by silica gel chromatography eluting with 1:4 ethyl acetate:hexanes to afford the title compound.

Example 396B

N,N-dimethyl-1H-indazole-3-carboxamide

1H-Indazole-3-carboxylic acid (5.0 g, 30.8 mmol) and carbonyl diimidazole (5.0 g, 33.9 mmol) were dissolved in N,N-dimethylformamide (150 mL) and heated to 60° C. After 2 hours, dimethylamine hydrochloride (4.0 g, 33.9) was added, and the reaction was stirred for an additional hour at 60° C. The reaction was poured into water, and the aqueous phase was extracted with ethyl acetate (3×150 mL). The combined organic phases were washed sequentially with aqueous sodium bicarbonate, 10% hydrochloric acid, water and brine. After drying over magnesium sulfate, filtering and concentrating in vacuo, the title compound was obtained.

Example 396C 5-iodo-N,N-dimethyl-1H-indazole-3-carboxamide

Example 396B (0.8 g, 4.23 mmol), bis(trifluoroacetoxy)iodobenzene (2.0 g, 4.65 mmol), and iodine (0.64 g, 2.53 mmol) were stirred in 30 mL 2:1 dichloromethane:tetrahydrofuran for 24 hours. The reaction was quenched with sodium bisulfite. The resultant precipitate was collected and washed with water and hexanes to give the title compound.

Example 396D 5-(1-benzyl-1H-1,2,3-triazol-4-yl)-N,N-dimethyl-1H-indazole-3-carboxamide Example 396A (166 mg, 0.37 mmol), Example 396C (116 mg, 0.37 mmol), tri(o-tolyl)phosphine (22 mg, 0.074 mmol), tris(dibenzylideneacetone)dipalladium(0) (40 mg, 0.044 mmol), and triethylamine (0.06 mL, 0.43 mmol) were combined in dimethylformamide (2 mL) in a sealed vial under an inert atmosphere. The vial was sealed and heated to 110° C. for 24 hours. The mixture was adsorbed onto silica gel and purified by silica gel chromatography eluting with 5/95 2 M ammonia in methanol/dichloromethane. $^1$H NMR (400 MHz, DMSO-d$_6$) δ ppm 13.50 (br s, 1H), 8.68 (s, 1H), 8.44 (s, 1H), 7.92 (d, 1H), 7.65 (d, 1H), 7.39 (m, 5H), 5.64 (s, 2H), 3.36 (br s, 3H), 3.09 (br s, 3H). MS (ESI+) m/z 347.0 (M+H)$^+$.

Example 397

Methyl 5-(1-benzyl-1H-1,2,3-triazol-4-yl)-1H-indazole-3-carboxylate

The title compound was prepared according to the procedure outlined in Example 396D substituting methyl 5-bromo-1H-indazole-3-carboxylate for Example 396C. $^1$H NMR (400 MHz, DMSO-d$_6$) δ ppm 13.97 (br s, 1H), 8.73 (s, 1H), 8.54 (s, 1H), 7.95 (d, 1H), 7.72 (d, 1H), 7.39 (m, 5H), 5.66 (s, 2H), 3.95 (s, 3H).

Example 398

5-(1-benzyl-1H-1,2,3-triazol-4-yl)-3-(1-methyl-1H-imidazol-2-yl)-1H-indazole

The title compound was prepared according to the procedure outlined in Example 396D substituting 5-bromo-3-(1-methyl-1H-imidazole-2-yl)-1H-indazole (Woods, K., et al. Bioorg. Med. Chem. 2006, 14, 6832-6846) for Example 396C. $^1$H NMR (400 MHz, DMSO-d$_6$) δ ppm 13.20 (br s, 1H), 8.86 (s, 1H), 8.66 (s, 1H), 7.90 (d, 1H), 7.64 (d, 1H), 7.39 (m, 5H), 7.31 (s, 1H), 7.13 (s, 1H), 5.65 (s, 2H), 4.06 (s, 3H). MS (ESI+) m/z 356.0 (M+H)$^+$.

Example 399

5-(1-benzyl-1H-1,2,3-triazol-4-yl)-3-morpholin-4-yl-1H-indazole

The title compound was prepared according to the procedure outlined in Example 396D substituting 4-(5-bromo-1H-indazole-3-yl)morpholine (Wrzeciono, U., et al. Pharmazie 1986, 41, 472-474) for Example 396C. $^1$H NMR (400 MHz, DMSO-d$_6$) δ ppm 12.10 (s, 1H), 8.61 (s, 1H), 8.17 (s, 1H), 7.83 (d, 1H), 7.36 (m, 6H), 5.64 (s, 2H), 3.81 (m, 4H), 3.32 (m, 4H). MS (ESI+) m/z 361.0 (M+H)$^+$.

Example 400

5-(1-benzyl-1H-1,2,3-triazol-4-yl)-3-(4-methylpiperazin-1-yl)-1H-indazole

The title compound was prepared according to the procedure outlined in Example 396D substituting 5-bromo-3-(4-methylpiperazine-1-yl)-1H-indazole (Wrzeciono, U., et al. *Pharmazie* 1986, 41, 472-474) for Example 396C. $^1$NMR (400 MHz, DMSO-d$_6$) δ ppm 12.08 (s, 1H), 8.62 (s, 1H), 8.16 (s, 1H), 7.82 (d, 1H), 7.36 (m, 6H), 5.64 (s, 2H), 3.39 (m, 2H), 3.31 (m, 2H), 2.67 (m, 4H), 2.35 (s, 3H). MS (ESI+) m/z 374.1 (M+H)$^+$.

Example 401

5-(1-benzyl-1H-1,2,3-triazol-4-yl)-3-thien-2-yl-1H-indazole

The title compound was prepared according to the procedure outlined in Example 396D substituting 5-bromo-3-(thiophen-2-yl)-1H-indazole (Woods, K., et al. *Bioorg. Med. Chem.* 2006, 14, 6832-6846) for Example 396C. $^1$H NMR (400 MHz, DMSO-d$_6$) δ ppm 13.25 (br s, 1H), 8.75 (s, 1H), 8.47 (s, 1H), 7.95 (d, 1H), 7.80 (d, 1H), 7.63 (d, 1H), 7.57 (d, 1H), 7.38 (m, 5H), 7.22 (m, 1H), 5.66 (s, 2H). MS (ESI+) m/z 357.9 (M+H)$^+$.

Example 402

5-(1-benzyl-5-cyclohexyl-1H-1,2,3-triazol-4-yl)-1H-indazol-3-amine

Example 402A 1-benzyl-5-cyclohexyl-4-(tributylstannyl)-1H-1,2,3-triazole

The title compound was prepared according to the procedure outlined in Example 151A substituting cyclohexaneacetylene for 4-fluorophenyl acetylene. MS (ESI+) m/z 531.1 (M+H)$^+$.

Example 402B 5-(1-benzyl-5-cyclohexyl-1H-1,2,3-triazol-4-yl)-2-fluorobenzonitrile The title compound was prepared according to the procedure outlined in Example 151B substituting Example 402A for Example 151A.

Example 402C 5-(1-benzyl-5-cyclohexyl-1H-1,2,3-triazol-4-yl)-1H-indazol-3-amine The title compound was prepared according to the procedure outlined in Example 151C substituting Example 402B for Example 151B. $^1$H NMR (500 MHz, DMSO-d$_6$) δ ppm 11.47 (s, 1H), 7.77 (s, 1H), 7.33 (m, 7H), 5.69 (s, 2H), 5.42 (s, 2H), 2.87 (m, 1H), 1.55 (m, 3H), 1.39 (m, 3H), 1.16 (m, 3H), 1.00 (m, 1H). MS (ESI+) m/z 373.1 (M+H)$^+$.

Example 403

5-[1-benzyl-5-(cyclohexylmethyl)-1H-1,2,3-triazol-4-yl]-1H-indazol-3-amine

Example 403A 1-benzyl-5-(cyclohexylmethyl)-4-(tributylstannyl)-1H-1,2,3-triazole The title compound was prepared according to the procedure outlined in Example 151A substituting 3-cyclohexyl-1-propyne for 4-fluorophenyl acetylene. MS (ESI+) m/z 546.3 (M+H)$^+$.

Example 403B 5-(1-benzyl-5-(cyclohexylmethyl)-1H-1,2,3-triazol-4-yl)-2-fluorobenzonitrile The title compound was prepared according to the procedure outlined in Example 151B substituting Example 403A for Example 151A.

Example 403C

5-[1-benzyl-5-(cyclohexylmethyl)-1H-1,2,3-triazol-4-yl]-1H-indazol-3-amine

The title compound was prepared according to the procedure outlined in Example 151C substituting Example 403B for Example 151B. $^1$H NMR (500 MHz, DMSO-d$_6$) δ ppm 11.43 (s, 1H), 7.99 (s, 1H), 7.54 (d, 1H), 7.33 (m, 6H), 5.64 (s, 2H), 5.43 (br s, 2H), 2.80 (d, 2H), 1.40 (m, 5H), 1.18 (m, 1H), 0.83 (m, 5H). MS (ESI+) m/z 387.1 (M+H)$^+$.

Example 404

5-(1-benzyl-1H-1,2,3-triazol-4-yl)-3-(1,3-thiazol-2-yl)-1H-indazole

The title compound was prepared according to the procedure outlined in Example 396D substituting 2-(5-bromo-1H-indazole-3-yl)thiazole (Woods, K., et al. *Bioorg. Med. Chem.* 2006, 14, 6832-6846) for Example 396C. $^1$H NMR (500 MHz, DMSO-d$_6$) δ ppm 13.62 (s, 1H), 8.85 (s, 1H), 8.74 (s, 1H), 8.05 (d, 1H), 7.95 (d, 1H), 7.78 (d, 1H), 7.70 (d, 1H), 7.36 (m, 5H), 5.67 (s, 2H). MS (ESI+) m/z 359.0 (M+H)$^+$.

Example 405

5-(1,5-dibenzyl-1H-1,2,3-triazol-4-yl)-1H-indazol-3-amine

Example 405A 1,5-dibenzyl-4-(tributylstannyl)-1H-1,2,3-triazole

The title compound was prepared according to the procedure outlined in Example 151A substituting 3-phenyl-1-propyne for 4-fluorophenyl acetylene.

Example 405B 5-(1,5-dibenzyl-1H-1,2,3-triazol-4-yl)-2-fluorobenzonitrile

The title compound was prepared according to the procedure outlined in Example 151B substituting Example 405A for Example 151A.

Example 405C 5-(1,5-dibenzyl-1H-1,2,3-triazol-4-yl)-1H-indazol-3-amine

The title compound was prepared according to the procedure outlined in Example 151C substituting Example 405B for Example 151B. $^1$H NMR (500 MHz, DMSO-d$_6$) δ ppm 11.44 (s, 1H), 8.07 (s, 1H), 7.53 (d, 1H), 7.19 (m, 9H), 6.95 (d, 2H), 5.62 (s, 2H), 5.39 (s, 2H), 4.34 (s, 2H). MS (ESI+) m/z 381.1 (M+H)$^+$.

Example 406

5-(1-benzyl-5-thien-2-yl-1H-1,2,3-triazol-4-yl)-1H-indazol-3-amine

Example 406A 1-benzyl-5-(thiophen-2-yl)-4-(tributylstannyl)-1H-1,2,3-triazole The title compound was prepared according to the procedure outlined in Example 151A substituting 2-ethynylthiophene for 4-fluorophenyl acetylene. MS (ESI+) m/z 532.1 (M+H)$^+$.

Example 406B 5-(1-benzyl-5-(thiophen-2-yl)-1H-1,2,3-triazol-4-yl)-2-fluorobenzonitrile The title compound was prepared according to the procedure outlined in Example 151B substituting Example 406A for Example 151A. MS (ESI+) m/z 361.0. (M+H)$^+$.

Example 406C 5-(1-benzyl-5-thien-2-yl-1H-1,2,3-triazol-4-yl)-1H-indazol-3-amine The title compound was prepared according to the procedure outlined in Example 151C substituting Example 406B for Example 151B. $^1$H NMR (500 MHz, DMSO-d$_6$) δ ppm 11.45 (s, 1H), 8.08 (s, 1H), 7.80 (d, 1H), 7.25 (m, 7H), 7.04 (d, 2H), 5.57 (s, 2H), 5.38 (s, 2H). MS (ESI+) m/z 373.0 (M+H)$^+$.

Example 407

5-(1-benzyl-1H-1,2,3-triazol-4-yl)-N-(2-morpholin-4-ylethyl)-1H-indazol-3-amine

The title compound was prepared according to the procedure outlined in Example 396D substituting 5-bromo-N-(2-morpholinoethyl)-1H-indazol-3-amine (Wrzeciono, U., et al. *Pharmazie* 1986, 41, 472-474) for Example 396C. $^1$H NMR (500 MHz, DMSO-d$_6$) δ ppm 11.64 (br s, 1H), 8.46 (s, 1H), 8.25 (s, 1H), 7.70 (d, 1H), 7.36 (m, 7H), 5.64 (s, 2H), 3.73 (m, 2H), 3.56 (m, 2H), 3.34 (m, 8H). MS (ESI+) m/z 404.1 (M+H)$^+$.

Example 408

5-[1-benzyl-5-(4-fluorophenyl)-1H-1,2,3-triazol-4-yl]-3-methyl-1H-indazole

The title compound was prepared according to the procedure outlined in Example 396D substituting Example 151A for Example 396A and 5-bromo-3-methyl-1H-indazole (Woods, K., et al. *Bioorg. Med. Chem.* 2006, 14, 6832-6846) for Example 396C. $^1$H NMR (500 MHz, DMSO-d$_6$) δ ppm 12.68 (br s, 1H), 7.77 (s, 1H), 7.31 (m, 9H), 6.99 (d, 2H), 5.51 (s, 2H), 3.38 (s, 3H). MS (ESI+) m/z 384.1 (M+H)$^+$.

Example 409

5-[1-benzyl-5-(cyclopentylmethyl)-1H-1,2,3-triazol-4-yl]-1H-indazol-3-amine

Example 409A 1-benzyl-5-(cyclopentylmethyl)-4-(tributylstannyl)-1H-1,2,3-triazole The title compound was prepared according to the procedure outlined in Example 151A substituting 3-cyclopentyl-1-propyne for 4-fluorophenyl acetylene.

Example 409B 5-(1-benzyl-5-(cyclopentylmethyl)-1H-1,2,3-triazol-4-yl)-2-fluorobenzonitrile The title compound was prepared according to the procedure outlined in Example 151B substituting Example 409A for Example 151A.

Example 409C

5-[1-benzyl-5-(cyclopentylmethyl)-1H-1,2,3-triazol-4-yl]-1H-indazol-3-amine

The title compound was prepared according to the procedure outlined in Example 151C substituting Example 409B for Example 151B. $^1$H NMR (500 MHz, DMSO-d$_6$) δ ppm 11.44 (s, 1H), 8.00 (s, 1H), 7.54 (d, 1H), 7.32 (m, 6H), 5.65 (s, 2H), 5.42 (s, 2H), 2.91 (d, 2H), 1.82 (m, 1H), 1.38 (m, 4H), 1.23 (m, 2H), 0.91 (m, 2H). MS (ESI+) m/z 373.1 (M+H)$^+$.

Example 410

5-(1-benzyl-1H-1,2,3-triazol-4-yl)-N-butyl-1H-indazol-3-amine

Example 62D (80 mg, 0.27 mmol) and butyraldehyde (29 mg, 0.40 mmol) were dissolved in N,N-dimethylformamide (3 mL). Glacial acetic acid was added until pH=6 then the mixture was stirred at room temperature for 3 hours. Sodium triacetoxyborohydride (229 mg, 1.1 mmol) was added and the mixture was stirred overnight. The solvent was removed under reduced pressure and the residue was purified by preparative HPLC on a C18 column using a gradient of 35% to 95% acetonitrile/water containing 0.1% trifluoroacetic acid to afford the title compound. $^1$H NMR (300 MHz, DMSO-d$_6$)

δ ppm 11.41 (s, 1H) 8.41 (s, 1H) 8.25 (s, 1H) 7.68 (d, J=8.73, 1H) 7.37-7.43 (m, 5H) 7.26 (d, J=8.73, 1H) 5.97 (t, J=5.55, 1H) 5.64 (s, 2H) 3.21-3.30 (m, 2H) 1.57-1.64 (m, 2H) 1.37-1.43 (m, 2H) 0.92 (t, J=7.34, 3H).

Example 411

N-benzyl-5-(1-benzyl-1H-1,2,3-triazol-4-yl)-1H-indazol-3-amine

The title compound was prepared according to the procedure outlined in Example 410 substituting benzaldehyde for butyraldehyde. $^1$H NMR (300 MHz, DMSO-d$_6$) δ ppm 11.50 (s, 1H) 8.41 (s, 1H) 8.31 (s, 1H) 7.69 (dd, J=8.73, 1.59, 1H) 7.22-7.43 (m, 12H) 5.64 (s, 2H) 4.47 (s, 2H).

Example 412

5-(1-benzyl-1H-1,2,3-triazol-4-yl)-N-(4-chlorobenzyl)-1H-indazol-3-amine

The title compound was prepared according to the procedure outlined in Example 410 substituting 4-chlorobenzaldehyde for butyraldehyde. $^1$H NMR (300 MHz, DMSO-d$_6$) δ ppm 11.48 (s, 1H) 8.42 (s, 1H) 8.29 (s, 1H) 7.69 (d, J=8.72, 1H) 7.34-7.44 (m, 9H) 7.28 (d, J=8.72, 1H) 6.71 (t, J=6.15, 1H) 5.63 (s, 2H) 4.45 (d, J=5.95, 2H).

Example 413

5-(1-benzyl-1H-1,2,3-triazol-4-yl)-N-(4-methoxybenzyl)-1H-indazol-3-amine

The title compound was prepared according to the procedure outlined in Example 410 substituting 4-methoxybenzaldehyde for butyraldehyde. $^1$H NMR (300 MHz, DMSO-d$_6$) δ ppm 11.46 (s, 1H) 8.40 (s, 1H) 8.29 (s, 1H) 7.68 (d, J=8.73, 1H) 7.36-7.40 (m, 5H) 7.34 (d, J=8.73, 2H) 7.27 (d, J=8.73, 1H) 6.87 (d, J=8.73, 2H) 6.50-6.54 (m, 1H) 5.64 (s, 2H) 4.39 (d, J=4.36, 2H) 3.72 (s, 3H).

Example 414

5-(1-benzyl-1H-1,2,3-triazol-4-yl)-N-(3-fluorobenzyl)-1H-indazol-3-amine

The title compound was prepared according to the procedure outlined in Example 410 substituting 3-fluorobenzaldehyde for butyraldehyde. $^1$H NMR (300 MHz, DMSO-d$_6$) δ ppm 11.51 (s, 1H) 8.43 (s, 1H) 8.30 (s, 1H) 7.70 (d, J=9.12, 1H) 7.19-7.41 (m, 9H) 7.03 (t, J=9.12, 1H) 6.72-6.76 (br s, 1H) 5.64 (s, 2H) 4.49 (s, 2H).

Example 415

4-({[5-(1-benzyl-1H-1,2,3-triazol-4-yl)-1H-indazol-3-yl]amino}methyl)benzonitrile The title compound was prepared according to the procedure outlined in Example 410 substituting 4-cyanobenzaldehyde for butyraldehyde. $^1$H NMR (300 MHz, DMSO-d$_6$) δ ppm 11.52 (s, 1H) 8.44 (s, 1H) 8.30 (s, 1H) 7.77 (d, J=8.33, 2H) 7.69 (d, J=8.73, 1H) 7.58 (d, J=8.33, 2H) 7.37-7.41 (m, 5H) 7.28 (d, J=8.73, 1H) 6.83-6.87 (br s, 1H) 5.64 (s, 2H) 4.56 (s, 2H).

Example 416

5-(1-benzyl-1H-1,2,3-triazol-4-yl)-N-(2,4-difluorobenzyl)-1H-indazol-3-amine

The title compound was prepared according to the procedure outlined in Example 410 substituting 2,4-difluorobenzaldehyde for butyraldehyde. $^1$H NMR (300 MHz, DMSO-d$_6$) δ ppm 11.54 (s, 1H) 8.44 (s, 1H) 8.30 (s, 1H) 7.69 (d, J=8.65, 1H) 7.24-7.53 (m, 8H) 7.20 (d, J=8.47, 1H) 6.71 (d, J=6.10, 1H) 5.64 (s, 2H) 4.47 (d, J=5.76, 2H).

Example 417

5-(1-benzyl-1H-1,2,3-triazol-4-yl)-N-(cyclohexylmethyl)-1H-indazol-3-amine

The title compound was prepared according to the procedure outlined in Example 410 substituting cyclohexanecarboxaldehyde for butyraldehyde. $^1$H NMR (300 MHz, DMSO-d$_6$) δ ppm 11.40 (s, 1H) 8.42 (s, 1H) 8.29 (s, 1H) 7.67 (d, J=8.65, 1H) 7.37-7.40 (m, 5H) 7.26 (d, J=9.49, 1H) 6.05 (t, J=5.76, 1H) 5.64 (s, 2H) 3.09 (t, J=6.10, 2H) 1.78-1.85 (m, 2H) 1.64-1.73 (m, 4H), 1.15-1.24 (m, 3H) 0.92-1.01 (m, 2H).

Example 418

5-(1-phenyl-1H-1,2,3-triazol-4-yl)-1H-indazole

To a solution of Example 1C (30 mg, 0.21 mmol) in dimethyl sulfoxide (0.25 mL) was added iodobenzene (0.024 mL, 0.21 mmol), a solution of L-proline (5 mg, 0.042 mmol) and sodium carbonate (5 mg, 0.04 mmol) in water (0.1 mL), sodium azide (16 mg, 0.25 mmol), a solution of sodium ascorbate (8 mg, 0.04 mmol) in water (0.05 mL) and a solution of copper (II) sulfate pentahydrate (6 mg, 0.02 mmol) in water (0.05 mL) and the mixture was heated at 65° C. overnight. The mixture was centrifuged, and the crude solids were washed with methanol. The methanol wash was removed with a pipette. It was then dissolved in dimethyl sulfoxide and passed through a silica gel plug eluting with ethyl acetate. The product containing fractions were combined, concentrated in vacuo, and then treated with water. The mixture was centrifuged, and the solid was washed with water and methanol. The washes were removed with a pipette affording the title compound. $^1$H NMR (400 MHz,) δ ppm 13.17 (s, 1H), 9.28 (s, 1H), 8.34 (s, 1H), 8.17 (s, 1H), 7.96 (m, 3H), 7.65 (m, 3H), 7.52 (m, 1H). MS (ESI) m/z 262 (M+H).

Biological Data

ROCK-2 Inhibitory Assay

The compounds of formula (I) were tested for their ability to inhibit N-terminal His6-tagged (SEQ ID NO: 6) recombinant human ROCK-2 residues 11-552 expressed by baculovirus in Sf21 cells (Upstate). In 384-well v-bottom polypropylene plates (Axygen), 1 nM (final concentration) in 10 μL recombinant N-terminal His6-tagged (SEQ ID NO: 6) recombinant human ROCK-2 residues 11-552 expressed by baculovirus in Sf21 cells (Upstate) was mixed with 2 μM (final concentration) in 10 μL biotinylated peptide substrate (biotin-Aha-KEAKEKRQEQIAKRRRLSSLRASTSKSGGSQK (SEQ ID NO: 1)) (Genemed), and various concentration of inhibitor (2% DMSO final) in reaction buffer (25 mM HEPES, pH 7.5, 0.5 mM DTT, 10 mM MgCl$_2$, 100 μM Na$_3$VO$_4$, 0.075 mg/mL Triton X-100), and the reaction was initiated by addition of 5 μM unlabelled ATP containing 0.01 uCi [$^{33}$P]-ATP (Perkin Elmer). The reaction was quenched after 1 hour by the addition of 50 μL stop buffer (50 mM EDTA, 2M NaCl final concentration). 80 μL of the stopped reactions were transferred to 384-well streptavidin-coated FlashPlates (Perkin Elmer), incubated 10 minutes at room temperature, washed 3 times with 0.05% Tween-20/PBS using an ELX-405 automated plate washer (BioTek), and counted on a TopCount Scintillation Plate Reader (Packard).

ROCK-1 Inhibitory Assay

The compounds of formula (I) were tested for their ability to inhibit N-terminal His6-tagged (SEQ ID NO: 6), recombinant, human ROCK-1 amino acids 17-535 expressed by baculovirus in Sf21 cells (Upstate). In 384-well v-bottom polypropylene plates (Axygen), 2 nM (final concentration) in 10 μL recombinant N-terminal His6-tagged (SEQ ID NO: 6), recombinant, human ROCK-1 amino acids 17-535 expressed by baculovirus in Sf21 cells (Upstate) in reaction buffer was mixed with 2 μM (final concentration) biotinylated peptide substrate (biotin-Aha-VRRLRRLTAREAA (SEQ ID NO: 2)) (Genemed), and various concentration of inhibitor (2% DMSO final) in 10 μL reaction buffer (25 mM HEPES, pH 7.5, 0.5 mM DTT, 10 mM MgCl$_2$, 100 μM Na$_3$VO$_4$, 0.075 mg/mL Triton X-100), and the reaction was initiated by addition of 5 μM unlabelled ATP containing 0.01 uCi [$^{33}$P]-ATP (Perkin Elmer). The reaction was quenched after 1 hour by the addition of 50 μL stop buffer (50 mM EDTA, 2M NaCl final concentration). 80 μL of the stopped reactions were transferred to 384-well streptavidin-coated FlashPlates (Perkin Elmer), incubated 10 minutes at room temperature, washed 3 times with 0.05% Tween-20/PBS using an ELX-405 automated plate washer (BioTek), and counted on a TopCount Scintillation Plate Reader (Packard).

GSK Inhibitory Assay

The compounds of formula (I) were tested for their ability to inhibit N-terminal His6-tagged (SEQ ID NO: 6) GSK-3 expressed by baculovirus in Sf21 cells (Upstate). In 384-well v-bottom polypropylene plates (Axygen), 10 μL recombinant N-terminal His-tagged GSK3 expressed by baculovirus in Sf21 cells (Upstate) was mixed with 10 μl biotinylated peptide substrate (biotin-ahx-YRRAAVPPSPSLSRHSSPHQS (p)EDEEE (SEQ ID NO: 3)), 2 μM final concentration (Genemed), and various concentration of inhibitor (2% DMSO final) in reaction buffer (20 mM HEPES, pH 7.5, 1 mM DTT, 10 mM MgCl$_2$ 100 μM Na$_3$VO$_4$, 0.075 mg/mL Triton X-100), and the reaction was initiated by addition of 20 μl [$^{33}$P]-ATP, 5 μM final concentration, 2 mCi/umol (Perkin Elmer). The reaction was quenched after 1 hour by the addition of 50 μL stop buffer (50 mM EDTA, 2M NaCl final concentration). 80 μL of the stopped reactions were transferred to 384-well streptavidin-coated FlashPlates (Perkin Elmer), incubated 10 minutes at room temperature, washed 3 times with 0.05°/0 Tween-20/PBS using an ELX-405 automated plate washer (BioTek), and counted on a TopCount Scintillation Plate Reader (Packard).

Human GSK-3β Inhibitory Assay

Compounds were tested for their ability to inhibit human Glycogen Synthase kinase-3 beta (hGSK-3β) to phosphorylate biotin-YRRAAVPPSPSLSRHSSPHQ(pS)EDEEE (SEQ ID NO: 3). Compounds were incubated with 0.5 μCi $^{33}$P-ATP, 10 μM ATP, 0.0125U hGSK-3β (Upstate cell signaling solutions) and 1 μM substrate (biotin-YRRAAVPPSPSLSRHSSPHQ(pS)EDEEE (SEQ ID NO: 3)) in 50 mM HEPES, 10 mM MgCl$_2$, 100 μM Na$_3$VO$_4$, 1 mM DTT, 0.0075% Triton, 2% DMSO (total volume 50 μL) for 30 minutes at room temperature. The incubation was stopped by addition of an equal volume of 100 mM EDTA, 4 M NaCl$_2$. 80 μL of this mixture was added to streptavidin-coated Flashplates (PerkinElmer). Following a wash step, $^{33}$P incorporation was quantified on a MicroBeta microplate liquid scintillation counter (PerkinElmer). IC50s were determined by fitting a sigmoidal dose-response curve to the counts obtained at the different concentrations in GraphPad Prism.

Human GSK-3α Inhibitory Assay

Compounds were tested for their ability to inhibit human Glycogen Synthase kinase-3 alpha (hGSK-3α) 0.5 nM final concentration of to phosphorylate biotin-YR-RAAVPPSPSLSRHSSPHQ(pS)EDEEE (SEQ ID NO: 3). Compounds were incubated with 0.5 Ci $^{33}$P-ATP, 10 M ATP, 0.0125 U hGSK-3 (Upstate cell signaling solutions) and 2 μM substrate (biotin-YRRAAVPPSPSLSRHSSPHQ(pS)EDEEE) (SEQ ID NO:3) in 50 mM HEPES, 10 mM MgCl$_2$, 100 μM Na$_3$VO$_4$, 1 mM DTT, 0.0075% Triton, 2% DMSO (total volume 50 μL) for 30 minutes at room temperature. The incubation was stopped by addition of an equal volume of 100 mM EDTA, 4M NaCl$_2$. 80 μL of this mixture was added to streptavidin-coated Flashplates (PerkinElmer). Following a wash step, $^{33}$P incorporation was quantified on a MicroBeta microplate liquid scintillation counter (PerkinElmer). IC50s were determined by fitting a sigmoidal dose-response curve to the counts obtained at the different concentrations in GraphPad Prism.

JAK2 Inhibition Assay

Jak2 kinase activity was assayed by a homogenous time-resolved fluorescence (HTRF) in vitro kinase assay (Mathis, G., HTRF(R) Technology. J Biomol Screen, 1999. 4(6): p. 309-314). Specifically, 10 μL C-terminal His6-tagged (SEQ ID NO: 6), recombinant, human JAK2, amino acids 808-end, expressed by baculovirus in Sf21 cells (Upstate) was mixed with 10 μL inhibitor (various concentrations, 2% final DMSO) and 10 μL of ATP (5 μM final concentration) in reaction buffer (50 mM HEPES, pH 7.5, 10 mM MgCl$_2$, 2 mM MnCl$_2$, 0.1% BSA and 1 mM DTT, 40 μL final volume). The reaction was initiated by addition of 10 μL of Bio-PDK peptide (Biotin-Ahx-KTFCGTPEYLAPEVRREPRILSEE-EQEMFRDFDYIADWC (SEQ ID NO: 4), 0.5 μM final concentration) in a black 384-well plate (Packard). After 60 minutes incubation at room temperature, the reaction was quenched by addition 60 μL stop/revelation buffer to give 30 mM EDTA, 1 μg/mL streptavidin-APC (Prozyme), 50 ng/mL anti-phosphotyrosine mAb PT66-K Europium Cryptate, 30 mM HEPES, pH 7.5, 120 mM KF, 0.005% Tween-20, 0.05% BSA). The quenched reaction was allowed to stand at room temperature for 1 hour and then read in a time-resolved fluorescence detector (Envision, Perkin Elmer) at 615 nm and 665 nm simultaneously. The ratio between the signal of 615 nm and 665 nm was used in the calculation of the IC$_{50}$.

Cdc7 Inhibition Assay

Cdc7 kinase assays were carried out in 25 mM HEPES, pH 7.5, 1 mM DTT, 10 mM MgCl$_2$, 100 μM Na$_3$VO$_4$, and 0.075 mg/ml Triton X-100 using 12 ng baculovirus-expressed Cdc7/Dbf4 and 2 μM Jerini peptide substrate A-A11 (biotin-C$_6$linker-TPSDSLIYDDGLS) (SEQ ID NO:5). Reactions were initiated with λ-[$^{33}$P]-ATP (1 μM, 20 mCi/μmol) and quenched after 1 hour with 5 volumes of stop buffer (50 mM EDTA, 2 M NaCl). The reactions were incubated for 30 minutes on streptavidin-coated plates, washed, and quantified using a TopCount scintillation plate reader (Packard). IC$_{50}$ values are determined via non-linear regression fitting of the data. K$_i$ values are generated assuming ATP-competitive (equilibrium) inhibition and using the experimentally determined apparent ATP K$_m$ of Cdc7 (0.7 μM).

| Example | Ki(μM) 11 data point | Ki(μM) 6 data point |
|---|---|---|
| 1 | 0.0523 | |
| 10 | 0.0563 | |
| 32 | 0.0127 | |
| 35 | | >1.23 |
| 60 | 0.0556 | |
| 61 | 0.0077 | |
| 62 | 0.012 | |
| 63 | | >1.23 |
| 64 | 0.015 | |
| 65 | | 0.242 |
| 66 | | 0.058 |
| 73 | 0.0006 | 0.0004 |
| 80 | | 0.127 |
| 87 | 0.000601 | |
| 89 | 0.035 | |
| 102 | 0.0021 | 0.0012 |
| 123 | 0.023 | 0.017 |
| 125 | | 0.035 |
| 146 | | 0.229 |
| 150 | 0.43 | |
| 151 | 0.0008 | 0.0022 |
| 157 | | 0.64 |
| 162 | 0.00225 | |
| 163 | 0.0034 | |
| 167 | 0.00105 | |
| 169 | | >1.23 |
| 171 | | 0.030 |
| 172 | | >1.23 |
| 185 | 0.0004 | |
| 189 | 0.0019 | |
| 194 | 0.068 | |
| 197 | | 1.23 |
| 198 | 0.0009 | 0.0008 |
| 199 | 0.34 | |
| 200 | 0.013 | |
| 201 | | 0.013 |
| 204 | 0.11 | |
| 205 | 0.0024 | 0.0009 |
| 207 | | 0.046 |
| 216 | 0.12 | |
| 217 | 1.0 | |
| 218 | >1.23 | |
| 220 | 0.98 | |
| 222 | 0.093 | |
| 224 | 0.0063 | |
| 227 | 0.015 | |
| 241 | | 0.473 |
| 242 | | >1.23 |
| 243 | | >1.23 |
| 254 | | >1.23 |
| 255 | | >1.23 |
| 262 | 0.041 | |
| 263 | 0.022 | |
| 311 | >1.23 | |
| 314 | 0.18 | |
| 316 | 0.50 | |
| 318 | >1.23 | |
| 319 | 0.068 | |
| 320 | 0.41 | |
| 321 | 0.57 | |
| 322 | 0.034 | |
| 323 | 0.18 | |
| 324 | >1.23 | |
| 395 | 0.0005 | 0.0010 |
| 396 | 0.681 | |
| 397 | 0.0811 | |
| 398 | 0.489 | |
| 399 | 0.63 | |
| 400 | 0.23 | |
| 401 | 0.00492 | |
| 402 | 0.037 | |
| 403 | 0.0082 | |
| 404 | 0.258 | |
| 405 | 0.0011 | |
| 406 | 0.0005 | |
| 407 | 0.22 | |
| 408 | 0.000428 | |
| 409 | 0.020 | |
| 410 | 0.040 | |
| 411 | 0.12 | |
| 412 | 0.14 | |
| 413 | 0.052 | |
| 414 | 0.038 | |
| 415 | 0.065 | |
| 416 | 0.037 | |
| 417 | 0.35 | |
| 418 | 0.192 | |

Phospho-MCM2 ELISA

HCT-116 cells (20,000/well; 96-well format) were treated for 6 hours with increasing concentrations of compounds (0.01-10 μM in half-log increments). After removing the medium/inhibitor, the cells were frozen for 5 minutes and treated on ice with 20 μL of lysis buffer (Invitrogen #FNN0011) for 30 minutes. 80 μL of cold 2% BSA (in PBS) were then added to each well before transferring 80 μL to MCM2 antibody-coated plates (Bethyl # A300-122A, lot A300-122A-1). The plates were incubated overnight at 4° C., washed, and then incubated with the sandwich antibody (1:100 rabbit anti-human phospho-MCM2 Ser53; Bethyl #A300-756A, lot A300-756A-2) for 2 hours at room temperature. After another series of washes the samples are incubated for 1 hour with detection antibody (XSA-grade goat anti-rabbit-HRP, KPL #074-15-061, lot 50884, diluted to 2 μg/mL in 2% BSA). Plates were washed, developed using luminescence substrate (SuperSignal Pico for ELISA, Pierce #37069, Lot. HB101408), and read on a Molecular Devices M5 luminometer.

| Example | EC50 (μM) |
|---|---|
| 60 | >10 |
| 61 | 8.787 |
| 62 | >10 |
| 64 | >10 |
| 73 | 1.972 |
| 87 | 5.952 |
| 89 | >10 |
| 102 | 3.134 |
| 123 | >10 |
| 151 | 3.757 |
| 162 | 5.744 |
| 163 | 9.432 |
| 167 | 4.307 |
| 185 | 5.473 |
| 189 | 5.324 |
| 194 | >10 |
| 198 | 4.162 |
| 204 | 6.209 |
| 205 | >10 |
| 222 | >10 |
| 224 | >10 |
| 227 | >10 |
| 262 | >10 |
| 263 | >10 |
| 319 | >10 |
| 322 | >10 |
| 395 | 2.989 |
| 401 | >10 |
| 403 | >10 |
| 405 | 3.100 |
| 406 | 0.671 |
| 408 | 1.961 |
| 409 | >10 |

AlamarBlue Cell Viability Assays

HCT-116 cells (3,000/well; 96-well format) were treated for 72 hours with increasing concentrations of compounds (0.01-30 µM in half-log increments). The cells were then incubated in fresh media with 10% AlamarBlue reagent (Invitrogen # DAL1100). AlamarBlue reactions were incubated according to the manufacturer's instructions (approximately 4 hours) and then analyzed using an fmax fluorescence microplate reader (Molecular Devices) using excitation/emission wavelengths of 544/595 nm. Data were analyzed using SOFTmax PRO software provided by the manufacturer.

| Example | EC50 (µM) |
|---------|-----------|
| 1 | >30 |
| 32 | >30 |
| 60 | 0.143 |
| 61 | 3.978 |
| 62 | 4.539 |
| 64 | 0.422 |
| 73 | 0.760 |
| 87 | 10.970 |
| 89 | 5.484 |
| 102 | 3.192 |
| 123 | 3.863 |
| 151 | 8.639 |
| 162 | 1.450 |
| 163 | 0.928 |
| 167 | 18.153 |
| 185 | 22.636 |
| 189 | 19.202 |
| 194 | 4.392 |
| 198 | 2.900 |
| 200 | 13.536 |
| 204 | 0.128 |
| 205 | 0.595 |
| 216 | 19.059 |
| 222 | 2.109 |
| 224 | 2.422 |
| 227 | 1.404 |
| 262 | 3.416 |
| 263 | 1.035 |
| 319 | 1.565 |
| 322 | 1.529 |
| 395 | 0.315 |
| 397 | 24.827 |
| 401 | 6.720 |
| 402 | 0.037 |
| 403 | 0.008 |
| 405 | 6.622 |
| 406 | 1.495 |
| 408 | >30 |
| 409 | 13.533 |

Methods—β-Catenin Reporter-Gene Assay

Compounds were tested for their ability to modulate β-catenin-modulated gene transcription in a LEF/TCF (T-cell factor) reporter gene assay. SY-SY5Y human neuroblastoma cells were transiently transfected with 80 ng/well TOPFLASH plasmid (Upstate cell signaling solutions) containing two sets of three copies of the TCF binding site upstream of the Thymidine kinase minimal promoter and firefly Luciferase open reading frame or with 80 ng/well FOPFLASH plasmid (Upstate cell signaling solutions) containing three copies of a mutated TCF binding site upstream of the Thymidine kinase minimal promoter and firefly Luciferase open reading frame. In addition, all cells were transiently transfected with the 20 ng/well pRL-TK plasmid (Promega) containing the herpes simplex virus thymidine kinase promoter to provide low to moderate levels of Renilla Luciferase expression. Transfection medium was exchanged for serum-free medium containing the test substance and incubated for 24 hours at 37° C. The incubation was stopped and quantified using the Dual Glo Luciferase Assay (Promega) as indicated and quantified on a Pherastar reader (BMG).

Firefly Luciferase activity was normalized for Renilla Luciferase activity per well. Subsequently, the normalised TOPFLASH response was compared to the normalised FOPFLASH response, thus giving the LEF/TCF specific signal. The maximal response is the maximal ratio between the normalised TOPFLASH and FOPFLASH signals. Sigmoidal dose-response curves were fitted using Graphpad Prism.

Murine Asthma Model of Acute Asthma

Female Balb/c mice were purchased from Taconic and housed at Abbott Bioresearch Center. Animals were utilized at 8-12 weeks of age. All protocols were approved by the Institutional Animal Care and Use Committee (IACUC). Dexamethasone (Dex), and ovalbumin (OVA) were purchased from Sigma. Endotoxin was removed from ovalbumin using DetoxiGel (Pierce) according to manufacturer's protocol and the final material contained less than 0.1 EU/mg protein. Alum Imject was purchased from Pierce.

Animals were sensitized to OVA on day 0 and 7 with an i.p. injection of 8 µg OVA in 2 mg alum. On days 14 and 16, animals received intra-nasal challenge of 0.3 µg OVA in 50 µl sterile PBS. Animals were dosed i.p. with a representative compound of formula (I), Example 179, (dissolved with 0.5% HMPC, 0.02% Tween 80 in water) twice per day at doses of 3, 10, and 30 mg/kg/dose beginning the afternoon of day 13. The final dose of compound was administered 30 minutes prior to measurement of airway hyperresponsiveness (AHR). Dexamethasone was administered orally once a day on days 13-17 at a dose of 3 mg/kg. All endpoints were analyzed on day 17, 24 hours after the second OVA challenge. AHR was assessed using unconscious restrained whole body plethysmography. Briefly, a surgical plane of anesthesia was induced with an i.p. injection of ketamine and xylazine. A tracheal canula was surgically inserted between the third and fourth tracheal rings. Spontaneous breathing was prevented by an intravenous (i.v.) jugular vein injection of pancuronium bromide. Animals were placed in a whole body plethysmograph (Buxco) and mechanically ventilated with 0.2 mL room air at 150 breaths per minute with a volume-controlled ventilator (Harvard Apparatus). Pressure in the lung and flow within the plethysmograph were measured using transducers, and lung resistance was calculated as pressure/flow using Biosystem Xa software. Baseline resistance as well as resistance following challenge with methacholine (3, 10 or 30 mg/mL) that was delivered with an inline ultrasonic-nebulizer were measured. Upon completion of pulmonary function testing, the lungs were lavaged 4 times with 0.5 mL sterile PBS. Lavage fluid was analyzed for IL-13, AMCase, Muc5ac and cellular infiltrates. The efficacy of the test compound was tested at doses of 3, 10 and 30 mg/kg b.i.d. (6, 20, 60 mg/kg/day). Challenge with OVA caused an increase in lung resistance to 6.90 cm H$_2$O/mL/sec vs. 4.65 cm H$_2$O/mL/sec in animals challenged with PBS. Treatment of mice with the test compound significantly inhibited (p<0.001) methacholine-induced airways resistance down to 4.55 cm H$_2$O/mL/sec and 4.77 cm H$_2$O/mL/sec at doses ranging between 1 and 100 mg/kg. The preferred compounds require a dose of less than 50 mg/kg to exhibit said response. The most preferred compounds require a dose of less than 30 mg/kg to exhibit said response. This inhibition was equivalent to measurements taken in the PBS challenged group (4.65 cm H$_2$O/mL/sec) and to treatment of 3 mg/kg dexamethasone (4.76 cm H$_2$O/mL/sec).

IL-13 Measurement:

IL-13 concentrations in the bronchioalveolar lavage fluid (BAL) were measured by ELISA (R & D Systems) according to manufacturer's instructions. IL-13 concentrations in the BAL fluid were significantly induced to 102.5 pg/mL in OVA challenged mice as compared to levels below detection in the PBS challenged group. This induction was significantly inhibited (p<0.05) by 60% after administration of a representative compound of formula (I), Example 179, at the 30 mg/kg dose. There was no significant inhibition at the 3 mg/kg or 10 mg/kg dose groups.

AMCase Measurement:

Acidic mammalian chitinase (AMCase) activity was determined in a 1:10 dilution of BAL fluid with 0.01% BSA, 30 mM sodium citrate, 60 mM sodium phosphate, pH 5.2 in the presence of 80 µM 4-methylumbelliferyl β-D-N,N'-diacetyl-chitobioside. Reactions were incubated for 15 minutes at room temperature and quenched by addition of 100 µL of 1 M glycine/NaOH pH 10.6. Product formation was determined by fluorescence emission at 460 nm using excitation at 385 nm on a Fluoroskan Ascent fluorometer. AMCase activity was induced to 28.5 U in OVA challenged animals compared to 2.17 U in the PBS challenged animals. This induction was significantly inhibited (p<0.01) in the 30 mg/kg group by 45% after a representative compound of formula (I), Example 179 was administered.

MUC5AC Measurement:

Concentrations of the mucin gene MUC5AC were quantitated by ELISA format. Briefly, BAL samples are diluted 1:2 in buffer (2% BSA in PBS) and plated onto high protein binding 96-well plates (Costar) and dried. After a series of washes, a 1:100 dilution of biotinylated MUC5AC antibody (Clone 45M, LabVision) was added for 1 hour. Plates are washed and a 1:3000 dilution of streptavidin-HRP (Southern Biotech) was added to the plate for 15 minutes. Plates were then developed using a TMB substrate (Sigma) for 30 minutes. The reaction was stopped using 1M $H_2SO_4$ and then read in a spectrophotometer at OD 450 nm. Levels of MUC5AC were reduced by 35% after administration of a representative compound of formula (I), Example 179 at 35 mg/kg.

Determination of Antinociceptive Effect: Models for Neuropathic Pain

Spinal Nerve (L5/L6) Ligation Model of Neuropathic Pain.

As previously described in detail by Kim and Chung (Kim S. H.; Chung J. M. An experimental model for peripheral neuropathy produced by segmental spinal nerve ligation in the rat. *Pain* 1992, 50, 355-363), a 1.5 cm incision was made dorsal to the lumbosacral plexus. In anesthetized rats, the paraspinal muscles (left side) were separated from the spinous processes, the L5 and L6 spinal nerves isolated, and tightly ligated with 3-0 silk threads. Following hemostasis, the wound was sutured and coated with antibiotic ointment. The rats were allowed to recover and then placed in a cage with soft bedding for 14 days before behavioral testing for mechanical allodynia.

Sciatic Nerve Ligation Model of Neuronathic Pain.

As previously described in detail by Bennett and Xie (Bennett G. J.; Xie Y-K. A peripheral mononeuropathy in rat that produces disorders of pain sensation like those seen in man. *Pain* 1988, 33, 87-107), in anesthetized rats, a 1.5 cm incision was made 0.5 cm below the pelvis and the biceps femoris and the gluteous superficialis (right side) were separated. The sciatic nerve was exposed, isolated, and four loose ligatures (5-0 chromic catgut) with 1 mm spacing were placed around it. The rats were allowed to recover and then placed in a cage with soft bedding for 14 days before behavioral testing for mechanical allodynia as described above. In addition, animals were also tested for cold allodynia by dipping their hind paw in a cold-water bath (4.5° C.) and determining the paw withdrawal latency.

Selected analogs of compounds of formula (I), Examples 160 and 179, dosed either i.p. or p.o. demonstrated greater than 30% inhibition of tactile allodynia in the Chung and Bennett models of neuropathic pain described herein at doses ranging from 1-150 mg/kg.

In summary, a representative compound of formula (I) in a mouse model of acute asthma was effective in inhibiting airway resistance in a dose range between 1 and 100 mg/kg. High dose (30 mg/kg) treatment also inhibited IL-13 induction as well as AMCase activity and MUC5AC levels in the BAL fluid.

Representative compounds of formula (I) in rat models of neuropathic pain were effective as demonstrated by a greater than 30% inhibition of tactile allodynia at doses ranging from 1-150 mg/kg.

The compounds of formula (I) were found to inhibit human ROCK-2, N-terminal His-tagged GSK-3β, human GSK-3β, His6-tagged (SEQ ID NO: 6), recombinant, human JAK2 and Firefly Luciferase exhibiting an $IC_{50}$ of less than 10 nM to about 10 µM, preferably less than 10 nM to about 1.0 µM. More preferably, compounds of formula (I) were found to inhibit human ROCK-2, N-terminal His-tagged GSK-3β, human GSK-3β, His6-tagged (SEQ ID NO: 6), recombinant, human JAK2 and Firefly Luciferase exhibiting an $IC_{50}$ of less than 10 nM to about 100 nM, and most preferably less than 10 nM.

In addition, certain compounds of formula (I) exhibited inhibition of human ROCK-2 with a selectivity of greater than 10 fold against a panel of 50 kinase targets. Certain compounds of formula (I) exhibited inhibition of human GSK-3β with a selectivity of greater than 10 fold against a panel of 50 kinase targets. Certain compounds of formula (I) exhibited inhibition of His6-tagged (SEQ ID NO: 6), recombinant, human JAK2 with a selectivity of greater than 10 fold against a panel of 50 kinase targets.

Certain compounds of formula (I) were also found to inhibit Cdc7 exhibiting a Ki of about 0.1 nM to about 10 µM. More preferably, compounds of formula (I) were found to inhibit Cdc7 exhibiting a Ki of about 0.1 nM to 100 nM, and most preferably less than 10 nM. Compounds found to inhibit Cdc7 preferably have an $EC_{50}$ less than 5 µM in both the AlamarBlue cell viability assay and Phospho-MCM2 ELISA assay and more preferably less than 1 µM.

Methods of Administration

The present invention also provides pharmaceutical compositions that comprise compounds of the present invention. The pharmaceutical compositions comprise compounds of the present invention formulated together with one or more non-toxic pharmaceutically acceptable carriers.

The pharmaceutical compositions of this invention can be administered to humans and other mammals orally, rectally, parenterally, intracisternally, intravaginally, topically (as by powders, ointments or drops), bucally or as an oral or nasal spray. The term "parenterally," as used herein, refers to modes of administration that include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable carrier or excipient, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants, which may be required. Ophthalmic formulations, eye ointments, powders and solutions are also contemplated as being within the scope of this invention.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The term "pharmaceutically acceptable salt," as used herein, means salts derived from inorganic or organic acids. The salts can be prepared in situ during the final isolation and purification of compounds of Formula (I) or separately by reacting the free base of a compound of Formula (I) with an inorganic or organic acid. Representative acid addition salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, fumarate, methanesulfonate, nicotinate, 2-naphthalenesulfonate, oxalate, pamoate, pectinate, persulfate, 3-phenylpropionate, picrate, pivalate, propionate, succinate, sulfate, (L) tartrate, (D) tartrate, (DL) tartrate, thiocyanate, phosphate, glutamate, bicarbonate, p-toluenesulfonate, and undecanoate.

The term "pharmaceutically acceptable prodrug" or "prodrug," as used herein, represents those prodrugs of the compounds of the present invention which are, within the scope of sound medical judgment, suitable for use in contact with the tissues of humans and lower animals without undue toxicity, irritation, allergic response, and the like. Prodrugs of the present invention may be rapidly transformed in vivo to compounds of Formula (I), for example, by hydrolysis in blood.

The present invention contemplates compounds of Formula (I) formed by synthetic means or formed by in vivo biotransformation.

The compounds of the invention can exist in unsolvated as well as solvated forms, including hydrated forms, such as hemi-hydrates. In general, the solvated forms, with pharmaceutically acceptable solvents such as water and ethanol among others, are equivalent to the unsolvated forms for the purposes of the invention.

The total daily dose of the compounds of this invention administered to a human or lower animal may range from about 0.003 to about 30 mg/kg/day. For purposes of oral administration, more preferable doses can be in the range of from about 0.01 to about 10 mg/kg/day. If desired, the effective daily dose can be divided into multiple doses for purposes of administration; consequently, single dose compositions may contain such amounts or submultiples thereof to make up the daily dose.

Methods of Use

Protein kinases can be classified into broad groups based upon the identity of the amino acid(s) that they target (serine/threonine, tyrosine, lysine, and histidine). For example, tyrosine kinases include receptor tyrosine kinases (RTKs), such as growth factors and non-receptor tyrosine kinases, such as the src kinase family. There are also dual-specific protein kinases that target both tyrosine and serine/threonine, such as cyclin dependent kinases (CDKs) and mitogen-activated protein kinases (MAPKs).

The protein tyrosine kinases (PTKs) compose a large family of kinases that regulate cell to cell signals involved in growth, differentiation, adhesion, motility, and death (Pearson, M. et al., In *Protein Tyrosine Kinases*; Fabbro, D., McCormick, F., Eds.; Humana Press Inc., 2006; pp 1-29.). Members of the tyrosine kinase include, but are not limited to, Yes, BMX, Syk, EphA1, FGFR3, RYK, MUSK, JAK1 and EGFR. Tyrosine kinases are distinguished into two classes, i.e., the receptor type and non-receptor type tyrosine kinases. Interestingly, the entire family of tyrosine kinases consists of at least 90 characterized kinases with at least 58 receptor type and at least 32 nonreceptor type kinases comprising at least 30 total subfamilies. Tyrosine kinases have been implicated in a number of diseases in humans, including diabetes and cancer (Pearson, M. et al., In *Protein Tyrosine Kinases*; Fabbro, D., McCormick, F., Eds.; Humana Press Inc., 2006; pp 1-29.). Tyrosine kinases are often involved in most forms of human malignancies and have been linked to a wide variety of congenital syndromes (Robertson et al., *Trends Genet.* 16:265-271, 2000).

The non-receptor tyrosine kinases represent a group of intracellular enzymes that lack extracellular and transmembrane sequences. Currently, over 32 families of non-receptor tyrosine kinases have been identified (Robinson et al., *Oncogene* 19, 5548-5557, 2000). Representative examples include Src, Btk, Csk, ZAP70 and Kak families. In particular, the Src family of non-receptor tyrosine kinase family is the largest, consisting of Src, Yes, Fyn, Lyn, Lck, Blk, Hck, Fgr and Yrk protein tyrosine kinases. The Src family of kinases have been linked to oncogenesis, cell proliferation and tumor progression. Many of the protein tyrosine kinases have been found to be involved in cellular signaling pathways involved in various pathological conditions including but not limited to cancer and hyperproliferative disorders and immune disorders.

The cyclin dependent kinases CDKs represent a group of intracellular enzymes that control progression through the cell cycle and have essential roles in cell proliferation (Cohen, P. *Nature Reviews Drug Discovery* 1, 309-315, 2002). Representative examples of CDKs include, but are not limited to, cyclin dependent kinase 2 (CDK2), cyclin dependent kinase 7 (CDK7), cyclin dependent kinase 6 (CDK6) and cell division control 2 protein (CDC2). CDKs have been implicated in the regulation of transitions between different phases of the cell cycle, such as the progression from a quiescent stage in G1 (the gap between mitosis and the onset of DNA replication for a new round of cell division) to S (the period of active DNA synthesis), or the progression from G2 to M phase, in which active mitosis and cell division occur (Rowell et al. *Critical Reviews in Immunology* 26(3), 189-212, 2006). CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). CDKs display an absolute dependence on the cyclin subunit in order to phosphorylate their target substrates, and different kinase/cyclin pairs function to regulate progression through specific portions of the cell cycle. Furthermore, CDKs have been implicated in various disease states, including but not limited to, those displaying the cancer phenotype, various neoplastic disorders and in neurological disorders (Pallas et al. *Current Medicinal Chemistry: Central Nervous System Agents* 5(2), 101-109, 2005).

The mitogen activated protein (MAP) kinases participate in the transduction of signals to the nucleus of the cell in response to extracellular stimuli. Representative examples of MAP kinases include, but are not limited to, mitogen activated protein kinase 3 (MAPK3), mitogen-activated protein kinase 1 (ERK2), mitogen-activated protein kinase 7 (MAPK7), mitogen-activated protein kinase 8 (JNK1), mitogen-activated protein kinase 14 (p38 alpha), mitogen-activated protein kinase 10 (MAPK 10), JNK3 alpha protein kinase, stress-activated protein kinase JNK2 and mitogen-activated protein kinase 14 (MAPK14). MAP kinases are a family of proline-directed serine/threonine kinases that mediate signal transduction from extracellular receptors or heath shock, or UV radiation (Barr et al., *Trends in Pharmacological Sciences* 27(10), 525-530, 2006). MAP kinases activate through the phosphorylation of threonine and tyrosine by dual-specificity protein kinases, including tyrosine kinases such as growth factors. Cell proliferation and differentiation have been shown to be under the regulatory control of multiple MAP kinase cascades (Sridhar et al., *Pharmaceutical Research*, 17:11 1345-1353, 2000). As such, the MAP kinase pathway plays critical roles in a number of disease states, for example, defects in activities of MAP kinases have been shown to lead to aberrant cell proliferation and carcinogenesis (Qi et al., *Journal of Cell Science* 118(16), 3569-3572, 2005). Moreover, MAP kinase activity has also been implicated in insulin resistance associated with type-2 diabetes (Fujishiro et al. *Recent Research Developments in Physiology* 1(Pt. 2), 801-812, 2003).

The p90 ribosomal S6 kinases (Rsk) are serine/threonine kinases which function in mitogen-activated cell growth and proliferation, differentiation, and cell survival. Examples of members of the Rsk family of kinases include, but are not limited to, ribosomal protein S6 kinase, 90 kDa, polypeptide 2 (Rsk3), ribosomal protein S6 kinase, 90 kDa, polypeptide 6 (Rsk4), ribosomal protein S6 kinase, 90 kDa, polypeptide 3 (Rsk2) and ribosomal protein S6 kinase, 90 kDa, polypeptide 1 (Rsk1/p90Rsk). The Rsk family members are activated by extracellular signal-related kinases and phosphoinositide-dependent protein kinase 1 (Frodin and Gammeltoft, *Mol. Cell. Endocrinol.* 151, 65-77, 1999). Under basal conditions, RSK kinases are localized in the cytoplasm of cells and upon stimulation by mitogens, the activated (phosphorylated by extracellular-related kinase) RSK transiently translocates to the plasma membrane where they become fully activated. The fully activated RSK phosphorylates substrates that are involved in cell growth, proliferation, differentiation, and cell survival (Clark et al. *Cancer Research* 65, 3108-3116, 2005). RSK signaling pathways have also been associated with the modulation of the cell cycle (Gross et al., *J. Biol. Chem.* 276, 46099-46103, 2001). Current data suggests that small molecules that inhibit Rsk may be useful therapeutic agents for the prevention and treatment of cancer and inflammatory diseases.

Members of the checkpoint protein kinase family (CHK) are serine/threonine kinases that play an important role in cell cycle progression. Examples of members of the checkpoint family include, but are not limited to, CHK1 and CHK2. Checkpoints kinases are control systems that coordinate cell cycle progression by influencing the formation, activation and subsequent inactivation of the cyclin-dependent kinases. Checkpoints kinases prevent cell cycle progression at inappropriate times, maintain the metabolic balance of cells while the cell is arrested, and in some instances can induce apoptosis (programmed cell death) when the requirements of the checkpoint have not been met (Nurse, *Cell,* 91, 865-867, 1997; Hartwell et al., *Science,* 266, 1821-1828, 1994). Members of the checkpoint family of kinases have been implicated in cell proliferative disorders, cancer phenotypes and other diseases related to DNA damage and repair (Kumagai and Dunphy *Cell Cycle,* 5, 1265-1268 (2006); Xiao et al., *Molecular Cancer Therapeutics* 5, 1935-1943, 2006).

Aurora kinases are a family of multigene mitotic serine-threonine kinases that functions as a class of novel oncogenes. These kinases comprise aurora-A and aurora-B members. Aurora kinases are hyperactivated and/or overexpressed in several solid tumors including but not limited to, breast, ovary, prostate, pancreas, and colorectal cancers. In particular aurora-A is a centrosome kinase that plays an important role cell cycle progression and cell proliferation. Aurora-A is located in the 20q13 chromosome region that is frequently amplified in several different types of malignant tumors such as colorectal, breast and bladder cancers. There is also a high correlation between aurora-A and high histoprognostic grade aneuploidy, making the kinase a potential prognostic vehicle. Inhibition of aurora kinase activity may reduce cell proliferation, tumor growth and potentially tumorigenesis. A detailed description of aurora kinase function is reviewed in *Journal of Cell Science,* 119, 3664-3675, 2006.

The Rho-associated coiled-coil-containing protein serine/threonine kinases ROCK-1 and ROCK-2 are thought to play a major role in cytoskeletal dynamics by serving as downstream effectors of the Rho/Rac family of cytokine- and growth factor-activated small GTPases. ROCKs phosphorylate various substrates, including, but not limited to, myosin light chain phosphatase, myosin light chain, ezrin-radixin-moesin proteins and LIM (for Linl1, Isl1 and Mec3) kinases. ROCKs also mediate the formation of actin stress fibers and focal adhesions in various cell types. ROCKs have an important role in cell migration by enhancing cell contractility and are required for tail retraction of monocytes and cancer cells. ROCK inhibitors have also been shown to reduce tumor-cell dissemination in vivo. Recent experiments have defined new functions of ROCKs in cells, including centrosome positioning and cell-size regulation, which might contribute to various physiological and pathological states (Mueller et al, *Nature Reviews Drug Discovery* 4, 387-398, 2005). The ROCK family members are attractive intervention targets for a variety of pathologies including cancer and cardiovascular disease. ROCK inhibitors can be useful therapeutic agents for hypertension, angina pectoris, and asthma. Furthermore, Rho is expected to play a role in peripheral circulation disorders, arteriosclerosis, inflammation, and autoimmune disease and as such, is a useful target for therapy (Shimokawa et al, *Arteriosclerosis*, Thrombosis, and Vascular Biology, 25, 1767-1775, 2005).

The limited success of pharmacotherapeutic approaches in spinal-cord injury is based to a large extent on the inability of injured nerve fibers in the white matter of the human spinal cord to regrow and re-establish synaptic contacts with their disconnected partner neurons. A hostile micro-environment, characterized by the presence of a large variety of molecular neurite-growth inhibitors at the lesion site, in the scar tissue and on CNS myelin, accounts for this irreversible arrest of neurite-growth. In tissue culture, these inhibitors of neurite growth often induce very dramatic responses, including the collapse of the formation and withdrawal of the neurite. Scar tissue in the human brain and spinal cord is a strong and persistent barrier for any regenerative neurite growth and ROCK inhibitors might help injured fibers to grow or sprout beyond this regeneration-inhibiting tissue. A variety of evidence indicates that injury to brain and spinal cord results in a strongly activated RhoA-ROCK pathway. Due to the persistent presence of the neurite growth inhibitors at or around the lesion site and in CNS myelin, such activation could potentially persist for a long time, making ROCK inhibition an attractive goal not only for acute and sub-acute treatment, but also for chronic treatment of spinal-cord injury. Inhibition of ROCK by two different small-molecule ROCK inhibitors (Y-27632 and fasudil) stimulated or accelerated functional recovery in different mouse and rat spinal-cord-injury models when given locally or systemically immediately after injury as a single dose or over several weeks (Dergham, P. et al. Rho signaling pathway targeted to promote spinal cord repair. *J. Neurosci.* 22, 6570-6577, 2002; Hara, M. et al. Protein kinase inhibition by fasudil hydrochloride promotes neurological recovery after spinal cord injury in rats. *J. Neurosurg. Spine* 93, 94-101, 2000. Fournier, A. E. et al. ROCK inhibition enhances axonal regeneration in the injured CNS. *J. Neurosci.* 23, 1416-1423, 2003; Sung, J. K. et al. A possible role of RhoA/Rho-kinase in experimental spinal cord injury in rat *Brain Res.* 959, 29-38, 2003; Tanaka, H. et al. Cytoplasmic p21(Cip1/WAF1) enhances axonal regeneration and functional recovery after spinal cord injury in rats. *Neuroscience* 127, 155-164, 2004). In these studies, ROCK inhibition not only enhanced nerve-fiber growth beyond the lesion site, but was also neuroprotective and decreased tissue damage and cavity formation. On the basis of these rodent studies, ROCK inhibitors, which possess neuroprotective and neuroregeneration-stimulating activities, could offer significant benefit for spinally injured patients. In addition, they could normalize spinal blood flow due to their vasodilatory effects, thereby further enhancing tissue preservation.

Pathologically, Alzheimer's disease is characterized at the microscopic level by intracellular neurofibrillary tangles and extracellular amyloid aggregates. Neurofibrillary tangles contain aberrantly phosphorylated tau protein, a microtubule-associated protein and substrate for ROCK, whereas the amyloid aggregates are formed primarily by toxic 42-amino-acid long amyloid-$\beta$(A$\beta$) peptides. It was recently shown (Zhou, Y. et al. Nonsteroidal anti-inflammatory drugs can lower amyloidogenic A$\beta$42 by inhibiting Rho. *Science* 302, 1215-1217, 2003) that in cells secreting A$\beta$42 and in transgenic PDAPP MICE producing large amounts of A$\beta$42, some NSAIDs lowered A$\beta$42 by inhibiting the RhoA-ROCK pathway. The ROCK inhibitor Y-27632 was effective in lowering A$\beta$42 levels both in cell culture and in PDAPP transgenic mice after intra-cerebroventricular injection. Activation of Rho by geranylgeranylpyrophosphate, a lipid required for the membrane attachment of Rho, increased A$\beta$42 levels; this increase was completely prevented by Y-27632. The ROCK inhibitor Y-27632 used in animal Alzheimer's disease models was efficient in lowering the amount of the toxic A$\beta$42 levels, but had no effect on total A$\beta$ levels and this effect of Rho or ROCK inhibitors is at least one mechanism by which NSAIDs reduce A$\beta$42 levels. In addition to many other therapeutic interventions, these inhibitors have the well-documented advantage of stimulating regenerative growth of neuritis and it is therefore possible that the inhibition of this pathway could result in repair of the amyloid-damaged neural circuitry.

Most important in disease pathogenesis is the migration of leukocytes beyond the brain endothelium into the CNS and the inflammatory cascade stimulated by these cells, which finally results in demyelination of CNS fiber tracts and in neurite damage and loss. Leukocytes require active RhoA and ROCK for their journey beyond brain endothelium, because their trans-endothelial migration was prevented by the ROCK inhibitor Y-2763294.

Neuroprotective activities of the ROCK inhibitors fasudil and hydroxy-fasudil are not restricted to spinal-cord injury models, but have also been reported in cerebral multi-infarct models in gerbils and rats (Toshima Y, Satoh S, Ikegaki I, Asano T. A new model of cerebral microthrombosis in rats and the neuroprotective effect of a Rho-kinase inhibitor. *Stroke* 31, 2245-2250, 2000; Satoh, S. et al. Pharmacological profile of hydroxy fasudil as a selective ROCK inhibitor on ischemic brain damage. *Life Sci.* 69, 1441-1453, 2001; Kitaoka, Y. et al. Involvement of RhoA and possible neuroprotective effect of fasudil, a ROCK inhibitor, in NMDA-induced neurotoxicity in the rat retina. *Brain Res.* 1018, 111-118, 2004). In rodent stroke models, several regeneration inhibitors, such as the ROCK-activating NgR1 complex and one of its ligands, NOGO-A, have been neutralized 24 hours or even 1 week after induction of a cerebral stroke and improved functional recovery has been observed (Lee, J. K., Kim, J. E., Sivula, M. & Strittmatter, S. M. Nogo receptor antagonism promotes stroke recovery by enhancing axonal plasticity. *J. Neurosci.* 24, 6209-6217, 2004; Wiessner, C. et al. Anti-Nogo-A antibody infusion 24 hours after experimental stroke improved behavioral outcome and corticospinal plasticity in normotensive and spontaneously hypertensive rats. *J. Cereb. Blood Flow Metab.* 23, 154-165, 2003). Blocking ROCK is therefore a feasible neuroregenerative strategy; furthermore, such a strategy has the advantage that the therapeutic treatment window for the use of these inhibitors might be larger than for thrombolytic or neuroprotective stroke treatment options.

Neuronal injuries in the peripheral nervous system or in the CNS of humans can lead to a chronic pain state known as neuropathic pain. Inflammatory mediators such as lysophosphatidic acid (LPA) which is produced in response to injury has recently been shown to be involved in initiation of neuropathic pain in a mouse model of peripheral nerve injury (Inoue, M. et al. Initiation of neuropathic pain requires lysophosphatidic acid receptor signaling. *Nature Med.* 10, 712-718, 2004). LPA is present at lesion sites in the PNS and CNS, and exerts its function by binding to G-protein-coupled LPA receptors which results in activation of the RhoA-ROCK pathway. The ROCK inhibitor Y-27632 prevented the initiation of neuropathic pain after nerve injury or LPA injection, whereas another ROCK inhibitor, H-1152, relieved neuropathic pain in an L5 spinal-nerve-transection model (Tatsumi, S. et al. Involvement of Rho-kinase in inflammatory and neuropathic pain through phosphorylation of myristoylated alanine-rich C-kinase substrate (MARCKS). Neuroscience 131, 491-498, 2005). The results of these studies indicate that ROCK is a potential drug target responsible for the induction and also maintenance of persistent pain states.

Moreover, Schueller et al. (Abstract 1216, 8th World Congress on Inflammation, Copenhagen, Denmark, Jun. 16-20, 2007) have demonstrated that SLx-2119, an orally bioavailable, potent and highly selective inhibitor of ROCK 2 reduces atherogenesis in the presence of dramatically elevated lipid levels in groups of 8 ApoE knockout mice, indicating that selective inhibition of ROCK 2 has the potential to limit atherosclerosis.

The 70 kDa ribosomal S6 kinase (p70S6K) is activated by numerous mitogens, growth factors and hormones. Activation of p70S6K occurs through phosphorylation at a number of sites and the primary target of the activated kinase is the 40S ribosomal protein S6, a major component of the machinery involved in protein synthesis in mammalian cells. In addition, p70S6K activation has been implicated in cell cycle control, neuronal cell differentiation, regulation of cell motility and a cellular response that is important in tumor metastases, immunity and tissue repair. Modulation of p70S6 kinase activity may also have therapeutic implications in disorders such as cancer, inflammation, and various neuropathies. A detailed discussion of p70S6K kinases can be found in *Prog. Cell Cycle Res.,* 1, 21-32, 1995, and *Immunol Cell Biol.* 78, 447-51, 2000.

Glycogen synthase kinase 3 (GSK-3) is a ubiquitously expressed constitutively active serine/threonine kinase that phosphorylates cellular substrates and thereby regulates a wide variety of cellular functions, including development, metabolism, gene transcription, protein translation, cytoskeletal organization, cell cycle regulation, and apoptosis. GSK-3 was initially described as a key enzyme involved in glycogen metabolism, but is now known to regulate a diverse array of cell functions. Two forms of the enzyme, GSK-3+ƒ and GSK-3+ƒ, have been previously identified. The activity of GSK-3+ƒ is negatively regulated by protein kinase B/Akt and by the Wnt signaling pathway. Small molecules inhibitors of GSK-3 may, therefore, have several therapeutic uses, including the treatment and prevention of neurodegenerative diseases and stimulation of neurogeneration in various neurological disorders (Gartner et al. *J. Cell Science,* 2006, 119, 3927-3934. Zhou et al. Neuron, 2004, 42, 897-912), type II diabetes, bipolar disorders, stroke, cancer, osteoarthritis, osteoporosis, rheumatoid arthritis (Cuzzocrea et al. *Clinical Immunology,* 2006, 120, 57-67) and chronic inflammatory disease. General review: Kockeritz et al., *Current Drug Targets,* 7, 1377-1388, 2006. Review of neurological applications: *Current Drug Targets,* 7(11), 1389-1397 and 1399-1409, 2006.

Protein kinases have become attractive targets for the treatment of cancers (Fabbro et al., *Pharmacology & Therapeutics* 93:79-98, 2002). It has been proposed that the involvement of protein kinases in the development of human malignancies may occur by: (1) genomic rearrangements (e.g., BCR-ABL in chronic myelogenous leukemia), (2) mutations leading to constitutively active kinase activity, such as acute myelogenous leukemia and gastrointestinal tumors, (3) deregulation of kinase activity by activation of oncogenes or loss of tumor suppressor functions, such as in cancers with oncogenic RAS, (4) deregulation of kinase activity by over-expression, as in the case of EGFR and (5) ectopic expression of growth factors that can contribute to the development and maintenance of the neoplastic phenotype (Fabbro et al., *Pharmacology & Therapeutics* 93:79-98, 2002).

Cdc7 is a serine/threonine kinase that functions in the initiation of DNA replication. Cdc7 is found in complexes with either Dbf4 or Drf1, regulatory subunits that are essential for activating the enzyme and targeting it to substrates. Cdc7 phosphorylates multiple subunits of the minichromosome maintenance (MCM) DNA replicative helicase, thereby activating it and triggering the unwinding of DNA double helixes at origins of replication. This activity is essential to the proper initiation of DNA replication, the process by which a cell's DNA is duplicated prior to cell division. Inhibiting regulators of replication initiation, such as Cdc6, Cdc7/Dbf4 or Cdc7/Drf1, has lethal consequences in cancerous cells, whereas normal cells are able to arrest and resume normal divisions once initiation activity is restored (Feng, D., et al. (2003). Inhibiting the expression of DNA replication-initiation proteins induces apoptosis in human cancer cells. *Cancer Res.* 63, 7356-7364; Montagnoli, A., et al. (2004). Cdc7 inhibition reveals a p53-dependent replication checkpoint that is defective in cancer cells. *Cancer Res* 64, 7110-7116; see Lau, E., et al. (2006). Is there a pre-RC checkpoint that cancer cells lack? *Cell Cycle* 5, 1602-1606, for review). Thus, small molecules that inhibit Cdc7 may be useful therapeutic agents for the prevention and/or treatment of cancer, inflammatory diseases, and other cell proliferative disorders.

Certain cancers are associated with angiogenesis. Angiogenesis is the growth of new capillary blood vessels from pre-existing vasculature (Risau, W., Nature 386:671-674, 1997). It has been shown that protein kinases can contribute to the development and maintenance of the neoplastic phenotype (Fabbro et al., *Pharmacology & Therapeutics* 93:79-98, 2002). For example, VEGF A-D and their four receptors have been implicated in phenotypes that involve neovascualrization and enhanced vascular permeability, such as tumor angiogenesis and lymphangiogenesis (Matter, A., *Drug Discov. Today* 6:1005-1023, 2001).

It has been recognized that a single agent approach that specifically targets one kinase or one kinase pathway may be inadequate to treat diseases and disorders, in particular cancer, for several reasons. Models have suggested that 5 to 7 mutations are necessary for the progression of a normal cell to a malignant one. Furthermore, it is widely recognized that cancer is the result of alterations in multiple pathways, in particular protein kinase pathways that are associated with processes such as cell growth, proliferation, apoptosis, motility, or invasion. In a majority of cancers, a common feature is the simultaneous overexpression and/or hyper-activation of a variety of protein kinases, such as receptor and non-receptor kinases, serine/threonine kinases, PI3 kinases and cell cycle associated kinases. In fact, several of these kinases, either alone or in conjunction with other kinases, have been implicated in a number of processes important for cell survival, proliferation, growth and malignant transformation, motility and invasion leading to metastasis and angiogenesis or inflammation, and diseases, disorders, and conditions associated therewith.

Accordingly, blocking one target kinase may not be clinically sufficient because there are multiple target kinases that affect the progression of a condition, disease, or disorder. In addition, blocking one target kinase may not be clinically sufficient because redundant kinase-mediated pathways and alternative oncogenic or inflammatory mechanisms may compensate for the blocked target kinase. Moreover, the use of a single agent can also increase the chances that resistance to that agent will develop.

Cardiovascular disease accounts for nearly one quarter of total annual deaths worldwide. Vascular disorders such as atherosclerosis and restenosis result from dysregulated growth of the vessel walls and the restriction of blood flow to vital organs. Various kinase pathways, e.g. JNK, are activated by atherogenic stimuli and regulated through local cytokine and growth factor production in vascular cells (Yang et al., *Immunity* 9:575, 1998). Ischemia and ischemia coupled with reperfusion in the heart, kidney or brain result in cell death and scar formation, which can ultimately lead to congestive heart failure, renal failure or cerebral dysfunction. In organ transplantation, reperfusion of previously ischemic donor organs results in acute leukocyte-mediated tissue injury and delay of graft function. Ischemia and reperfusion pathways are mediated by various kinases. For example, the JNK pathway has been linked to leukocyte-mediated tissue damage (Li et al., *Mol. Cell. Biol.* 16:5947-5954, 1996). Finally, enhanced apoptosis in cardiac tissues has also been linked to kinase activity (Pombo et al., *J. Biol. Chem.* 269:26546-26551, 1994).

What is claimed is:

1. A compound of formula (I)

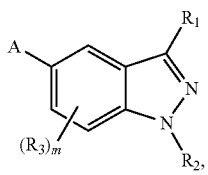

(I)

or a pharmaceutically acceptable salt thereof,
wherein A is (ii)

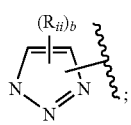

(ii)

$R_1$ is hydrogen or $R_aR_bN$;

$R_2$ is hydrogen, heterocyclecarbonyl, alkylcarbonyl, arylcarbonyl, or $R_eR_fN$-alkyl-C(O)—;

$R_3$ is alkyl, alkoxy, aryl, cyano, cycloalkyl, halogen, haloalkyl, heteroaryl, nitro, or $R_gR_hN$—;

$R_a$ and $R_b$ are each hydrogen;

$R_e$ and $R_f$ are each independently hydrogen or alkyl; $R_g$ and $R_h$ are each independently hydrogen, alkyl, or alkylcarbonyl;

$R_j$ and $R_k$ are each independently hydrogen, alkyl, aryl, arylalkyl, or heteroaryl;

$R_{ii}$ is alkoxyalkyl, alkoxycarbonyl, aryl, arylalkyl, aryl(hydroxy)alkyl, aryloxyalkyl, arylcarbonyl, arylthioalkyl, carboxy, cycloalkyl, cycloalkylalkyl, cycloalkylcarbonyl, halogen, heteroaryl, heteroarylalkyl, heterocycle, heterocyclealkyl, heterocyclecarbonyl, hydroxyalkyl, trialkylsilylalkyl, $Z_aZ_bN$—, $Z_aZ_b$Nalkyl- or $Z_cZ_dNC(O)$—;

$Z_a$ and $Z_b$ are each independently hydrogen, alkyl or $H_2$NalkylC(O)—;

$Z_c$ and $Z_d$ are each independently hydrogen, alkyl, alkoxyalkyl, aryl, arylalkyl, cycloalkyl, cycloalkylalkyl, heteroarylalkyl, heterocyclealkyl, hydroxyalkyl or dialkylN-alkyl-;

m is 0; and b is 1 or 2.

2. The compound according to claim 1, wherein $R_2$ is hydrogen, or $R_eR_fN$-alkyl-C(O)—;

$R_4$ is alkyl, alkoxyalkyl, aryl, cycloalkyl, $R_jR_kN$— or $R_jR_kN$-alkyl-;

$R_5$ is alkyl, aryl or heteroaryl;

$R_j$ and $R_k$ are each independently hydrogen, alkyl, or aryl;

$R_{ii}$ is alkoxyalkyl, aryl, arylalkyl, aryloxyalkyl, arylcarbonyl, arylthioalkyl, carboxy, cycloalkyl, cycloalkylalkyl, cycloalkylcarbonyl, halogen, heteroaryl, heteroarylalkyl, heterocyclealkyl, heterocyclecarbonyl, hydroxyalkyl, $Z_aZ_b$Nalkyl-, or $Z_cZ_dNC(O)$—;

$Z_a$ and $Z_b$ are each independently hydrogen or alkyl;

$Z_c$ and $Z_d$ are each independently hydrogen, alkyl, alkoxyalkyl, aryl, arylalkyl, cycloalkylalkyl or heterocyclealkyl;

m is 0; and
b is 1 or 2.

3. The compound according to claim 1, wherein
$R_2$ is hydrogen;
$R_4$ is alkyl, alkoxyalkyl or aryl;
$R_5$ is alkyl or aryl;
$R_{ii}$ is aryl, arylalkyl, cycloalkyl, cycloalkylalkyl or halogen;
b is 1 or 2; and
m is 0.

4. The compound according to claim 1, wherein
$R_4$ is alkoxyalkyl, alkyl, aryl, or $R_jR_kN$—;
$R_5$ is alkyl, aryl, or heteroaryl;
$R_j$ and $R_k$ are alkyl;
$R_{ii}$ is alkoxyalkyl, aryl, arylalkyl, aryl(hydroxy)alkyl, aryloxyalkyl, arylcarbonyl, arylthioalkyl, carboxy, cycloalkyl, cycloalkylalkyl, cycloalkylcarbonyl, halogen, heteroaryl, heteroarylalkyl, heterocyclealkyl, heterocyclecarbonyl, hydroxyalkyl, $Z_aZ_b$Nalkyl or $Z_cZ_d$NC(O)—;
$Z_a$ and $Z_b$ are each independently hydrogen or $H_2$Nalkyl-C(O)—;
$Z_c$ and $Z_d$ are each independently hydrogen, alkoxyalkyl, alkyl, arylalkyl, cycloalkyl, cycloalkylalkyl, or heterocyclealkyl;
b is 1; and
m is 0.

5. The compound according to claim 1, wherein
$R_2$ is hydrogen, heterocyclecarbonyl, or arylcarbonyl;
$R_4$ is alkyl, alkoxyalkyl, aryl, $R_jR_kN$— or $R_jR_kN$-alkyl-;
$R_5$ is alkyl, or aryl;
$R_j$ and $R_k$ are each independently hydrogen, alkyl, aryl, or arylalkyl;
$R_{ii}$ is aryl, arylalkyl, arylcarbonyl, cycloalkyl, cycloalkylalkyl, halogen, heteroaryl, heterocyclealkyl, heterocyclecarbonyl, or $Z_cZ_d$NC(O)—;
$Z_c$ and $Z_d$ are each independently hydrogen, alkyl, alkoxyalkyl, aryl;
m is 0; and
b is 1 or 2.

6. The compound of claim 1, that is selected from the group consisting of:
5-(1-benzyl-1H-1,2,3-triazol-4-yl)-1H-indazole;
5-[1-(2-methylbenzyl)-1H-1,2,3-triazol-4-yl]-1H-indazole;
5-[1-(3-methylbenzyl)-1H-1,2,3-triazol-4-yl]-1H-indazole;
5-[1-(4-methylbenzyl)-1H-1,2,3-triazol-4-yl]-1H-indazole;
5-[1-(3-methoxybenzyl)-1H-1,2,3-triazol-4-yl]-1H-indazole;
5-[1-(2-fluorobenzyl)-1H-1,2,3-triazol-4-yl]-1H-indazole;
5-[1-(3-fluorobenzyl)-1H-1,2,3-triazol-4-yl]-1H-indazole;
5-[1-(4-fluorobenzyl)-1H-1,2,3-triazol-4-yl]-1H-indazole;
5-[1-(2-chlorobenzyl)-1H-1,2,3-triazol-4-yl]-1H-indazole;
5-[1-(3-chlorobenzyl)-1H-1,2,3-triazol-4-yl]-1H-indazole;
5-[1-(4-chlorobenzyl)-1H-1,2,3-triazol-4-yl]-1H-indazole;
5-[1-(2-bromobenzyl)-1H-1,2,3-triazol-4-yl]-1H-indazole;
5-[1-(2-nitrobenzyl)-1H-1,2,3-triazol-4-yl]-1H-indazole;
5-[1-(3-nitrobenzyl)-1H-1,2,3-triazol-4-yl]-1H-indazole;
5-[1-(4-nitrobenzyl)-1H-1,2,3-triazol-4-yl]-1H-indazole;
2-{[4-(1H-indazol-5-yl)-1H-1,2,3-triazol-1-yl]methyl}benzonitrile;
3-{[4-(1H-indazol-5-yl)-1H-1,2,3-triazol-1-yl]methyl}benzonitrile;
4-{[4-(1H-indazol-5-yl)-1H-1,2,3-triazol-1-yl]methyl}benzonitrile;
5-{1-[2-(trifluoromethyl)benzyl]-1H-1,2,3-triazol-4-yl}-1H-indazole;
5-{1-[3-(trifluoromethyl)benzyl]-1H-1,2,3-triazol-4-yl}-1H-indazole;
5-{1-[4-(trifluoromethyl)benzyl]-1H-1,2,3-triazol-4-yl}-1H-indazole;
5-{1-[3-(trifluoromethoxy)benzyl]-1H-1,2,3-triazol-4-yl}-1H-indazole;
5-{1-[4-(trifluoromethoxy)benzyl]-1H-1,2,3-triazol-4-yl}-1H-indazole;
5-[1-(4-tert-butylbenzyl)-1H-1,2,3-triazol-4-yl]-1H-indazole;
methyl 3-{[4-(1H-indazol-5-yl)-1H-1,2,3-triazol-1-yl]methyl}benzoate;
methyl 4-{[4-(1H-indazol-5-yl)-1H-1,2,3-triazol-1-yl]methyl}benzoate;
5-[1-(2,4-dimethylbenzyl)-1H-1,2,3-triazol-4-yl]-1H-indazole;
5-[1-(3,5-dimethylbenzyl)-1H-1,2,3-triazol-4-yl]-1H-indazole;
5-[1-(2,3-dichlorobenzyl)-1H-1,2,3-triazol-4-yl]-1H-indazole;
5-[1-(2,4-dichlorobenzyl)-1H-1,2,3-triazol-4-yl]-1H-indazole;
5-[1-(2,5-dichlorobenzyl)-1H-1,2,3-triazol-4-yl]-1H-indazole;
5-[1-(3,5-dichlorobenzyl)-1H-1,2,3-triazol-4-yl]-1H-indazole;
5-{1-[2,4-bis(trifluoromethyl)benzyl]-1H-1,2,3-triazol-4-yl}-1H-indazole;
5-(1-benzyl-1H-1,2,3-triazol-4-yl)-1H-indazol-3-amine;
5-(1-benzyl-1H-1,2,3-triazol-4-yl)-1-[(1-methylpiperidin-4-yl)carbonyl]-1H-indazol-3-amine;
5-(1-benzyl-5-cyclopropyl-1H-1,2,3-triazol-4-yl)-1H-indazole;
5-(1-benzyl-4-cyclopropyl-1H-1,2,3-triazol-5-yl)-1H-indazole;
5-[1-(tetrahydro-2H-pyran-4-ylmethyl)-1H-1,2,3-triazol-4-yl]-1H-indazole;
5-(1-benzyl-5-phenyl-1H-1,2,3-triazol-4-yl)-1H-indazole;
5-(4-benzyl-1H-1,2,3-triazol-1-yl)-1H-indazole;
5-(1-benzyl-5-cyclopropyl-1H-1,2,3-triazol-4-yl)-1H-indazol-3-amine;
5-(1-benzyl-4-cyclopropyl-1H-1,2,3-triazol-5-yl)-1H-indazol-3-amine;
5-(1-benzyl-5-phenyl-1H-1,2,3-triazol-4-yl)-1H-indazol-3-amine;
2-[1-(1H-indazol-5-yl)-1H-1,2,3-triazol-4-yl]propan-2-ol;
5-[4-(methoxymethyl)-1H-1,2,3-triazol-1-yl]-1H-indazole;
1-[1-(1H-indazol-5-yl)-1H-1,2,3-triazol-4-yl]-1-phenylethanol;
1-[1-(1H-indazol-5-yl)-1H-1,2,3-triazol-4-yl]propan-2-ol;
3-[1-(1H-indazol-5-yl)-1H-1,2,3-triazol-4-yl]propan-1-ol;

1-{[1-(1H-indazol-5-yl)-1H-1,2,3-triazol-4-yl]methyl}-1H-1,2,3-benzotriazole;
5-{4-[(phenylthio)methyl]-1H-1,2,3-triazol-1-yl}-1H-indazole;
5-(4-cyclopropyl-1H-1,2,3-triazol-1-yl)-1H-indazole;
5-[4-(2-phenylethyl)-1H-1,2,3-triazol-1-yl]-1H-indazole;
5-[4-(cyclohexylmethyl)-1H-1,2,3-triazol-1-yl]-1H-indazole;
5-(4-cyclopentyl-1H-1,2,3-triazol-1-yl)-1H-indazole;
1-[1-(1H-indazol-5-yl)-1H-1,2,3-triazol-4-yl]cyclohexanol;
5-[4-(phenoxymethyl)-1H-1,2,3-triazol-1-yl]-1H-indazole;
5-{4-[(1,1-dioxidothiomorpholin-4-yl)methyl]-1H-1,2,3-triazol-1-yl}-1H-indazole;
5-[4-(3-phenylpropyl)-1H-1,2,3-triazol-1-yl]-1H-indazole;
[1-benzyl-4-(1H-indazol-5-yl)-1H-1,2,3-triazol-5-yl](phenyl)methanone;
N,N-diethyl-N-{[1-(1H-indazol-5-yl)-1H-1,2,3-triazol-4-yl]methyl}amine;
5-(1-benzyl-5-methyl-1H-1,2,3-triazol-4-yl)-1H-indazole;
5-(1-benzyl-5-methyl-1H-1,2,3-triazol-4-yl)-1H-indazol-3-amine;
5-(1-benzyl-5-iodo-1H-1,2,3-triazol-4-yl)-1H-indazol-3-amine;
N-{3-[4-(3-amino-1H-indazol-5-yl)-1-benzyl-1H-1,2,3-triazol-5-yl]phenyl}-N'-(3-methylphenyl)urea;
[1-benzyl-4-(1H-indazol-5-yl)-1H-1,2,3-triazol-5-yl](3-chlorophenyl)methanone;
[1-benzyl-4-(1H-indazol-5-yl)-1H-1,2,3-triazol-5-yl](cyclopropyl)methanone;
5-[5-cyclopropyl-1-(tetrahydro-2H-pyran-4-ylmethyl)-1H-1,2,3-triazol-4-yl]-1H-indazole;
N¹-{[1-benzyl-4-(1H-indazol-5-yl)-1H-1,2,3-triazol-5-yl]methyl}glycinamide;
(4-fluorophenyl)[4-(1H-indazol-5-yl)-1-(tetrahydro-2H-pyran-4-ylmethyl)-1H-1,2,3-triazol-5-yl]methanone;
(4-chlorophenyl)[4-(1H-indazol-5-yl)-1-(tetrahydro-2H-pyran-4-ylmethyl)-1H-1,2,3-triazol-5-yl]methanone;
(3-chlorophenyl)[4-(1H-indazol-5-yl)-1-(tetrahydro-2H-pyran-4-ylmethyl)-1H-1,2,3-triazol-5-yl]methanone;
(2-chlorophenyl)[4-(1H-indazol-5-yl)-1-(tetrahydro-2H-pyran-4-ylmethyl)-1H-1,2,3-triazol-5-yl]methanone;
cyclopentyl[4-(1H-indazol-5-yl)-1-(tetrahydro-2H-pyran-4-ylmethyl)-1H-1,2,3-triazol-5-yl]methanone;
1-benzyl-4-(1H-indazol-5-yl)-1H-1,2,3-triazole-5-carboxylic acid;
5-{5-(4-fluorophenyl)-1-[4-(trifluoromethyl)benzyl]-1H-1,2,3-triazol-4-yl}-1H-indazol-3-amine;
5-[1-benzyl-5-(4-fluorophenyl)-1H-1,2,3-triazol-4-yl]-1H-indazol-3-amine;
[4-(1H-indazol-5-yl)-1-(tetrahydro-2H-pyran-4-ylmethyl)-1H-1,2,3-triazol-5-yl](tetrahydro-2H-pyran-4-yl)methanone;
5-[1-benzyl-5-(2-methylphenyl)-1H-1,2,3-triazol-4-yl]-1H-indazole;
5-{1-benzyl-5-[(4-methylpiperazin-1-yl)carbonyl]-1H-1,2,3-triazol-4-yl}-1H-indazole;
1-{[1-benzyl-4-(1H-indazol-5-yl)-1H-1,2,3-triazol-5-yl]carbonyl}piperidin-4-ol;
1-acetyl-5-[5-(4-fluorophenyl)-1-(tetrahydro-2H-pyran-4-ylmethyl)-1H-1,2,3-triazol-4-yl]-1H-indazole;
1-benzyl-4-(1H-indazol-5-yl)-N,N-dimethyl-1H-1,2,3-triazole-5-carboxamide;
N,1-dibenzyl-4-(1H-indazol-5-yl)-1H-1,2,3-triazole-5-carboxamide;
5-[1-benzyl-5-(2-methylphenyl)-1H-1,2,3-triazol-4-yl]-1H-indazol-3-amine;
2-{2-[1-(1H-indazol-5-yl)-1H-1,2,3-triazol-4-yl]ethyl}-1H-isoindole-1,3(2H)-dione;
5-{4-[(2,4-dichlorophenoxy)methyl]-1H-1,2,3-triazol-1-yl}-1H-indazole;
5-{4-[(2,6-dichlorophenoxy)methyl]-1H-1,2,3-triazol-1-yl}-1H-indazole;
5-[5-(4-fluorophenyl)-1-(tetrahydro-2H-pyran-4-ylmethyl)-1H-1,2,3-triazol-4-yl]-1H-indazole;
1-{[1-(1H-indazol-5-yl)-1H-1,2,3-triazol-4-yl]methyl}-1H-indazole;
5-[1-benzyl-5-(piperidin-1-ylcarbonyl)-1H-1,2,3-triazol-4-yl]-1H-indazole;
5-[5-(2-methylphenyl)-1-(tetrahydro-2H-pyran-4-ylmethyl)-1H-1,2,3-triazol-4-yl]-1H-indazole;
5-[5-(2-methylphenyl)-1-(tetrahydro-2H-pyran-4-ylmethyl)-1H-1,2,3-triazol-4-yl]-1H-indazol-3-amine;
5-[1-benzyl-5-(morpholin-4-ylcarbonyl)-1H-1,2,3-triazol-4-yl]-1H-indazole;
5-[1-benzyl-5-(4-methoxyphenyl)-1H-1,2,3-triazol-4-yl]-1H-indazol-3-amine;
5-{1-benzyl-5-[3-(dimethylamino)phenyl]-1H-1,2,3-triazol-4-yl}-1H-indazol-3-amine;
5-{1-benzyl-5-[4-(dimethylamino)phenyl]-1H-1,2,3-triazol-4-yl}-1H-indazol-3-amine;
N-{3-[4-(3-amino-1H-indazol-5-yl)-1-benzyl-1H-1,2,3-triazol-5-yl]phenyl}acetamide;
N-{4-[4-(3-amino-1H-indazol-5-yl)-1-benzyl-1H-1,2,3-triazol-5-yl]phenyl}acetamide;
5-{1-benzyl-5-[3-(1H-pyrazol-1-yl)phenyl]-1H-1,2,3-triazol-4-yl}-1H-indazol-3-amine;
5-[1-benzyl-5-(1-methyl-1H-pyrazol-4-yl)-1H-1,2,3-triazol-4-yl]-1H-indazol-3-amine;
3-[4-(3-amino-1H-indazol-5-yl)-1-benzyl-1H-1,2,3-triazol-5-yl]-N-phenylbenzamide;
3-[4-(3-amino-1H-indazol-5-yl)-1-benzyl-1H-1,2,3-triazol-5-yl]-N-benzylbenzamide;
5-[1-benzyl-5-(1-methyl-1H-indol-5-yl)-1H-1,2,3-triazol-4-yl]-1H-indazol-3-amine;
5-[1-benzyl-5-(3-methoxyphenyl)-1H-1,2,3-triazol-4-yl]-1H-indazol-3-amine;
5-[1-benzyl-5-(3-morpholin-4-ylphenyl)-1H-1,2,3-triazol-4-yl]-1H-indazol-3-amine;
1-{[1-benzyl-4-(1H-indazol-5-yl)-1H-1,2,3-triazol-5-yl]carbonyl}piperidin-4-amine;
3-[4-(3-amino-1H-indazol-5-yl)-1-benzyl-1H-1,2,3-triazol-5-yl]phenol;
3-[4-(3-amino-1H-indazol-5-yl)-1-benzyl-1H-1,2,3-triazol-5-yl]benzamide;
5-{1-benzyl-5-[4-(methylsulfonyl)phenyl]-1H-1,2,3-triazol-4-yl}-1H-indazol-3-amine;
1-benzyl-4-(1H-indazol-5-yl)-N-[(2S)-tetrahydrofuran-2-ylmethyl]-1H-1,2,3-triazole-5-carboxamide;
1-benzyl-4-(1H-indazol-5-yl)-N-(2-isopropoxyethyl)-1H-1,2,3-triazole-5-carboxamide;
1-benzyl-4-(1H-indazol-5-yl)-N-[(2R)-tetrahydrofuran-2-ylmethyl]-1H-1,2,3-triazole-5-carboxamide;
1-benzyl-4-(1H-indazol-5-yl)-N-(tetrahydrofuran-3-ylmethyl)-1H-1,2,3-triazole-5-carboxamide;
1-benzyl-N-cyclopentyl-4-(1H-indazol-5-yl)-1H-1,2,3-triazole-5-carboxamide;
1-benzyl-N-(cyclopentylmethyl)-4-(1H-indazol-5-yl)-1H-1,2,3-triazole-5-carboxamide;

1-benzyl-N-ethyl-4-(1H-indazol-5-yl)-N-methyl-1H-1,2,3-triazole-5-carboxamide;
1-benzyl-4-(1H-indazol-5-yl)-N-isopropyl-N-methyl-1H-1,2,3-triazole-5-carboxamide;
1-benzyl-4-(1H-indazol-5-yl)-N-(2-methoxyethyl)-N-methyl-1H-1,2,3-triazole-5-carboxamide;
1-benzyl-4-(1H-indazol-5-yl)-N-phenyl-1H-1,2,3-triazole-5-carboxamide;
1-benzyl-N-(4-chlorophenyl)-4-(1H-indazol-5-yl)-1H-1,2,3-triazole-5-carboxamide;
1-benzyl-4-(1H-indazol-5-yl)-N-(2-morpholin-4-yl-ethyl)-1H-1,2,3-triazole-5-carboxamide;
1-benzyl-N-[2-(dimethylamino)ethyl]-4-(1H-indazol-5-yl)-N-methyl-1H-1,2,3-triazole-5-carboxamide;
1-benzyl-N-(2-hydroxyethyl)-4-(1H-indazol-5-yl)-N-propyl-1H-1,2,3-triazole-5-carboxamide;
1-benzyl-N-[3-(dimethylamino)propyl]-4-(1H-indazol-5-yl)-N-methyl-1H-1,2,3-triazole-5-carboxamide;
1-benzyl-N-[2-(diethylamino)ethyl]-4-(1H-indazol-5-yl)-N-methyl-1H-1,2,3-triazole-5-carboxamide;
N,1-dibenzyl-N-ethyl-4-(1H-indazol-5-yl)-1H-1,2,3-triazole-5-carboxamide;
N,1-dibenzyl-N-(2-hydroxyethyl)-4-(1H-indazol-5-yl)-1H-1,2,3-triazole-5-carboxamide;
(3R)-1-{[1-benzyl-4-(1H-indazol-5-yl)-1H-1,2,3-triazol-5-yl]carbonyl}piperidin-3-ol;
1-{[1-benzyl-4-(1H-indazol-5-yl)-1H-1,2,3-triazol-5-yl]carbonyl}piperidine-4-carboxamide;
5-{1-benzyl-5-[(2,6-dimethylmorpholin-4-yl)carbonyl]-1H-1,2,3-triazol-4-yl}-1H-indazole;
5-{5-[(4-acetylpiperazin-1-yl)carbonyl]-1-benzyl-1H-1,2,3-triazol-4-yl}-1H-indazole;
5-{1-benzyl-5-[(4-phenylpiperazin-1-yl)carbonyl]-1H-1,2,3-triazol-4-yl}-1H-indazole;
1-benzyl-N-[(1R)-1-(hydroxymethyl)-2-methylpropyl]-4-(1H-indazol-5-yl)-1H-1,2,3-triazole-5-carboxamide;
1-benzyl-N-[(1S)-1-(hydroxymethyl)-2-methylpropyl]-4-(1H-indazol-5-yl)-1H-1,2,3-triazole-5-carboxamide; and
1-benzyl-N-[3-(1H-imidazol-1-yl)propyl]-4-(1H-indazol-5-yl)-1H-1,2,3-triazole-5-carboxamide.

7. A pharmaceutical composition comprising a therapeutically effective amount of a compound of formula (I) according to claim 1, in combination with a pharmaceutically suitable carrier.

* * * * *

SEQUENCE LISTING

```
<160> NUMBER OF SEQ ID NOS: 6

<210> SEQ ID NO 1
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Lys Glu Ala Lys Glu Lys Arg Gln Glu Gln Ile Ala Lys Arg Arg Arg
1               5                   10                  15

Leu Ser Ser Leu Arg Ala Ser Thr Ser Lys Ser Gly Gly Ser Gln Lys
            20                  25                  30

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Arg Arg Leu Arg Arg Leu Thr Ala Arg Glu Ala Ala
1               5                   10

<210> SEQ ID NO 3
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Phosphorylated Ser

<400> SEQUENCE: 3

Tyr Arg Arg Ala Ala Val Pro Pro Ser Pro Ser Leu Ser Arg His Ser
1               5                   10                  15

Ser Pro His Gln Ser Glu Asp Glu Glu Glu
            20                  25

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 4

Lys Thr Phe Cys Gly Thr Pro Glu Tyr Leu Ala Pro Glu Val Arg Arg
1               5                   10                  15

Glu Pro Arg Ile Leu Ser Glu Glu Glu Gln Glu Met Phe Arg Asp Phe
                20                  25                  30

Asp Tyr Ile Ala Asp Trp Cys
            35

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Pro Ser Asp Ser Leu Ile Tyr Asp Asp Gly Leu Ser
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 6

His His His His His His
1               5
```